United States Patent
Serhan et al.

(10) Patent No.: US 8,933,270 B2
(45) Date of Patent: Jan. 13, 2015

(54) USE OF DOCASATRIENES, RESOLVINS, AND THEIR STABLE ANALOGS IN THE TREATMENT OF AIRWAY DISEASES AND ASTHMA

(71) Applicant: The Brigham and Women's Hospital, Inc., Boston, MA (US)

(72) Inventors: Charles N. Serhan, Needham, MA (US); Bruce D. Levy, West Roxbury, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 14/064,803

(22) Filed: Oct. 28, 2013

(65) Prior Publication Data
US 2014/0179630 A1    Jun. 26, 2014

Related U.S. Application Data

(63) Continuation of application No. 13/007,600, filed on Jan. 15, 2011, now Pat. No. 8,569,542, which is a
(Continued)

(51) Int. Cl.
C07C 59/10    (2006.01)
C07C 57/02    (2006.01)
(Continued)

(52) U.S. Cl.
CPC .............. *C07C 59/42* (2013.01); *C07C 59/48* (2013.01); *A61K 31/537* (2013.01);
(Continued)

(58) Field of Classification Search
None
See application file for complete search history.

(56) References Cited

U.S. PATENT DOCUMENTS 4,201,211 A    5/1980    Chandrasekaran et al.
4,442,099 A    4/1984    Nicolaou et al.
(Continued)

FOREIGN PATENT DOCUMENTS

EP    0736509 A2    10/1996
EP    0736509 B1    10/1996
(Continued)

OTHER PUBLICATIONS

Hong et al., Journal of Biological Chemistry (2003), 278(17), 14677-14687.*
(Continued)

*Primary Examiner* — Karl J Puttlitz
(74) *Attorney, Agent, or Firm* — Colin L. Fairman; Christensen Fonder P.A.

(57) ABSTRACT

The present invention is generally drawn to novel isolated therapeutic agents, termed resolvins, generated from the interaction between a dietary omega-3 polyunsaturated fatty acid (PUFA) such as eicosapentaenoic acid (EPA) or docosahexaenoic acid (DHA), cyclooxygenase-II (COX-2) and an analgesic, such as aspirin (ASA). Surprisingly, careful isolation of compounds generated from the combination of components in an appropriate environment provide di- and tri-hydroxy EPA or DHA compounds having unique structural and physiological properties. The present invention therefore provides for many new useful therapeutic di- or tri-hydroxy derivatives of EPA or DHA (resolvins) that diminish, prevent, or eliminate inflammation or PMN migration, for example. The present invention also provides methods of use, methods of preparation, and packaged pharmaceuticals for use as medicaments for the compounds disclosed throughout the specification.

33 Claims, 31 Drawing Sheets

Related U.S. Application Data continuation of application No. 11/836,460, filed on Aug. 9, 2007, now Pat. No. 7,872,152, which is a continuation of application No. 11/081,203, filed on Mar. 16, 2005, now Pat. No. 7,759,395, and a continuation-in-part of application No. 10/639,714, filed on Aug. 12, 2003, now Pat. No. 7,585,856.

(60) Provisional application No. 60/553,918, filed on Mar. 17, 2004, provisional application No. 60/402,798, filed on Aug. 12, 2002.

(51) Int. Cl.

| | | |
|---|---|---|
| C07C 59/48 | (2006.01) | |
| A61K 31/537 | (2006.01) | |
| A61K 31/445 | (2006.01) | |
| A61K 31/202 | (2006.01) | |
| A61K 31/551 | (2006.01) | |
| A61K 31/495 | (2006.01) | |
| C07F 7/18 | (2006.01) | |
| C07C 59/42 | (2006.01) | |
| A61K 31/655 | (2006.01) | |
| A61K 31/275 | (2006.01) | |

(52) U.S. Cl.
CPC ............ *A61K 31/445* (2013.01); *A61K 31/202* (2013.01); *A61K 31/551* (2013.01); *A61K 31/495* (2013.01); *C07F 7/1868* (2013.01); *A61K 31/655* (2013.01); *A61K 31/275* (2013.01)
USPC ............................ 562/587; 562/598; 514/578

(56) References Cited

U.S. PATENT DOCUMENTS

| | | | |
|---|---|---|---|
| 4,567,290 A | 1/1986 | Nicolaou et al. |
| 4,576,758 A | 3/1986 | Morris et al. |
| 4,666,701 A | 5/1987 | Horrobin et al. |
| 4,710,521 A | 12/1987 | Soukup et al. |
| 4,759,880 A | 7/1988 | Nicolaou et al. |
| 4,810,424 A | 3/1989 | Gerwick et al. |
| 5,087,790 A | 2/1992 | Petasis et al. |
| 5,136,501 A | 8/1992 | Silverman et al. |
| 5,177,046 A | 1/1993 | Savoca et al. |
| 5,409,955 A | 4/1995 | Bockow et al. |
| 5,411,988 A | 5/1995 | Bockow et al. |
| 5,441,951 A | 8/1995 | Serhan |
| 5,594,732 A | 1/1997 | Bell et al. |
| 5,604,258 A | 2/1997 | Ferrante et al. |
| 5,648,512 A | 7/1997 | Serhan |
| 5,650,157 A | 7/1997 | Bockow |
| 5,709,855 A | 1/1998 | Bockow |
| 5,752,238 A | 5/1998 | Dedrick |
| 5,756,789 A | 5/1998 | Bruce et al. |
| 5,814,599 A | 9/1998 | Mitragotri et al. |
| 5,842,040 A | 11/1998 | Hughes et al. |
| 5,845,265 A | 12/1998 | Woolston |
| 5,846,974 A | 12/1998 | Kallman et al. |
| 5,861,399 A | 1/1999 | Seed et al. |
| 5,870,717 A | 2/1999 | Wiecha |
| 5,878,400 A | 3/1999 | Carter, III |
| 5,878,423 A | 3/1999 | Anderson et al. |
| 5,890,138 A | 3/1999 | Godin et al. |
| 5,896,379 A | 4/1999 | Haber |
| 5,912,006 A | 6/1999 | Bockow et al. |
| 5,932,598 A | 8/1999 | Talley et al. |
| 5,946,467 A | 8/1999 | Pathakis et al. |
| 6,030,715 A | 2/2000 | Thompson et al. |
| 6,030,917 A | 2/2000 | Weinberg et al. |
| 6,048,897 A | 4/2000 | Serhan |
| 6,069,109 A | 5/2000 | Kao et al. |
| 6,117,911 A | 9/2000 | Grainger et al. |
| 6,201,022 B1 | 3/2001 | Mease et al. |
| 6,232,467 B1 | 5/2001 | Petasis et al. |
| 6,259,699 B1 | 7/2001 | Opalka et al. |
| 6,272,474 B1 | 8/2001 | Garcia |
| 6,316,648 B1 | 11/2001 | Serhan |
| 6,336,105 B1 | 1/2002 | Conklin et al. |
| 6,336,138 B1 | 1/2002 | Caswell et al. |
| 6,377,937 B1 | 4/2002 | Paskowitz |
| 6,397,212 B1 | 5/2002 | Biffar |
| 6,415,270 B1 | 7/2002 | Rackson et al. |
| 6,427,132 B1 | 7/2002 | Bowman et al. |
| 6,428,990 B1 | 8/2002 | Mukerji et al. |
| 6,569,075 B2 | 5/2003 | Serhan |
| 6,602,817 B1 | 8/2003 | Petasis |
| 6,620,919 B2 | 9/2003 | Serhan |
| 6,635,776 B2 | 10/2003 | Serhan |
| 6,653,493 B2 | 11/2003 | Serhan |
| 6,670,396 B2 | 12/2003 | Serhan et al. |
| 6,750,360 B2 | 6/2004 | Serhan |
| 6,887,901 B1 | 5/2005 | Serhan |
| 6,949,664 B2 | 9/2005 | Patasis |
| 7,030,159 B2 | 4/2006 | Serhan et al. |
| 7,053,230 B2 | 5/2006 | Serhan et al. |
| 7,341,840 B2 | 3/2008 | Serhan et al. |
| 2001/0023500 A1 | 9/2001 | Serhan |
| 2001/0031882 A1 | 10/2001 | Serhan |
| 2002/0010351 A1 | 1/2002 | Serhan |
| 2002/0045579 A1 | 4/2002 | Madara et al. |
| 2002/0055538 A1 | 5/2002 | Serhan et al. |
| 2002/0055539 A1 | 5/2002 | Bockow et al. |
| 2002/0082435 A1 | 6/2002 | Serhan |
| 2002/0091279 A1 | 7/2002 | Serhan |
| 2002/0094549 A1 | 7/2002 | Serhan et al. |
| 2002/0107289 A1 | 8/2002 | Serhan |
| 2002/0111505 A1 | 8/2002 | Serhan |
| 2002/0120013 A1 | 8/2002 | Serhan |
| 2002/0132847 A1 | 9/2002 | Serhan |
| 2002/0143069 A1 | 10/2002 | Serhan |
| 2002/0193431 A1 | 12/2002 | Serhan et al. |
| 2003/0032827 A1 | 2/2003 | Serhan |
| 2003/0055275 A1 | 3/2003 | Serhan |
| 2003/0060512 A1 | 3/2003 | Madara et al. |
| 2003/0069435 A1 | 4/2003 | Serhan |
| 2003/0134901 A1 | 7/2003 | Serhan |
| 2003/0166716 A1 | 9/2003 | Serhan et al. |
| 2003/0191184 A1 | 10/2003 | Serhan et al. |
| 2003/0191332 A1 | 10/2003 | Serhan |
| 2003/0195248 A1 | 10/2003 | Serhan et al. |
| 2003/0236423 A1 | 12/2003 | Petasis |
| 2004/0019110 A1 | 1/2004 | Van Dyke et al. |
| 2004/0044050 A1 | 3/2004 | Goodman et al. |
| 2004/0053998 A1 | 3/2004 | Serhan et al. |
| 2004/0059144 A1 | 3/2004 | Serhan et al. |
| 2004/0116408 A1 | 6/2004 | Serhan |
| 2004/0151712 A1 | 8/2004 | Madara et al. |
| 2004/0192785 A1 | 9/2004 | Serhan |
| 2005/0075398 A1 | 4/2005 | Bazan et al. |
| 2005/0228047 A1 | 10/2005 | Petasis |
| 2005/0261255 A1 | 11/2005 | Serhan et al. |
| 2006/0128804 A1 | 6/2006 | Serhan et al. |
| 2006/0293288 A1 | 12/2006 | Serhan et al. |

FOREIGN PATENT DOCUMENTS

| | | |
|---|---|---|
| GB | 2033745 A1 | 5/1980 |
| JP | 5186342 | 7/1993 |
| WO | WO 91/16914 | 11/1991 |
| WO | WO 97/19415 | 5/1997 |
| WO | WO 98/19259 | 5/1998 |
| WO | WO 98/35469 | 8/1998 |
| WO | WO 98/46588 | 10/1998 |
| WO | WO 99/06913 | 2/1999 |
| WO | WO 99/13417 | 3/1999 |
| WO | WO 99/56727 | 11/1999 |
| WO | WO 00/32210 A1 | 6/2000 |
| WO | WO 00/74632 | 12/2000 |
| WO | WO 01/60778 | 8/2001 |
| WO | WO 03/051350 | 6/2003 |
| WO | WO 03/053423 | 7/2003 |

(56) References Cited

FOREIGN PATENT DOCUMENTS

| | | |
|---|---|---|
| WO | WO 03/084305 A | 10/2003 |
| WO | WO 03/105776 A | 12/2003 |
| WO | WO 2004/014835 | 2/2004 |
| WO | WO 2005/089744 A | 9/2005 |

OTHER PUBLICATIONS

A.J. Marcus, "Platelets: their role in hemostasis, thrombosis, and inflammation", Inflammation: Basic Principles and Clinical Correlates 1999,. pp. 77•95.

A.P. Simopoulos, "Workshop on the essentiality of an recommended dietary intakes for omega-6 and omega-3 fatty acids", J. Am. Coli. Nutr. 1999, pp. 487-489.

Alami, et al., "A versatile route to conjugated hydroxyl (E,Z,E,E)-Tetraenoic acids: highly chemo- and stereoselective synthesis of lipoxin B4 tetrahedra Asym.", 8(17) 2949-2958, 1997.

Arita et al., "Stereochemical Assignment, Antiinflammatory Properties, and Receptor for the Omega-3 Lipid Mediator Resolvin E1", J. Exp. Med. 201(5): 713-722, 2005.

Arita et al., "Resolvin E1, An Endogenous Lipid Mediator Derived from Omega-3 Eicosapentaenoic Acid, Protects Against 2, 4,6-Trinitrobenzene Sulfonic Acid-Induced Colitis", Proc. Nat/. A cad. Sci., USA, 1 02(21 ): 7671-7676, 2005.

Babine, R.E. and S.L. Bender., "Molecular Recognition of Protein-Ligand Complexes: Applications to Design," Chem. Rev. 97:1359-1472 (1997).

Bannenberg, et al., "Molecular Circuits of Resolution: Formation and Actions of Resolvins and Protectins", Immunol. 174(7): 4345-4355, 2005.

Beamer L.J. et al. "Crystal structure of Human BPI and two bound phospholipids at 2.4 angstrom resolution", Science, vol. 276, 1997, pp. 1861-1864.

Bhaley, G. et al., "Solid Phase Synthesis of Diverse Tetrahydro-1,4-Benzodiazepine-2-ones," Tetrahedron Letters 38(48):8375-8378 (1997).

Blaser, E. et al., "Asymmetrix Steering of oxa Diels-Alder Reactions with Silyloxydienes Employing Proline Esters as Chiral Auxiliary Groups," Eur. J. Org. Chem., 329-333, (1999).

Boland et al., "Stereospecific Syntheses and Spectroscopis Properties of Isomeric 2,4,6,8-Undecatetraenes. New Hydrocarbons from the Marine Brown Alga Giffordia Mitchellae", Helv. Chim. Acta 70;1025-1040, 1987.

CA 101:19194 for Van Rollins et al., Journal of Biological Chemistry,(1984) 259(9), pp. 5776-5783.

CA 119:265901 for Reynaud et al., Analytical Biochemistry (1993), 214(1 ), pp. 165-170.

Canny,G. et al., "Lipid mediator-induced expression of bactericidal/permeability increasing protein (BPI) in human mucosal epihelia", Proc. Natl. Acad., Sci., USA, vol. 99, No. 6, 2002, pp. 3902-390.

Chemical Abstracts online citation, AN:2004:143088, retrieved Aug. 15, 2007 from STN, Columbus, OH, USA.

Dharmsathaphorn, K. et al., "Established intestinal cell lines as model systems for electrolyte transport studies", Methods in Enzymology, vol. 192, 1990, pp. 354-389.

Dioux, Laurent and Morris Srebnik "Asymmetric Boron-Catalyzed Reactions", Chem Rev. 93:763-784, (1993).

Durantel et al., "Study of the mechanism of Antiviral Action of Iminosugar Derivatives against Bovine Viral Diarrhea Virus," J. Virology 75(19): 8987-8998, (2001).

E.M. Hill, et al. "Identification and egg hatching activity of monohydroxy fatty acid eicosanoids in the barnacle Balanus balanoides", Abstract, XP-002200247, 1992.

Eckmann, L. et al., "Epithelial cell secrete the chemokines interleukin-8 in response to bacterial entry", Infection and Immunity, vol. 61, No. 11, 1193, pp. 4569-4574, 1993.

Eritsland et al., "Effects of Highly Concentrated Omega-3 PUF As and Acetylsalicylic Acid, Alone and Combined, on Bleeding Time and Serum Liquid Profile", J, Olso City Hosp., vol. 39(8-9), pp. 97-101, 1989.

Garro-Helion et al., "Mild and Selective Palladium (0)-Catalyzed Deallylation of Allylic Amines, Allylamine and Diallylamines as Very Convenient Ammonia Equivalents for the Synthesis of Primary Amines", J. Org. Chem., 58:6109-6113, (1993).

Golebiowski, A. and J. Jurczak, "Alpha-Amino-Beta-Hydroxy Acids in the Total Synthesis of Amino Sugars," Synlett, pp. 241-245, (Apr. 1993).

Guiller et al., "Linkers and Cleavage Strategies in Solid-Phase Organic Synthesis and Commbinatorial Chemistry," Chem. Rev., 100; 2091-2157, (2000).

Hanessia, S. et al., "Design and Synthesis of Conformationally Constrained Amino Acids as Versatile Scaffolds and Peptide Manners," Tetrahedron, 53: 12789-12854, (1997).

Hill, EM. Proc R. Soc. London Ser. B., 247 (1318) pp. 41-46, 1992.

Hong, et al., "Novel Docosatrienes and 17S-Resolvins Generated from Docosahexaenoic Acid in Murine Brain, Human Blood, and Glial Cells, Autacoids in Anti-Inflammation", J. Bioi. Chem. 278(17): 14677-14687,2003.

Hoyng, C.F. and A.D. Patel, "Aldehyde Components for Use in Four-Component Condensation ("CC") UGI Reaction Peptide Synthesis," Tetranderon Lett., 21 :4795-4798, (1980).

Humphrey, J.M. and A.R. Chamberlain, "Chemical Synthesis of Natural Product Peptides: Coupling Mehtods for the Incorporation of Noncoded Amino Acids Into Peptides," Chem. Rev., 97:2243-2266, (1997).

Ikeda et al., "Chiral Allenylboronic Esters as Practical Reagent for Enantioselective Carbon-Carbon Bond formation Facile Synthesis of(-) Ipsenol", J. Am. Chem. Soc. 108:483-4486, 1986.

J. Claria et al., "Aspirin triggers previously undescribed bioactive eicosanoids by human endothelial cell-leukocyte interactions", Proc. Nat/. Acad. Sci., USA, 1995, pp. 9475-9479.

Karanian, J.W., et al., "Physiological functions of hydroxyl-docosahexaenoic acid", Abstract, XP-002200246, 1993.

Konig et al., "Synthesis of N-tert-Aikylglyoxylic Acid Amides", Synthesis, pp. 1233• 1234, (1993), [in German, English language abstract on p. 1.

L. De Montarby, et al. "Synthesis stereoselectives de metabolites hydroxyles d'acides gras polinsatures", Bulletin De La Societe Chimique de France, No. 3, pp. 419-432, 1989.

Lacoviello et al., "Modulation of Fibrinolytic Response to Venous Occlusion in Humans by a Combination of Low-Dose Aspirin and n-3 PUFAs", Arteriosclerosis Thrombosis, vol. 10, pp. 1191-1197, 1992.

Lau et al., "Effects of Fish Oil Supplementation on Non-Steroidal Anti-Inflammatory Drug (NSAID) Requirement in Patients with Mild Rheumatoid Arthritis—A Double-Blind Placebo Controlled Study", British Journal of Rheumatology, vol. 32 (11 ), pp. 982-989, 1993.

M. Ligo et al., "Inhibitory effects of docosahexaenoic acid on colon carcinoma 26 metastasis to the lung", Br. J. Cancer, pp. 650-655, 1997.

M.Yamane, et al., "Docosahexaenolc/arachidonic acid w-hydroxylation system and differentiation in the human clonic adenocarcinoma cell line, Caco-2", Cancer Letters, vol. 122, pp. 51•59, 1998.

Serhan, "A Search for Endogenous Mechanisms of Anti-Inflammation Uncovers Novel Chemical Mediators: Missing Links to Resolution", Histochem Cell Biol.122(4): 305-321, 2004.

Serhan, "Novel Eicosanoid and Docosanoid Mediators: Resolvins, Docosatrienes, and Neuroprotectins", Curr Opin Clin Nutr Metab Care, 8(2): 1-7, 2005.

Serhan, "Novel Omega-3-Derived Local Mediators in Anti-Inflammation and Resolution", Pharmacal. Ther. 105(1): 7-21, 2005.

Serhan, et al., "Resolvins, Docosatrienes and Neuroprotectins, Novel Omega-3 Derived Mediators and their Endogenous Aspirin-Triggered Epimers", Lipids, vol. 39, pp. 1125-1132, 2004.

Serhan, et al., "Novel Endogenous Small Molecules as the Checkpoint Controllers in Inflammation and Resolution: Entree for Resoleomics" Rheum Dis Clin North Am. 30(1): 69-95, 2004.

Serhan, et al., "Novel Pathways and Endogenous Mediators in Anti-Inflammation and Resolution", Chem Immunol Allergy, 83: 115-145, 2003.

(56) References Cited

OTHER PUBLICATIONS

Serhan, et al., "Resolvins: a family of bioactive products of omega-3 fatty acids transformation circuits initiated by aspirin treatment that counter proinflammation signals", J. Exp. Med., vol. 196, No. 8, pp. 1025-1037, 2002.
T. Kato, et al., "Production of Hydroxy Unsaturated Fatty Acids Using Crude Lipoxygenase Obtained from Infected Rice Plants", Bull. Chem. Soc. Jpn., vol. 69, pp. 1663-1666, 1996.
Takeshi Terano, Ensho, Chemical Abstract 107:22439, pp. 63-71, 1987.
Terano T. et al., "Eicosapentaenoic acid and docosahexaenoic acid inhibit vascular smooth muscle cell proliferation by inhibiting phosphorylation of Cdk2-cyclinE complex", Biochem. Biophys. Res. Comm., vol. 254, pp. 502-506, 1999.
Van Dyke, et al., "Resolution of Inflammation: A New Paradigm for the Pathogenesis of Periodontal Diseases", J. Dent. Res., 82(2): 82-90, 2003.
Vu Bois et al., "Novel, Stereoselective Synthesis of 2 Amino Saccharides," J. Am. Chem. Soc. 119: 3179-3180, 1997.
W.E.M. Lands, "Proceedings of the AOCS Short Course on Polyunsaturated Fatty Acids and Eicosanoids", American Oil Chemists' Society, 1987.
Serhan et al, "Design of lipoxin A4 stable analogs that block transmigration and adhesion of human neutrophils", Biochemistry, 1995, pp. 14609-14615.
N. Chiang et al., "Leukotriene 84 receptor transgenic mice reveal novel protective roles for lipoxins and aspirin-triggered lipoxins in reperfusion", J. Clin. Invest., 1999, pp. 309•316.
C.N. Serhan et al., "Novel functional sets of lipid-derived mediators with Anti•inflammatory Actions generated from omega-3 fatty acids via cyclooxygenase 2• nonsteroidal anti-Inflammatory drugs and transcellular processing", J. Exp. Med., vol. 192, No. 8, 2000, pp. 1197-1204.
H.R. Herschman, "Recent progress in the cellular and molecular biology of prostaglandin synthesis", Trends Cardiovasc. Med. ,1998, pas. 145-150.
P. Needleman et al., "The discovery and function of COX-2", J. Rheumatol, 1997, pp. 6• 8.
N. Chiang et al., "Aspirin-triggered 15-epi-lipoxin A4 (ATL) generation by human leukocytes and murine peritonitis exudates: Development of a specific 15-epi•LXA4 ELISA", J. Pharmacal. Exp. Ther. ,1998, pp. 779-790.
G. Xiao et al., "Analysis of hydroperoxide-induced tyrosyl radicals and lipoxygenase activity in aspirin-treated human prostaglandin H synthase-2", Biochemistry 1997, pp. 1836-1845.
K. Node et al., "Anti-inflammatory properties of cytochrome P450 epoxygenase-derived elcosanoids", Science 1999, pp. 1276-1279.
S. Sethi et al., "Inhibition of phagocyte-endothelium interactions by oxidized fatty acids: A natural antI•flammatory mechanism?", J. Lab. ClIn. Med. 1996, pp. 27-38.
G.N. Levy, "Prostaglandin H synthases, nonsteriodal anti-inflammatory drugs, and colon cancer", FASEB J. 1997, pp. 234-247.
K. Gronert, et al., "Transcellular regulation of eicosanoid biosynthesis", Eicosanoid Protocols 1999, pp. 119-144.
H.J. George et al., "Expression purification and characterization of recombinant human inductible prostaglandin G/H synthase from baculovirus-infected insect cells", Protein Expres. Purif. 1996, pp. 19-26.
J.H. Capdevila et al., "The highly stereoselective oxidation of polyunsaturated fatty acids by cytochrome P450BM•3", J. Bioi. Chem. 1996, pp. 22663-22671.
R.T. Ruettinger et al., "Epoxidation of unsaturated fatty acids by a soluble cytochrome P-45-dependent system from *Bacillus megaterium*", J. Biol. Chem. 1981, pp. 5728-5734.
T.H. Lee et al., "Characterization and biologic properties of 5,12-dihydroxy derivatives of eicosapentaenoic acid, including leukotriene B5 and the double lipoxygenase product", J. Biol. Chem. 1984, pp. 2383•2389.

C.N. Serhan et al., "Nomenclature of lipoxins and related compounds derviyed from arachidonic acid and eicosapentaenoic acid", Prostaglandins ,1 987, figs. 201•204.
D.J. Hill et al., "Trout thrombocytes contain 12-but not 5-lipoxygenase activity", Biochem. Biophys. Acta 1999, pp. 63-70.
B.N. Cronstein et al., "A mechanism for the anti-inflammatory effects of corticosterlods: The glucocorticoid receptor regulates leukocyte adhesion to endotheliasl cells and expression of endothelial-leukocyte adhesion molecule 1 and intercellular adhesion molecule 1", Proc. Nat/. A cad. Sci. 1992, pp. 9991-9995.
T. Yokomizo et al., "A G•protein-coupled receptor for leukotriene B4 that mediates chemotaxis", Nature, 1997, pp. 620-624.
M.R. Buchanan et al., "Regulation of endothelial cell and platelet receptor-ligand binding by the 12- and 15-lipoxygenase monohydroxldes, 12-, 15-HETE and 13-HODE", Prostaglandins Leukot. Essent. Fatty Acids 1998, pp. 339-346.
P.M. Ridker et al., "Inflammation, aspirin, and the risk of cardiovascular disease in apparently healthy men", N. Engl. J. Med. 1997, pp. 973-979.
Knapp, Howard R., et al., "Bactericidal Effects of Polyunsaturated Fatty Acids", The Journal of Infectious Diseases, vol. 154, No. 1, 1986 pp. 84-94.
Cooper, S.F., et al., "Identification of Antibacterial Fatty Acids from *Phaeodactylum tricomtum* grown in dialysis culture", The Faculty Press, 1985, pp. 28-36.
Ganz T. et al., "Antimicrobial peptides of phagocytes and epithelia", Seminars in Hematology, vol. 34, No. 4, 1997, pp. 343-354.
Elsbach, P .et al., "Role of the bactericidal/permeability-increasing protein in host defence", Current Opinion in Immunology, vol. 1 0, No. 1, 1998, pp. 45-49.
Levy, O., "A neutrophil-derived anti-infective molecule: bactericidal/permeability increasing protein", Antimicrobial Agents and Chemotherapy, vol. 44, No. 11, 2000, pp. 2925-2931.
Levy, O., "Antimicrobial proteins and peptides of blood: templates for novel D D antimicrobial agents", Blood, vol. 96, No. 8, 2000, pp. 2664-2672.
Lockhart, D.J. et al., "Expression monitoring by hybridixation to high-density oligonucleotide arrays", Nature Biotechnology, vol. 14, No. 13, 1996, pp. 1675•1680.
Higuchi, R. et al., "Kinetic PCR analysis: real time monitoring of DNA amplification reactions", "Biotechnology", vol. 11, 1993, pp. 1026-1030.
Taylor, C.T. et al., "Critical role of cAMP response element binding protein expression in hypoxia-elicited induction of epithelial tumor necrosis factor-a", J. Bioi. Chem., vol. 274, No. 27,1999, pp. 19447-19454.
Pfaffl, M.W., "A new mathematical model for relative quantification in real-time RT-PCR", Nucleic Acids Research, vol. 29, No. 9, 2001,. pp. 2002-2007.
Colgan, S.P .et al., "Defective in vitro motility of polymorphonuclear leuocytes of homozygote and heterozygote Chediak-Higashi cats", Vet. Immunol. Immunopathology, 1992, pp. 205-227.
Weersink, A., et al., "Human granulocytes express a 550-kDa lipopolysaccharidebinding protein on the cell surface that is identical to the bactericidal/permeability-increasing protein", J. Immunology, vol. 150, No. 1, 1993, pp. 253-263.
Weiss, J. et al., "Purification and characterization of a potent bactericidal and membrane active protein from the granules of human polymorphonuclear leukocytes", J. Biol. Chem., vol. 253, No. 8, 1987, pp. 2664-2672.
Marx et al., "Synthetic Design for Combinatorial Chemistry. Solution and Polymer-Supported Synthesis of Polycyclic Lactams by Intramolecular Cyclization of Azomethane Ylides," J. Chem. Soc., 119:6153-6167, (1997).
Mehta et al., "Structure-Activity Relationship of a New Class of Anti-Hepatitis B Virus Agents", Antimicrobial Agents and Chemotherapy, 46(12):4004-4008 (2002).
Nicolaou et al., NoveiiBX-Mediated Process for the Synthesis of Amino Sugars and Libraries Thereof, Angew. Chem. Int. Ed. Engl., 39:2525-2529, (2000).
Nicolaou et al., "Lipoxins and Related Eicosanoids: Biosynthesis, Biological Properties and Chemical Synthesis," Angew. Chem. Ed. Engl. 30: 1100•1116, (1991).

(56) References Cited

OTHER PUBLICATIONS

Noyori, R. (Ed), "Enantioselective Addition of Organometallic Reagents to Carbonyl Compounds: Chirality Transfer, Multiplication and Amplification," Chapter 5 in Asymmetrical Catalysts in Organic Synthesis, New York; Wiley & Sons, Inc. pp. 225-297 (1994).
Nugent, William A., "Chiral Lewis Acid Catalysts. Enantioselective Additon of Azide to Meso Epoxides", J. Am. Chem. Soc., 114(7); 2768-2769 (1992).
O'Donnell, Martin J. and J. Falmagne, "The Synthesis of Amino Acids via Organoboranes." J. Chem. Soc. Chem. Commun., No. 17, pp. 1168-1169, (Sep. 1, 1985).
Petasis, N.A. and I.A. Zavialov, "The Boronic Acid Mannich Reaction: A New Method for the Synthesis of Geometrically Pure Allylamines." Tetrahedron Letters, 34(4): 538-586, (1993).
Rodriguez and Spur, "Total Synthesis of aspirin-triggered 15-epi-lipoxin A4", Tetrahedron Letters, 42: 6057-6060, 2001.
Petasis, N.A. and I.A. Zavialov, "A New and Practical Synthesis of Alpha Amino Acids from Alkenyl Boronic Acids," J. Am. Chem. Soc., 119(2): 445-446, (1997).
"Scope and Editorial Policy", Organometallics, published by the American Chemical Society 21(1): 13A, 14A (2002).
Thompson, L.A. and J.A. Ellman, "Synthesis and Applications of Small Molecule Libraries", Chem. Rev., 96:555-6000 (1996).
Waki, M. and J. Meienhofer, "Peptide Synthesis Using the Four-Component Condensation (Ugi Reaction)," J. Am. Chem. Soc., 99:6075-6082, (1977).
Yamamoto, Y. and N. Asao, "Selective Reactions Using Allylic Metals", Chem Rev., 93;2207-2293, (1993).
McCormick, B.A. et al., "*Salmonella typhimurium* attachment to human intestinal epithelial mono layers: transcellular signaling to subepithllal neurophlls", J. Cell Biology, vol. 123, No. 4, 1993, pp. 895-907.
Loeschke D. et al., Dig. Dis. Sci., vol. 41,2087-94, (1996).
N.G. Bazan, et al., Docosahexaneoic Acid (22:6, n-3) is metabolized to lipoxygenase reaction products in the retina, BIochem. BIophys. Res. Comm., vol. 125, pp. 741•747, 1984.
J. Booyens et al., "Some effects of the essential fatty acids linoleic acid and alpha•linolenic acid and of their metabolites gamma-linolenic acid, arachidonic acid, eicosapentaenoic acid docosahexaenoic acid, and of prostaglandins A1 and e1 on the proliferation of human osteogenic sarcoma cells in culture", Prostaglandins Leukot. Med., vol. 15, pp. 15•33, 1984.
J. Catella-Lawson et al., "Cycloxygenase inhibitors and the antiplatelet effects of aspirin", N. Engl. J. Med., vol. 345, pp. 1809-1817, 2001.
L.J. Crofford. "Rational use of analgesic and anti-Inflammatory drugs", N. Engl. J. Med., vol. 345, pp. 1844-1846, 2001.
C.M. Fored et al., "Acetaminophen, aspirin, and chronic renal failure", N. Engl. J. Med., vol. 345, pp. 18001-1808,2001.
B.J. Greeling et al., "Fat intake and fatty acid profile in plasma phospholipids and adipose tissue in patients with Crohn's disease, compared with controls", Am. J. Gastroenterol., vol. 94, pp. 410-417, 1999.
L.J. Jenski et al., "Docosahexaenoic acid-induced alteration of Thy-1 and CDS expression on murine splenocytes", Biochem. Biophys., Acta. 1236, pp. 39-50, 1995.
T. Khair-El-Din et al., "Transcription of the murine Inos gene is inhibited by docosahexanaenoic acid, a major constituent of fetal serum and fish oils diets inhibits IFN alpha-induced Ia-expression by murine macrophases in vitro", J. Immuno., vol. 154, 1995, pp. 1296-1306.
K. Kitajka et al., "The role of n-3 ployi=unsaturated fatty acids in brain: Modulation of rat brain gene expression by dietary n-3 fatty acids", Proc. Natl. Acad. Sci., USA 9, pp. 2619-2624, 2002.
M. Martinez et al., "Docohexaenoic acid—a new therapeutic approach to peroxisomal disorder patients: Experience with two cases", Neurology, vol. 43, 1993, pp. 1389-1397.
I. Marzo et al., "Biosynthesis of docohexaenoic acid in human cells, evidence that two different-desaturase activities may exist", Biochem. Biophys. Acta 1301, 1996, pp. 263-272.

C.C. Miller et al., "Oxidative metabolism of dihomogammalinolenic acid by guinea pig epidermis: Evidence of generation of anti-inflammatory products", Prostaglandins, vol. 35, 1988, pp. 917-938.
R. K. Pullarkat et al., "Leukocyte docosahexaenoic acid in juvenile form of ceroidlipofuscinosis", Neuropadiatrie, vol. 9, pp. 127-130, 1987.
J.H. Rapp et al., "Dietary eicosapentaenoic acid and docosahexaenoic acid form fish oil", Arteriosclerosis and Thrombosis, vol. 11, 1991 pp. 903-911.
T.D. Reddy et al., "Change in content, incorporation and lipoxygenation of docosahexaenoic acid in retina and retinal pigment epithelium in canine ceroid lipofuscinosis", Neuroscience Lett., vol. 59, pp. 67-72, 1985.
K.C. Srivastava, "Docosahexaenoic acid (C22:6w3) and linoleic acid are anti-aggregatory, and alter arachodonic acid metabolism in human platelets", Prostaglandins Leukot. Med., vol. 17, pp. 319-327, 1985.
M. VanRollins et al., "Oxidation of docosahexanaenoic acid by rat liver mirosomes", J. Biol. Chern., vol. 259, pp. 5776-5782, 1984.
M. VanRollins et al., "Autooxidation of docosahexaenoic acid: Analysis of ten isomers of hydroxydocosahexaenoate", J. Lipid Res., vol. 25, pp. 507-517, 1984.
V.A. Ziboth et al., "Inhibition of sheep vesicular gland oxygenase by unsaturated fatty acids from skin of essential acid deficient rats", Prostaglandins, vol. 5, pp. 233-240, 1974.
C.N. Serhan, et al., "Novel functional sets of Lipid-derived mediators with antiinflammatory actions generated from omega-3 fatty acids via Cyclooxygenase 2-nonsteroidal Anti-inflammatory drugs and transcelllular processing", J. Exp. Med. col. 192, pp. 1197-1204, 2000.
B. Samuelson et al., "Leukotrienes and lipoxins: structure, biosynthesis, and biological effects", Science, vol. 237, pp. 1171-1176, 1987.
F. D. Gunstone et al., "The Lipid Handbook", $2^{nd}$ ED., Chapman & Hall, London, pp. 1-551, 1994.
B. Samuelson et al., "From studies of biochemical mechanisms to novel biological mediators: prostaglandin endoperoxides, thromboxanes and leukotrienes", In Les Prix Nobel, pp. 165-174, 1982.
D.C. Zeldin, "Epoxygenase pathways of arachidonic acid metabolism", J. Biol. Cherm, vol. 276, pp. 36059-36062, 2001.
R. Palmantieri, et al., "Transcellular metabolism of arachidonic acid in platelets and polymorphonuclear leukocytes activated by physiological agonists: enhancement of leukotriene B4 synthesis", Cell-cell Interactions in the Release of Inflammatory Mediators, vol. 314, pp. 73-89, 1991.
C.N. Serhan et al., "Unorthodox routes to prostanoid formation: new twists in cyclooxygenase-initiated pathways", J. Clin. Invest., vol. 107, pp. 1481-1489, 2001.
B.D. Levy et al., "Lipid mediator class switching during acute inflammation: signals in resolution", Nature Immunol., vol. 2 pp. 612-619, 2001.
B. McMahon et al., "Lipoxins: Revelations on Resolution", Trends in Pharmacological Sciences, vol. 22, pp. 391-395, 2001.
C. Bandeira-Mielo et al., "Cyclooxygenase-2 derived prostaglandin $E_2$ and lipoxin $A_4$ accelerate resolution of allergic edema in *Antiostrongylus costaricensis*-infected rats: relationship with concurrent eosinophilia", J. Immunol., vol. 164, pp. 1029-1036, 2000.
A. F. Rowley et al.,"Homeostasis in fish—an evolutionary perspective", Throm. Homeost., vol. 77, pp. 227-233, 1997.
R. De Caterina et al., "n-e Fatty Acids and Vascular Disease", Current Topics in Cardiovascular Disease, Springer-Verlag, London, 1993.
J.R. Hibbeln, "Fish consumption and major depression", Lancet, vol. 351, pp. 1213, 1998.
M. Olfson et al., "National trends in the outpatient treatment of depression", JAMA, vol. 287, pp. 203-209, 2002.
C.M. Albert, et al., "Blood levels of long-chain n-e fatty acids and the risk of sudden death", N. Engl. J. Med., vol. 346, pp. 1113-1118, 2002.
K. Shinmura et al., "Cyclooxygenase-2 medaites the cardioprotectie effects of the late phase of ischemic preconditioning in conscious rabbits", Proc. Natl. Acad. Sci. USA, vol. 97, pp. 10197-10202, 2000.

(56) References Cited

OTHER PUBLICATIONS

GISSI-Preventive Investigators, "Dietary supplementation with n-3 polyunsaturated fatty acids and vitamin E after myocardial infarction: Results of the GISSI-Prevenzione trial", Lancet, vol. 354, pp. 447-455, 1999.
R. Marchioli et al., "Early protection against sudden death by n-3 polyunsaturated fatty acids after myocardial infarction: time-course analysis of the results of the Gruppo-Italiano per lo Studion della Sopravivenze nell'Infarto Miocardico", Circulation, vol. 105, pp. 1897-1903, 2002.
P. McLennan et al., "The cardiovascular protective role of the docosahexaenoic acid", Eur. J. Pharmacol. vol. 300, pp. 83-89, 1996.
P. Libby, "Atherosclerosis, The New View", Sci. Am., vol. 286, pp. 46-55, 2002.
J.M. Drazen et al., "Heterogeneity of therapeutic responses in asthma", Br. Med. Bull., vol. 56, pp. 1 054-1070, 2000.
J.R. Vane et al., "Therapeutic Roles of Selective COX-2 Inhibitors", William Harvey Press, London, 2001.
S.W. Rolinson et al., "Spatial requirements for 15-(R)-hydroxyl 5Z, 8Z, 11Z, 13 Eeicosatetraenoic acid synthesis with the cyclooxygenase active site of murine COX-2 ", J. Biol. Cherm. , vol. 275, pp. 6586-6591, 2000.
D.W. Gilroy et al., "Inducible cyclooxygenase may have anti-inflammatory properties", Nature Med., vol. 5, pp. 698-701, 1999.
N.G. Balzan et al., "Pathways for the uptake and conservation of docosahexaenoic acid in photoreceptors and synapses: biochemical and autoradiographic studies", Can. J. Physiol. Pharmacol., vol. 71, pp. 690-698, 1993.
J. Whelan et al., "The unique characteristics of the purified 5-lipoxygenase from potato tubers and the proposed mechanism of formation of leukotrienes and lipoxins", Biological Oxidation Systems, vol. 2, pp. 765-778, 1990.
S. Fischer et al., "Uptake, release and metabolism of docosahexaenoic acid (DHA, C22:6w3) in human platelets and neutrophils", Biochem, Biophys. RES. Commun., vol. 120, pp. 907-918, 1984.
T.H. Lee et al., "Effects of exogenous arachidonic, eicosapentaenoic, and docosahexaenoic acids on the generation of 5-lipoxygenase pathway products by ionophore-activated human neutrophils", J. Clin. Invest., vol. 74, pp. 1922-1933, 1984.
J.A.Yergey et al., "High-performance liquid chromatography/ thermospray mass spectrometry of eicosanoids and novel oxygenated metabolites of docosahexaenoic acid", Anal. Cherm., vol. 58, pp. 1344-1348, 1986.
C.B. Clish et al.,"Oxidoreductases in lipoxin A,. metabolic inactivation", J. Biol. Cherm., vol. 375, pp. 25372-25380, 2000.
S.P. Colgan et al.,"Lipoxin $A_4$ modulates transmigration of human neutrophils across intestinal epithelial monolayers", J. Clin. Invest., vol. 92, pp. 75-82, 1993.
F.H. Qiu et al., "Aspirin-triggered lipoxin $A_4$ and lipoxin $A_4$ up-regulate transcriptional corepressor NAB1 in human neutrophils", FASEB J. 1096/ fj. 1 001-0576fje, vol. 10, 2001.
S. Sawazaki et al., "Lipoxygenation of docosaxaenoic acid by the rate pineal body", J. Neurochem., vol. 62, pp. 2437-2447, 1994.
C.C. Miller et al., "Dietary supplementation with ethyl ester concentrates of fish oil (n-3) and borage oil (n-6) polyunsaturated fatty acids induces epidermal generation of local putative anti-inflammatory metabolites", J. Invest. Dermat., vol. 96, pp. 98-103, 1991.
E.J. Corey et al., "Docosahexaaenoic acid is a strong inhibitor of prostaglandin but not leukotriene biosynthesis", Proc. Natl. Acad. Sci. USA, vol. 80, pp. 3581-3584, 1983.
M.K. O' Banion et al., "Cdna Cloning and functional activity of a glucocorticoidregulated inflammatory cyclooxygenase", Proc. Natl., Acad., Sci. USA, vol. 89, pp. 4888-4892, 1992.
T. Shimizu et al., "Enzyme with dual lipooxygenase activities catalyzes luekotriene $A_4$ synthesis from arachidonic acid", Proc. Natl. Acad Sci. USA, vol. 81, pp. 689-693, 1994.

V.A. Ziboth et al., "Metabolism of polyunsaturated fatty acids by skin epidermal enzymes: generation of anti-inflammatory and antiproliferative metabolites", Am. J. Clin. Nutr., vol. 71 (Suppl.), pp. 361S-366S, 2000.
N. Salem et al., "Arachidonic and docosahexaenoic acids are biosynthesized from their 18-carbon precursors in human infants", Proc. Natl. Acad. Sci. USA, vol. 93, pp. 49-54,1996.
J. Tou, "Acylation of docosahexaenoic acid into phospholipids by intact human neutrophils", Lipids, vol. 21, pp. 324-327, 1986.
J.S. Poling, et al., "Docosahexaenoic acid block of neuronal voltage-gated K+ channels: subunit selective antagonism by zinc", Neuropharmacology, vol. 35, pp. 969-982, 1986.
A. Mata de Urquiza et al., "Docosahaenoic acids, a ligand for the retinoid X receptor in mouse brain", Science, vol. 290, pp. 2140-2144, 2000.
S.D. Freeman et al., "Characterization of EPS-induced lung inflammation in ctfr mice and the effect of docosahexaenoic acid", J. Appl. Physiol., vol. 92, pp. 2169-2176, 2002.
E.E. Reich et al., "Formation of novel D-ring and E-ring isoprostane-like compounds ($D_4$ /$E_4$-neuroprostanes) in vivo from docosahexaenoic acid", Biochemistry, vol. 39, pp. 2376-2383, 2000.
G. Garcia-Gardena et al., "Biomechanical activation of cascular endothelium as a determinant of its functional phenotype", Proc. Natl. Acad. Sci. USA, vol. 98, pp. 4478-4485, 2001.
P.A. Gum et al., "Aspirin use and all-cause mortality among patients being valuated for known or suspected coronary artery disease: a propensity analysis", J.A.M.A., vol. 286, pp. 1187-1194, 2001.
I. H. Rosenberg et al., "Fish-food to calm the heart", N. Engl. J. Med., vol. 346, pp. 1102-1103, 2002.
J.F. Maddox et al., "Lipoxin $A_4$ and $B_4$ are potent stimuli for human monocyte migration and adhesion selective inactivation by dehydrogenation and reduction", J. Exp. Med., vol. 183, pp. 137-146, 1996.
T. Khair-El-Din et al., "Transcription of the Murine Inos gene is inhibited by Docosahexaenoic Acid, a Major Constituent of Fetal and Neonatal Sera as Well as Fish Oils", J. Exp. Med., vol. 183, pp. 1241-1246, 1996.
J.F. Schmedtje, Jr. et al., "Hypoxia Induces Cyclooxygenase-2 via the NF-Kb p65 Transcription Factor in Human Vascular Endothelial Cells", J. Biol. Chem., vol. 272, No. 1 pp. 601-608, 1997.
Stahl, G.L. et al., Pharmacologic profile of lipoxins AS and B5: new biologically active eicosanoids European Journal of Pharmacology, 1989, vol. 163, No. 1, 99. 55-60.
Lloyd-Evans, P. et al., Eicosanoid generation and effects on the aggregation of thrombocytes from the rainbow trout, *Oncorhynchus mykiss*, Biochimica et Biophysica Acta, Lipids and Lipid Metabolism, 1994, vol. 1215, No. 3. pp. 291-299.
Yamane, M. et al., High-performance liquid chromatography-thermospray mass spectrometry of epoxy polyunsaturated fatty acids and epoxyhydroxy polyunsaturated fatty acids from an incubation mixture of rat tissue homogenate, Journal of Chromatography, B: Biomedical Sciences and Applications, 1994, vol. 652, No. 2, pp. 123-136.
Inhibitory potencies of fish oil hydroxyl fatty acids on cellular lipoxygenases and platelet aggregation, Biochemical Pharmacology, 1991, vol. 42, No. 4, p. 959-962.
Slots, et al., "General Health Risk of Periodontal Disease", International Dental Journal, Dec. 2001,51(6), pp. 417-422.
Green, Gary A., "Understanding NSAIDS: From Aspirin to COX-2", Clinical Cornerstone, Sports Medicine 2001, 3(5), pp. 50-59.
Merck Index, "Gingivitis", Copyright © 1995-2007 Merck & Co., Inc., Whitehouse Station, NJ, USA, Last Full Version, Feb. 2003, 3 pgs.
Stella, Valentino J., "Expert Opinion of Therapeutic Patents", Prodrugs as Therapeutics, 2004, 14(3), pp. 277-280.
Wolff et al., "Burger's Medicinal Chemistry and Drug Discovery", 5th Ed., vol. 1, pp. 975-977, 1994.
Dragoli et al., "Parallel Synthesis of Prostaglandin $E_1$ Analogues", J. Comb. Chem., 1999, pp. 534-539.
"Epolinsatures", Bulletin De La Societe Chimique de France, No. 3, pp. 419-432, 1989.

(56) References Cited

OTHER PUBLICATIONS

Levy, Bruce D. et al. "Protectin D1 is Generated in Asthma and Dampens Airway Inflammation and Hyperresponsiveness," The Journal of Immunology, 2007, 178: 496-502.

Serhan, et al. "Resolvins, Oocosatrienes, and Neuroprotectins, Novel Omega-3-Derived Mediators, and their Endogenous Aspirin-Triggered Epimers", Lipids, 73: 155-172, 2004.

Hong, et al. "Rainbow trout (*Oncorhynchus mykiss*) brain cells biosynthesize novel docasahexaenoic acid-derived resolvins and protectins-mediator lipidomic analysis", Prostaglandins & Other Lipid Mediators, Elsevier, vol. 78, No. 1-4, Jun. 13, 2005, pp. 107-116. XP005174168.

Serhan, Charles N. et al. "Anti-Inflammatory Actions of Neuroprotectin D1/Protectin D1 and it's Natural Stereoisomers: Assignments of Oihydroxy-Containing Oocosatrienes", Journal of Immunology, 176(3), 1848-1959 Coden: J01MA3; ISSN 0022-1767, Feb. 1, 2006. XP002429095.

PCT/US2006/038326 International Search Report dated Apr. 23, 2007.

PCT/US2006/000306 International Search Report dated Jul. 14, 2006.

PCT/US2003/25336 International Search Report dated Feb. 16, 2004.

PCT/US2001/05196 International Search Report dated Jul. 19, 2002.

EP 06 02 2386 European Search Report dated Oct. 5, 2007.

PCT/US2005/12552 International Search Report dated Aug. 24, 2005 (in name of Trustees of Boston University).

PCT/US2006/011222 International Search Report dated Oct. 5, 2007.

PCT/US2005/009056 International Search Report dated Nov. 16, 2005.

Karanian, J.W. et al., "Inhibitory Effects of n-6 and n-3 Hydroxy Fatty Acids on Thromboxane (U46619)-Induced Smooth Muscle Contraction", The Journal of Pharmacology and Experimental Therapeutics, vol. 270, No. 3, pp. 1105-1109, 1994, XP-009087752.

Croset, M. et al., "Inhibition by Lipoxygenase Products of TXA2-Like Responses of Platelets and Vascular Smooth Muscle", Biochemical Pharmacology, vol. 37, No. 7, pp. 1275-1280, 1988, XP-002445509.

Hong, et al. Journal of Biological Chemistry, 278(17) 1467714687, 2003.

Evans, B.E. et al., "Design of Nonpeptidal ligands for a Peptide Receptor: Cholecystokinin Antagonists", J. Med. Chem., 30:1229•1239 (1987).

Fletcher, M.D. and M.C. Campbell, "Partially Modified Retro-Inverso Peptides: Development, Synthesis, and Conformational Behavior," Chem. Rev., 98:763-795, (1998).

G. Weissmann, "Aspirin", Sci. Am. 1991, pp. 84-90.

G.E. Billman et al., "Prevention of sudden cardiac death by dietary pure ω-3 polyunsaturated fatty acids in dogs", Circulation 99, 1999, p. 2452-2457.

Marcheselli, et al. "Novel Docosanoids Inhibit Brain Ischemia-Reperfusion-Mediated Leukocyte Infiltration and Pro-Inflammatory Gene Expression", J. Biol. Chem. 278(44): 43807-43817, 2003.

Miller et al., "Lipids", Chemical Abstract 112:117062, pp. 998-1003, 1989.

R. Marchioloi, "Dietary supplementation with n-3 polyunsaturated fatty acids and vitamin E after myocardial infarction: results of the GISSI-Prevenzione trial", Lancet 1999, pp. 447-455.

Rao et al, "Comparative Pharmacology of Cyclooxygenase Inhibitors on Platelet Function", Prostaglandins Leukot. Med., vol. 18 (1), pp. 119-131, 1985.

Serhan et al.,"Resolvins, Docosatrienes, and Neuroprotectins, Novel Omega-3-Derived Mediators, and their Aspirin-Triggered Endogenous Epimers: An Overview of Their Protective Roles in Catabasis", Prostaglandins Other Lipid Mediat. 5543, 1-18, 2004.

Khalfoun, B. et al., "Docosahexaenoic and Eicosapentaenoic Acids Inhibit Human Lymphoproliferative Responses in Vitro but not the Expression of T Cell Surface Activation Markers", Scand. J. Immunol., 43, pp. 248-256, 1996, XP-000878923.

XP002184773—Antiinflammatory drug with immuno-modulating effect—contains (5Z, 8Z, 11Z, 13E, 15(S), 17Z)-15-hydroxy :eicosa:penta:enoic acid or its salts or ester(s) as the effective ingredient. Publisher accession No. 1993-269748.

Database CAS Online citation 2002:815669 retrieved Oct. 30, 2009; from STN' Columbus, OH, USA.

Database CAS Online citation 2003:304562 retrieved Oct. 30, 2009; from STN' Columbus, OH, USA.

Kim, H.Y., et al. "Preparation and the structural determination of hydroperoxy derivatives of docosahexaenoic acid and other polyunsaturates by thermospray LC/MS", Prostaglandins, 1989, vol. 37, No. 1, pp. 105-119.

Yamauchi, et al. "Autoxidation and Photosensitized Oxidation of Methyl Eicosapentaenoate: Secondary Oxidation Products", Agric. Biol. Chem, vol. 49 No. 7, 1985, pp. 2077-2082.

\* cited by examiner

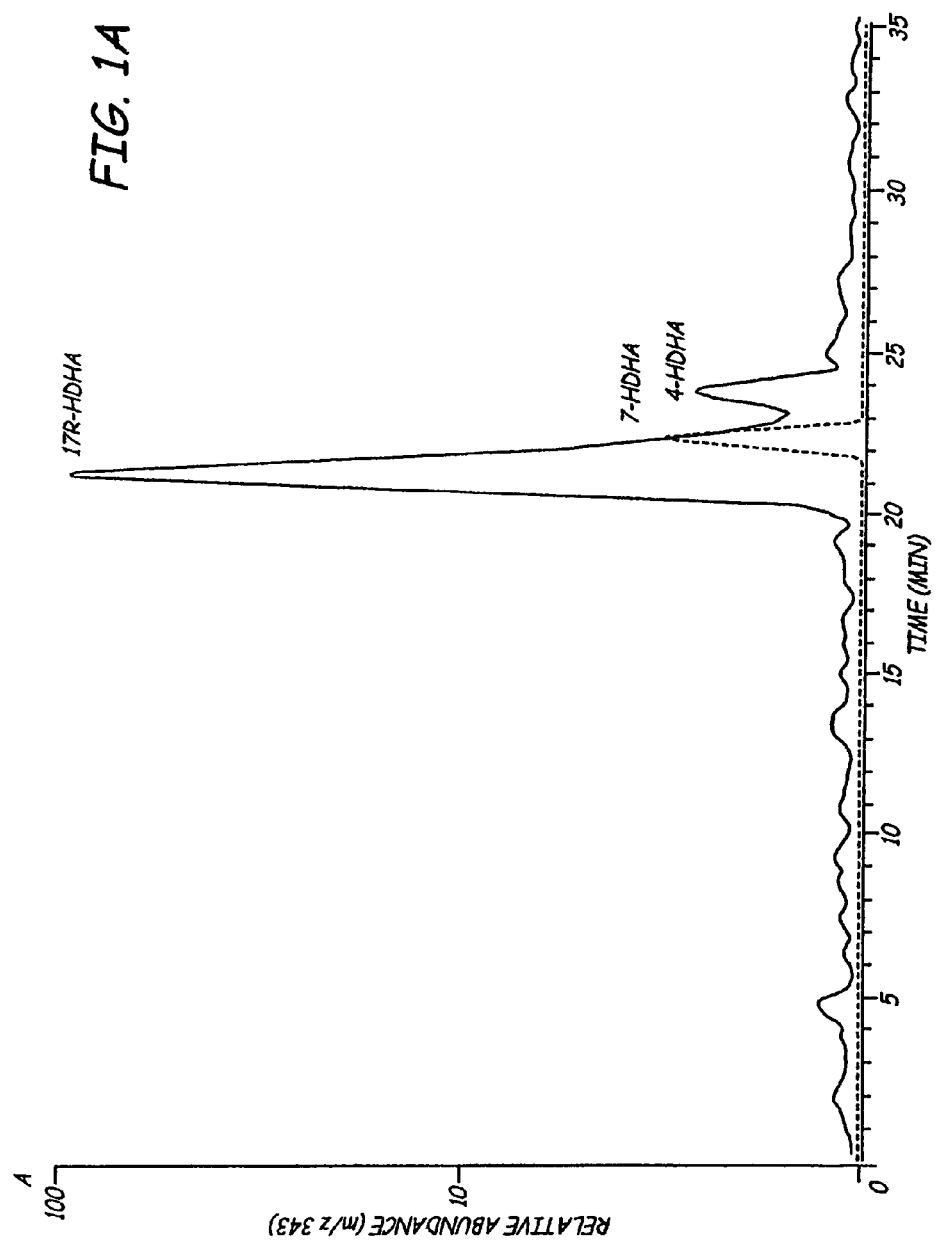

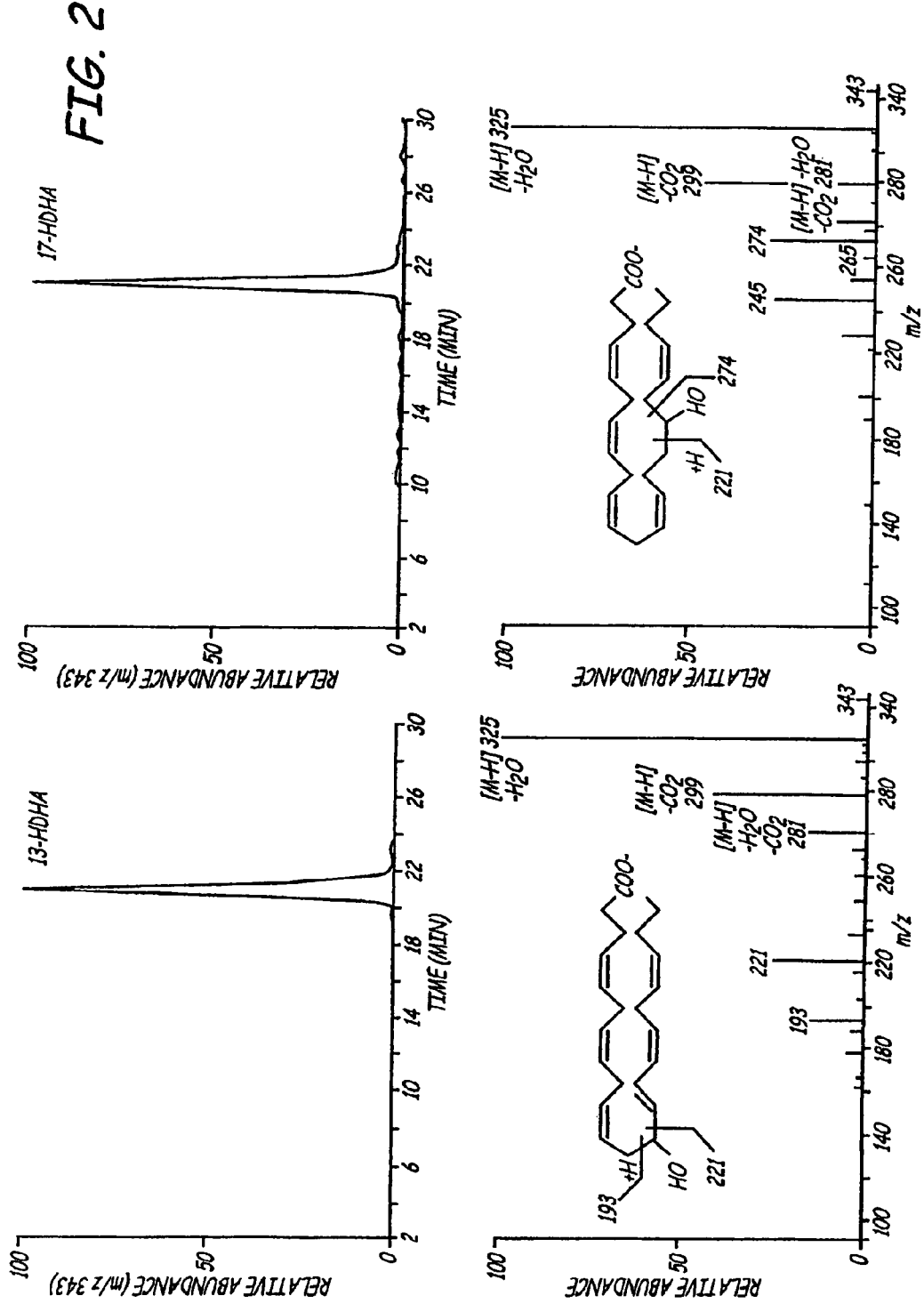

NOVEL 4, 17S-diHDHA AND 10, 17S-DOCOSATRIENE:
REDUCE LEUKOCYTE INFILTRATION IN ZYMOSAN-INDUCED PERITONITIS

§ Compounds (100 ng or 200 ng in 100 µl sterile saline) were injected by intravenous bolus injection into male FVB mouse tail vein followed by 1 ml zymosan A (1 mg/ml) into peritoneum. Peritoneal lavages were collected (2 h) and cell types were enumerated.

Fig. 20
a   10,17S-DT  200 ng
 
b   10,17S-DT  20 ng
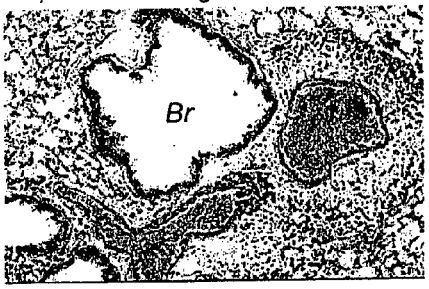 
c   vehicle
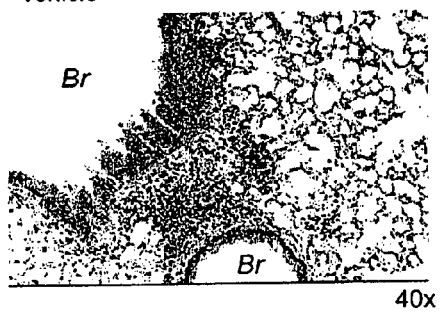 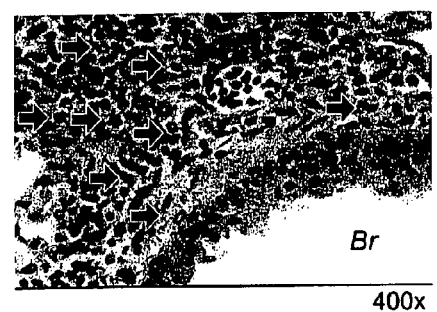
40x                                    400x

Regulation of Allergic Airway Inflammation By Resolvin E1

Resolvin E1 (200 ng) administered (iv) to sensitized animals 1 h prior to OVA aerosol challenge.
* $P < 0.05$

USE OF DOCASATRIENES, RESOLVINS, AND THEIR STABLE ANALOGS IN THE TREATMENT OF AIRWAY DISEASES AND ASTHMA

CROSS REFERENCE TO RELATED APPLICATION(S)

This application is a Continuation of U.S. patent application Ser. No. 13/007,600, filed Jan. 15, 2011, entitled "Use of Docosatrienes, Resolvins, and Their Stable Analogs in the Treatment of Airway Diseases and Asthma", which is a Continuation of U.S. patent application Ser. No. 11/836,460, filed Aug. 9, 2007, entitled "Use of Docosatrienes, Resolvins, and Their Stable Analogs in the Treatment of Airway Diseases and Asthma", issued as U.S. Pat. No. 7,872,152 on Jan. 18, 2011, which is a Continuation of U.S. patent application Ser. No. 11/081,203, filed Mar. 16, 2005, "entitled "Use of Docosatrienes, Resolvins, and Their Stable Analogs in the Treatment of Airway Diseases and Asthma" issued as U.S. Pat. No. 7,759,395 on Jul. 20, 2010, which is a Continuation-In-Part and claims priority to U.S. Provisional Application Ser. No. 60/553,918, filed on Mar. 17, 2004, entitled "Use of Docosatrienes, Resolvins and Their Stable Analogs in the Treatment of Airway Diseases and Asthma", U.S. Ser. No. 10/639,714, filed Aug. 12, 2003, Issued as U.S. Pat. No. 7,585,856 on Sep. 8, 2009, and U.S. Provisional Application Ser. No. 60/402,798, filed on Aug. 12, 2002, entitled "Resolvins: Biotemplates for Novel Therapeutic Interventions", the contents of which are incorporated herein in their entirety for all purposes.

STATEMENT REGARDING FEDERALLY SPONSORED RESEARCH

The work leading to this invention was supported in part by National Institutes of Health (NIH) grants HL68669 and P01-DE13499. The U.S. Government therefore may have certain rights in the invention.

FIELD OF THE INVENTION

The present invention relates to previously unknown therapeutic agents derived from novel signaling and biochemical pathways that use eicosapentaenoic acid (EPA) and/or docosahexaenoic acid (DHA), both of which are polyunsaturated fatty acids (PUFAs) as precursors to the production of bioactive novel endogenous products that control physiologic events in inflammation and resolution in vascular endothelial reactions and neural systems (brain). More specifically, the present invention relates to di- and trihydroxy potent bioactive products termed "Resolvins," which are derived from the biochemical interactions of a 5 lipoxygenases, such as cyclooxygenase and a polyunsaturated fatty acid. In addition, therapeutic stable analogs of resolvins that enhance their biologic properties are described that can be used to expedite resolution by inhibiting the pro-inflammatory amplification of leukocyte entry.

BACKGROUND OF THE INVENTION

The roles of eicosanoids in diverse physiologic and pathologic scenarios provide clear examples of the importance of fatty acid precursors such as arachidonic acid in cell communication, a sharp departure from their structural and storage assignments (3-5). Among the classes of bioactive eicosanoids, including prostaglandins, leukotrienes (LT), lipoxins (LX) and cis-epoxyeicosatrienoic acids or EETs (4, 6), it is now apparent that counter-regulatory autacoids exist within these classes of eicosanoids. Of the cyclooxygenase pathways, prostacyclin and thromboxane are important vascular counter-regulators (7). In inflammation, leukotriene products of the 5-lipoxygenase are pro-inflammatory mediators (4, 8), and lipoxins generated via lipoxygenase interactions can counter-regulate certain leukotriene-mediated events (for a recent review, see 9). The emergence of temporal and spacial separation in biosynthesis of eicosanoids during inflammation sheds light on distinct functional settings for lipoxins as "stop" or pro-resolution signals (10). Moreover, aspirin (ASA) treatment can pirate the lipoxin system, triggering formation of their 15-epimeric or their R-containing isoform (ASA-triggered LX) that serve as LX mimetics, to mount pro-resolution status (9, 11, 12), as well as enhancers in epithelial-based anti-microbial host defense (13).

Leukocytes from several species of fish rich in omega-3 fatty acids generate prostaglandins, leukotrienes and lipoxins from both arachidonic acid (C20:4) and eicosapentaenoic acid (C20:5). Their immune functions in marine organisms appear similar to those in humans; namely, as drivers of cell motility. Yet, fish cells generate quantitatively similar levels of both 4 and 5 series (EPA-derived) leukotrienes and lipoxins, which is sharply different than human tissues that use predominantly C20:4-derived mediators (reviewed in 14). Omega-3 fatty acids such as eicosapentaenoic acid (EPA, C20:5) and docosahexaenoic acid (DHA, C22:6) may be beneficial in several human diseases including atherosclerosis, asthma, cardiovascular, cancer (reviewed in 15), and, more recently, mental depression (16, 17) and preventing sudden death after myocardial infarction (18, 19). Of interest are results from the GISSI-Prevenzione trial that evaluated omega-3 polyunsaturated fatty acid supplementation with more than 11,300 patients that provide evidence for a decrease of ~45% in cardiovascular death (20).

It is noteworthy that both patient groups received aspirin in the GISSI trial while comparing tocopherol vs. omega-3 supplementation (20) as did a significant number of participants in the most recent Physician Health study report (18). The impact of ASA to the results of these studies was not tested although firmly concluding the benefits of omega-3 fatty acids in risk reduction (18, 20, 21). Eating fish rich in omega-3's is now recommended by the American Heart Association (see http://www.americanheart.org). However, what is evident from animal studies is that DHA is the bioactive cardiovascular protective component of fish oils (22). The mechanism(s) for omega-3 protective properties in heart disease and in prostate cancer remains unclear and the molecular bases are still sought to explain the clinical phenomena associated with fish oil trials.

The heightened awareness that unresolved inflammation is important in many chronic disorders including heart disease, atherosclerosis, asthma, and Alzheimer's disease (23, 24) leads to question whether omega-3 utilization during ASA therapy is converted to endogenous bioactive compounds relevant in human disease and health. Recently, data suggests that at sites of inflammation omega-3 PUFA eicosapentaenoic acid (EPA) is converted to potent bioactive products that target neutrophil recruitment (2). Hence, COX-2, which has a larger substrate tunnel/channel than COX-1 (25, 26), acts on C20:4 as well as additional substrates that can be productively accommodated as exemplified by the ability to convert the omega-3 polyene family of lipids (i.e., C18:3 and C20:5), possibly for tissue-specific COX-2 missions (2) such as those associated with ischemic preconditioning (19), resolution (10, 12, 27) and/or other disease processes. EPA and COX-2 (2) or DHA (28-32) raise the possibility that, in addition to arachidonic acid, omega-3 fatty acids in certain biologic processes, e.g., ischemia-induced cardiac arrhythmias (22), may serve as substrates for conversion to potent bioactive products (2). However, the biological role and significance of products that could be derived from DHA in inflammation has remained to be established.

A need therefore exists for an improved understanding of the function of these materials in physiology as well as the isolation of bioactive agents that can serve to eliminate or diminish various disease states or conditions, such as those associated with inflammation.

BRIEF SUMMARY OF THE INVENTION

The present invention, in one embodiment, is drawn to isolated therapeutic agents generated from the interaction between a dietary omega-3 polyunsaturated fatty acid (PUFA) such as eicosapentaenoic acid (EPA) or docosahexaenoic acid (DHA), cyclooxygenase-II (COX-2) and an analgesic, such as aspirin (ASA). Surprisingly, careful and challenging isolation of previously unknown and unappreciated compounds are generated from exudates by the combination of components in an appropriate environment to provide di- and tri-hydroxy EPA or DHA compounds having unique structural and physiological properties. The present invention therefore provides for many new useful therapeutic di- or tri-hydroxy derivatives of EPA or DHA that diminish, prevent, or eliminate inflammation, for example.

The di- and tri-hydroxy EPA and DHA therapeutic agents of the invention include, for example:

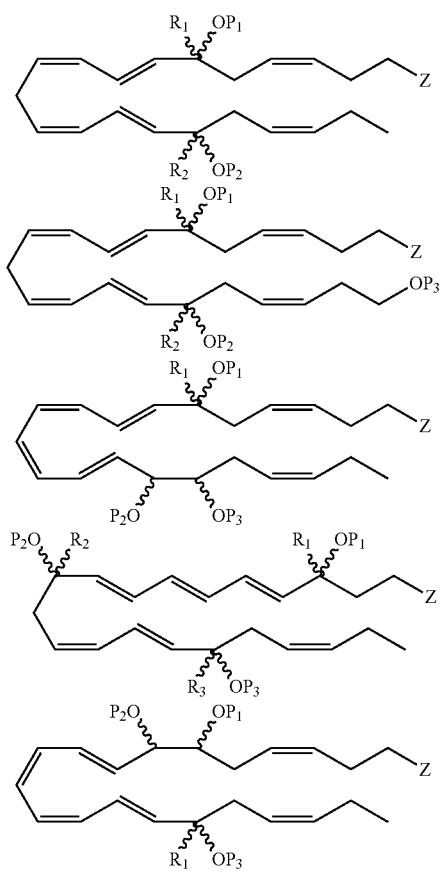

-continued

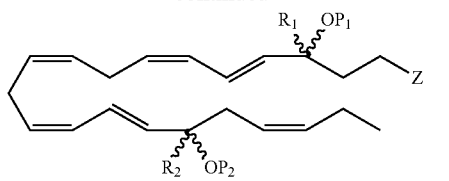

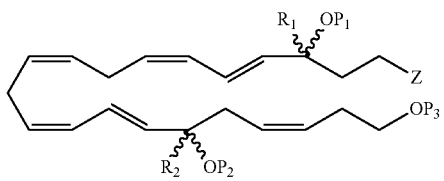

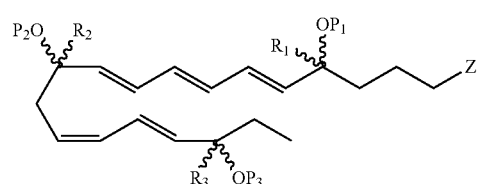

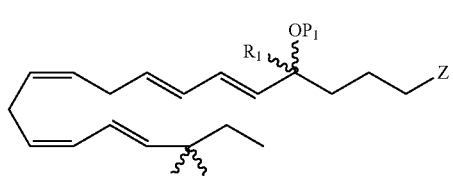

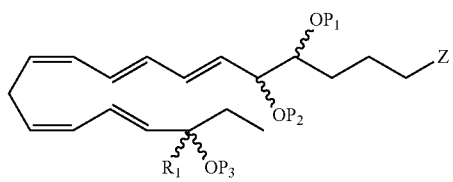

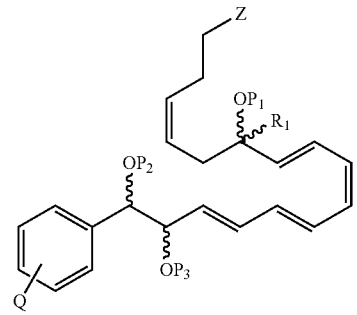

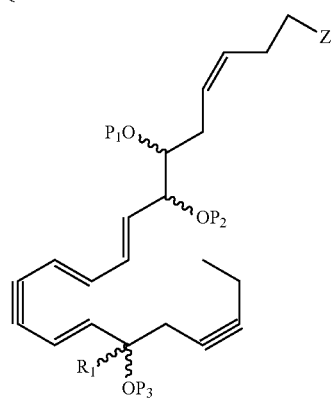

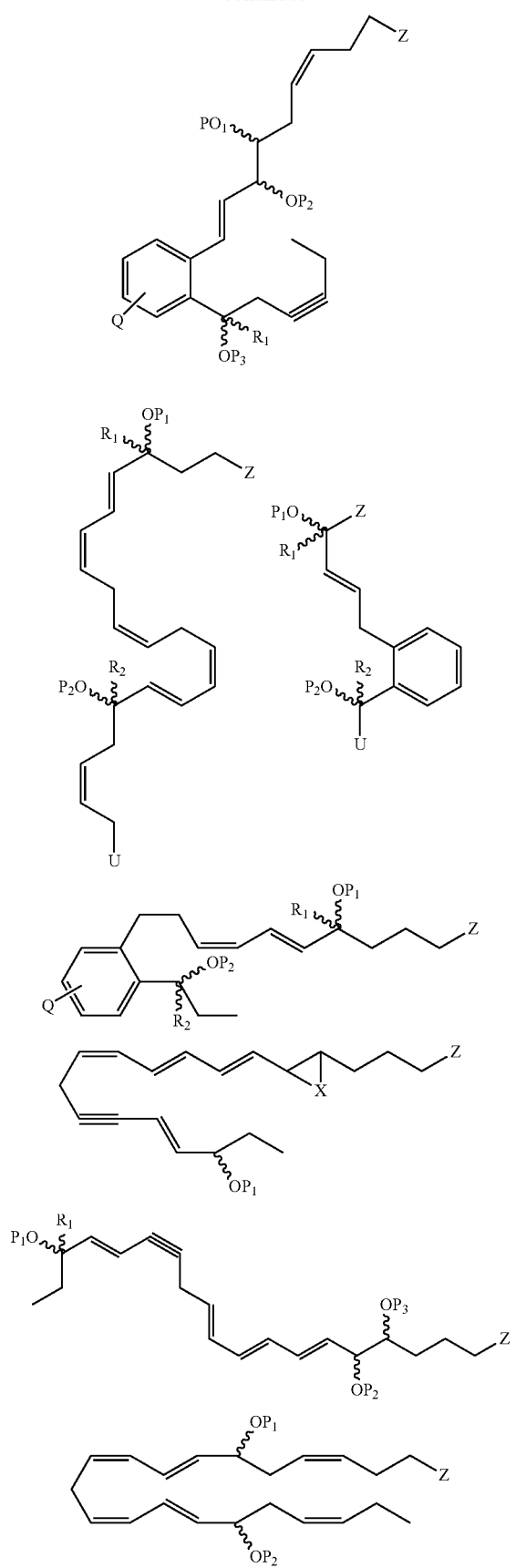
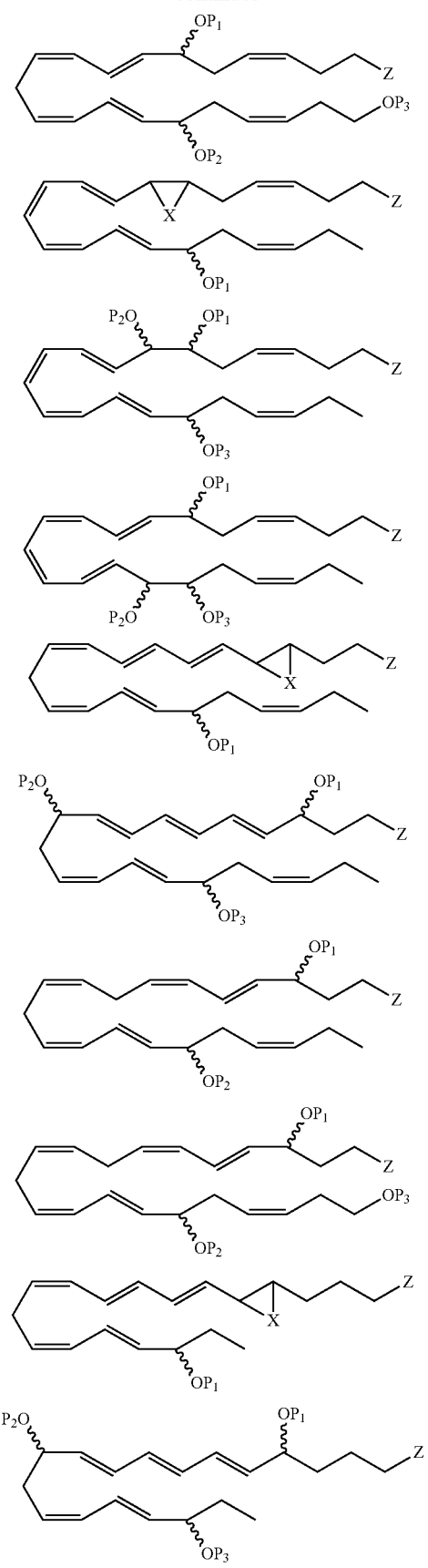

-continued

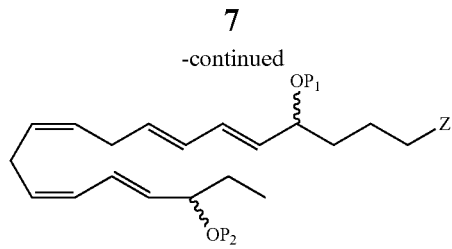
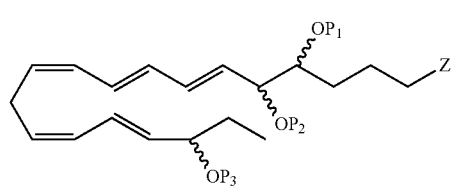
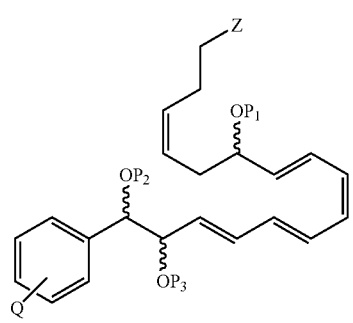
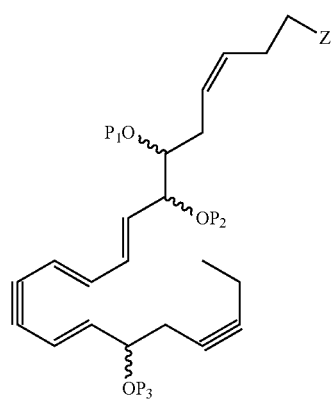
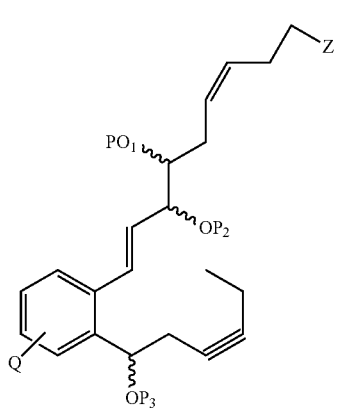

-continued

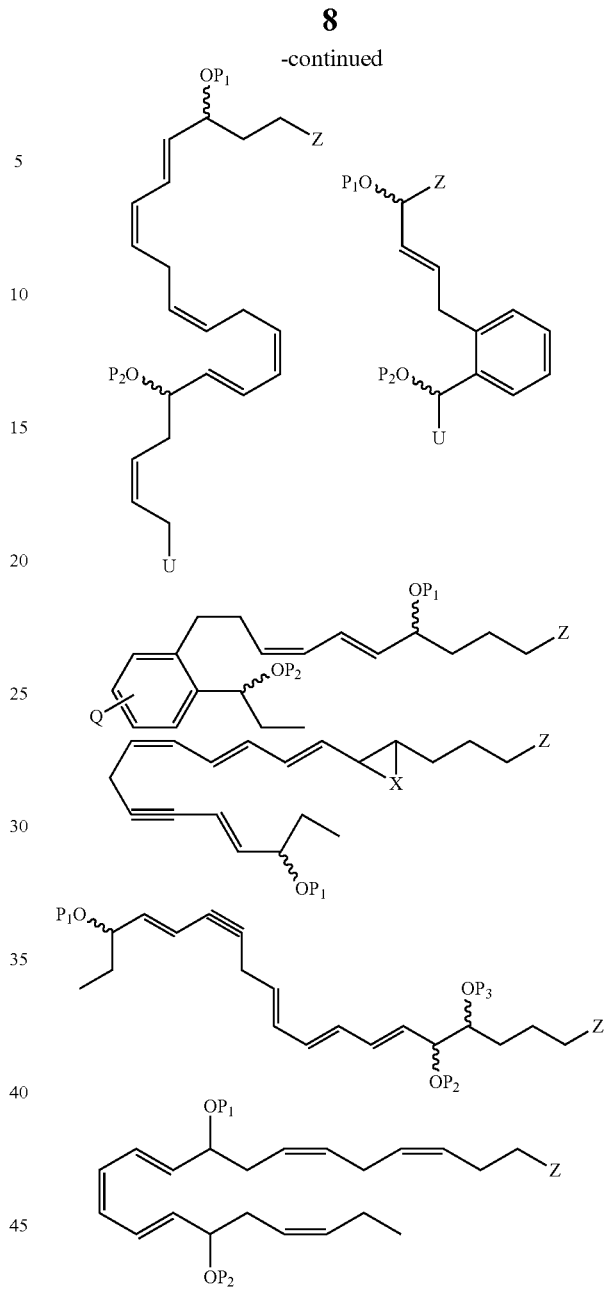

wherein $P_1$, $P_2$ and $P_3$, if present, each individually are protecting groups, hydrogen atoms or combinations thereof;

wherein $R_1$, $R_2$ and $R_3$, if present, each individually are substituted or unsubstituted, branched or unbranched alkyl groups, substituted or unsubstituted aryl groups, substituted or unsubstituted, branched or unbranched alkylaryl groups, halogen atoms, hydrogen atoms or combinations thereof;

wherein Z is —C(O)OR$^d$, —C(O)NR$^c$R$^c$, —C(O)H, —C(NH)NR$^c$R$^c$, —C(S)H, —C(S)OR$^d$, —C(S)NR$^c$R$^c$, —CN;

each R$^a$, if present, is independently selected from the group consisting of hydrogen, (C1-C6) alkyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl and 6-16 membered heteroarylalkyl;

each $R^b$, if present, is a suitable group independently selected from the group consisting of =O, —$OR^d$, (C1-C3) haloalkyloxy, —$OCF_3$, =S, —$SR^d$, =$NR^d$, =$NOR^d$, —$NR^cR^c$, halogen, —$CF_3$, —CN, —NC, —OCN, —SCN, —NO, —$NO_2$, =$N_2$, —$N_3$, —S(O)$R^d$, —S(O)$_2R^d$, —S(O)$_2$$OR^d$, —S(O)$NR^cR^c$, —S(O)$_2NR^cR^c$, —OS(O)$R^d$, —OS(O)$_2$$R^d$, —OS(O)$_2OR^d$, —OS(O)$_2NR^cR^c$, —C(O)$R^d$, —C(O)$OR^d$, —C(O)$NR^cR^c$, —C(NH)$NR^cR^c$, —C($NR^a$)$NR^cR^c$, —C(NOH)$R^a$, —C(NOH)$NR^cR^c$, —OC(O)$R^d$, —OC(O)$OR^d$, —OC(O)$NR^cR^c$, —OC(NH)$NR^cR^c$, —OC($NR^a$)$NR^cR^c$, —[NHC(O)]$_nR^d$, —[$NR^a$C(O)]$_nR^d$, —[NHC(O)]$_nOR^d$, —[$NR^a$C(O)]$_nOR^d$, —[NHC(O)]$_nNR^cR^c$, —[$NR^a$C(O)]$_n$$NR^cR^c$, —[NHC(NH)]$_nNR^cR^c$ and —[$NR^a$C($NR^a$)]$_nNR^cR^c$;

each $R^c$, if present, is independently a protecting group or $R^a$, or, alternatively, each $R^c$ is taken together with the nitrogen atom to which it is bonded to form a 5 to 8-membered cycloheteroalkyl or heteroaryl which may optionally include one or more of the same or different additional heteroatoms and which may optionally be substituted with one or more of the same or different $R^a$ or suitable $R^b$ groups;

each n, independently, if present, is an integer from 0 to 3;

each $R^d$, independently, if present, is a protecting group or $R^a$;

in particular, Z is a carboxylic acid, ester, amide, thiocarbamate, carbamate, thioester, thiocarboxamide or a nitrile;

wherein X, if present, is a substituted or unsubstituted methylene, an oxygen atom, a substituted or unsubstituted nitrogen atom, or a sulfur atom;

wherein Q represents one or more substituents and each Q individually, if present, is a halogen atom or a branched or unbranched, substituted or unsubstituted alkyl, alkenyl, alkynyl, cycloalkyl, aryl, alkoxy, aryloxy, alkylcarbonyl, arylcarbonyl, alkoxycarbonyl, aryloxycarbonyl, amino, hydroxy, cyano, carboxyl, alkoxycarbonyloxy, aryloxycarbonyloxy or aminocarbonyl group;

wherein U is a branched or unbranched, substituted or unsubstituted alkyl, alkenyl, alkynyl, cycloalkyl, aryl, alkoxy, aryloxy, alkylcarbonyl, arylcarbonyl, alkoxycarbonyl, aryloxycarbonyl, alkoxycarbonyloxy, and aryloxycarbonyloxy group;

and pharmaceutically acceptable salts thereof.

In certain embodiments, $P_1$, $P_2$, and $P_3$, if present, each individually are hydrogen atoms and Z is a carboxylic acid or ester. In other embodiments, X is an oxygen atom, one or more P's are hydrogen atoms, Z is a carboxylic acid or ester. In still other embodiments, Q is one or more halogen atoms, one or more P's are hydrogen atoms, and Z is a carboxylic acid or ester.

In certain embodiments, $R_1$, $R_2$ and $R_3$, if present, are each individually lower alkyl groups, such as methyl, ethyl, and propyl and can be halogenated, such as trifluoromethyl. In one aspect, at least one of $R_1$, $R_2$ and $R_3$, if present, is not a hydrogen atom. Generally, Z is a carboxylic acid and one or more P's are hydrogen atoms.

In certain embodiments, when $OP_3$ is disposed terminally within the resolvin analog, the protecting group can be removed to afford a hydroxyl. Alternatively, in certain embodiments, the designation of $OP_3$ serves to denote that the terminal carbon is substituted with one or more halogens, i.e., the terminal C-18, C-20, or C-22 carbon, is a trifluoromethyl group, or arylated with an aryl group that can be substituted or unsubstituted as described herein. Such manipulation at the terminal carbon serves to protect the resolvin analog from omega $P_{450}$ metabolism which can lead to biochemical inactivation.

In one aspect, the resolvins described herein that contain epoxide, cyclopropane, azine, or thioazine rings within the structure also serve as enzyme inhibitors that increase endogenous resolvin levels in vivo and block "pro" inflammatory substances, their formation and action in vivo, such as leukotrienes and/or $LTB_4$.

Another embodiment of the present invention is directed to pharmaceutical compositions of the novel compounds described throughout the specification.

The present invention also provides methods to treat various disease states and conditions, including for example, inflammation.

The present invention further provides various methods to prepare the novel compounds described throughout the specification.

The present invention also provides packaged pharmaceuticals that contain the novel di- and tri-hydroxy EPA and DHA compounds described throughout the specification for use in treatment with various disease states and conditions.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIG. 2 depicts novel ASA triggered HDHA products generated by human recombinant COX-2-aspirin: 17R-HDHA. Human recombinant COX-2 treated in the presence and absence of ASA (2 mM) was incubated with DHA (10 μM, 30 min, 37° C.). Incubations were stopped with 2 ml cold methanol, extracted and taken for LC-MS-MS analyses. Results are representative of incubations from >8 separate experiments, some with 1-$^{14}$C-labeled DHA. Upper Panels: LC-MS-MS chromatogram of m/z 343 showing the presence of mono-HDHA. Lower: MS-MS spectrum of (left) 13-HDHA without ASA treatment and (right) 17R-HDHA with ASA treatment.

Air pouch—Compounds (dissolved in 500 μL of PBS without $Ca^{2+}$ or $Mg^{2+}$) injected into the air pouch via intrapouch injection or via intravenous administration (in 120 μl sterile saline) followed by intrapouch injection of TNFα. Four hours later air pouch lavages were collected and cells were enumerated and differentiated. Compounds were prepared by biogenic synthesis or isolated from in vivo exudates. The ratio of 7,17R-diHDHA to 4,17R-diHDHA was ~8:1; the ratio of 4,11,17R-triHDHA and 7,16,17R-triHDHA was ~2:1; and the ratio of di to triHDHA was ~1:1.3. Exudate transfers to a native mouse (described herein). ATLa denotes 15-epi-16-para(fluoro)-phenoxy-$LXA_4$ (administered at 100 ng/mouse). Values represent mean+/−SEM from 3-4 different mice; *P<0.05 when infiltrated PMN is compared to vehicle control.

Figure 6:
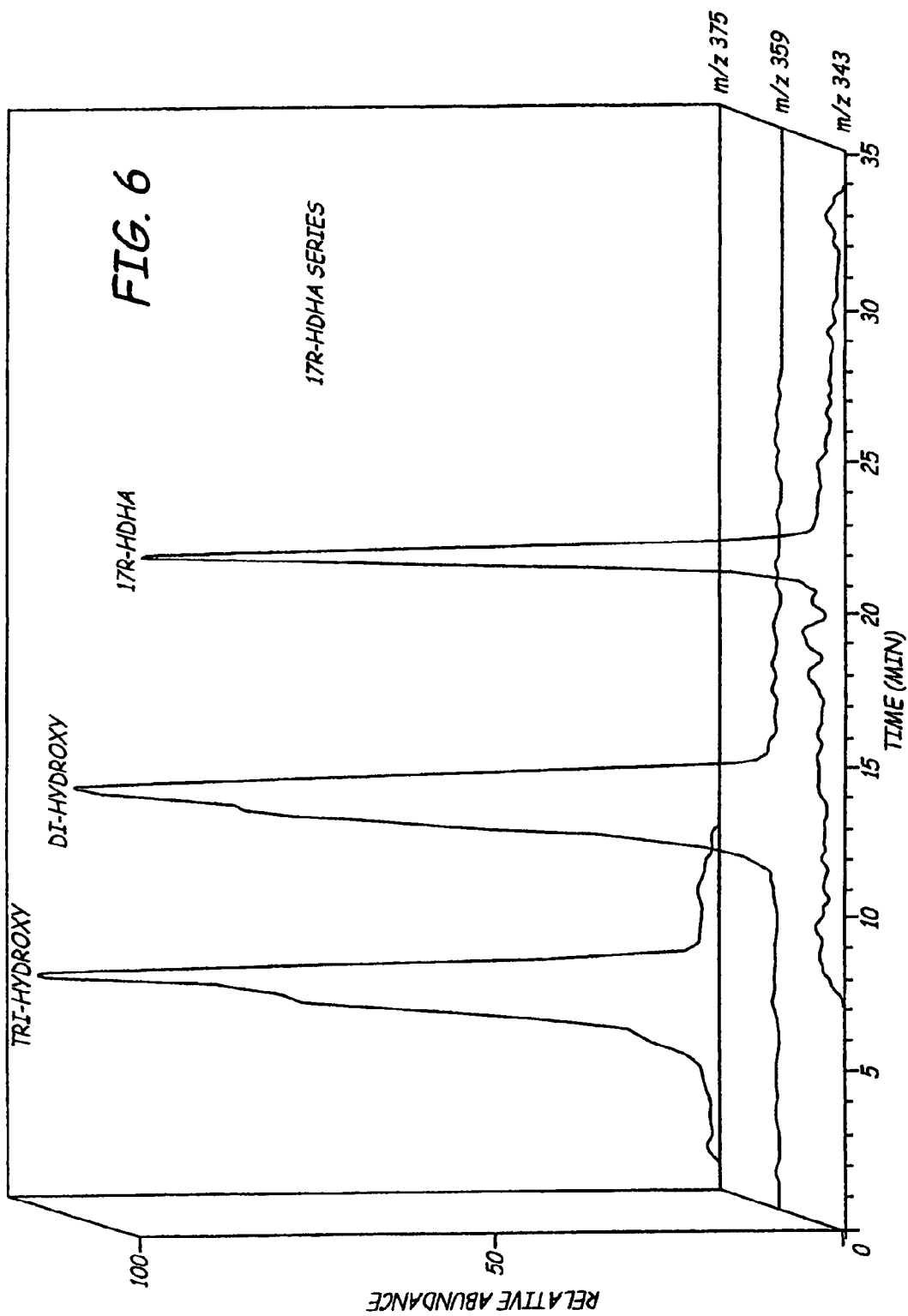

FIG. 6 depicts resolvin production by human PMNs exposed to microbial zymosan: novel 17R di- and triHDHA. Human PMNs ($50\times10^6$ cells/ml) incubated with zymosan A (100 ng/ml) and 17R-HDHA (5 μg/ml, 40 min, 37° C.). Results are representative of n=4.

Figure 1B:
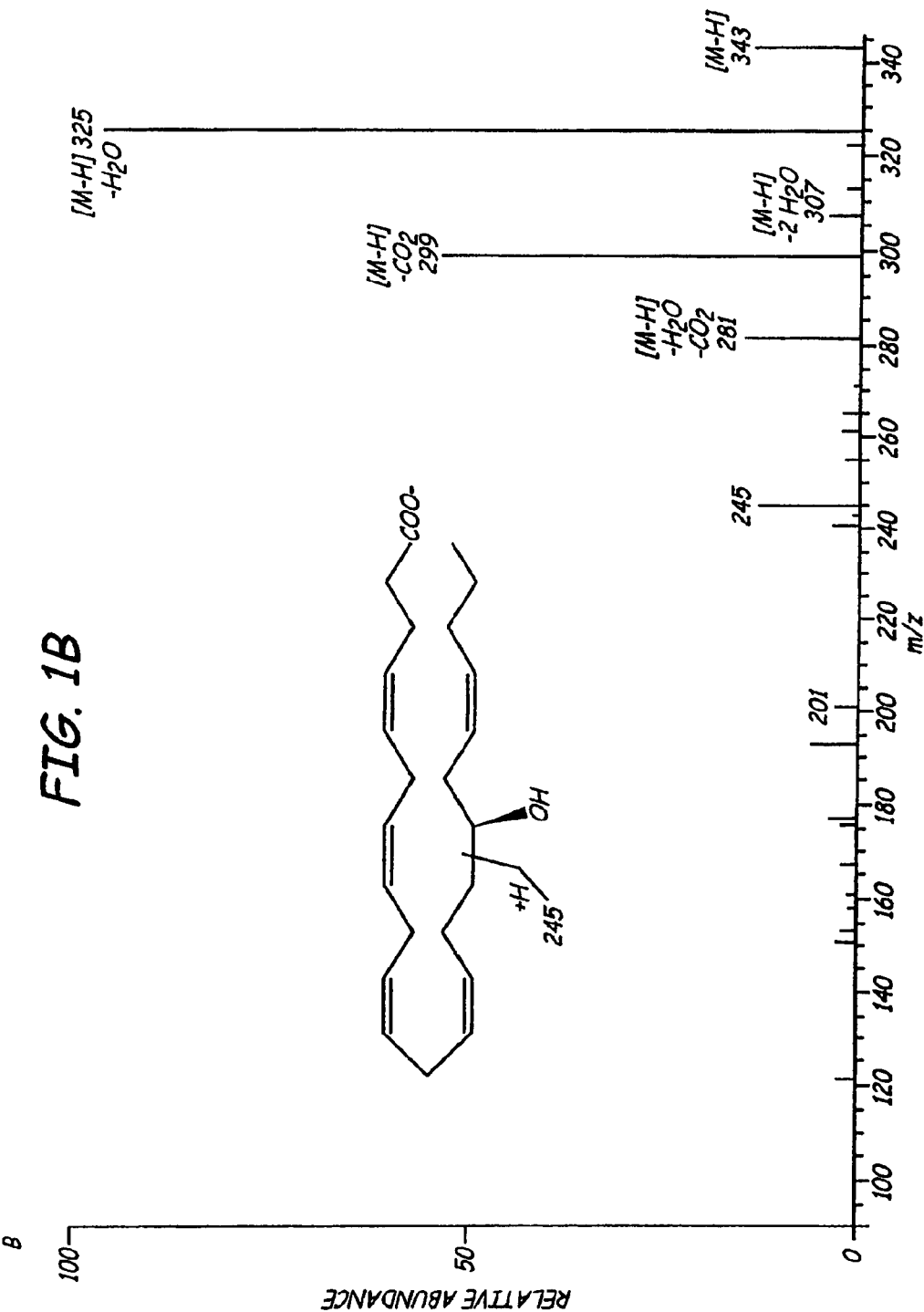
FIG. 1 depicts inflammatory exudates from mice treated with ASA to generate novel compounds: LC-MS-MS-based lipodomic analysis. Panel A: TNFα-induced leukocyte exudates from dorsal air pouches. Samples were collected at 6 h from FVB mice given ASA and DHA (See Methods). Selected ion chromatogram (m/z 343) showing the production of 17R-HDHA, 7S-HDHA, and 4S-HDHA. Using the diene UV chromophores for quantitation, 7-HDHA was ~15% of the exudate materials and was identified using a SIM trace for m/z 141 with ms/ms 343. In some exudates 17S-HDHA was also present from lipoxygenase-dependent routes. MS-MS for Panel B: 17R-HDHA (m/z 343); Panel C: 7S,17R-diHDHA (m/z 359); and Panel D: 4,11,17R-triH-DHA (m/z 375). See below for diagnostic ions. Results are representative of n=7.
Figure 1C:
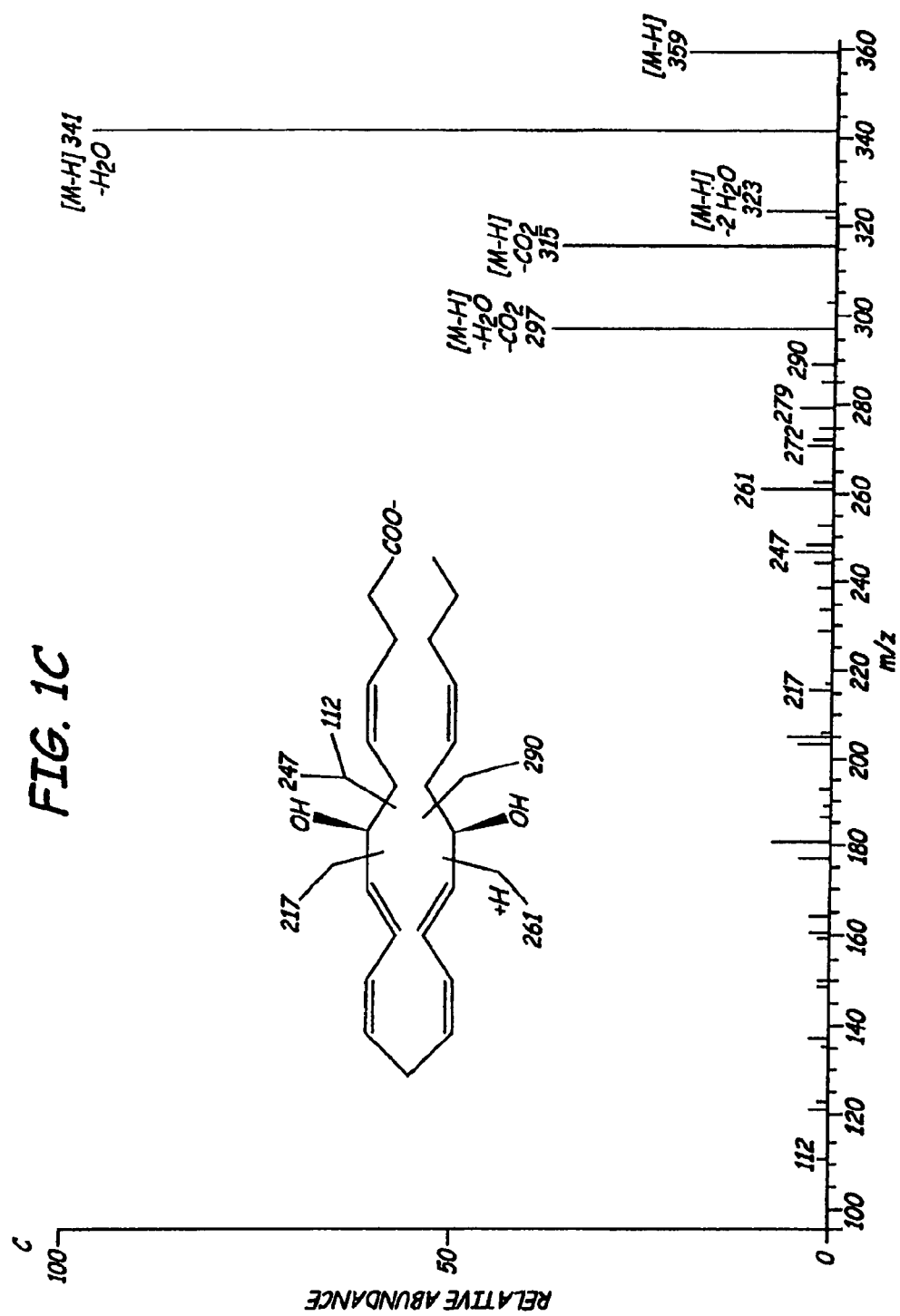
Figure 1D:
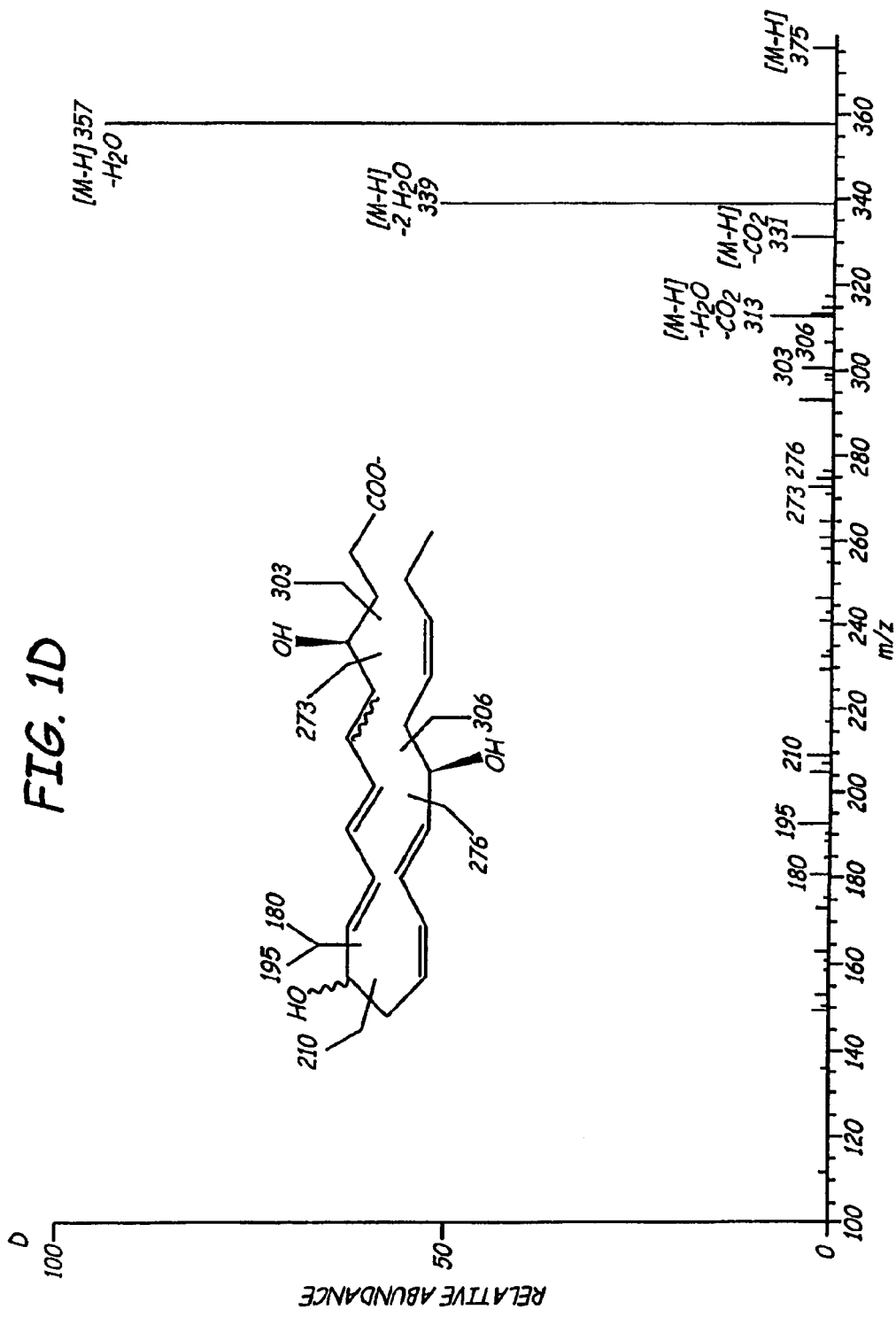
Figure 7:
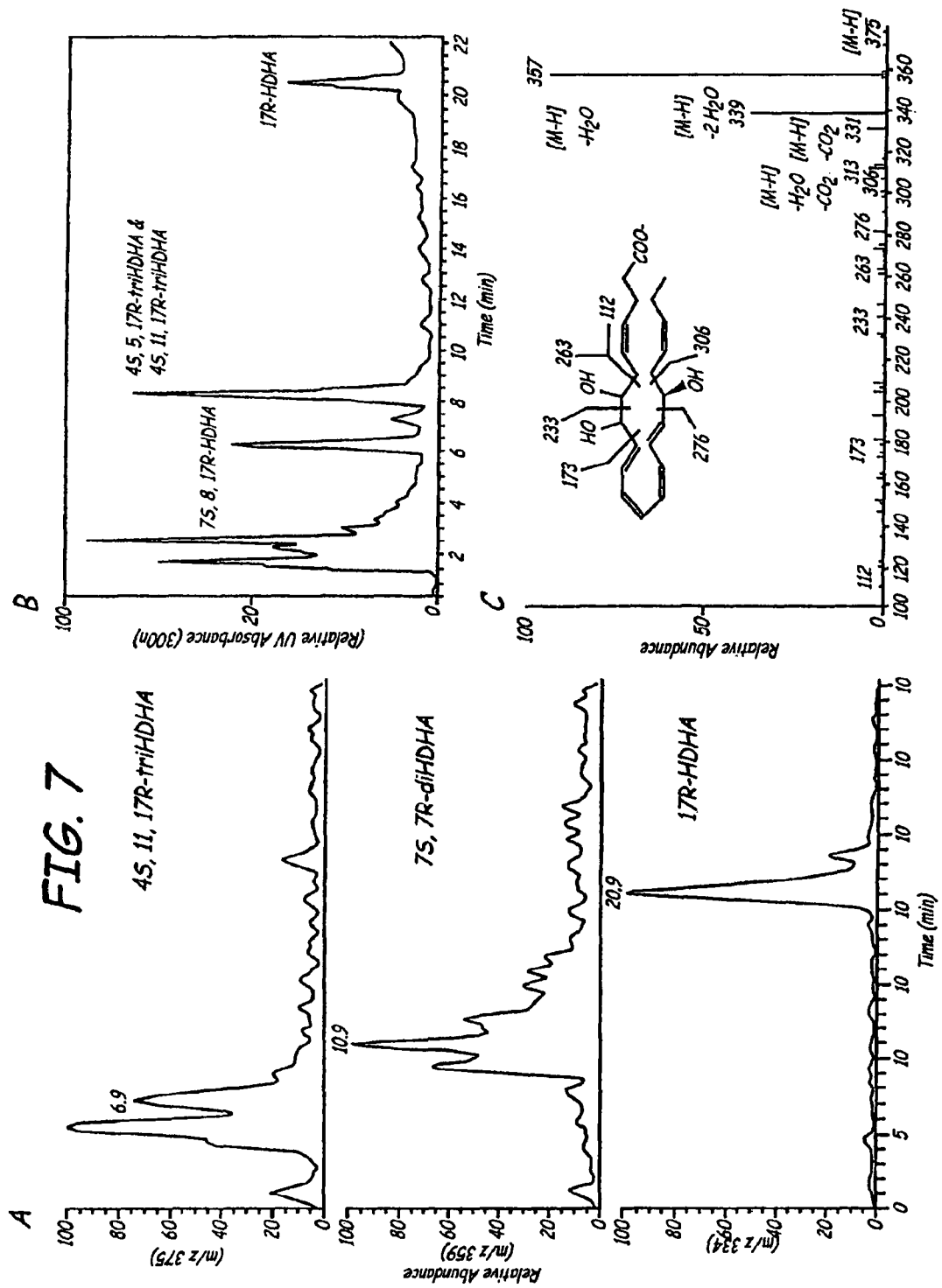

FIG. 7 depicts that inflammatory exudate produces 17R-containing di- and trihydroxy tetraenes and triene-containing compounds: LC-MS-MS. See FIG. 1 for details. Exudates were obtained and analyzed by procedures essentially identical to those described in FIG. 1. Panel A: m/z were plotted at 375 (upper), 359 (middle), and 343 (lower). Panel B: UV absorbance was plotted at 300 nm to mark tetraene-containing chromatophores. Panel C: MS-MS of 7S,8,17R-triHDHA.

Figure 8:
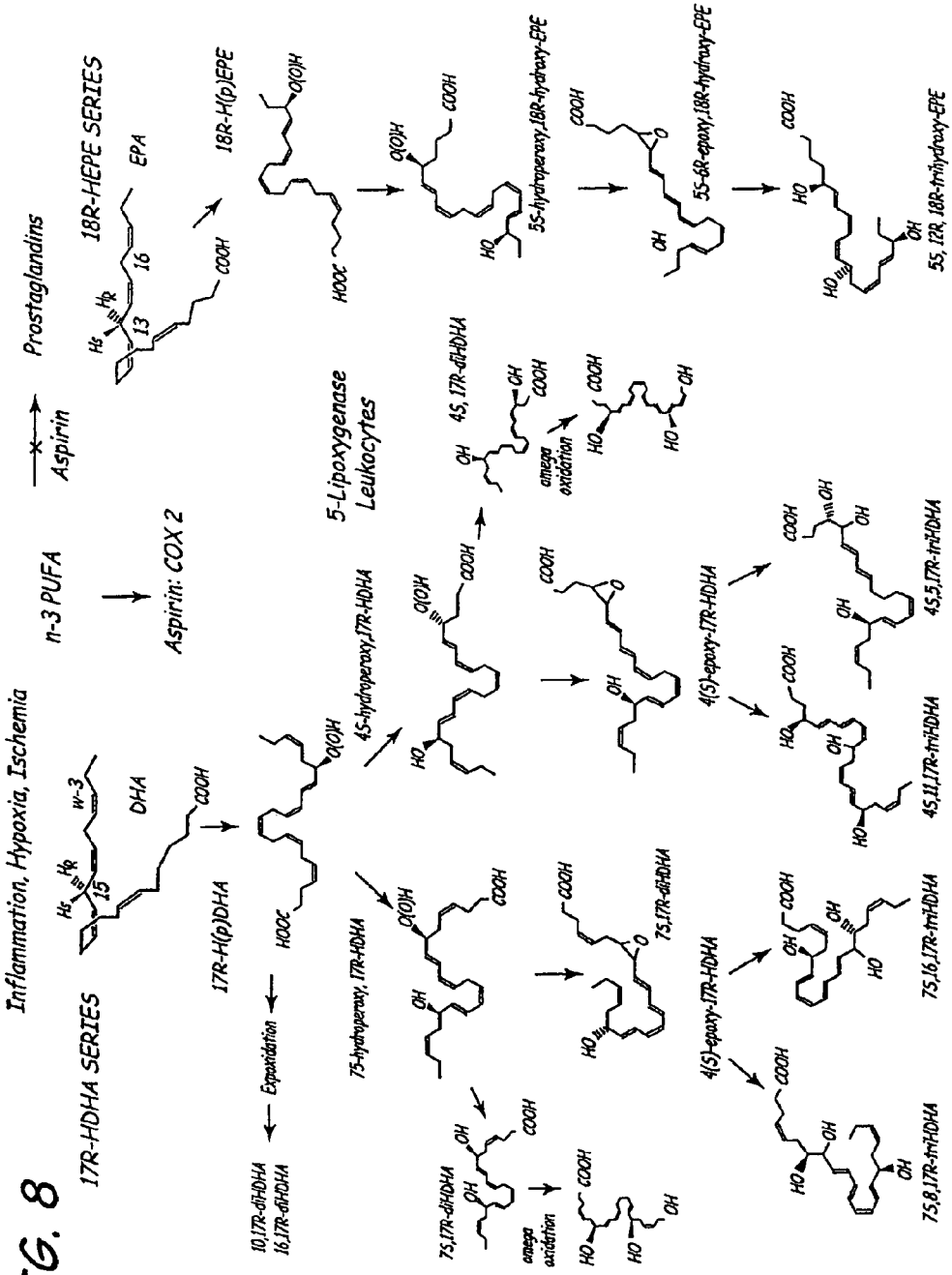

FIG. 8 depicts a biosynthetic scheme proposed for resolvins: aspirin triggered omega-3-derived products. Acetylation of COX-2 by ASA treatment generates novel 17R-H(p)DHA from DHA that is reduced to its corresponding alcohol and converted via sequential actions of a leukocyte 5-lipoxygenase and leads to formation of both dihydroxy- and trihydroxy-containing docosanoids that retain their 17R configuration. Pathways are denoted for omega oxidation products that are likely to be in vivo markers of enzymatic inactivation. The resolvin pathways appear to be maximally induced during the "spontaneous resolution" phase of inflammation and compounds are activated to dampen PMN infiltration, which reduces exudate PMN numbers to promote pro-resolution of inflammatory (Resolvins from EPA, the 18R-HEPE series, are denoted) that leads to potent inhibitors of PMN recruitment in vitro and in vivo (see pathway, right, text and Ref. 2). The complete stereochemistries of the new di- and trihydroxy-containing compounds remain to be established and are depicted here in their likely configuration based on biogenic total synthesis. See Table 2 and text for further details.

Figure 9:
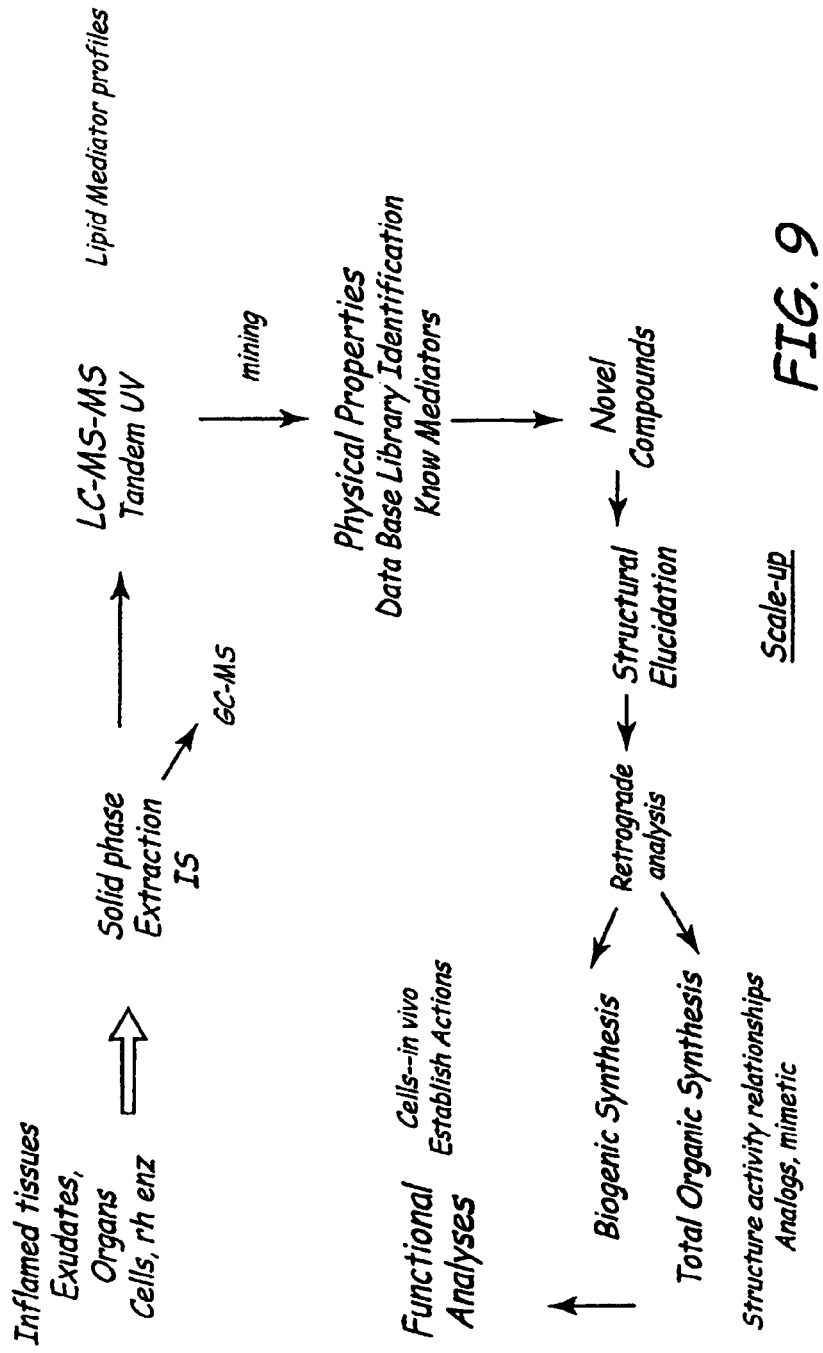

FIG. 9 provides a lipodomics based analysis/flow diagram for the approach to isolate and characterize the complex and unknown compounds of the present invention.

Figure 10:
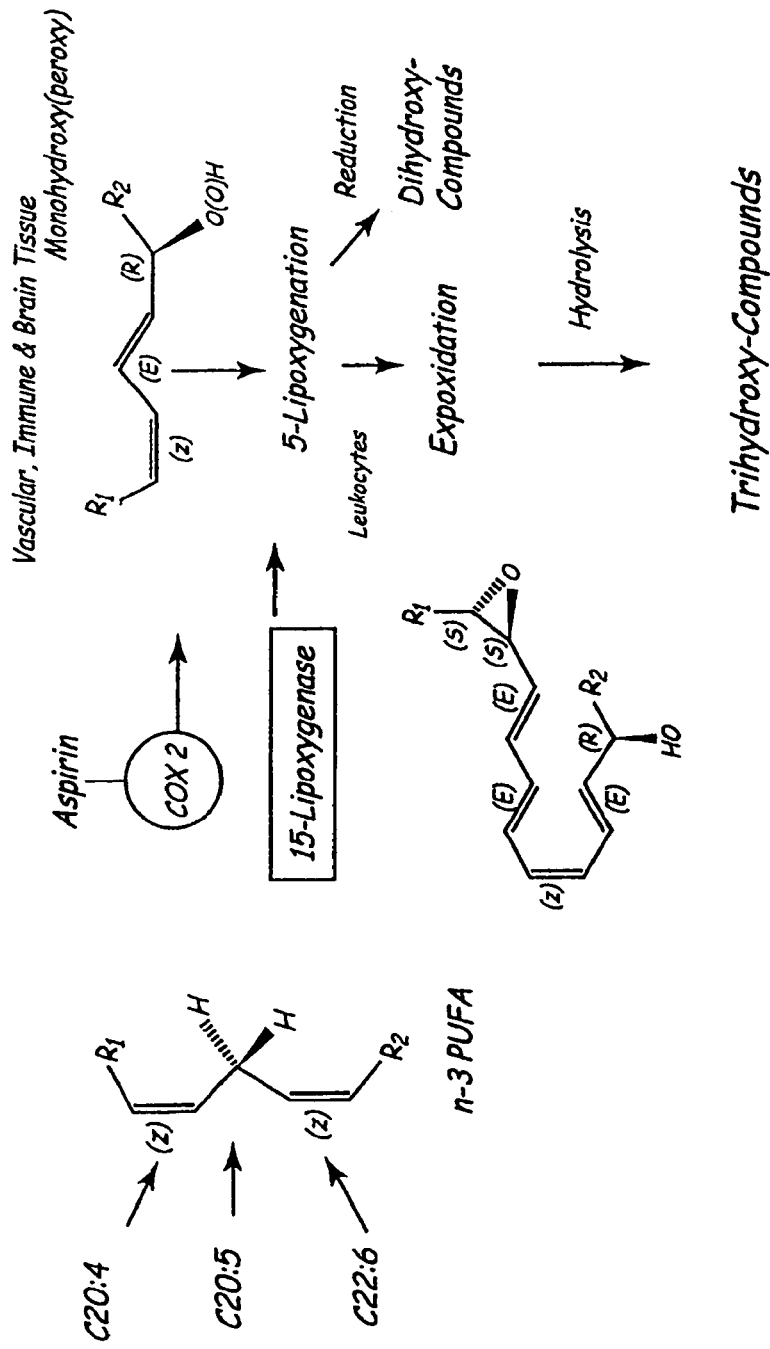

FIG. 10 provides a depiction of the general metabolic pathway in which production of resolvin di and tri-hydroxy compounds are produced.

Figure 11:
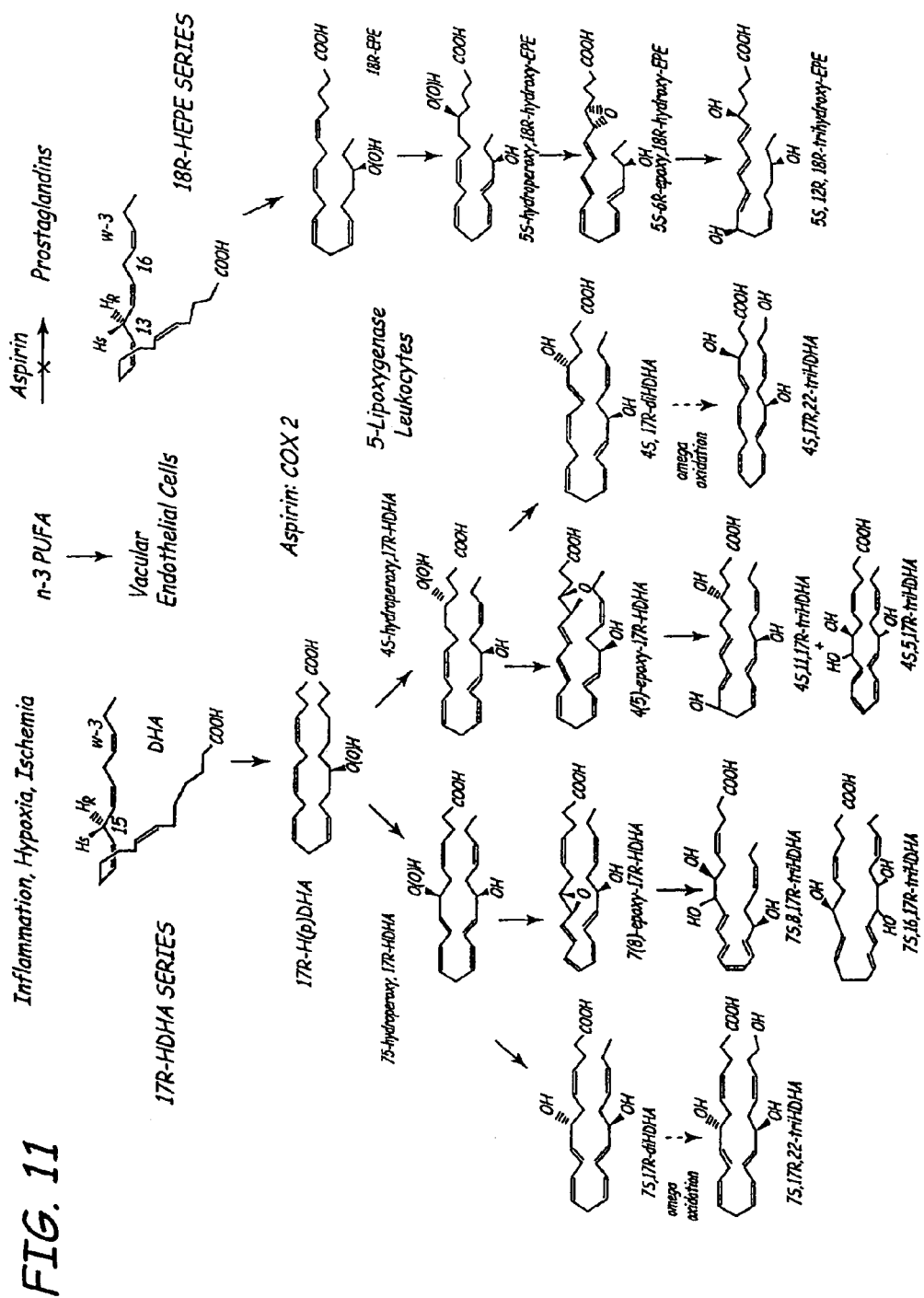

FIG. 11 is a more detailed illustration which depicts the production of resolving di and tri-hydroxy compounds from HDA or EPA from a PUFA and aspirin within inflamed tissue.

Figure 12:
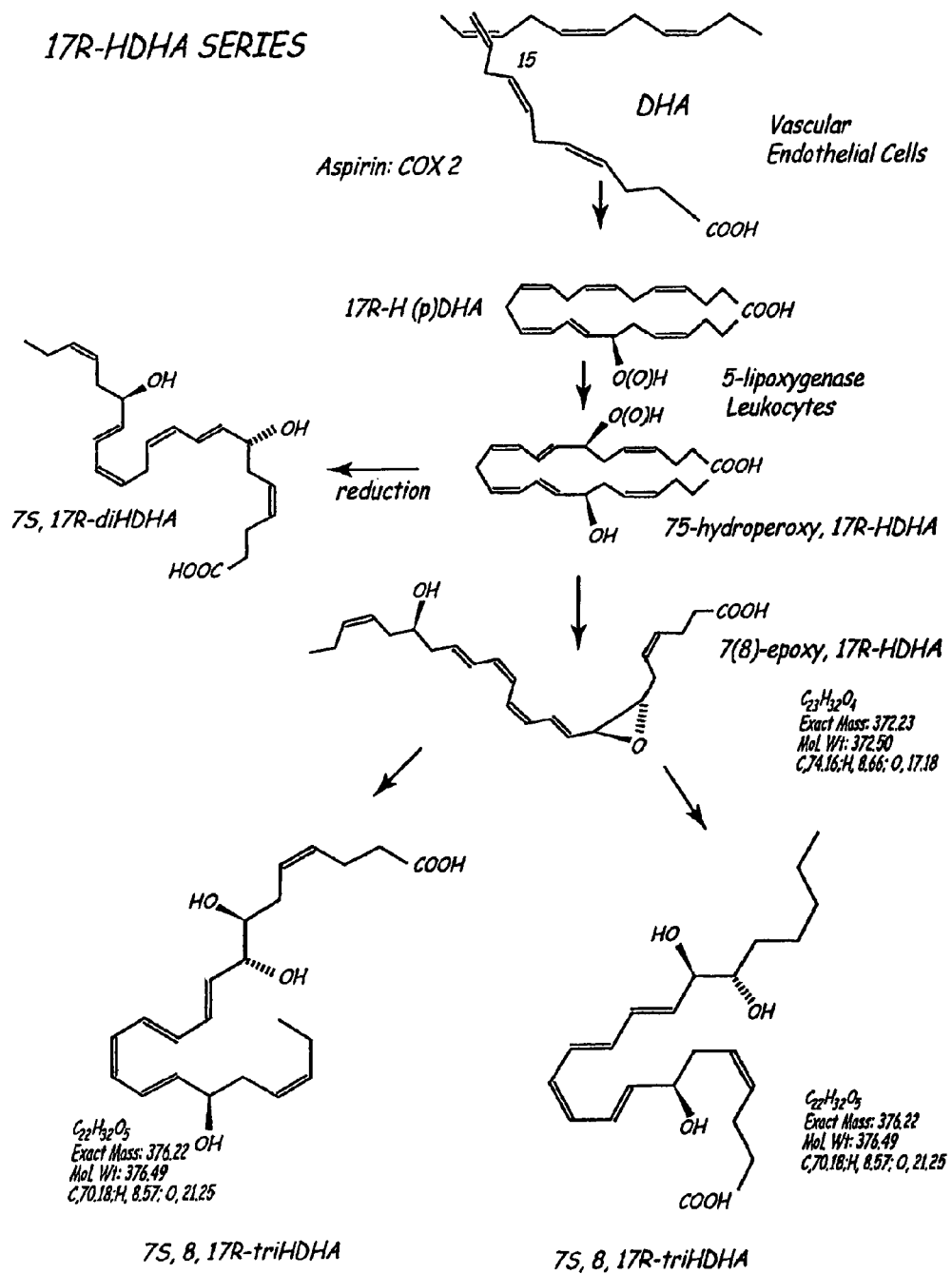

FIG. 12 provides a schematic depiction of some of the di and tri-HDHA compounds of the invention.

Figure 13:
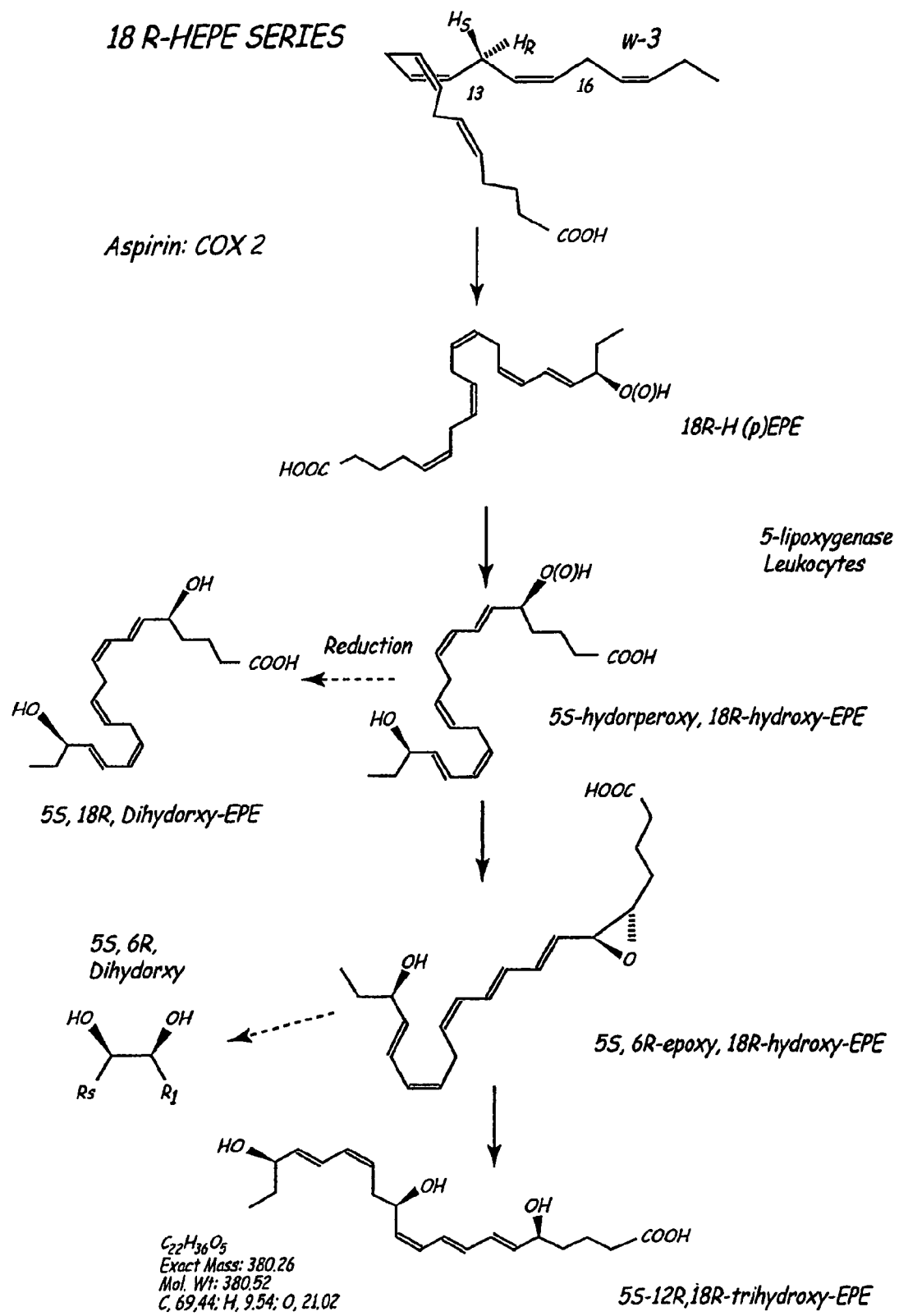

FIG. 13 shows a biochemical pathway/conversion of EPA with COX-2 to form di and tri-hydroxy EPA compounds.

Figure 14:
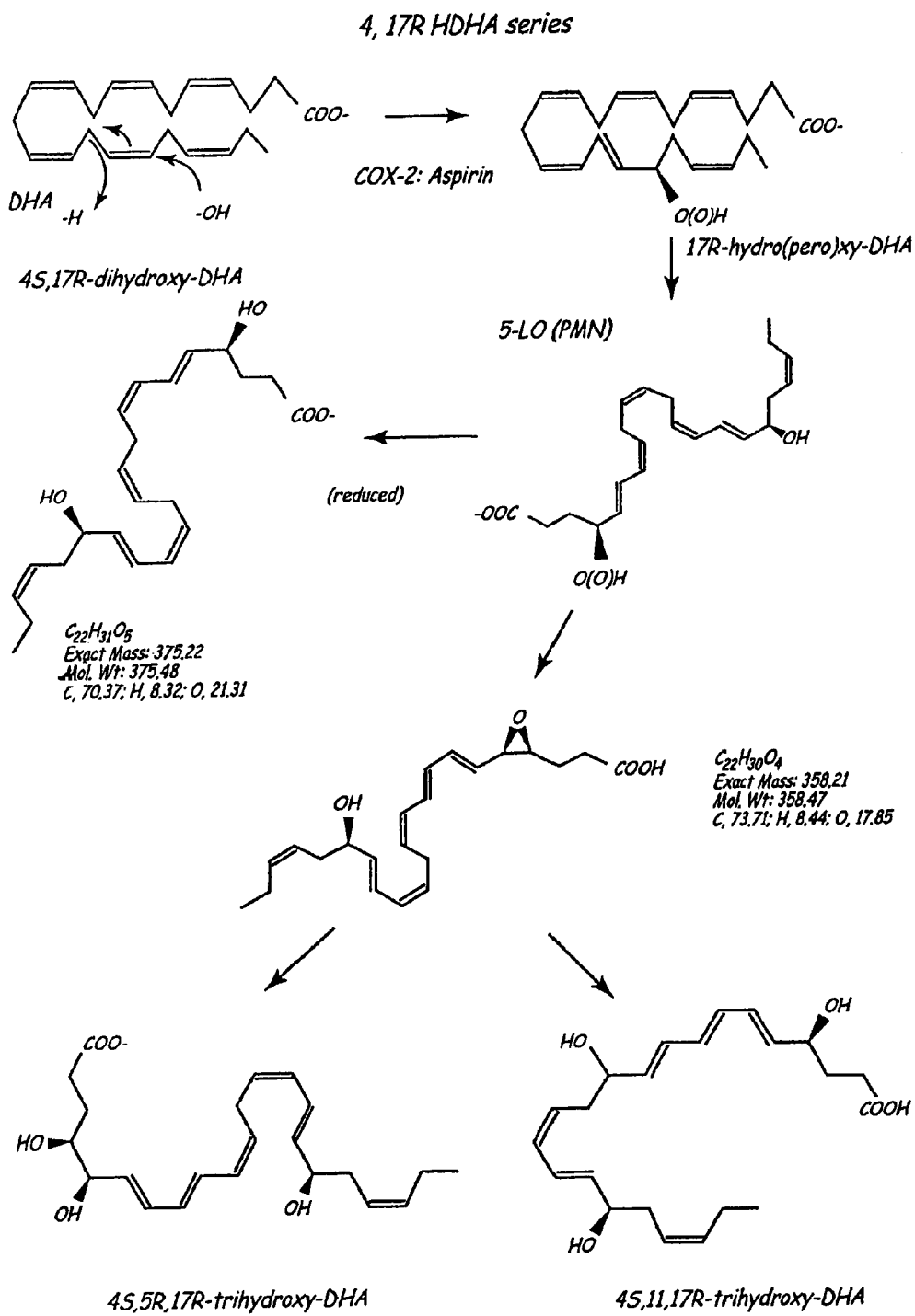

FIG. 14 is another schematic depiction of a biochemical pathway/conversion of DHA with COX-2 to form di and tri-hydroxy DHA compounds.

Figure 15:
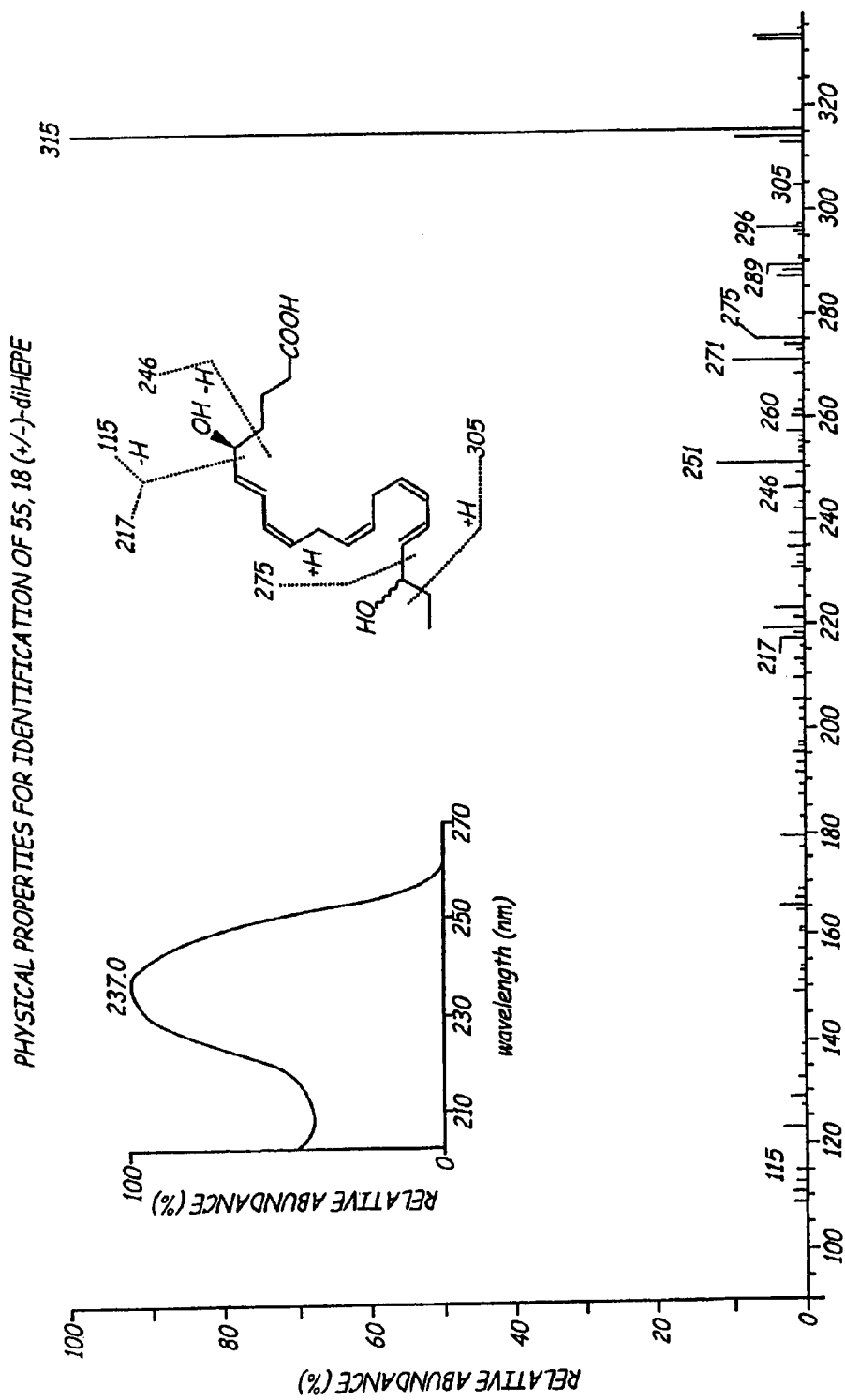

FIG. 15 shows the physical properties for 5S,18(+/−)-di-HEPE.

Figure 16:
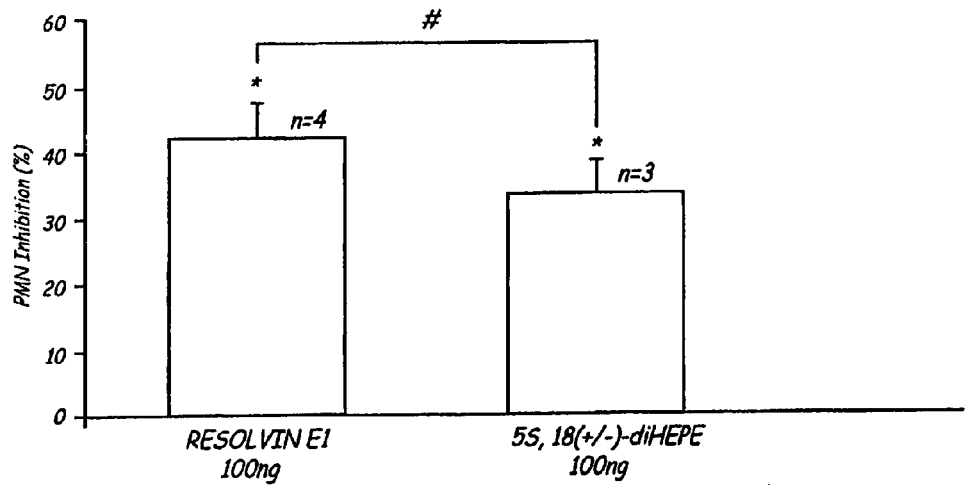

FIG. 16 is a direction comparison of 5S,18(+/−)-diHEPE and Resolvin E1, demonstrating a reduction of neutrophil infiltration in Zymosan-induced peritonitis.

Figure 17:
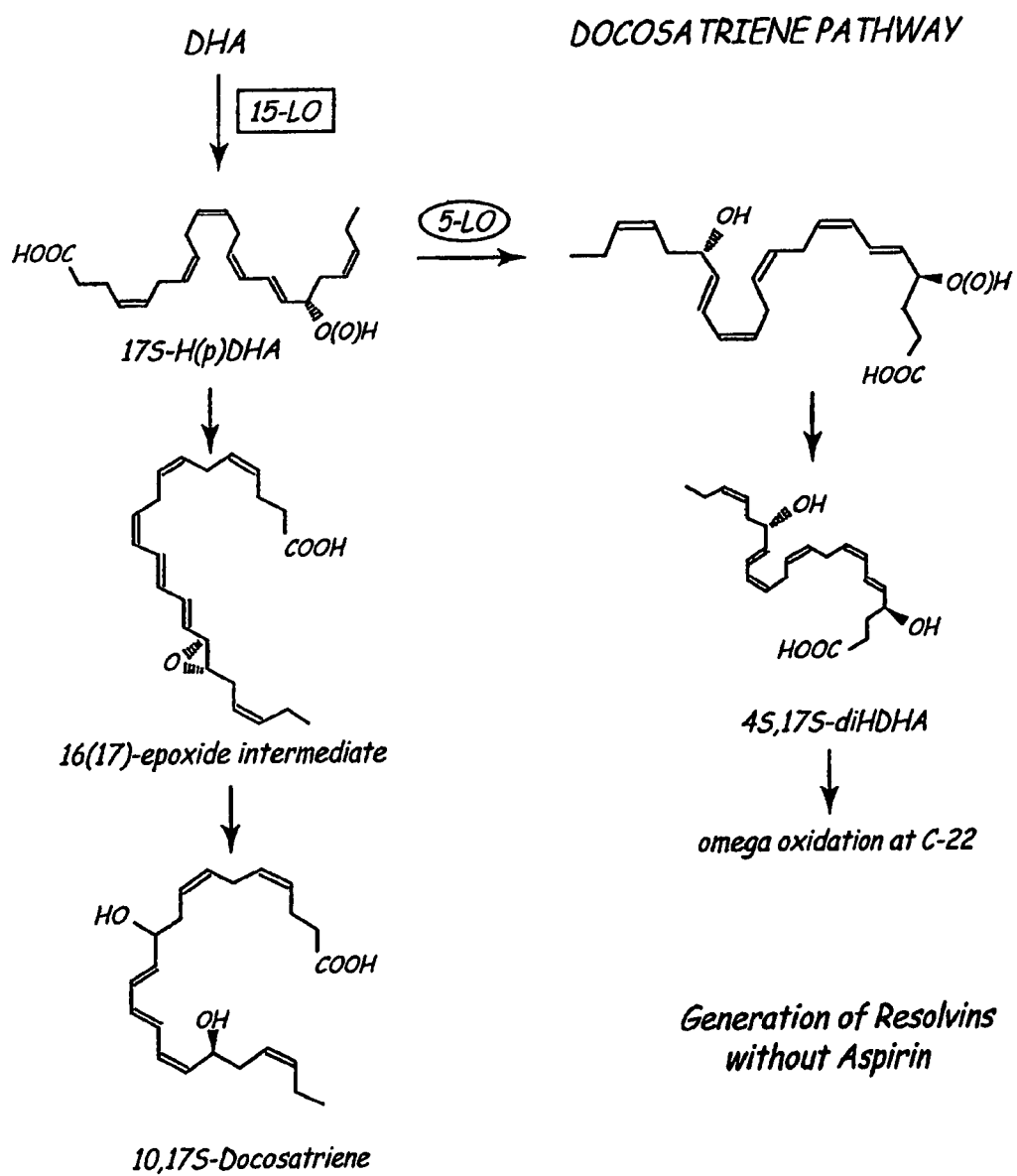

FIG. 17 depicts a docosatriene pathway.

Figure 18:
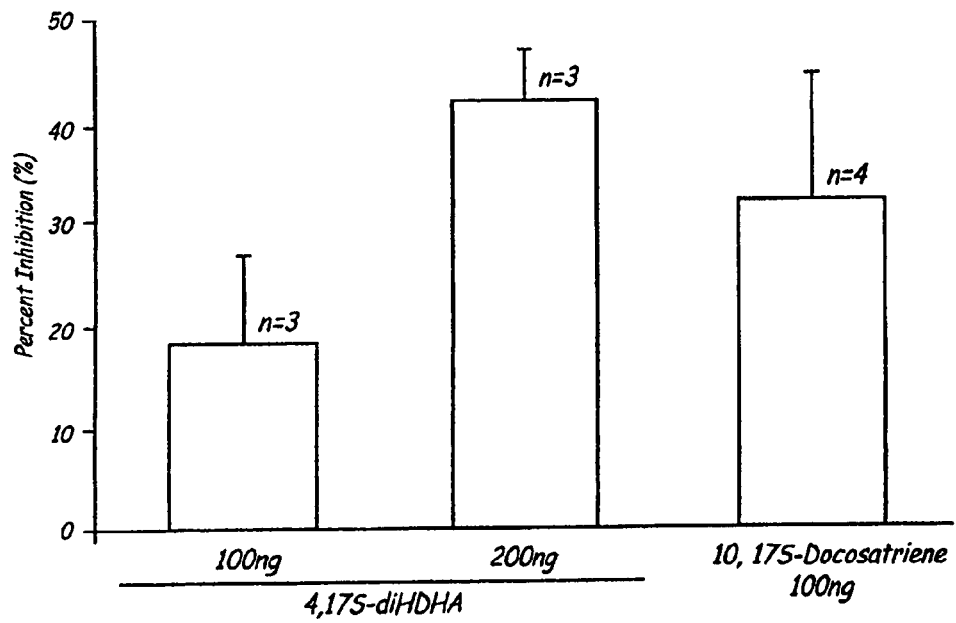

FIG. 18 is a comparison of 4,17S-diHDHA and 10,17S docosatriene in reduction of leukocyte infiltration in Zymosan-induced peritonitis.

Figure 19:
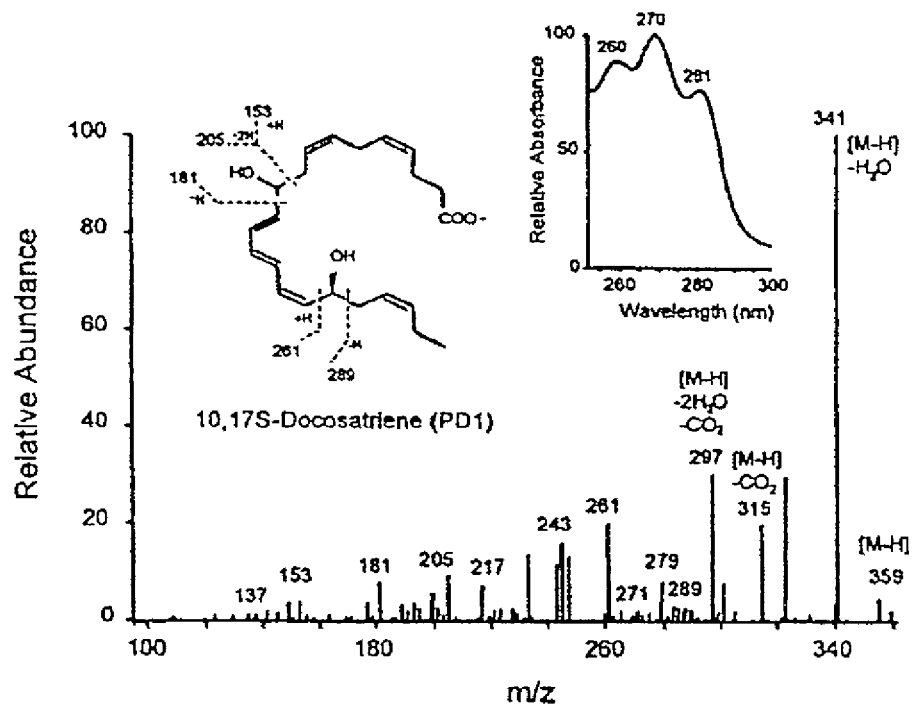

FIG. 19 provides generation of PD1 by inflamed lung. Prior to LC-PDA-MS-MS analysis, products were extracted from murine lungs after animals underwent allergen sensitization and aerosol challenge. Without addition of exogenous DHA, material was present in the lung extracts with the retention time, UV absorbance spectrum, and diagnostic mass spectrum of authentic PD1 (i.e., 10,17S-docosatriene). Inset, the fragmentation ions are denoted for PD1. Note that the absolute stereochemistry depicted is tentative in that the chirality at carbon 10 remains to be established. Results are representative of n=6.

FIG. 20 provides lung histopathology from mice given PD1. Mice were sensitized and aerosol challenged with OVA in the presence of PD 1 (a, 20 ng—upper row, b, 2 ng—middle row) or c, vehicle (lower row). Representative (n=3) lung tissue sections (magnifications: ×200 (left column), ×400 (right column)) were obtained from formalin-fixed, paraffin-embedded lung tissue, prepared and stained with hematoxylin and eosin. Arrows denote representative EOS; Br, bronchus. Bronchoalveolar lavage fluids (BALF) were obtained from OVA sensitized and challenged mice. Leukocytes in BALF were enumerated and identified after Wright-Giemsa stain. Results are expressed as mean±SEM (n≥5). *P<0.05 by Student's t-test compared to control animals.

Figure 21:
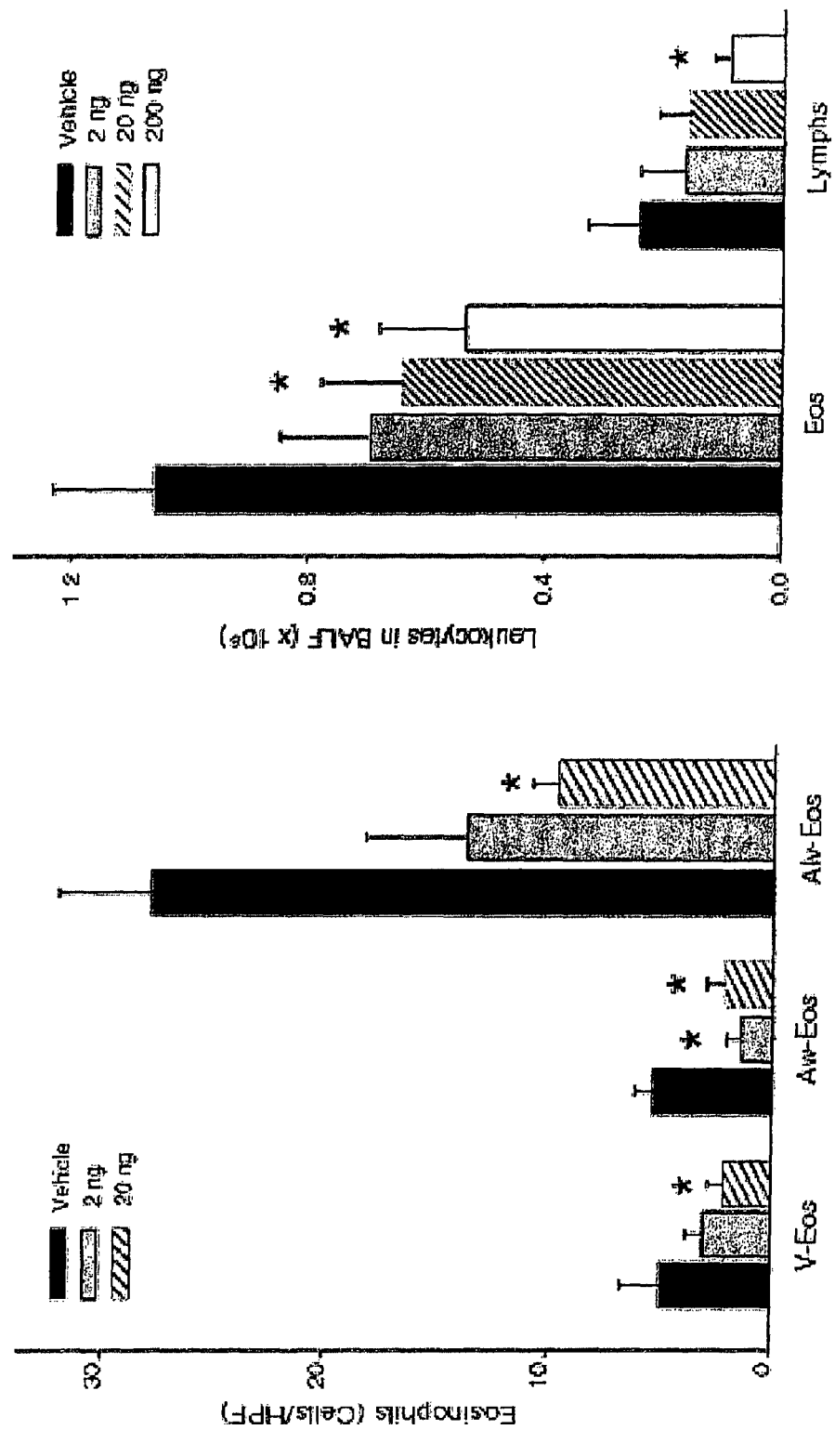

FIG. 21 provides that PD 1 sharply reduces leukocyte infiltration. 21a, Tissue morphometric analyses were performed to determine the impact of PD1 on EOS accumulation in pulmonary vessels (V-EOS), large airways (Aw-EOS) and alveoli (Alv-EOS). 21b, Bronchoalveolar lavage fluids (BALF) were obtained from OVA sensitized and challenged mice. Leukocytes in BALF were enumerated and identified after Wright-Giemsa stain. Results are expressed as mean±SEM (n≥3). *P<0.05 by Student's t-test compared to control animals.

Figure 22:
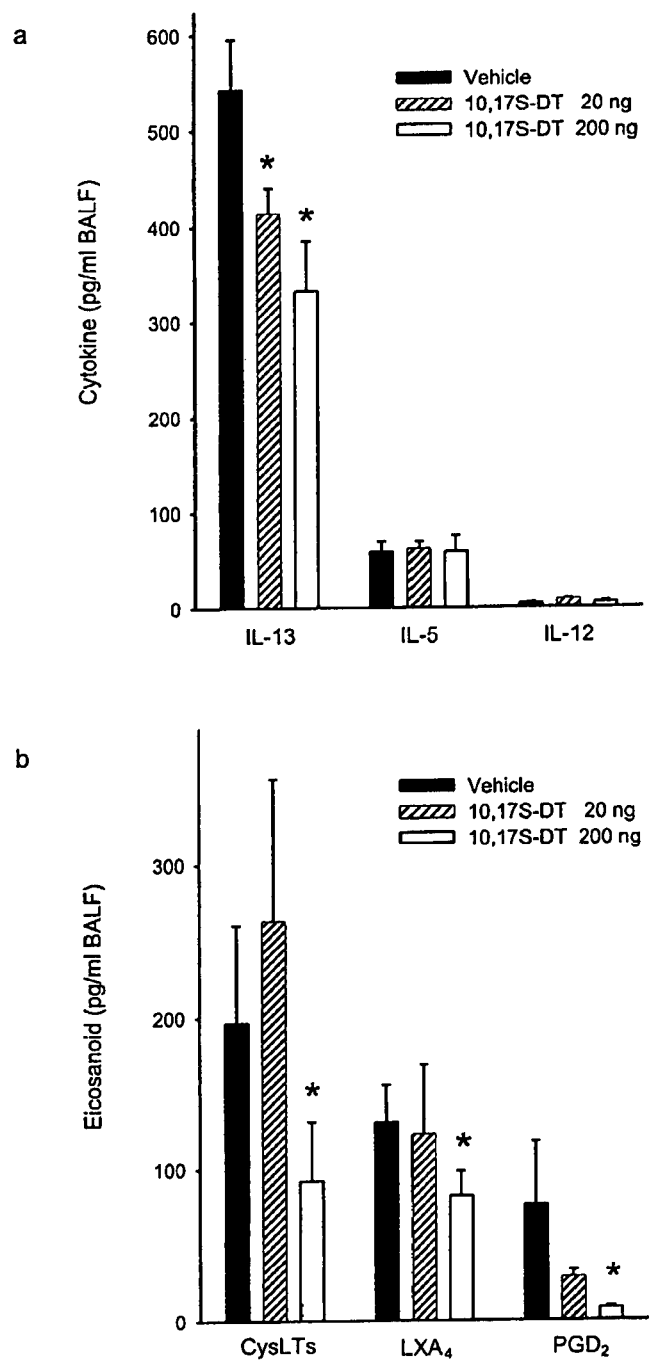

FIG. 22 depicts that PD1 selectively decreases airway inflammatory mediators. In the presence or absence of PD1, the mediator profile in BALF was determined in materials from OVA sensitized and challenged mice for specific (a) cytokines (IL-13, IL-5, IL-12), and (b) lipid mediators (cys-LTs and $PGD_2$). Results are expressed as mean±SEM (n≥5, d=2). *P<0.05 by Student's t-test compared to control animals.

Figure 23:
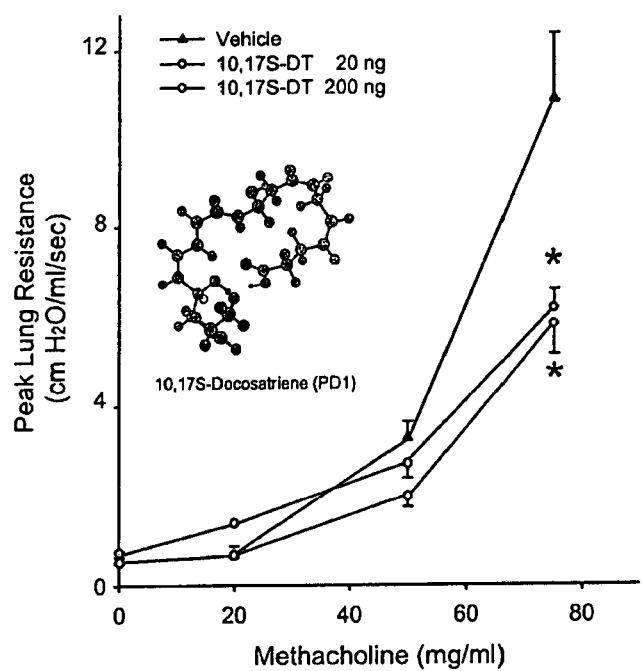

FIG. 23 depicts reduction of airway hyper-responsiveness by PD1. OVA sensitized mice were treated with PD1 (inset) (○) or vehicle (▲) prior to OVA aerosol challenge. Airway reactivity was determined by methacholine-dependent change in peak lung resistance. Results are expressed as mean±SEM (n≥5). *P<0.05 by Student's t-test compared to control animals.

Figure 24:
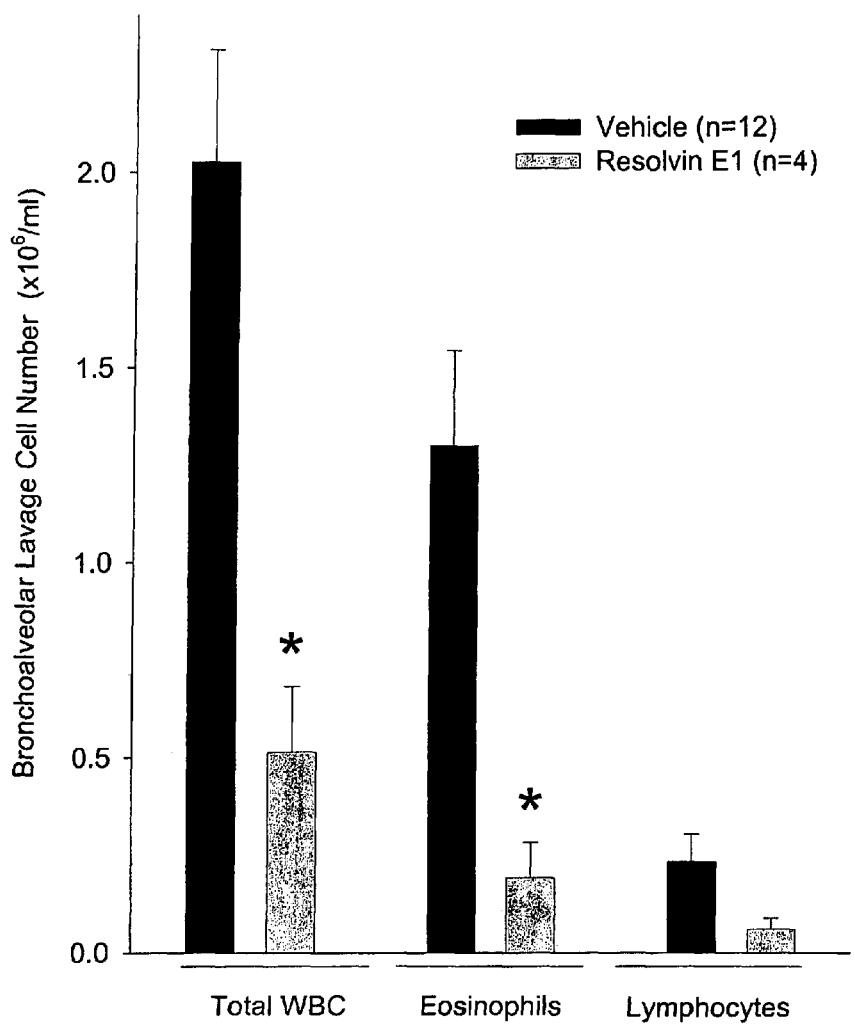

FIG. 24 depicts regulation of allergic airway inflammation by Resolvin E1 at 200 ng concentration.

Figure 25:
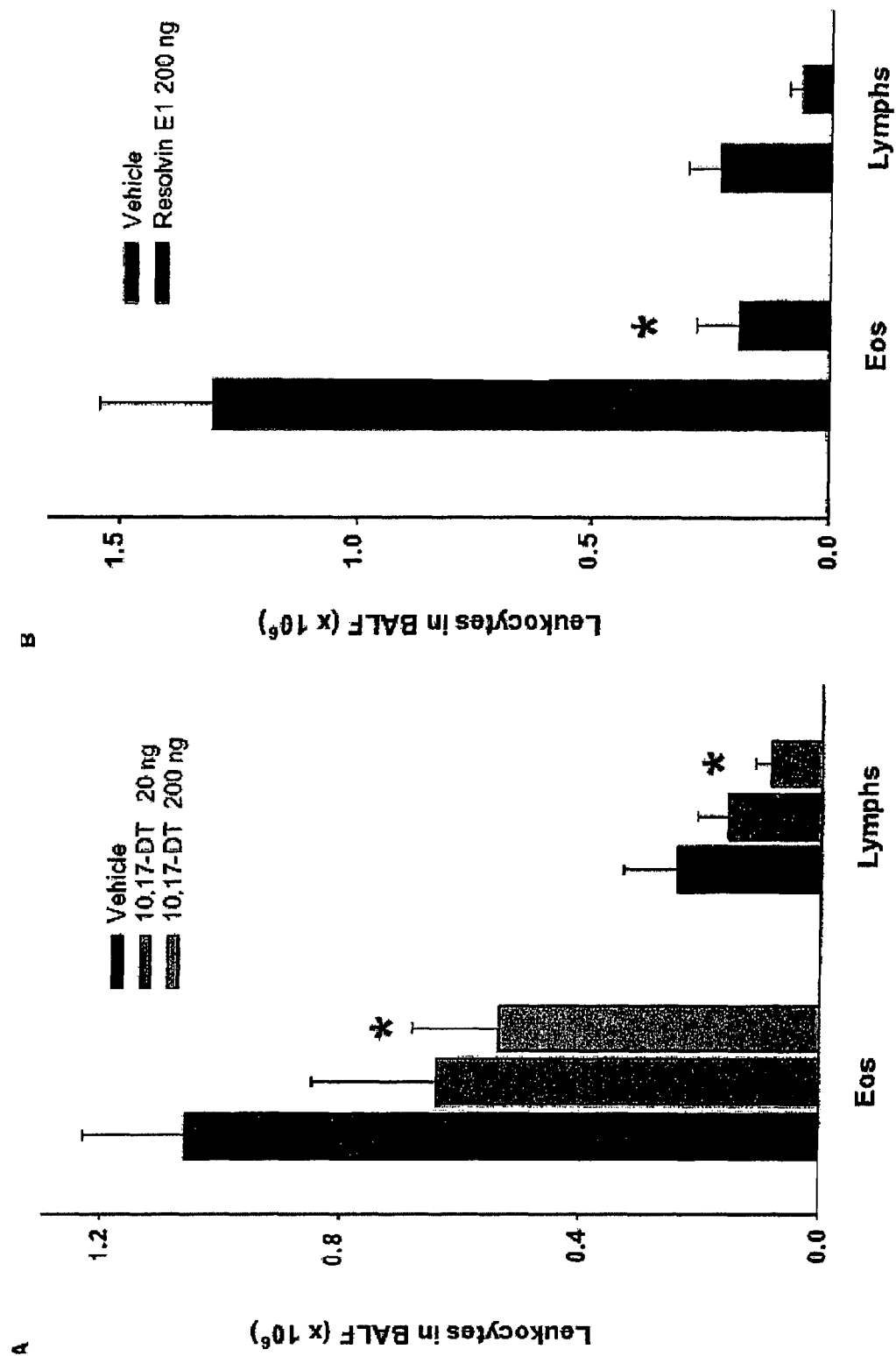

FIG. 25 depicts in panel A that eosinophil and lymphs are reduced in the present of 10,17-DT at 20 ng and 200 ng; panel B similarly shows a reduction in eosinophil and lympsh in the presence of Resolvin E1 at 200 ng.

DETAILED DESCRIPTION

The present invention provides methods for preparing novel anti-inflammatory agents and discloses the structures of novel endogenously generated anti-inflammatory mediators that are generated in resolution. The invention is based on the structural elucidation of several new classes of compounds that are generated in vivo during inflammation, which are termed "resolvins." The structural elucidation of the compounds and the mechanisms of their biosynthesis at sites of inflammation in vivo in murine systems via vascular leukocyte interactions and in brain when aspirin is taken are presented throughout the specification. This structural elucidation of novel biochemical pathways and compounds that serve as endogenous mediators in anti-inflammation and/or pro-resolution forms the basis of a novel approach to active anti-inflammatories that expedites resolution.

From structural elucidation, these novel compounds are "active ingredients" that the body converts via novel biochemical pathways to endogenous omega-3 fatty acid-derived mediators that have anti-inflammatory properties that we've uncovered in murine models. These results provide that these compounds, when generated in vivo in humans, are responsible, at least in part, for the beneficial actions of eating fish and aspirin therapy.

The structural elucidation of these pathways, biological properties and structural elucidation of novel compounds formulates the basis for a novel therapeutic approach, namely administering these compounds and/or related structures/analogs with greater biostability and chemical stability as new therapeutic approaches to expedite resolution and evoke anti-inflammation status.

Along these lines, the new structures, pathways, and examples of novel chemical classes of analogs based on these natural resolvin compounds are presented in the illustrations and figures throughout this specification. Most importantly, with the description of these novel pathways and physical properties of the resolvins, one claim can be directed for assaying these compounds in human fluids (blood, urine, breast milk), biopsied material, etc. as treatment markers to gauge effective n-3 status levels as indices for developing a therapeutic basis for anti-inflammation. This includes LC-MS-MS and GC-MS properties and could also lead to the development of much easier to handle ELISA assays monitoring these novel products.

Aspirin is unique among current therapies because it acetylates cyclooxygenase-2 (COX-2) enabling the biosynthesis of R-containing precursors of endogenous anti-inflammatory and pro-resolving mediators (1, 2). The present invention provides that lipidomic analysis of TNFα-induced exudates obtained in the resolution phase from mice treated with aspirin (ASA) and docosahexaenoic acid (DHA; C22:6) produce a novel family of bioactive 17R-hydroxy-containing di-, and trihydroxy-docosanoids via COX-2 initiated pathways. Murine brain treated with aspirin produced 17R-hydroxy-docosahexaenoic acid (17R-HDHA) from endogenous sources as did cytokine activated human microglial cells.

Human recombinant COX-2 converted DHA to 13-hydroxy-DHA that switched with ASA treatment to 17R-HDHA, which proved to be a major route in hypoxic human vascular endothelial cells that express COX-2. Human neutrophils engaged in phagocytosis transformed COX-2-ASA-derived 17R-hydroxy-DHA into two sets of novel 17R-hydroxy retaining di- and trihydroxy products; one initiated via oxygenation at carbon 7 and the other at carbon 4 that generates epoxide intermediates. COX-2-ASA generated docosanoids (i.e., 17R-HDHA) inhibited cytokine expression ($IC_{50}$~50 pM) by microglial cells. In both murine dermal inflammation and peritonitis, the 17R series compounds at ng doses (e.g. 4S,11,17R-triHDHA, 7S,8,17R-triHDHA, and 7S,17R-diHDHA) reduced 40-80% leukocytic exudates.

These results indicate that COX-2-bearing murine and human cells (i.e. neural, vascular, leukocytes and exudates) with aspirin treatment convert DHA to novel 17R-hydroxy-containing series of docosanoids that are potent regulators in acute inflammation-resolution. These redundant biosynthetic pathways utilize omega-3 fatty acids during multi-cellular events in resolution to produce endogenous protective compounds (termed Resolvins) that enhance pro-resolution status. Moreover, these results can provide a molecular rationale for the utilization of omega-3 DHA and aspirin as well as omega-3 fatty acid dietary supplementation in chronic inflammatory diseases, neoplasia, and cardiovascular disease.

The present invention provides that aspirin treatment of murine in vivo and human tissues in vitro carrying COX-2 initiates the production of novel 17R-hydroxy series docosanoids via previously undescribed biosynthetic circuits that counter-regulate pro-inflammatory responses (i.e., cytokine production, peritonitis). During stress, these cellular pathways utilize omega-3 fatty acids to biosynthesize endogenous compounds that serve in anti-inflammation signaling. Thus, the new family of compounds are referred to as Resolvins because they are i) generated during the resolution phase and ii) chemically redundant signals that play protective roles in dampening inflammation to promote a pro-resolution status.

The present invention is drawn to methods for treating or preventing inflammation in a subject by administration of a combination of a polyunsaturated fatty acid(s) (PUFA(s)) and aspirin, i.e., polyunsaturated fatty acids including C20:5 and C22:6. In one embodiment, the omega fatty acid, e.g., C20:3 or C22:6, and an analgesic, such as aspirin, are administered at two different times.

The phrase "resolvin mediated interaction" is intended to include disease states or conditions caused by or associated with one or more types of inflammation associated with cytokine, leukocyte or PMN regulation and regulation by one or more of the therapeutic analogs described throughout the specification for the pharmacologic inhibition of inflammatory diseases, vascular disorders and neuronal inflammation. In one embodiment, the disease state includes, for example, those diseases that afflict a subject by associating with or interfering with cytokine, leukocyte or PMN regulation within the subject. Such disease states or conditions are described throughout the specification, vide infra, and are incorporated herein in their entirety. Presently unknown conditions related to cytokine, leukocyte or PMN regulation that may be discovered in the future are encompassed by the present invention, since the characterization as conditions related to resolvin mediated interaction(s) will be readily determinable by persons skilled in the art.

Resolvins are natural counter regulatory lipid mediators in host defense mechanisms that protect host tissues from effector cell mediated injury and over amplification of acute inflammation to dampen the inflammatory response, i.e., counter-regulative. Some known chronic inflammatory diseases may represent the loss of and/or genetically program low resolvin endogenous responders and/or levels. The resolvin analogs described throughout the specification can be used to replace, enhance and/or treat the loss of these substances therapeutically and thereby pharmacologically resolve inflammation by inhibiting leukocyte recruitment and amplification, namely inhibition of the amplification of inflammation.

The present invention is also drawn to methods for treating arterial inflammation, arthritis, psoriasis, urticaria, vasculitis, asthma, ocular inflammation, pulmonary inflammation, pulmonary fibrosis, seborrheic dermatitis, pustular dermatosis, or cardiovascular diseases in a subject by administration of a combination of an omega fatty acid and an analgesic, such as aspirin to the subject. Disease states or conditions that are associated with inflammation (hence "resolving"), the recruitment of neutrophils, leukocytes and/or cytokines are included within the general scope of inflammation and include, for example, Addiction, AIDS, Alcohol-related disorders, Allergy, Alzheimer's disease, Anesthesiology, Anti-infectives, Anti-inflammatory agents, Arthritis, Asthma, Atherosclerosis, Bone diseases, Breast cancer, Cancer, Cardiovascular diseases, Child heath, Colon cancer, Congenital defects, Decision analysis, Degenerative neurologic disorders, Dementia, Dermatology, Diabetes mellitus, Diagnostics, Drug delivery, Drug discovery/screen, Endocrine disorders, ENT, Epidemiology, Eye diseases, Fetal and maternal medicine, Gastrointestinal disorders, Gene therapy, Genetic diagnostics, Genetics, Genitourinary disorders, Geriatric medicine, Growth and Development, Hearing, Hematologic disorders, Hepatobiliary disorders, Hypertension, Imaging, Immunology, Infectious diseases, Leukemia/lymphoma, Lung cancer, Metabolic disorders, Neonatology, Neurological disorders, Neuromuscular disorders, Nuclear medicine, Obesity/eating disorders, Orthopedic, Other, Parasitic diseases, Perinatal disorders, Pregnancy, Preventative medicine, Prostate cancer, Psychiatric disorders, Pulmonary disorders, Radiology, Renal disorders, Reproduction, Rheumatic diseases, Stroke, Surgical, Transplantation, Vaccines, Vascular medicine, Wound healing, oral infections, periodontal disease, brain injury, trauma and neuronal inflammation, and Women's health.

The present invention is also drawn to methods for treating or preventing chronic bronchitis, bronchiectasis, cystic fibrosis, non-cystic fibrosis-related bronchiectasis, eosinophilic lung diseases including parasitic infection, idiopathic eosinophilic pneumonias and Churg-Strauss vasculitis, allergic bronchopulmonary aspergillosis, allergic inflammation of the respiratory tract, including rhinitis, and sinusitis, bronchiolitis, bronchiolitis obliterans, bronchiolitis obliterans with organizing pneumonia, eosinophilic granuloma, Wegener's granulomatosis, sarcoidosis, hypersensitivity pneumonitis, idiopathic pulmonary fibrosis, pulmonary manifestations of connective tissue diseases, acute or chorionic lung injury, adult respiratory distress syndrome, Terms and abbreviations used throughout the specification include:
ASA, aspirin
BAL, bronchoalveolar lavage
COX, cyclooxygenase
CysLT, cysteinyl leukotriene
DHA, docosahexaenoic acid
DT, docosatriene
EOS, eosinophil
EPA, eicosapentaenoic acid
GC-MS, gas chromatography-mass spectrometry
4S-HDHA, 4S-hydroxy-5E,7Z,10Z,13Z,16Z,19Z-docosahexaenoic acid
17S-HDHA, 17S-hydroxy-4Z,7Z,10Z,13Z,15E,19Z-docosahexaenoic acid
17R/S-HDHA, 17R/S-hydroxy-4Z,7Z,10Z,13Z,15E,19Z-docosahexaenoic acid
17R-HDHA, 17-hydroxy-docosa-4Z,7Z,10Z,13Z,15E,19Z-hexaenoic acid
7S,17R-dihydroxy-DHA, 7S,17R-dihydroxy-docosa-4Z,8E,10Z,13Z,15E,19Z-hexaenoic acid
4S,17R-dihydroxy-DHA, 4S-17R-dihydroxy-docosa-5E,7Z,10Z,13Z,15E,19Z-hexaenoic acid
7S,17R,22-trihydroxy-DHA, 7S,17R,22-trihydroxy-docosa-4Z,8Z,10Z,13Z,15E,19Z-hexaenoic acid
4S,11,17R-trihydroxy-DHA, 4S,11,17S,-trihydroxy-docosa-5E,7E,9Z,13Z,15E,19Z-hexaenoic acid
LC-UV-MS-MS, liquid chromatography-UV diode array detector-tandem mass spectrometry
LO, lipoxygenase
LT, leukotriene
LX, lipoxins
Lymph, lymphocyte
MS, mass spectrometry
PDA, photodiode array detector
PD1,10,17S-docosatriene
PMN, neutrophil
PD1, protectin D1

PUFA, polyunsaturated fatty acids 10,17S-docosatriene, 10,17S-dihydroxy-4,7,15,19-cis-11,13-trans-docosahexaenoic acid "Alkyl" by itself or as part of another substituent refers to a saturated or unsaturated branched, straight-chain or cyclic monovalent hydrocarbon radical having the stated number of carbon atoms (i.e., C1-C6 means one to six carbon atoms) that is derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" is used, as defined below. In preferred embodiments, the alkyl groups are (C1-C6) alkyl.

"Alkanyl" by itself or as part of another substituent refers to a saturated branched, straight-chain or cyclic alkyl derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like. In preferred embodiments, the alkanyl groups are (C1-C6) alkanyl.

"Alkenyl" by itself or as part of another substituent refers to an unsaturated branched, straight-chain or cyclic alkyl having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. In preferred embodiments, the alkenyl group is (C2-C6) alkenyl.

"Alkynyl" by itself or as part of another substituent refers to an unsaturated branched, straight-chain or cyclic alkyl having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. In preferred embodiments, the alkynyl group is (C2-C6) alkynyl.

"Alkyldiyl" by itself or as part of another substituent refers to a saturated or unsaturated, branched, straight-chain or cyclic divalent hydrocarbon group having the stated number of carbon atoms (i.e., C1-C6 means from one to six carbon atoms) derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to, methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Where it is specifically intended that the two valencies are on the same carbon atom, the nomenclature "alkylidene" is used. In preferred embodiments, the alkyldiyl group is (C1-C6) alkyldiyl. Also preferred are saturated acyclic alkanyldiyl groups in which the radical centers are at the terminal carbons, e.g., methandiyl (methano); ethan-1,2-diyl (ethano); propan-1,3-diyl (propano); butan-1,4-diyl (butano); and the like (also referred to as alkylenos, defined infra).

"Alkyleno" by itself or as part of another substituent refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The locant of a double bond or triple bond, if present, in a particular alkyleno is indicated in square brackets. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In preferred embodiments, the alkyleno group is (C1-C6) or (C1-C3) alkyleno. Also preferred are straight-chain saturated alkano groups, e.g., methano, ethano, propano, butano, and the like.

"Heteroalkyl," Heteroalkanyl," Heteroalkenyl," Heteroalkynyl," Heteroalkyldiyl" and "Heteroalkyleno" by themselves or as part of another substituent refer to alkyl, alkanyl, alkenyl, alkynyl, alkyldiyl and alkyleno groups, respectively, in which one or more of the carbon atoms are each independently replaced with the same or different heteroatoms or heteroatomic groups. Typical heteroatoms and/or heteroatomic groups which can replace the carbon atoms include, but are not limited to, —O—, —S—, —S—O—, —NR'—, —PH—, —S(O)—, —S(O)$_2$—, —S(O)NR'—, —S(O)$_2$NR'—, and the like, including combinations thereof, where each R' is independently hydrogen or (C1-C6) alkyl.

"Cycloalkyl" and "Heterocycloalkyl" by themselves or as part of another substituent refer to cyclic versions of "alkyl" and "heteroalkyl" groups, respectively. For heteroalkyl groups, a heteroatom can occupy the position that is attached to the remainder of the molecule. Typical cycloalkyl groups include, but are not limited to, cyclopropyl; cyclobutyls such as cyclobutanyl and cyclobutenyl; cyclopentyls such as cyclopentanyl and cyclopentenyl; cyclohexyls such as cyclohexanyl and cyclohexenyl; and the like. Typical heterocycloalkyl groups include, but are not limited to, tetrahydrofuranyl (e.g., tetrahydrofuran-2-yl, tetrahydrofuran-3-yl, etc.), piperidinyl (e.g., piperidin-1-yl, piperidin-2-yl, etc.), morpholinyl (e.g., morpholin-3-yl, morpholin-4-yl, etc.), piperazinyl (e.g., piperazin-1-yl, piperazin-2-yl, etc.), and the like.

"Acyclic Heteroatomic Bridge" refers to a divalent bridge in which the backbone atoms are exclusively heteroatoms and/or heteroatomic groups. Typical acyclic heteroatomic bridges include, but are not limited to, —O—, —S—, —S—O—, —NR'—, —PH—, —S(O)—, —S(O)$_2$—, —S(O)NR'—, —S(O)$_2$NR'—, and the like, including combinations thereof, where each R' is independently hydrogen or (C1-C6) alkyl.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, tetrahydronaphthalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, tetrahydronaphthalene, triphenylene, trinaphthalene, and the like, as well as the various hydro isomers thereof.

"Aryl" by itself or as part of another substituent refers to a monovalent aromatic hydrocarbon group having the stated number of carbon atoms (i.e., C5-C15 means from 5 to 15 carbon atoms) derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like, as well as the various hydro isomers thereof. In preferred embodiments, the aryl group is (C5-C15) aryl, with (C5-C10) being even more preferred. Particularly preferred aryls are cyclopentadienyl, phenyl and naphthyl.

"Arylaryl" by itself or as part of another substituent refers to a monovalent hydrocarbon group derived by the removal of one hydrogen atom from a single carbon atom of a ring system in which two or more identical or non-identical parent aromatic ring systems are joined directly together by a single bond, where the number of such direct ring junctions is one less than the number of parent aromatic ring systems involved. Typical arylaryl groups include, but are not limited to, biphenyl, triphenyl, phenyl-naphthyl, binaphthyl, biphenyl-naphthyl, and the like. Where the number of carbon atoms in an arylaryl group are specified, the numbers refer to the carbon atoms comprising each parent aromatic ring. For example, (C5-C15) arylaryl is an arylaryl group in which each aromatic ring comprises from 5 to 15 carbons, e.g., biphenyl, triphenyl, binaphthyl, phenylnaphthyl, etc. Preferably, each parent aromatic ring system of an arylaryl group is independently a (C5-C15) aromatic, more preferably a (C5-C10) aromatic. Also preferred are arylaryl groups in which all of the parent aromatic ring systems are identical, e.g., biphenyl, triphenyl, binaphthyl, trinaphthyl, etc.

"Biaryl" by itself or as part of another substituent refers to an arylaryl group having two identical parent aromatic systems joined directly together by a single bond. Typical biaryl groups include, but are not limited to, biphenyl, binaphthyl, bianthracyl, and the like. Preferably, the aromatic ring systems are (C5-C15) aromatic rings, more preferably (C5-C10) aromatic rings. A particularly preferred biaryl group is biphenyl.

"Arylalkyl" by itself or as part of another substituent refers to an acyclic alkyl group in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylakenyl and/or arylalkynyl is used. In preferred embodiments, the arylalkyl group is (C6-C21) arylalkyl, e.g., the alkanyl, alkenyl or alkynyl moiety of the arylalkyl group is (C1-C6) and the aryl moiety is (C5-C15). In particularly preferred embodiments the arylalkyl group is (C6-C13), e.g., the alkanyl, alkenyl or alkynyl moiety of the arylalkyl group is (C1-C3) and the aryl moiety is (C5-C10).

"Parent Heteroaromatic Ring System" refers to a parent aromatic ring system in which one or more carbon atoms are each independently replaced with the same or different heteroatoms or heteroatomic groups. Typical heteroatoms or heteroatomic groups to replace the carbon atoms include, but are not limited to, N, NH, P, O, S, S(O), S(O)$_2$, Si, etc. Specifically included within the definition of "parent heteroaromatic ring systems" are fused ring systems in which one or more of the rings are aromatic and one or more of the rings are saturated or unsaturated, such as, for example, benzodioxan, benzofuran, chromane, chromene, indole, indoline, xanthene, etc. Also included in the definition of "parent heteroaromatic ring system" are those recognized rings that include common substituents, such as, for example, benzopyrone and 1-methyl-1,2,3,4-tetrazole. Typical parent heteroaromatic ring systems include, but are not limited to, acridine, benzimidazole, benzisoxazole, benzodioxan, benzodioxole, benzofuran, benzopyrone, benzothiadiazole, benzothiazole, benzotriazole, benzoxaxine, benzoxazole, benzoxazoline, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Heteroaryl" by itself or as part of another substituent refers to a monovalent heteroaromatic group having the stated number of ring atoms (e.g., "5-14 membered" means from 5 to 14 ring atoms) derived by the removal of one hydrogen atom from a single atom of a parent heteroaromatic ring system. Typical heteroaryl groups include, but are not limited to, groups derived from acridine, benzimidazole, benzisoxazole, benzodioxan, benzodiaxole, benzofuran, benzopyrone, benzothiadiazole, benzothiazole, benzotriazole, benzoxazine, benzoxazole, benzoxazoline, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like, as well as the various hydro isomers thereof. In preferred embodiments, the heteroaryl group is a 5-14 membered heteroaryl, with 5-10 membered heteroaryl being particularly preferred.

"Heteroaryl-Heteroaryl" by itself or as part of another substituent refers to a monovalent heteroaromatic group derived by the removal of one hydrogen atom from a single atom of a ring system in which two or more identical or non-identical parent heteroaromatic ring systems are joined directly together by a single bond, where the number of such direct ring junctions is one less than the number of parent heteroaromatic ring systems involved. Typical heteroaryl-heteroaryl groups include, but are not limited to, bipyridyl, tripyridyl, pyridylpurinyl, bipurinyl, etc. Where the number of atoms are specified, the numbers refer to the number of atoms comprising each parent heteroaromatic ring systems. For example, 5-15 membered heteroaryl-heteroaryl is a heteroaryl-heteroaryl group in which each parent heteroaromatic ring system comprises from 5 to 15 atoms, e.g., bipyridyl, tripyridyl, etc. Preferably, each parent heteroaromatic ring system is independently a 5-15 membered heteroaromatic, more preferably a 5-10 membered heteroaromatic. Also preferred are heteroaryl-heteroaryl groups in which all of the parent heteroaromatic ring systems are identical.

"Biheteroaryl" by itself or as part of another substituent refers to a heteroaryl-heteroaryl group having two identical parent heteroaromatic ring systems joined directly together by a single bond. Typical biheteroaryl groups include, but are not limited to, bipyridyl, bipurinyl, biquinolinyl, and the like. Preferably, the heteroaromatic ring systems are 5-15 membered heteroaromatic rings, more preferably 5-10 membered heteroaromatic rings.

"Heteroarylalkyl" by itself or as part of another substituent refers to an acyclic alkyl group in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylalkenyl and/or heteroarylalkynyl is used. In preferred embodiments, the heteroarylalkyl group is a 6-21 membered heteroarylalkyl, e.g., the alkanyl, alkenyl or alkynyl moiety of the heteroarylalkyl is (C1-C6) alkyl and the heteroaryl moiety is a 5-15-membered heteroaryl. In particularly preferred embodiments, the heteroarylalkyl is a 6-13 membered heteroarylalkyl, e.g., the alkanyl, alkenyl or alkynyl moiety is (C1-C3) alkyl and the heteroaryl moiety is a 5-10 membered heteroaryl.

"Halogen" or "Halo" by themselves or as part of another substituent, unless otherwise stated, refer to fluoro, chloro, bromo and iodo.

"Haloalkyl" by itself or as part of another substituent refers to an alkyl group in which one or more of the hydrogen atoms is replaced with a halogen. Thus, the term "haloalkyl" is meant to include monohaloalkyls, dihaloalkyls, trihaloalkyls, etc. up to perhaloalkyls. For example, the expression "(C1-C2) haloalkyl" includes fluoromethyl, difluoromethyl, trifluoromethyl, 1-fluoroethyl, 1,1-difluoroethyl, 1,2-difluoroethyl, 1,1,1-trifluoroethyl, perfluoroethyl, etc.

The above-defined groups may include prefixes and/or suffixes that are commonly used in the art to create additional well-recognized substituent groups. As examples, "alkyloxy" or "alkoxy" refers to a group of the formula —OR", "alkylamine" refers to a group of the formula —NHR" and "dialkylamine" refers to a group of the formula —NR"R", where each R" is independently an alkyl. As another example, "haloalkoxy" or "haloalkyloxy" refers to a group of the formula —OR'", where R'" is a haloalkyl.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, $3^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPPS groups), glycol ethers, such as ethylene glycol and propylene glycol derivatives and allyl ethers.

The present invention provides compounds and pharmaceutical compositions useful for the treatment of various disease states and conditions, having the formula:

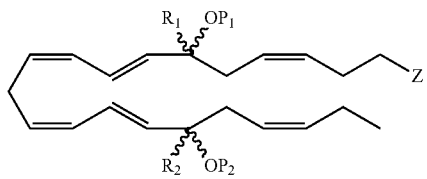

wherein $P_1$ and $P_2$ each individually are protecting groups, hydrogen atoms or combinations thereof;

wherein $R_1$ and $R_2$ each individually are substituted or unsubstituted, branched or unbranched alkyl groups, substituted or unsubstituted aryl groups, substituted or unsubstituted, branched or unbranched alkylaryl groups, halogen atoms, hydrogen atoms or combinations thereof;

wherein Z is —C(O)OR$^d$, —C(O)NR$^c$R$^c$, —C(O)H, —C(NH)NR$^c$R$^c$, —C(S)H, —C(S)OR$^d$, —C(S)NR$^c$R$^c$, —CN;

each R$^a$, is independently selected from the group consisting of hydrogen, (C1-C6) alkyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl and 6-16 membered heteroarylalkyl;

each R$^b$, is a suitable group independently selected from the group consisting of =O, —OR$^d$, (C1-C3) haloalkyloxy, —OCF$_3$, =S, —SR$^d$, =NR$^d$, =NOR$^d$, —NR$^c$R$^c$, halogen, —CF$_3$, —CN, —NC, —OCN, —SCN, —NO, —NO$_2$, =N$_2$, —N$_3$, —S(O)R$^d$, —S(O)$_2$R$^d$, —S(O)$_2$OR$^d$, —S(O)NR$^c$R$^c$, —S(O)$_2$NR'R$^c$, —OS(O)R$^d$, —OS(O)$_2$R$^d$, —OS(O)$_2$OR$^d$, —OS(O)$_2$NR$^c$R$^c$, —C(O)R$^d$, —C(O)OR$^d$, —C(O)NR$^c$R$^c$, —C(NH)NR$^c$R$^c$, —C(NR$^a$)NR$^c$R$^c$, —C(NOH)R$^a$, —C(NOH)NR$^c$R$^c$, —OC(O)R$^d$, —OC(O)OR$^d$, —OC(O)

$NR^cR^c$, $-OC(NH)NR^cR^c$, $-OC(NR^a)NR^cR^c$, $-[NHC(O)]_n R^d$, $-[NR^aC(O)]_n R^d$, $-[NHC(O)]_n OR^d$, $-[NR^aC(O)]_n OR^d$, $-[NHC(O)]_n NR^cR^c$, $-[NR^aC(O)]_n NR^cR^c$, $-[NHC(NH)]_n NR^cR^c$ and $-[NR^aC(NR^a)]_n NR^cR^c$;

each $R^c$, is independently a protecting group or $R^a$, or, alternatively, each $R^c$ is taken together with the nitrogen atom to which it is bonded to form a 5 to 8-membered cycloheteroalkyl or heteroaryl which may optionally include one or more of the same or different additional heteroatoms and which may optionally be substituted with one or more of the same or different $R^a$ or suitable $R^b$ groups;

each n, independently is an integer from 0 to 3;

each $R^d$, independently is a protecting group or $R^a$;

in particular, Z is a carboxylic acid, ester, amide, thiocarbamate, carbamate, thioester, thiocarboxamide or a nitrile;

and pharmaceutically acceptable salts thereof. In certain embodiments, $P_1$ and $P_2$ are hydrogen atoms, $R_1$ and $R_2$ each individually are methyl groups or hydrogen atoms or combinations thereof, and Z is carboxylic acid or a carboxylic ester.

The present invention also provides compounds and pharmaceutical compositions useful for the treatment of various disease states and conditions, having the formula:

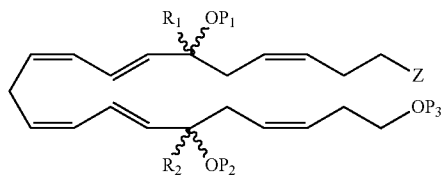

wherein $P_1$, $P_2$ and $P_3$ each individually are protecting groups, hydrogen atoms or combinations thereof wherein $R_1$ and $R_2$ each individually are substituted or unsubstituted, branched or unbranched alkyl groups, substituted or unsubstituted aryl groups, substituted or unsubstituted, branched or unbranched alkylaryl groups, halogen atoms, hydrogen atoms or combinations thereof wherein Z is as defined above, and in particular can be a carboxylic acid, ester, amide, thiocarbamate, carbamate, thioester, thiocarboxamide or a nitrile;

and pharmaceutically acceptable salts thereof. In certain embodiments, $P_1$, $P_2$ and $P_3$ each are hydrogen atoms, $R_1$ and $R_2$ each individually are methyl groups or hydrogen atoms or combinations thereof and Z is a carboxylic acid or a carboxylic ester.

In certain aspects the designation of $OP_3$ serves to denote that the terminal carbon is substituted with one or more halogens (I, Cl, F, Br, mono, di or tri substitution) to form, for example, a trifluoromethyl group, or is an aryl group or phenoxy group that can be substituted or unsubstituted as described herein.

The present invention still further provides compounds and pharmaceutical compositions useful for the treatment of various disease states and conditions, having the formula:

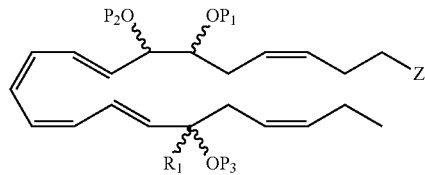

wherein $P_1$, $P_2$ and $P_3$ each individually are protecting groups, hydrogen atoms or combinations thereof;

wherein $R_1$ is a substituted or unsubstituted, branched or unbranched alkyl group, substituted or unsubstituted aryl group, substituted or unsubstituted, branched or unbranched alkylaryl group, halogen atom, or a hydrogen atom;

wherein Z is as defined above, and in particular can be a carboxylic acid, ester, amide, thiocarbamate, carbamate, thioester, thiocarboxamide or a nitrile;

and pharmaceutically acceptable salts thereof. In an embodiment, $P_1$, $P_2$ and $P_3$ each are hydrogen atoms, $R_1$ is a methyl group or a hydrogen atom and Z is a carboxylic acid or a carboxylic ester.

The present invention provides compounds and pharmaceutical compositions useful for the treatment of various disease states and conditions, having the formula:

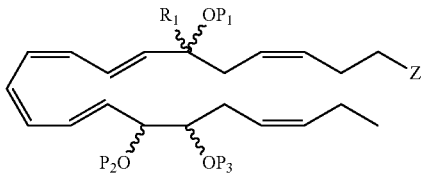

wherein $P_1$, $P_2$ and $P_3$ each individually are protecting groups, hydrogen atoms or combinations thereof;

wherein $R_1$ is a substituted or unsubstituted, branched or unbranched alkyl group, substituted or unsubstituted aryl group, substituted or unsubstituted, branched or unbranched alkylaryl group, halogen atom, or a hydrogen atom;

wherein Z is as defined above, and in particular can be a carboxylic acid, ester, amide, thiocarbamate, carbamate, thioester, thiocarboxamide or a nitrile;

and pharmaceutically acceptable salts thereof. In a particular embodiment, $P_1$, $P_2$ and $P_3$ each are hydrogen atoms, $R_1$ is a methyl group or a hydrogen atom and Z is a carboxylic acid or a carboxylic ester.

The present invention further provides compounds and pharmaceutical compositions useful for the treatment of various disease states and conditions, having the formula:

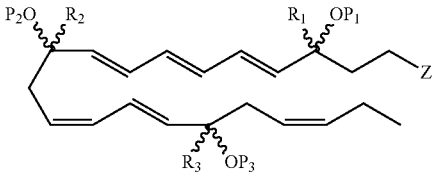

wherein $P_1$, $P_2$ and $P_3$ each individually are protecting groups, hydrogen atoms or combinations thereof;

wherein $R_1$, $R_2$ and $R_3$, each individually are substituted or unsubstituted, branched or unbranched alkyl groups, substituted or unsubstituted aryl groups, substituted or unsubstituted, branched or unbranched alkylaryl groups, halogen atoms, hydrogen atoms or combinations thereof;

wherein Z is as defined above, and in particular can be a carboxylic acid, ester, amide, thiocarbamate, carbamate, thioester, thiocarboxamide or a nitrile;

and pharmaceutically acceptable salts thereof. In a particular embodiment, $P_1$, $P_2$ and $P_3$ each are hydrogen atoms, $R_1$, $R_2$ and $R_3$ each individually are methyl groups or hydrogen atoms or combinations thereof and Z is a carboxylic acid or a carboxylic ester.

The present invention also provides compounds and pharmaceutical compositions useful for the treatment of various disease states and conditions, having the formula:

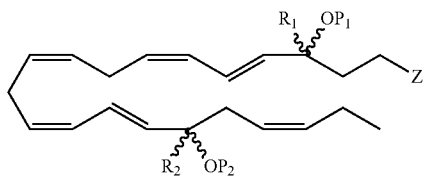

wherein $P_1$ and $P_2$ each individually are protecting groups, hydrogen atoms or combinations thereof;

wherein $R_1$ and $R_2$ each individually are substituted or unsubstituted, branched or unbranched alkyl groups, substituted or unsubstituted aryl groups, substituted or unsubstituted, branched or unbranched alkylaryl groups, halogen atoms, hydrogen atoms or combinations thereof;

wherein Z is as defined above, and in particular can be a carboxylic acid, ester, amide, thiocarbamate, carbamate, thioester, thiocarboxamide or a nitrile;

and pharmaceutically acceptable salts thereof. In certain embodiments, $P_1$ and $P_2$ are hydrogen atoms, $R_1$ and $R_2$ each individually are methyl groups or hydrogen atoms or combinations thereof and Z is carboxylic acid or a carboxylic ester.

The present invention provides compounds and pharmaceutical compositions useful for the treatment of various disease states and conditions, having the formula:

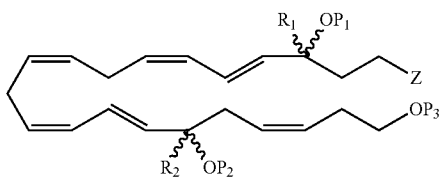

wherein $P_1$, $P_2$ and $P_3$ each individually are protecting groups, hydrogen atoms or combinations thereof;

wherein $R_1$ and $R_2$ each individually are substituted or unsubstituted, branched or unbranched alkyl groups, substituted or unsubstituted aryl groups, substituted or unsubstituted, branched or unbranched alkylaryl groups, halogen atoms, hydrogen atoms or combinations thereof;

wherein Z is as defined above, and in particular can be a carboxylic acid, ester, amide, thiocarbamate, carbamate, thioester, thiocarboxamide or a nitrile;

and pharmaceutically acceptable salts thereof. In a particular embodiment, $P_1$, $P_2$ and $P_3$ each are hydrogen atoms and Z is a carboxylic acid or a carboxylic ester.

In certain aspects the designation of $OP_3$ serves to denote that the terminal carbon is substituted with one or more halogens (I, Cl, F, Br, mono, di or tri substitution) to form, for example, a trifluoromethyl group, or is an aryl group or phenoxy group that can be substituted or unsubstituted as described herein.

The present invention also provides compounds and pharmaceutical compositions useful for the treatment of various disease states and conditions, having the formula:

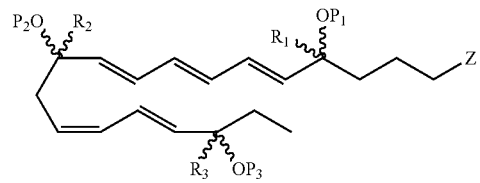

wherein $P_1$, $P_2$ and $P_3$ each individually are protecting groups, hydrogen atoms or combinations thereof wherein $R_1$, $R_2$ and $R_3$, each individually are substituted or unsubstituted, branched or unbranched alkyl groups, substituted or unsubstituted aryl groups, substituted or unsubstituted, branched or unbranched alkylaryl groups, halogen atoms, hydrogen atoms or combinations thereof wherein Z is as defined above, and in particular can be a carboxylic acid, ester, amide, thiocarbamate, carbamate, thioester, thiocarboxamide or a nitrile;

and pharmaceutically acceptable salts thereof. In one embodiment, $P_1$, $P_2$ and $P_3$ each are hydrogen atoms, $R_1$, $R_2$ and $R_3$ each individually are methyl groups or hydrogen atoms or combinations thereof and Z is a carboxylic acid or a carboxylic ester.

In certain embodiments, the invention includes 5,12,18-trihydroxy-EPA, i.e., (5S,12R,18R-trihydroxy-6Z,8E,10E,14Z,16E-eicosapentaenoic acid, known as Resolvin E1 (Reso E1) and more specifically, 5,12,18-trihydroxy EPA analogs (resolvins), as described in U.S. patent application Ser. No. 09/785,866, filed Feb. 16, 2001.

The present invention further still provides compounds and pharmaceutical compositions useful for the treatment of various disease states and conditions, having the formula:

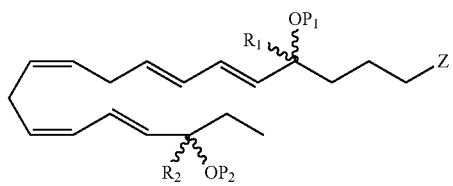

wherein $P_1$ and $P_2$ each individually are protecting groups, hydrogen atoms or combinations thereof;

wherein $R_1$ and $R_2$ each individually are substituted or unsubstituted, branched or unbranched alkyl groups, substituted or unsubstituted aryl groups, substituted or unsubstituted, branched or unbranched alkylaryl groups, halogen atoms, hydrogen atoms or combinations thereof;

wherein Z is as defined above, and in particular can be a carboxylic acid, ester, amide, thiocarbamate, carbamate, thioester, thiocarboxamide or a nitrile;

and pharmaceutically acceptable salts thereof. In one particular embodiment, $P_1$ and $P_2$ are hydrogen atoms, $R_1$ and $R_2$ each individually are methyl groups or hydrogen atoms or combinations thereof and Z is carboxylic acid or a carboxylic ester.

The present invention further still provides compounds and pharmaceutical compositions useful for the treatment of various disease states and conditions, having the formula:

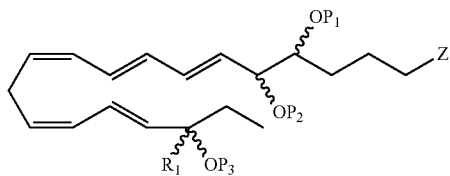

wherein $P_1$, $P_2$ and $P_3$ each individually are protecting groups, hydrogen atoms or combinations thereof;

wherein $R_1$ is a substituted or unsubstituted, branched or unbranched alkyl group, substituted or unsubstituted aryl group, substituted or unsubstituted, branched or unbranched alkylaryl group, halogen atom, or a hydrogen atom;

wherein Z is as defined above, and in particular can be a carboxylic acid, ester, amide, thiocarbamate, carbamate, thioester, thiocarboxamide or a nitrile;

and pharmaceutically acceptable salts thereof. In one embodiment, $P_1$, $P_2$ and $P_3$ each are hydrogen atoms, $R_1$ is a methyl group or a hydrogen atom and Z is a carboxylic acid or a carboxylic ester.

The present invention provides compounds and pharmaceutical compositions useful for the treatment of various disease states and conditions, having the formula:

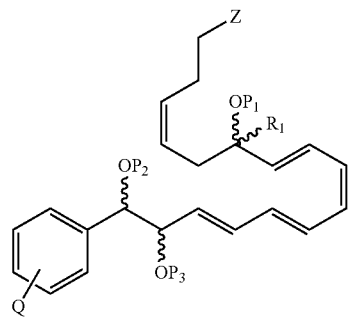

wherein $P_1$, $P_2$ and $P_3$ each individually are protecting groups, hydrogen atoms or combinations thereof;

wherein $R_1$ is a substituted or unsubstituted, branched or unbranched alkyl group, substituted or unsubstituted aryl group, substituted or unsubstituted, branched or unbranched alkylaryl group, halogen atom, or a hydrogen atom;

wherein Q represents one or more substituents and each Q, independently, is a hydrogen atom, a halogen atom or a branched or unbranched, substituted or unsubstituted alkyl, alkenyl, alkynyl, cycloalkyl, aryl, alkoxy, aryloxy, alkylcarbonyl, arylcarbonyl, alkoxycarbonyl, aryloxycarbonyl, amino, hydroxy, cyano, carboxyl, alkoxycarbonyloxy, aryloxycarbonyloxy or aminocarbonyl group;

wherein Z is as defined above, and in particular can be a carboxylic acid, ester, amide, thiocarbamate, carbamate, thioester, thiocarboxamide or a nitrile;

and pharmaceutically acceptable salts thereof. In one particular aspect, $P_1$, $P_2$ and $P_3$ each are hydrogen atoms, $R_1$ is a methyl group or a hydrogen atom, each Q is a hydrogen atom and Z is a carboxylic acid or a carboxylic ester.

The present invention also provides compounds and pharmaceutical compositions useful for the treatment of various disease states and conditions, having the formula:

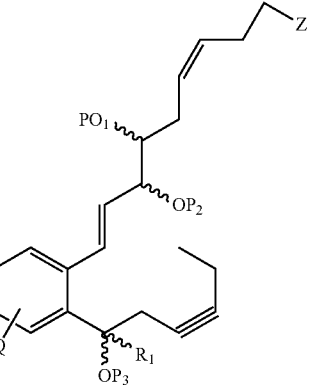

wherein $P_1$, $P_2$ and $P_3$ each individually are protecting groups, hydrogen atoms or combinations thereof wherein $R_1$ is a substituted or unsubstituted, branched or unbranched alkyl group, substituted or unsubstituted aryl group, substituted or unsubstituted, branched or unbranched alkylaryl group, halogen atom, or a hydrogen atom;

wherein Z is as defined above, and in particular can be a carboxylic acid, ester, amide, thiocarbamate, carbamate, thioester, thiocarboxamide or a nitrile;

and pharmaceutically acceptable salts thereof. In one embodiment, $P_1$, $P_2$ and $P_3$ each are hydrogen atoms, $R_1$ is a methyl group or a hydrogen atom, and Z is a carboxylic acid or a carboxylic ester.

The present invention further still provides compounds and pharmaceutical compositions useful for the treatment of various disease states and conditions, having the formula:

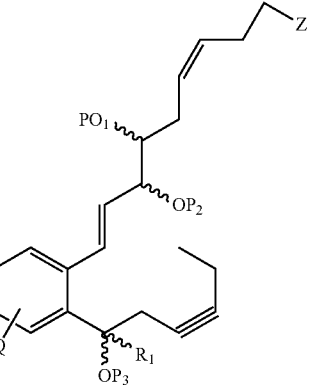

wherein $P_1$, $P_2$ and $P_3$ each individually are protecting groups, hydrogen atoms or combinations thereof wherein $R_1$ is a substituted or unsubstituted, branched or unbranched alkyl group, substituted or unsubstituted aryl group, substituted or unsubstituted, branched or unbranched alkylaryl group, halogen atom, or a hydrogen atom;

wherein Q represents one or more substituents and each Q, independently, is a hydrogen atom, halogen atom or a branched or unbranched, substituted or unsubstituted alkyl, alkenyl, alkynyl, cycloalkyl, aryl, alkoxy, aryloxy, alkylcarbonyl, arylcarbonyl, alkoxycarbonyl, aryloxycarbonyl, amino, hydroxy, cyano, carboxyl, alkoxycarbonyloxy, aryloxycarbonyloxy or aminocarbonyl group;

wherein Z is as defined above, and in particular can be a carboxylic acid, ester, amide, thiocarbamate, carbamate, thioester, thiocarboxamide or a nitrile;

and pharmaceutically acceptable salts thereof. In one particular embodiment, $P_1$, $P_2$ and $P_3$ each are hydrogen atoms, R is a methyl group or a hydrogen atom, each Q is a hydrogen atom and Z is a carboxylic acid or a carboxylic ester.

In still another aspect, the present invention provides compounds and pharmaceutical compositions useful for the treatment of various disease states and conditions, having the formula:

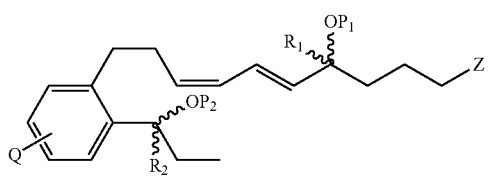

wherein $P_1$, and $P_2$ each individually are protecting groups, hydrogen atoms or combinations thereof;

wherein $R_1$ and $R_2$ each individually are substituted or unsubstituted, branched or unbranched alkyl groups, substituted or unsubstituted aryl groups, substituted or unsubstituted, branched or unbranched alkylaryl groups, halogen atoms, hydrogen atoms or combinations thereof;

wherein Q represents one or more substituents and each Q, independently, is a hydrogen atom, halogen atom or a branched or unbranched, substituted or unsubstituted alkyl, alkenyl, alkynyl, cycloalkyl, aryl, alkoxy, aryloxy, alkylcarbonyl, arylcarbonyl, alkoxycarbonyl, aryloxycarbonyl, amino, hydroxy, cyano, carboxyl, alkoxycarbonyloxy, aryloxycarbonyloxy or aminocarbonyl group;

wherein Z is as defined above, and in particular can be a carboxylic acid, ester, amide, thiocarbamate, carbamate, thioester, thiocarboxamide or a nitrile;

and pharmaceutically acceptable salts thereof. In one embodiment, $P_1$, and $P_2$ each are hydrogen atoms, $R_1$ and $R_2$ each individually are methyl groups or hydrogen atoms or combinations thereof, each Q is a hydrogen atom and Z is a carboxylic acid or a carboxylic ester.

The present invention also provides compounds and pharmaceutical compositions useful for the treatment of various disease states and conditions, having the formula:

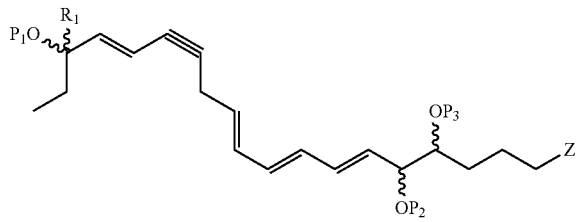

wherein $P_1$, $P_2$ and $P_3$ each individually are protecting groups, hydrogen atoms or combinations thereof;

wherein $R_1$, $R_2$ and $R_3$, each individually are substituted or unsubstituted, branched or unbranched alkyl groups, substituted or unsubstituted aryl groups, substituted or unsubstituted, branched or unbranched alkylaryl groups, halogen atoms, hydrogen atoms or combinations thereof;

wherein Z is as defined above, and in particular can be a carboxylic acid, ester, amide, thiocarbamate, carbamate, thioester, thiocarboxamide or a nitrile;

and pharmaceutically acceptable salts thereof. In one embodiment, $P_1$, $P_2$ and $P_3$ each are hydrogen atoms, $R_1$, $R_2$ and $R_3$ each individually are methyl groups or hydrogen atoms or combinations thereof and Z is a carboxylic acid or a carboxylic ester.

The present invention further provides compounds and pharmaceutical compositions useful for the treatment of various disease states and conditions, having the formula:

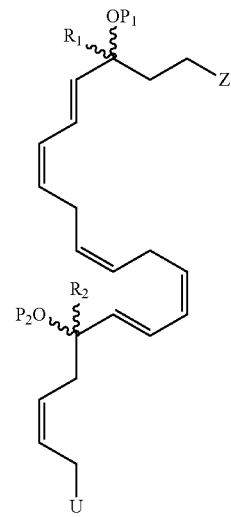

wherein $P_1$, and $P_2$ each individually are protecting groups, hydrogen atoms or combinations thereof;

wherein $R_1$ and $R_2$ each individually are substituted or unsubstituted, branched or unbranched alkyl groups, substituted or unsubstituted aryl groups, substituted or unsubstituted, branched or unbranched alkylaryl groups, halogen atoms, hydrogen atoms or combinations thereof;

wherein U is a branched or unbranched, substituted or unsubstituted alkyl, alkenyl, alkynyl, cycloalkyl, aryl, alkoxy, aryloxy, alkylcarbonyl, arylcarbonyl, alkoxycarbonyl, aryloxycarbonyl, alkoxycarbonyloxy, and aryloxycarbonyloxy group;

wherein Z is as defined above, and in particular can be a carboxylic acid, ester, amide, thiocarbamate, carbamate, thioester, thiocarboxamide or a nitrile;

and pharmaceutically acceptable salts thereof. In one aspect, $P_1$, and $P_2$ each are hydrogen atoms, $R_1$ and $R_2$ each individually are methyl groups or hydrogen atoms or combinations thereof, U is a trifluoromethyl group and Z is a carboxylic acid or a carboxylic ester.

In still another aspect, the present invention provides compounds and pharmaceutical compositions useful for the treatment of various disease states and conditions, having the formula:

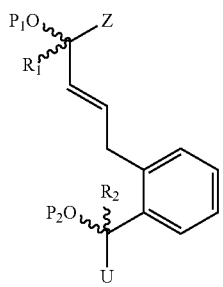

wherein $P_1$ and $P_2$ each individually are protecting groups, hydrogen atoms or combinations thereof;

wherein $R_1$ and $R_2$ each individually are substituted or unsubstituted, branched or unbranched alkyl groups, substituted or unsubstituted aryl groups, substituted or unsubstituted, branched or unbranched alkylaryl groups, halogen atoms, hydrogen atoms or combinations thereof;

wherein U is a branched or unbranched, substituted or unsubstituted alkyl, alkenyl, alkynyl, cycloalkyl, aryl, alkoxy, aryloxy, alkylcarbonyl, arylcarbonyl, alkoxycarbonyl, aryloxycarbonyl, alkoxycarbonyloxy, and aryloxycarbonyloxy group;

wherein Z is as defined above, and in particular can be a carboxylic acid, ester, amide, thiocarbamate, carbamate, thioester, thiocarboxamide or a nitrile;

and pharmaceutically acceptable salts thereof. For example, $P_1$ and $P_2$ each are hydrogen atoms, $R_1$ and $R_2$ each individually are methyl groups or hydrogen atoms or combinations thereof, U is a trifluoromethyl group and Z is a carboxylic acid or a carboxylic ester.

The present invention provides compounds and pharmaceutical compositions useful for the treatment of various disease states and conditions, having the formula:

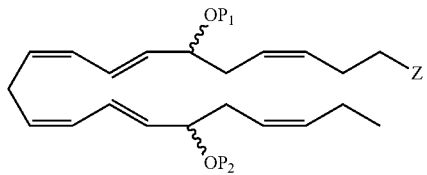

wherein $P_1$ and $P_2$ each individually are protecting groups, hydrogen atoms or combinations thereof;

wherein Z is as defined above, and in particular can be a carboxylic acid, ester, amide, thiocarbamate, carbamate, thioester, thiocarboxamide or a nitrile;

and pharmaceutically acceptable salts thereof. In certain embodiments, $P_1$ and $P_2$ are hydrogen atoms and Z is carboxylic acid or a carboxylic ester.

The analogs are designated as 7,17-diHDHAs. In certain aspects, the chiral carbon atom at the 7 position (C-7) has an R configuration. In another aspect, the C-7 carbon atom preferably has an S configuration. In still another aspect, the C-7 carbon atom is as an R/S racemate. Additionally, the chiral carbon atom at the 17 position (C-17) can have an R configuration. Alternatively, the C-17 carbon can have an S configuration. In still yet another aspect, the C-17 carbon can preferably exist as an R/S racemate. Exemplary analogs include, for example, 7S,17R/S-diHDHA, 7S,17R/S-dihydroxy-docosa-4Z,8E,10Z,13Z,15E,19Z-hexaenoic acid.

The present invention also provides compounds and pharmaceutical compositions useful for the treatment of various disease states and conditions, having the formula:

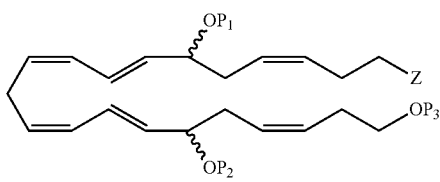

wherein $P_1$, $P_2$ and $P_3$ each individually are protecting groups, hydrogen atoms or combinations thereof wherein Z is as defined above, and in particular can be a carboxylic acid, ester, amide, thiocarbamate, carbamate, thioester, thiocarboxamide or a nitrile;

and pharmaceutically acceptable salts thereof. In certain embodiments, $P_1$, $P_2$ and $P_3$ each are hydrogen atoms and Z is a carboxylic acid or a carboxylic ester.

In certain aspects the designation of $OP_3$ serves to denote that the terminal carbon is substituted with one or more halogens (I, Cl, F, Br, mono, di or tri substitution) to form, for example, a trifluoromethyl group, or is an aryl group or phenoxy group that can be substituted or unsubstituted as described herein.

The present invention further provides compounds and pharmaceutical compositions useful for the treatment of various disease states and conditions, having the formula:

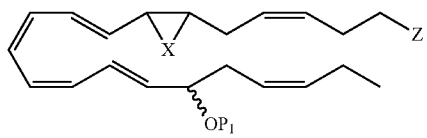

wherein $P_1$ is a protecting group or a hydrogen atom;

wherein X is a substituted or unsubstituted methylene, an oxygen atom, a substituted or unsubstituted nitrogen atom, or a sulfur atom;

wherein Z is as defined above, and in particular can be a carboxylic acid, ester, amide, thiocarbamate, carbamate, thioester, thiocarboxamide or a nitrile;

and pharmaceutically acceptable salts thereof. In one embodiment, $P_1$ is a hydrogen atom, X is an oxygen atom and Z is a carboxylic acid or a carboxylic ester.

The present invention still further provides compounds and pharmaceutical compositions useful for the treatment of various disease states and conditions, having the formula:

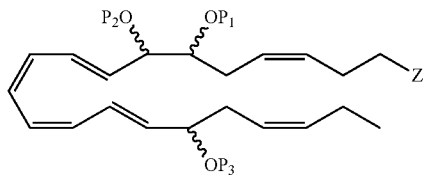

wherein $P_1$, $P_2$ and $P_3$ each individually are protecting groups, hydrogen atoms or combinations thereof;

wherein Z is as defined above, and in particular can be a carboxylic acid, ester, amide, thiocarbamate, carbamate, thioester, thiocarboxamide or a nitrile;

and pharmaceutically acceptable salts thereof. In an embodiment, $P_1$, $P_2$ and $P_3$ each are hydrogen atoms and Z is a carboxylic acid or a carboxylic ester.

The analogs are designated as 7,8,17-trihydroxy-DHAs. In certain embodiments, the chiral carbon atom at the 7 position (C-7) has an R configuration. In other embodiments, the C-7 carbon atom preferably has an S configuration. In still other embodiments, the C-7 carbon atom is as an R/S racemate. In certain aspects, the chiral carbon atom at the 8 position (C-8) has an R configuration. In another aspect, the C-8 carbon atom has an S configuration. In still another aspect, the C-8 carbon atom preferably is as an R/S racemate. Additionally, the chiral carbon atom at the 17 position (C-17) can have an R configuration. Alternatively, the C-17 carbon can preferably have an S configuration. In still yet another aspect, the C-17 carbon can exist as an R/S racemate.

The present invention provides compounds and pharmaceutical compositions useful for the treatment of various disease states and conditions, having the formula:

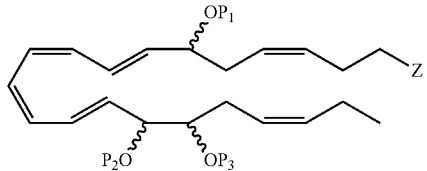

wherein $P_1$, $P_2$ and $P_3$ each individually are protecting groups, hydrogen atoms or combinations thereof;

wherein Z is as defined above, and in particular can be a carboxylic acid, ester, amide, thiocarbamate, carbamate, thioester, thiocarboxamide or a nitrile;

and pharmaceutically acceptable salts thereof. In a particular embodiment, $P_1$, $P_2$ and $P_3$ each are hydrogen atoms and Z is a carboxylic acid or a carboxylic ester.

The analogs are designated as 7,16,17-trihydroxy-DHAs. In certain embodiments, the chiral carbon atom at the 7 position (C-7) has an R configuration. In other embodiments, the C-7 carbon atom preferably has an S configuration. In still other embodiments, the C-7 carbon atom is as an R/S racemate. In certain aspects, the chiral carbon atom at the 16 position (C-16) has an R configuration. In another aspect, the C-16 carbon atom has an S configuration. In still another aspect, the C-16 carbon atom preferably is as an R/S racemate. Additionally, the chiral carbon atom at the 17 position (C-17) can have an R configuration. Alternatively, the C-17 carbon can preferably have an S configuration. In still yet another aspect, the C-17 carbon can exist as an R/S racemate.

The present invention also provides compounds and pharmaceutical compositions useful for the treatment of various disease states and conditions, having the formula:

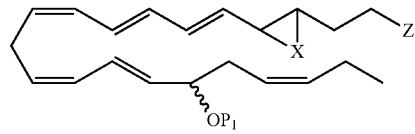

wherein $P_1$ is a protecting group or a hydrogen atom;

wherein X is a substituted or unsubstituted methylene, an oxygen atom, a substituted or unsubstituted nitrogen atom, or a sulfur atom;

wherein Z is as defined above, and in particular can be a carboxylic acid, ester, amide, thiocarbamate, carbamate, thioester, thiocarboxamide or a nitrile;

and pharmaceutically acceptable salts thereof. In one embodiment, $P_1$ is a hydrogen atom, X is an oxygen atom and Z is a carboxylic acid or a carboxylic ester.

The present invention further provides compounds and pharmaceutical compositions useful for the treatment of various disease states and conditions, having the formula:

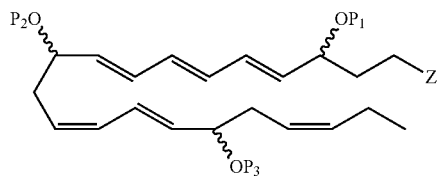

wherein $P_1$, $P_2$ and $P_3$ each individually are protecting groups, hydrogen atoms or combinations thereof;

wherein Z is as defined above, and in particular can be a carboxylic acid, ester, amide, thiocarbamate, carbamate, thioester, thiocarboxamide or a nitrile;

and pharmaceutically acceptable salts thereof. In a particular embodiment, $P_1$, $P_2$ and $P_3$ each are hydrogen atoms and Z is a carboxylic acid or a carboxylic ester.

The analogs are designated as 4,11,17-trihydroxy-DHAs. In certain embodiments, the chiral carbon atom at the 4 position (C-4) has an R configuration. In other embodiments, the C-4 carbon atom preferably has an S configuration. In still other embodiments, the C-4 carbon atom is as an R/S racemate. In certain aspects, the chiral carbon atom at the 11 position (C-11) has an R configuration. In another aspect, the C-11 carbon atom has an S configuration. In still another aspect, the C-11 carbon atom preferably is as an R/S racemate. Additionally, the chiral carbon atom at the 17 position (C-17) can have an R configuration. Alternatively, the C-17 carbon can preferably have an S configuration. In still yet another aspect, the C-17 carbon can exist as an R/S racemate.

The present invention also provides compounds and pharmaceutical compositions useful for the treatment of various disease states and conditions, having the formula:

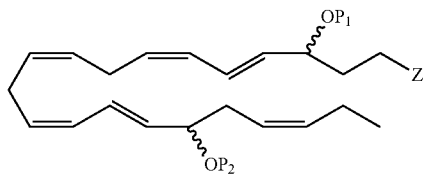

wherein $P_1$ and $P_2$ each individually are protecting groups, hydrogen atoms or combinations thereof;

wherein Z is as defined above, and in particular can be a carboxylic acid, ester, amide, thiocarbamate, carbamate, thioester, thiocarboxamide or a nitrile;

and pharmaceutically acceptable salts thereof. In certain embodiments, $P_1$ and $P_2$ are hydrogen atoms and Z is carboxylic acid or a carboxylic ester.

The present invention provides compounds and pharmaceutical compositions useful for the treatment of various disease states and conditions, having the formula:

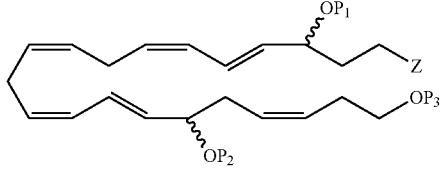

wherein $P_1$, $P_2$ and $P_3$ each individually are protecting groups, hydrogen atoms or combinations thereof;

wherein Z is as defined above, and in particular can be a carboxylic acid, ester, amide, thiocarbamate, carbamate, thioester, thiocarboxamide or a nitrile;

and pharmaceutically acceptable salts thereof. In a particular embodiment, $P_1$, $P_2$ and $P_3$ each are hydrogen atoms and Z is a carboxylic acid or a carboxylic ester.

In certain aspects the designation of $OP_3$ serves to denote that the terminal carbon is substituted with one or more halogens (I, Cl, F, Br, mono, di or tri substitution) to form, for example, a trifluoromethyl group, or is an aryl group or phenoxy group that can be substituted or unsubstituted as described herein.

The present invention provides compounds and pharmaceutical compositions useful for the treatment of various disease states and conditions, having the formula:

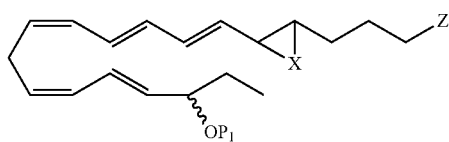

wherein $P_1$ is a protecting group or a hydrogen atom;

wherein X is a substituted or unsubstituted methylene, an oxygen atom, a substituted or unsubstituted nitrogen atom, or a sulfur atom;

wherein Z is as defined above, and in particular can be a carboxylic acid, ester, amide, thiocarbamate, carbamate, thioester, thiocarboxamide or a nitrile;

and pharmaceutically acceptable salts thereof. In one embodiment $P_1$ is a hydrogen atom, X is an oxygen atom and Z is a carboxylic acid or a carboxylic ester.

The present invention also provides compounds and pharmaceutical compositions useful for the treatment of various disease states and conditions, having the formula:

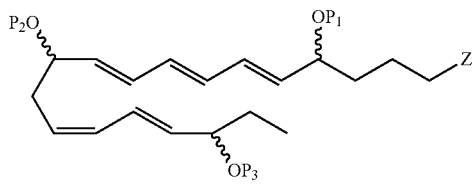

wherein $P_1$, $P_2$ and $P_3$ each individually are protecting groups, hydrogen atoms or combinations thereof;

wherein Z is as defined above, and in particular can be a carboxylic acid, ester, amide, thiocarbamate, carbamate, thioester, thiocarboxamide or a nitrile;

and pharmaceutically acceptable salts thereof. In one embodiment, $P_1$, $P_2$ and $P_3$ each are hydrogen atoms and Z is a carboxylic acid or a carboxylic ester.

The present invention further still provides compounds and pharmaceutical compositions useful for the treatment of various disease states and conditions, having the formula:

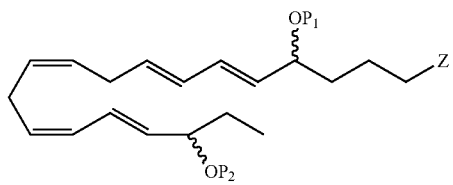

wherein $P_1$ and $P_2$ each individually are protecting groups, hydrogen atoms or combinations thereof;

wherein Z is as defined above, and in particular can be a carboxylic acid, ester, amide, thiocarbamate, carbamate, thioester, thiocarboxamide or a nitrile;

and pharmaceutically acceptable salts thereof. In one particular embodiment, $P_1$ and $P_2$ are hydrogen atoms and Z is carboxylic acid or a carboxylic ester.

In one particular embodiment, the compound is 5S,18 (+/−)-diHEPA, wherein the carboxyl group can be an acid, ester or salt. 5S,18(+/−)-diHEPA has been synthesized with 5-lipoxygenase potato and its physical properties are depicted in FIG. 15 based on LC-MS-MS. Additionally, 5S,18(+/−)-diHEPA is biologically active and has anti-inflammatory activity as noted by the downregulation of PMN infiltration in a peritonitis model. It is equipotent to Resolvin E1 at an equal dose amount (See FIG. 16).

The present invention further still provides compounds and pharmaceutical compositions useful for the treatment of various disease states and conditions, having the formula:

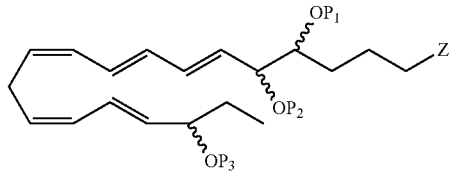

wherein $P_1$, $P_2$ and $P_3$ each individually are protecting groups, hydrogen atoms or combinations thereof;

wherein Z is as defined above, and in particular can be a carboxylic acid, ester, amide, thiocarbamate, carbamate, thioester, thiocarboxamide or a nitrile;

and pharmaceutically acceptable salts thereof. In one embodiment, $P_1$, $P_2$ and $P_3$ each are hydrogen atoms and Z is a carboxylic acid or a carboxylic ester.

The present invention provides compounds and pharmaceutical compositions useful for the treatment of various disease states and conditions, having the formula:

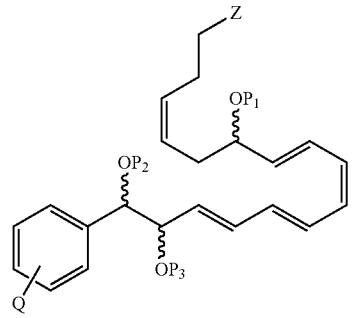

wherein $P_1$, $P_2$ and $P_3$ each individually are protecting groups, hydrogen atoms or combinations thereof;

wherein Q independently is a hydrogen atom, halogen atom or a branched or unbranched, substituted or unsubstituted alkyl, alkenyl, alkynyl, cycloalkyl, aryl, alkoxy, aryloxy, alkylcarbonyl, arylcarbonyl, alkoxycarbonyl, aryloxycarbonyl, amino, hydroxy, cyano, carboxyl, alkoxycarbonyloxy, aryloxycarbonyloxy or aminocarbonyl group;

wherein Z is as defined above, and in particular can be a carboxylic acid, ester, amide, thiocarbamate, carbamate, thioester, thiocarboxamide or a nitrile;

and pharmaceutically acceptable salts thereof. In one particular aspect, $P_1$, $P_2$ and $P_3$ each are hydrogen atoms, each Q is a hydrogen atom and Z is a carboxylic acid or a carboxylic ester.

The present invention also provides compounds and pharmaceutical compositions useful for the treatment of various disease states and conditions, having the formula:

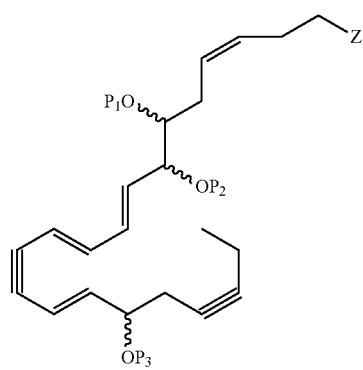

wherein $P_1$, $P_2$ and $P_3$ each individually are protecting groups, hydrogen atoms or combinations thereof;

wherein Z is as defined above, and in particular can be a carboxylic acid, ester, amide, thiocarbamate, carbamate, thioester, thiocarboxamide or a nitrile;

and pharmaceutically acceptable salts thereof. In one embodiment, $P_1$, $P_2$ and $P_3$ each are hydrogen atoms and Z is a carboxylic acid or a carboxylic ester.

The present invention further still provides compounds and pharmaceutical compositions useful for the treatment of various disease states and conditions, having the formula:

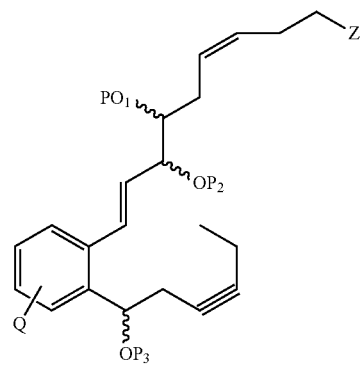

wherein $P_1$, $P_2$ and $P_3$ each individually are protecting groups, hydrogen atoms or combinations thereof;

wherein Q represents one or more substituents and each Q, independently, is a hydrogen atom, halogen atom or a branched or unbranched, substituted or unsubstituted alkyl, alkenyl, alkynyl, cycloalkyl, aryl, alkoxy, aryloxy, alkylcarbonyl, arylcarbonyl, alkoxycarbonyl, aryloxycarbonyl, amino, hydroxy, cyano, carboxyl, alkoxycarbonyloxy, aryloxycarbonyloxy or aminocarbonyl group;

wherein Z is as defined above, and in particular can be a carboxylic acid, ester, amide, thiocarbamate, carbamate, thioester, thiocarboxamide or a nitrile;

and pharmaceutically acceptable salts thereof. In one particular embodiment, $P_1$, $P_2$ and $P_3$ each are hydrogen atoms, each Q is a hydrogen atom and Z is a carboxylic acid or a carboxylic ester.

In still another aspect, the present invention provides compounds and pharmaceutical compositions useful for the treatment of various disease states and conditions, having the formula:

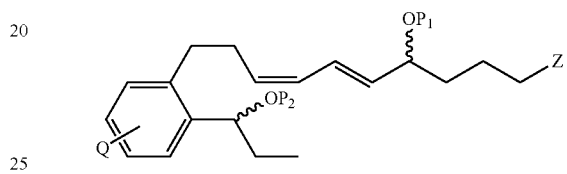

wherein $P_1$, and $P_2$ each individually are protecting groups, hydrogen atoms or combinations thereof;

wherein Q represents one or more substituents and each Q, independently, is a hydrogen atom, halogen atom or a branched or unbranched, substituted or unsubstituted alkyl, alkenyl, alkynyl, cycloalkyl, aryl, alkoxy, aryloxy, alkylcarbonyl, arylcarbonyl, alkoxycarbonyl, aryloxycarbonyl, amino, hydroxy, cyano, carboxyl, alkoxycarbonyloxy, aryloxycarbonyloxy or aminocarbonyl group;

wherein Z is as defined above, and in particular can be a carboxylic acid, ester, amide, thiocarbamate, carbamate, thioester, thiocarboxamide or a nitrile;

and pharmaceutically acceptable salts thereof. In one embodiment, $P_1$, and $P_2$ each are hydrogen atoms, each Q is a hydrogen atom and Z is a carboxylic acid or a carboxylic ester.

In still another aspect, the present invention provides compounds and pharmaceutical compositions useful for the treatment of various disease states and conditions, having the formula:

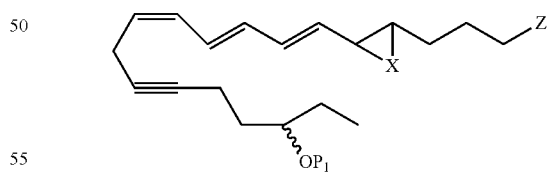

wherein $P_1$ is a protecting group or a hydrogen atom;

wherein X is a substituted or unsubstituted methylene, an oxygen atom, a substituted or unsubstituted nitrogen atom, or a sulfur atom;

wherein Z is as defined above, and in particular can be a carboxylic acid, ester, amide, thiocarbamate, carbamate, thioester, thiocarboxamide or a nitrile;

and pharmaceutically acceptable salts thereof. In one aspect, $P_1$ is a hydrogen atom, X is an oxygen atom and Z is a carboxylic acid or a carboxylic ester.

The present invention also provides compounds and pharmaceutical compositions useful for the treatment of various disease states and conditions, having the formula:

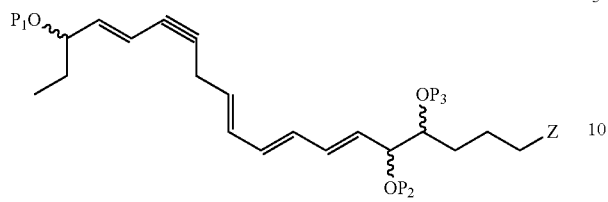

wherein $P_1$, $P_2$ and $P_3$ each individually are protecting groups, hydrogen atoms or combinations thereof wherein Z is as defined above, and in particular can be a carboxylic acid, ester, amide, thiocarbamate, carbamate, thioester, thiocarboxamide or a nitrile;

and pharmaceutically acceptable salts thereof. In one embodiment, $P_1$, $P_2$ and $P_3$ each are hydrogen atoms and Z is a carboxylic acid or a carboxylic ester.

The present invention further provides compounds and pharmaceutical compositions useful for the treatment of various disease states and conditions, having the formula:

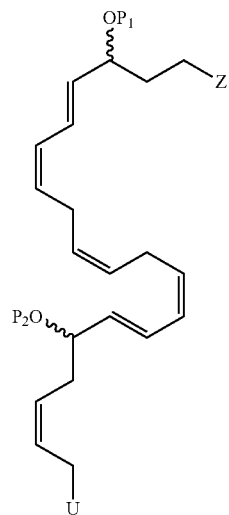

wherein $P_1$, and $P_2$ each individually are protecting groups, hydrogen atoms or combinations thereof;

wherein U is a branched or unbranched, substituted or unsubstituted alkyl, alkenyl, alkynyl, cycloalkyl, aryl, alkoxy, aryloxy, alkylcarbonyl, arylcarbonyl, alkoxycarbonyl, aryloxycarbonyl, alkoxycarbonyloxy, and aryloxycarbonyloxy group;

wherein Z is as defined above, and in particular can be a carboxylic acid, ester, amide, thiocarbamate, carbamate, thioester, thiocarboxamide or a nitrile;

and pharmaceutically acceptable salts thereof. In one aspect, $P_1$, and $P_2$ each are hydrogen atoms, U is a trifluoromethyl group and Z is a carboxylic acid or a carboxylic ester.

In still another aspect, the present invention provides compounds and pharmaceutical compositions useful for the treatment of various disease states and conditions, having the formula:

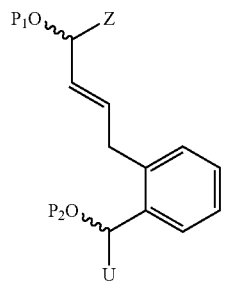

wherein $P_1$, and $P_2$ each individually are protecting groups, hydrogen atoms or combinations thereof;

wherein U is a branched or unbranched, substituted or unsubstituted alkyl, alkenyl, alkynyl, cycloalkyl, aryl, alkoxy, aryloxy, alkylcarbonyl, arylcarbonyl, alkoxycarbonyl, aryloxycarbonyl, alkoxycarbonyloxy, and aryloxycarbonyloxy group;

wherein Z is as defined above, and in particular can be a carboxylic acid, ester, amide, thiocarbamate, carbamate, thioester, thiocarboxamide or a nitrile;

and pharmaceutically acceptable salts thereof. For example, $P_1$, and $P_2$ each are hydrogen atoms, U is a trifluoromethyl group and Z is a carboxylic acid or a carboxylic ester.

"Q" includes, for example, hydrogen atoms, halogens (fluorine, iodine, chlorine, bromine), alkyl, alkenyl, alkynyl, cycloalkyl, aryl, alkoxy, aryloxy, alkylcarbonyl, arylcarbonyl, alkoxycarbonyl, aryloxycarbonyl, amino, hydroxy, cyano, carboxyl, alkoxycarbonyloxy, aryloxycarbonyloxy or aminocarbonyl. The organic moieties described herein can further be branched or unbranched, substituted or unsubstituted.

"U" includes, for example, alkyl, alkenyl, alkynyl, cycloalkyl, aryl, alkoxy, aryloxy, alkylcarbonyl, arylcarbonyl, alkoxycarbonyl, aryloxycarbonyl, alkoxycarbonyloxy, and aryloxycarbonyloxy. The organic moieties described herein can further be branched or unbranched, substituted or unsubstituted.

In one embodiment, the present invention pertains to monohydroxy docosahexaenoic acid (DHA) analogs having the formula

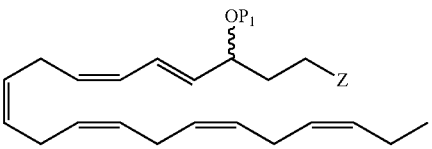

The analogs are designated as 4-hydroxy-DHAs, where $P_1$ is a protecting group or a hydrogen atom and Z is as defined above. In particular, Z can be a carboxylic acid, ester, amide, thiocarbamate, carbamate, thioester, thiocarboxamide or a nitrile. In one embodiment, the chiral carbon atom at the 4 position (C-4) has an S configuration. In another embodiment, the C-4 carbon atom has an R configuration. In still another embodiment, the C-4 carbon atom is as a racemic mixture, e.g., an R/S configuration. In particular, the present invention includes monohydroxy DHA analogs (as described herein) of 4S-HDHA, 4S-hydroxy-docosa-5E,7Z,10Z,13Z, 16Z,19Z-hexaenoic acid and salts and esters thereof.

In another embodiment, the monohydroxy DHA is 7S-monohydroxy-docosahexaenoic acid. The analogs are designated as 7-hydroxy-DHAs, where $P_1$ (where the hydroxyl is protected) and Z are as defined above. In particular, Z can be a carboxylic acid, ester, amide, thiocarbamate, carbamate, thioester, thiocarboxamide or a nitrile. In one embodiment, the chiral carbon atom at the 7 position (C-7) has an S configuration. In another embodiment, the C-7 carbon atom has an R configuration. In still another embodiment, the C-7 carbon atom is as a racemic mixture, e.g., an R/S configuration.

The present invention, further pertains to dihydroxy-docosahexaenoic acid analogs (diHDHA) having the formula

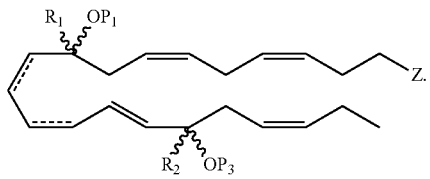

The analogs are designated as 10,17-diHDHAs. $P_1$, $P_2$, $R_1$ and $R_2$ are as defined above and can be the same or different. Z is as defined above and in particular can be a carboxylic acid, ester, amide, thiocarbamate, carbamate, thioester, thiocarboxamide or a nitrile. The broken double bond line indicates that either the E or Z isomer is within the scope of the analog(s). In certain aspects, the chiral carbon atom at the 10 position (C-10) has an R configuration. In another aspect, the C-10 carbon atom has an S configuration. In still another aspect, the C-10 carbon atom preferably is as an R/S racemate. Additionally, the chiral carbon atom at the 17 position (C-17) can have an R configuration. Alternatively, the C-17 carbon can preferably have an S configuration. In still yet another aspect, the C-17 carbon can exist as an R/S racemate. In one example, the present invention includes 10,17S-docosatriene, 10,17S-dihydroxy-docosa-4Z,7Z,11E,13,15E,19Z-hexaenoic acid analogs such as 10R/S-OCH$_3$,17S-HDHA, 10R/S, methoxy-17S hydroxy-docosa-4Z,7Z,11E,13,15E, 19Z-hexaenoic acid derivatives.

In still yet another embodiment, the present invention pertains to diHDHA analogs having the formula

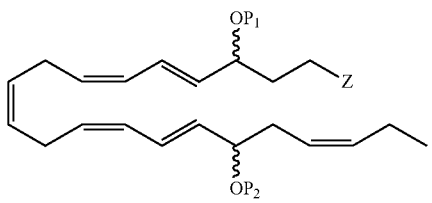

The analogs are designated as 4,17-diHDHAs. $P_1$, $P_2$ and Z are as defined above. $P_1$ and $P_2$ can be the same or different. In particular, Z can be a carboxylic acid, ester, amide, thiocarbamate, carbamate, thioester, thiocarboxamide or a nitrile. In certain aspects, the chiral carbon atom at the 4 position (C-4) has an R configuration. In another aspect, the C-4 carbon atom preferably has an S configuration. In still another aspect, the C-4 carbon atom is as an R/S racemate. Additionally, the chiral carbon atom at the 17 position (C-17) can have an R configuration. Alternatively, the C-17 carbon can have an S configuration. In still yet another aspect, the C-17 carbon can preferably exist as an R/S racemate.

For example, the present invention includes 4S,17R/S-di-HDHA, 4S,17R/S-dihydroxy-docosa-5E,7Z,10Z,13Z,15E, 19Z-hexaenoic acid analogs.

It should be understood that "Z" can be altered from one particular moiety to another by a skilled artisan. In order to accomplish this in some particular instances, one or more groups may require protection. This is also within the skill of an ordinary artisan. For example, a carboxylic ester (Z) can be converted to an amide by treatment with an amine. Such interconversion are known in the art.

In the EPA and DHA analogs, it should be understood that reference to "hydroxyl" stereochemistry is exemplary, and that the term is meant to include protected hydroxyl groups as well as the free hydroxyl group. In certain embodiments, the C-17 position has an R configuration. In other embodiment, the C-17 position has an S configuration. In other aspects, certain embodiments of the invention have an R configuration at the C-18 position.

In certain aspects of the present invention, ASA pathways generate R>S and therefore, 4S, 5R/S,7S,8R/S,11R,12R/S16S,17R. With respect to species generated from the 15-LO pathway the chirality of C-17 is S, C-16R and C-10, preferably R.

In certain embodiments, the invention does not include 5,12,18-trihydroxy-EPA, and more specifically, does not include 6,8,10,14,16-eicosapentaenoic acid, 5,12,18-trihydroxy and analogs thereof, as described in U.S. patent application Ser. No. 09/785,866, filed Feb. 16, 2001.

In certain embodiments, the endogenous compounds are isolated and/or purified or substantially purified by one or more purification methods described herein or known by those skilled in the art. Generally, the purities are at least 90%, in particular 95% and often greater than 99%.

In certain embodiments, the naturally occurring compound is excluded from the general description of the broader genus.

The hydroxyl(s) in the EPA and DHA analogs can be protected by various protecting groups (P), such as those known in the art. An artisan skilled in the art can readily determine which protecting group(s) may be useful for the protection of the hydroxyl group(s). Standard methods are known in the art and are more fully described in literature. For example, suitable protecting groups can be selected by the skilled artisan and are described in Green and Wuts, "Protecting Groups in Organic Synthesis", John Wiley and Sons, Chapters 5 and 7, 1991, the teachings of which are incorporated herein by reference. Preferred protecting groups include methyl and ethyl ethers, TMS or TIPPS groups, acetate (esters) or proprionate groups and glycol ethers, such as ethylene glycol and propylene glycol derivatives.

For example, one or more hydroxyl groups can be treated with a mild base, such as triethylamine in the presence of an acid chloride or silyl chloride to facilitate a reaction between the hydroxyl ion and the halide. Alternatively, an alkyl halide can be reacted with the hydroxyl ion (generated by a base such as lithium diisopropyl amide) to facilitate ether formation.

It should also be understood that for the EPA and DHA analogs, not all hydroxyl groups need be protected. One, two or all three hydroxyl groups can be protected. This can be accomplished by the stoichiometric choice of reagents used to protect the hydroxyl groups. Methods known in the art can be used to separate the mono, di- or tri-protected hydroxy compounds, e.g., HPLC, LC, flash chromatography, gel permeation chromatography, crystallization, distillation, etc.

It should be understood that there are one or more chiral centers in each of the above-identified compounds. It should understood that the present invention encompasses all stereochemical forms, e.g., enantiomers, diastereomers and racemates of each compound. Where asymmetric carbon atoms are present, more than one stereoisomer is possible, and all possible isomeric forms are intended to be included within the structural representations shown. Optically active (R) and (S) isomers may be resolved using conventional techniques known to the ordinarily skilled artisan. The present invention is intended to include the possible diastereomers as well as the racemic and optically resolved isomers.

The resolvin analogs depicted throughout the specification contain acetylenic and/or ethylenically unsaturated sites. Where carbon carbon double bonds exist, the configurational chemistry can be either cis (E) or trans (Z) and the depictions throughout the specification are not meant to be limiting. The depictions are, in general, presented based upon the configurational chemistry of related DHA or EPA compounds, and although not to be limited by theory, are believed to possess similar configuration chemistry.

Throughout the specification carbon carbon bonds in particular have been "distorted" for ease to show how the bonds may ultimately be positioned relative one to another. For example, it should be understood that acetylenic portions of the resolvins actually do include a geometry of approximately 180 degrees, however, for aid in understanding of the synthesis and relationship between the final product(s) and starting materials, such angles have been obfuscated to aid in comprehension.

Throughout the organic synthesis presented below, it should be understood that hydrogenation of acetylenic portions of the resolvin analog may result in one or more products. It is intended that all possible products are included within this specification. For example, hydrogenation of a diacetylenic resolvin analog can produce up to 8 products (four diene products, i.e., cis, cis; cis, trans; trans, cis; trans, trans) if hydrogenation of both acetylenic portions is completed (this can be monitored by known methods) and four monoacetylene-monoethylene products (cis or trans "monoene"-acetylene; acetylene-cis or trans "monoene". All products can be separated and identified by HPLC, GC, MS, NMR, IR.

Known techniques in the art can be used to convert the carboxylic acid/ester functionality of the resolvin analog into carboxamides, thioesters, nitrile, carbamates, thiocarbamates, etc. and are incorporated herein. The appropriate moieties, such as amides, can be further substituted as is known in the art.

In general, the resolvin analogs of the invention are bioactive as alcohols. Enzymatic action or reactive oxygen species attack at the site of inflammation or degradative metabolism. Such interactions with the hydroxyl(s) of the resolvin molecule can eventually reduce physiological activity as depicted below:

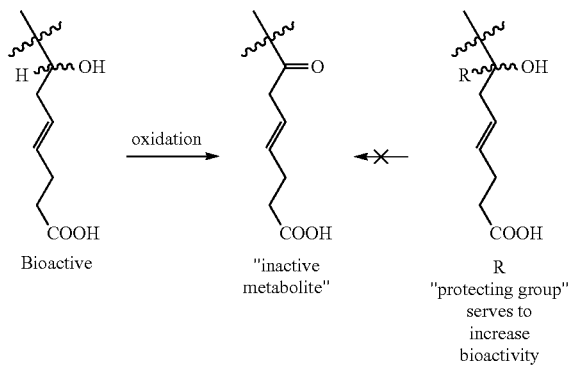

The use of "R" groups with secondary bioactive alcohols, in particular, serves to increase the bioavailability and bioactivity of the resolvin analog by inhibiting or diminishing the potential for oxidation of the alcohol to a ketone producing an inactive metabolite. The R "protecting groups" include, for example, linear and branched, substituted and unsubstituted alkyl groups, aryl groups, alkylaryl groups, phenoxy groups, and halogens.

Generally the use of "R protection chemistry" is not necessary with vicinal diols within the resolvin analog. Typically vicinal diols are not as easily oxidized and therefore, generally do not require such protection by substitution of the hydrogen atom adjacent to the oxygen atom of the hydroxyl group. Although it is generally considered that such protection is not necessary, it is possible to prepare such compounds where each of the vicinal diol hydroxyl groups, independently, could be "protected" by the substitution of the hydrogen atom adjacent to the oxygen atom of the hydroxyl group with an "R protecting group" as described above.

The term "tissue" is intended to include intact cells, blood, blood preparations such as plasma and serum, bones, joints, muscles, smooth muscles, and organs.

The term "subject" is intended to include living organisms susceptible to conditions or diseases caused or contributed bacteria, pathogens, disease states or conditions as generally disclosed, but not limited to, throughout this specification. Examples of subjects include humans, dogs, cats, cows, goats, and mice. The term subject is further intended to include transgenic species.

When the compounds of the present invention are administered as pharmaceuticals, to humans and mammals, they can be given per se or as a pharmaceutical composition containing, for example, 0.1 to 99.5% (more preferably, 0.5 to 90%) of active ingredient, i.e., at least one EPA or DHA analog, in combination with a pharmaceutically acceptable carrier.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting a compound(s) of the present invention within or to the subject such that it can perform its intended function. Typically, such compounds are carried or transported from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

In certain embodiments, the compounds of the present invention may contain one or more acidic functional groups and, thus, are capable of forming pharmaceutically acceptable salts with pharmaceutically acceptable bases. The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. These may include cations based on the alkali and alkaline earth metals, such as sodium, lithium, potassium, calcium, magnesium and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M., et al., "Pharmaceutical Salts," J. Pharm. Sci., 1977; 66:1-19 which is incorporated herein by reference).

The term "pharmaceutically acceptable esters" refers to the relatively non-toxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. The term is further intended to include lower hydrocarbon groups capable of being solvated under physiological conditions, e.g., alkyl esters, methyl, ethyl and propyl esters.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for intravenous, oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients. In one aspect, a solution of a EPA or DHA analog can be administered as ear drops to treat otitis.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention. Such solutions are useful for the treatment of conjunctivitis.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Intravenous injection administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systematically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of ordinary skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 0.1 to about 40 mg per kg per day. For example, between about 0.01 microgram and 20 micrograms, between about 20 micrograms and 100 micrograms and between about 10 micrograms and 200 micrograms of the compounds of the invention are administered per 20 grams of subject weight.

If desired, the effective daily dose of the active compound may be administered as two, three, four, five, six or more sub-doses administered separately at appropriate intervals throughout the day, optionally, in unit dosage forms.

The pharmaceutical compositions of the invention include a "therapeutically effective amount" or a "prophylactically effective amount" of one or more of the EPA or DHA analogs of the invention. A "therapeutically effective amount" refers to an amount effective, at dosages and for periods of time necessary, to achieve the desired therapeutic result, e.g., a diminishment or prevention of effects associated with various disease states or conditions. A therapeutically effective amount of the EPA or DHA analog may vary according to factors such as the disease state, age, sex, and weight of the individual, and the ability of the therapeutic compound to elicit a desired response in the individual. A therapeutically effective amount is also one in which any toxic or detrimental effects of the therapeutic agent are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the EPA or DHA analog and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of a EPA or DHA analog of the invention is 0.1-20 mg/kg, more preferably 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Delivery of the EPA or DHA analogs of the present invention to the lung by way of inhalation is an important method of treating a variety of respiratory conditions (airway inflammation) noted throughout the specification, including such common local conditions as bronchial asthma and chronic obstructive pulmonary disease. The EPA or DHA analogs can be administered to the lung in the form of an aerosol of particles of respirable size (less than about 10 μm in diameter). The aerosol formulation can be presented as a liquid or a dry powder. In order to assure proper particle size in a liquid aerosol, as a suspension, particles can be prepared in respirable size and then incorporated into the suspension formulation containing a propellant. Alternatively, formulations can be prepared in solution form in order to avoid the concern for proper particle size in the formulation. Solution formulations should be dispensed in a manner that produces particles or droplets of respirable size.

Once prepared an aerosol formulation is filled into an aerosol canister equipped with a metered dose valve. The formulation is dispensed via an actuator adapted to direct the dose from the valve to the subject.

Formulations of the invention can be prepared by combining (i) at least one EPA or DHA analog in an amount sufficient to provide a plurality of therapeutically effective doses; (ii) the water addition in an amount effective to stabilize each of the formulations; (iii) the propellant in an amount sufficient to propel a plurality of doses from an aerosol canister; and (iv) any further optional components e.g. ethanol as a cosolvent; and dispersing the components. The components can be dispersed using a conventional mixer or homogenizer, by shaking, or by ultrasonic energy. Bulk formulation can be transferred to smaller individual aerosol vials by using valve to valve transfer methods, pressure filling or by using conventional cold-fill methods. It is not required that a stabilizer used in a suspension aerosol formulation be soluble in the propellant. Those that are not sufficiently soluble can be coated onto the drug particles in an appropriate amount and the coated particles can then be incorporated in a formulation as described above.

Aerosol canisters equipped with conventional valves, preferably metered dose valves, can be used to deliver the formulations of the invention. Conventional neoprene and buna valve rubbers used in metered dose valves for delivering conventional CFC formulations can be used with formulations containing HFC-134a or HFC-227. Other suitable materials include nitrile rubber such as DB-218 (American Gasket and Rubber, Schiller Park, Ill.) or an EPDM rubber such as Vistalon™ (Exxon), Royalene™ (UniRoyal), bunaEP (Bayer). Also suitable are diaphragms fashioned by extrusion, injection molding or compression molding from a thermoplastic elastomeric material such as FLEXOMER™ GERS 1085 NT polyolefin (Union Carbide).

Formulations of the invention can be contained in conventional aerosol canisters, coated or uncoated, anodized or unanodized, e.g., those of aluminum, glass, stainless steel, polyethylene terephthalate.

The formulation(s) of the invention can be delivered to the respiratory tract and/or lung by oral inhalation in order to effect bronchodilation or in order to treat a condition susceptible of treatment by inhalation, e.g., asthma, chronic obstructive pulmonary disease, etc. as described throughout the specification.

The formulations of the invention can also be delivered by nasal inhalation as known in the art in order to treat or prevent the respiratory conditions mentioned throughout the specification.

While it is possible for a compound of the present invention to be administered alone, it is preferable to administer the compound as a pharmaceutical composition.

The invention features an article of manufacture that contains packaging material and a EPA or DHA analog formulation contained within the packaging material. This formulation contains an at least one EPA or DHA analog and the packaging material contains a label or package insert indicating that the formulation can be administered to the subject to treat one or more conditions as described herein, in an amount, at a frequency, and for a duration effective to treat or prevent such condition(s). Such conditions are mentioned throughout the specification and are incorporated herein by reference. Suitable EPA analogs and DHA analogs are described herein.

More specifically, the invention features an article of manufacture that contains packaging material and at least one EPA or DHA analog contained within the packaging material. The packaging material contains a label or package insert indicating that the formulation can be administered to the subject to asthma in an amount, at a frequency, and for a duration effective treat or prevent symptoms associated with such disease states or conditions discussed throughout this specification.

Materials and Methods

Zymosan A, hematin, NADPH, 15-lipoxygenase, ASA and other NSAIDs were from Sigma. Potato 5-lipoxygenase (LO), DHA, and EPA were from Cayman Chemical Co. (Ann Arbor, Mich.); and other synthetic standards, hydroxy fatty acids and intermediates used for MS identification and fragment ion references were purchased from Cascade Biochem Ltd. (Reading, U. K.). Authentic standards for 4S-hydroxy-5E,7Z,10Z,13Z,16Z,19Z-docosahexaenoic acid (4S-HDHA), 17S-hydroxy-4Z,7Z,10Z,13Z,15E,19Z-docosahexaenoic acid (17S-HDHA), and the racemate 17R/S-hydroxy-4Z,7Z,10Z,13Z,15E,19Z-docosahexaenoic acid (denoted 17R/S-HDHA) were from Penn Bio-Organics (Bellefonte, Pa.), and NMR analyses established the respective double bond configurations. Additional materials used in LC-MS-MS analyses were from vendors reported in Refs. (2, 33).

Incubations

Human PMN were freshly isolated from venous blood of healthy volunteers (that declined taking medication for ~2 weeks before donation; BWH protocol #88-02642) by Ficoll gradient and enumerated. Cells were divided into $50 \times 10^6$ cells, 1 ml DPBS with $Ca^{2+}$ and $Mg^{2+}$, denoted +/+, and incubations (40 min, 37° C.) were carried out with either 17R/S-HDHA (Penn Bio-Organics) or 17R-HDHA with zymosan A (100 ng/ml, Sigma). Human umbilical vein (HUVEC) or microvascular (HMVEC; Cascade Biologics, Portland, Oreg.) endothelial cells were cultured for transendothelial migration (34) and incubations with HMVEC monolayers (1, 2, or 3 passages) seeded ($\sim 2 \times 10^5$ cells/cm$^2$) on polycarbonate permeable supports pre-coated with 0.1% gelatin for ASA and DHA. For hypoxia experiments, plates of HUVEC treated with TNFα and IL-1β (both 1 ng/ml) were placed in a hypoxic chamber (3 h, 37° C.) and returned to normoxia (21 h, 37° C.). Next, ASA (500 μM, 30 min) was added followed by DHA (~5 μM) and A23187 (2 μM; 60 min, 37° C.). Individual whole brains were rapidly isolated from sacrificed mice immediately prior to incubations (each half/2 ml), washed with cold DPBS$^{+/+}$ and incubated with ASA (45 min, 37° C., 500 μM). Incubations were stopped with 5 ml cold methanol, and held at −20° C. for analyses.

Recombinant Cyclooxygenase-2 (COX-2) and Product Analyses

Human recombinant COX-2 was overexpressed in Sf9 insect cells (ATCC). The microsomal fractions (~8 μl) were suspended in Tris (100 mM, pH 8.0) as in (35). ASA was incubated (~2 mM, 37° C., 30 min) with COX-2 before addition of DHA (10 μM), or in some experiments $[1-^{14}C]$-labeled DHA (from American Radiolabeled Chemicals, Inc.), and conversions were monitored in parallel using $[1-^{14}C]$-labeled C20:4 (with ASA) (as in FIG. 2; also see text).

Incubations were extracted with deuterium-labeled internal standards (15-HETE and C20:4) for LC-MS-MS analysis as in (33) using a Finnigan LCQ liquid chromatography ion trap tandem mass spectrometer (San Jose, Calif.) equipped with a LUNA C18-2 (150×2 mm×5 μm or 100×2 mm×5 μm) column and a rapid spectra scanning UV diode array detector that monitored UV absorbance ~0.2 min prior to samples entering the MS-MS. All intact cell incubations and in vivo exudates were stopped with 2 ml cold methanol and kept at −80° C. for >30 minutes. Samples were extracted using C18 solid phase extraction and analyzed using GC-MS (see Table 2) (Hewlett-Packard), thin layer chromatography or tandem liquid chromatography-mass spectrometry (LC-MS-MS). Also, a Chiralcel OB-H column (4.6×250 mm; J. T. Baker) was used to determine R and S alcohol configurations of monohydroxy-PUFA using isocratic mobile phase (hexane: isopropanol; 97.5:2.5, vol:vol, with a 0.6 ml/min flow rate). Detailed procedures for isolation, quantitation and structural determination of lipid-derived mediators were recently reported (36) and used here essentially as reported for elucidation of novel products. Biogenic synthesis of the novel docosanoids were carried out using isolated enzymes, i.e. potato 5-LO, rhCOX-2 or ASA treated rhCOX-2 and 15-LO each incubated in tandem sequential reactions with either DHA or 17R-HDHA to produce the novel compounds in scale up quantities for isolation and confirmation of physical and biological properties.

PMN Migration, Murine Air Pouch Exudates and Peritonitis

Human PMN transendothelial migration was quantitated by monitoring myeloperoxidase (MPO) an azurophilic granule marker as in (34, 37). Inflammatory exudates were initiated with intrapouch injection of recombinant mouse TNFα (100 ng/pouch; R&D Systems) into dorsal air pouches (10) of 6-8 wk male FVB mice fed laboratory rodent diet 5001 (Lab Diet, Purina Mills) containing less than 0.25% arachidonic acid, 1.49% EPA and 1.86% DHA followed by ASA (500 μg) at 3.5 h and 300 μg DHA/pouch at 4 h post-TNFα injection. At 6 h (within the resolution phase), pouches were lavaged (3 ml saline) and exudate cells were enumerated Inhibition of TNFα stimulated (100 ng/pouch) PMN infiltration with i.v. tail injection of either 17R-HDHA (as prepared with COX-2 vide infra), 5S,12,18R-HEPE, or a 15-epi-LXA$_4$ analog were determined with pouch lavages taken at 4 h. Peritonitis was performed using 6 to 8-week-old FVB male mice (Charles River Laboratories) fed laboratory Rodent Diet 5001 (Purina Mills) that were anesthetized with isoflurane, and compounds to be tested (125 μl) were administered intravenously. Zymosan A in 1 ml (1 mg/ml) was injected ~1-1.5 min later in the peritoneum. Each test compound (100 ng/incubation, i.e. 17R-HDHA in ethanol) or vehicle alone was suspended in ~5 μl and mixed in sterile saline 120 μl. Two hours after the intraperitoneal injections, and in accordance with the Harvard Medical Area Standing Committee on Animals protocol #02570, mice were euthanized and peritoneal lavages rapidly collected for enumeration.

Cell Culture

Human glioma cells DBTRG-05MG cells (ATCC) were cultured as recommended by ATCC. For analyses, $10 \times 10^6$ cells per well in 6-well plates (Falcon) were stimulated for 16 h with 50 ng/ml of human recombinant TNFα (Gibco) in the presence of specified concentrations of test compounds (ie., 17R-HDHA) or vehicle (0.04° A ethanol). Cells were washed in DPBS$^{+/+}$ and harvested in 1 ml of Trizol (Gibco). For RT-PCR, RNA purification and RT-PCR were performed as in (38). Primers used in amplifications were: 5'GGAAGAT-GCTGGTTCCCTGC3' (SEQ ID NO: 1) and 5'TCAACACG-CAGGACAGGTACA3' (SEQ ID NO: 2) for IL-1β; 5'TCCACCACCGTGTTGCTGTAG3' (SEQ ID NO: 3); and 5' GACCACAGTCCATGACATCACT3' (SEQ ID NO: 4) for GAPDH. PCR products obtained with these primers were confirmed by sequencing. Analyses were performed for both genes (i.e., GAPDH and IL-1β) in the linear range of the reaction. Results were analyzed using the NIH Image program (http://rsb.info.nih.gov/nih-image).

Biogenic Synthesis of Natural Resolvins and Analogs

Biogenic Synthesis of 17 R-Containing HDHA Products:

For scale-up production of diHDHA products, human recombinant cyclooxygenase-2 (COX-2) was expressed in insect Sf9 cells and isolated microsomal fractions were prepared and suspended in Tris Buffer (100 mM, pH 8.0). Aspirin was added (2 mM) (30 min, RT) to assess 17R HDHA formation from DHA(10 uM) before large scale preparations that was confirmed as by LC-MS-MS analysis as in FIG. 2 (see specification). Next, DHA (100 mg from Sigma D-2534) was suspended in EtOH and added at 1% v/v to Borate buffer (0.1 mM H$_3$ BO$_3$, pH 8.5) and vortexed in a round-bottom flask (5 to 10 min under a stream of nitrogen) to form micelle suspensions (optical density>650 nm) to react first with the acetylated -COX-2 (60 min, RT) to generate the 17R oxygenation (see illustration scheme A).

These reaction mixtures were immediately transferred and spun through a Millipore YM-30 centrifuge column for 20 min, RT. Next, isolated potato 5-lipoxygenase purchased from Cayman Chemical was added at 400 ul (in accordance with each preparation's specific enzymatic activity) to 10 ml reactions for 30 min, 4° C. in a round-bottom flask flushed with O$_2$ rotating in an ice water bath. At time intervals, samples were taken from the reactions to monitor product formation using LC-MS-MS with tandem UV spectra recorded online with a PDA detector with a MeOH:H2O mobile phase and linear gradient.

Next, the 4 position and 7 position hydroperoxy adducts respectively introduced into the 17RHDHA substrate by the actions of the 5-lipoxygenase were reduced as a mixture with the addition of solid grains of sodium borohydride (5 min, RT) and the incubations were stopped with the addition of 2 vol cold MeOH. The diHDHA products were extracted using liquid-liquid acidic ether (pH 3.5) and washed to approximately neutral pH with water. The structures of the 45,17R and 7S,17R-diHDHA positional isomers were established by LC-MS-MS (using conditions cited in the specification). These compounds were well resolved in rp-HPLC using MeOH:H2O (65:35 v/v) for isolation and biologic actions.

Scheme A

17R-HDHA SERIES
Biogenic Synthesis

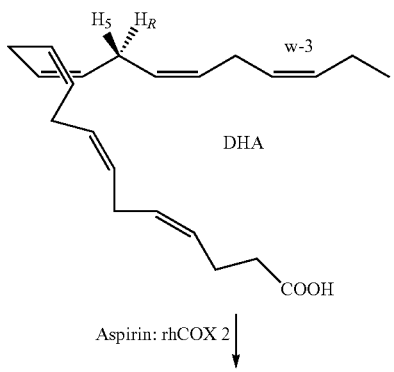

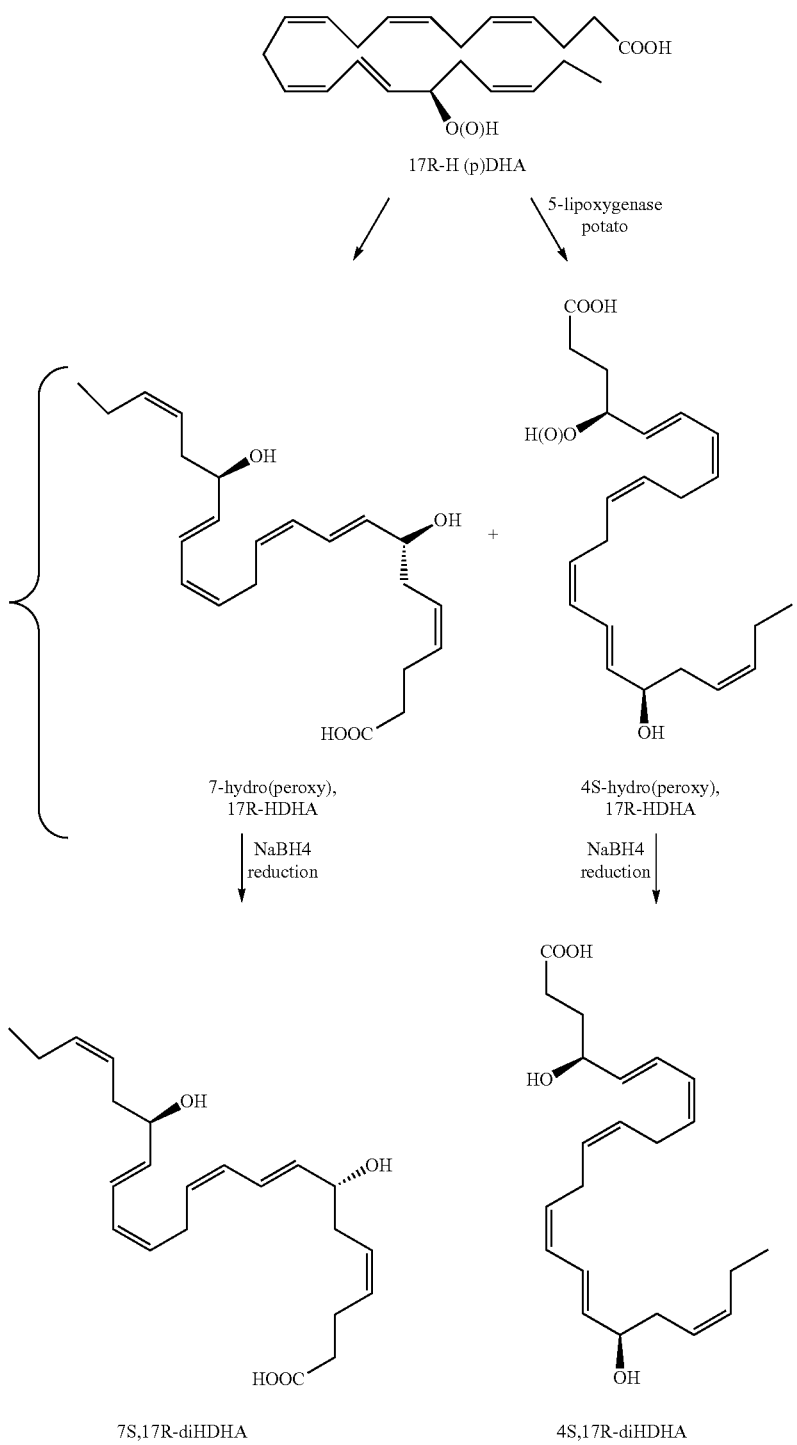

Biogenic Synthesis of 17 S Containing HDHA Products:

The preparation of the 17S products was carried out using sequential 15-lipoxyenase (soybean lipoxygenase; Sigma) followed by addition of potato 5-lipoxygenase (Cayman Chemical) for scale-up reactions to produce the 4S,17S-diHDHA and 7S,17S-diHDHA shown in scheme B. Both of these lipoxygenases insert molecular oxygen predominantly in the S configuration with antarafacial abstraction of hydrogen at specific positions in DHA (see specification). For these preparations, DHA (100 mg) was suspended in 10 ml Borate buffer (0.1M, pH 9.2), vortexed in a round bottom flask (250 ml vol) to form micelles, and the soybean 15-lipoxygenase was added to the micelle suspension at 4° C. in an ice water bath using spinning rotation for continuous mixing for 30-40 mins to convert DHA to the 17S-H(p) DHA. This hydroperoxy DHA was reduced with the addition of a few grains of NaBH$_4$ to the flask to produce the corresponding 17S hydroxy-DHA (see Scheme B). Next, the isolated potato 5-lipoxygenase was added to the flask kept at 4° C., pH 9.0 with rotation and oxygen to insert the 4S hydroperoxy—and 7S hydroperoxy—into 17S-HDHA followed by reduction with NaBH4. The reactions were monitored using LC-MSM-MS (vide supra), stopped with 2 vol MeOH, and acidic ether extracted and the positional isomers isolated using RP-HPLC. These 17S-containing products gave similar biologic in murine inflammation and physical properties (i.e. UV chromophores) to their corresponding 17 R products (see Table 2), but displayed different retention times in GC-MS.

Scheme B

17S-HDHA SERIES
Biogenic Synthesis

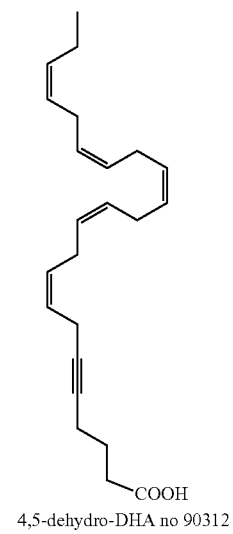

4,5-dehydro-DHA no 90312

15-Lipoxygenase
Soybean

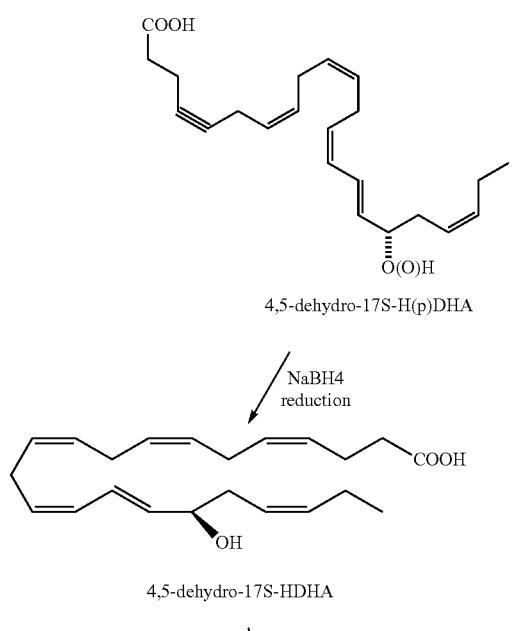

4,5-dehydro-17S-H(p)DHA

NaBH4
reduction 4,5-dehydro-17S-HDHA 5-lipoxygenase
potato

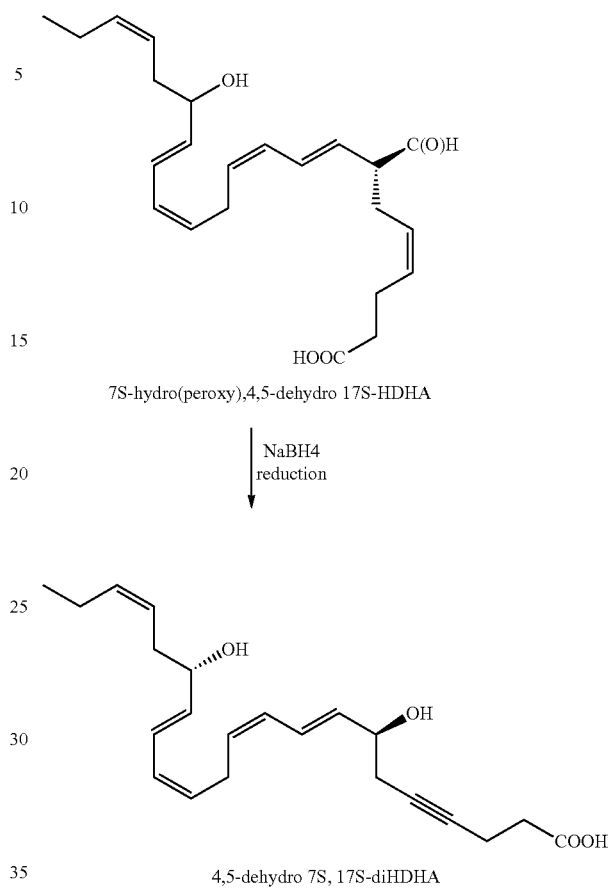

7S-hydro(peroxy),4,5-dehydro 17S-HDHA

NaBH4
reduction 4,5-dehydro 7S, 17S-diHDHA

Biogenic Synthesis of 5S,18R/S diHEPA and 5,12,18-Tri-EPE:

(+/−) 18-HEPE was purchased from Cayman Chemical (cat. Number 32840 CAS registry No. 141110-17-0) and used to produce the new EPA-derived compounds (see scheme C) by reactions and procedures described (vide supra) using the potato 5-lipoxygenase for scale up reactions. The racemate 18+/−HEPE (100 ug aliquots in EtOH) was suspended in Borate buffer (pH 9.2) in round-bottom flasks (250 ml) in 0.1% EtOH v/v, vortexed 5-10 min to form micelles and placed at 4° C., rotating as noted above in an ice water bath. The 5-lipoxygenase was added in 25 ul aliquots in two consecutive bolus additions for the isolated enzyme. The first bolus initiated reactions leading to production of 5S,18R/S-diHEPE after NaBH$_4$ reduction as the main product (see scheme C) generated after 30-40 min reactions as monitored by LC-MS-MS. The second bolus addition of 5-lipoxygenase to the mixture gave rise to the 5,12,18R/S-triHEPA via production of a 5(6)-epoxide intermediate formed by the LTA synthase reaction of the potato 5-lipoxygenase at this pH and substrate concentration. The epoxide opens in an SN2 type reaction in the presence of water adding at the least hindered carbon of the carbonium cation generated at the end (carbon 12) of the conjugated triene system (see below, scheme C). The structures were confirmed by LC-MS-MS and isolated by HPLC for assessment of biologic actions.

Scheme C
Biogenic Synthesis of 5S, 18+/-diHEPA
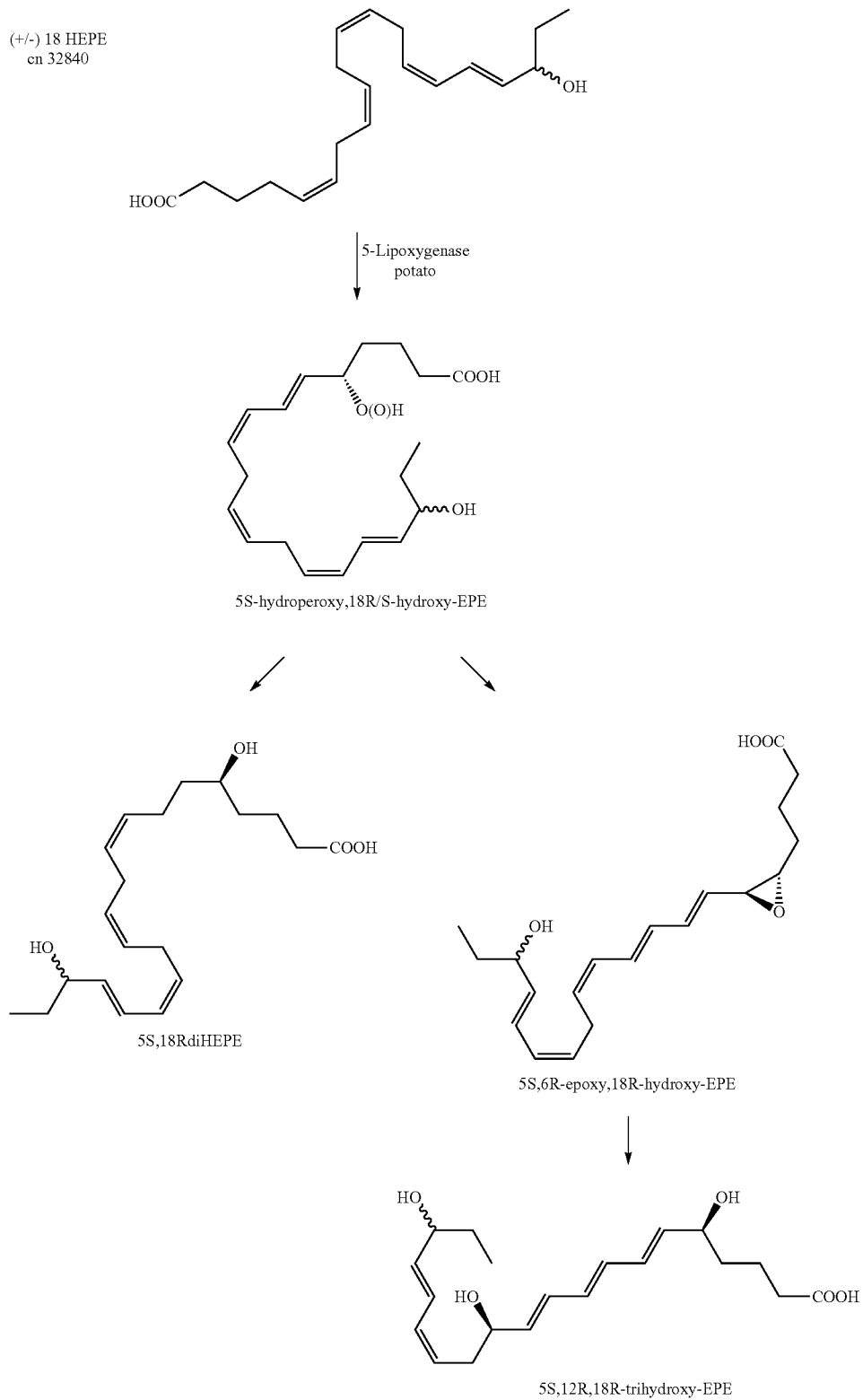

Examples of Analogs Via Biogenic Synthesis

Synthesis of 4,5-dehydro-7S,17 S-diHDHA 4,5-dehydro Docosahexaenoic Acid (cat number 90312) was purchased from Cayman Chemical (MI) and used without additional purification to produce analogs for scale-up biological analysis. The 4,5 dehydro DHA in 100 ug aliquot suspensions was prepared in 0.1M Borate Buffer (pH 9.2) in 25 ml round-bottom flask for vortexing and micelle formation before addition of the 15-lipoxygenase in 25 ul aliquots. After reduction with NaBH$_4$ of the hydroperox—added in the S configuration at position 17, the corresponding alcohol was next converted with the addition of potato 5-lipoxygenase followed by reduction to give the 4,5-dehydro 7S,17 S-diHDHA (see scheme D). This scheme can also be used to generate the corresponding 17R containing analogs by substituting the ASA-treat recombinant COX-2 in the position 1 enzyme instead of 15-lipoxygenase.

Scheme D

17S-HDHA SERIES
Biogenic Synthesis

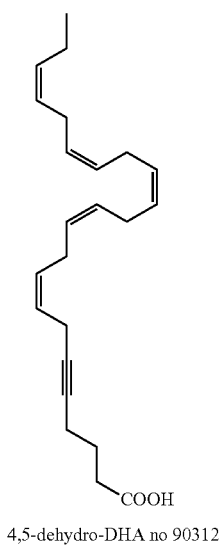

4,5-dehydro-DHA no 90312

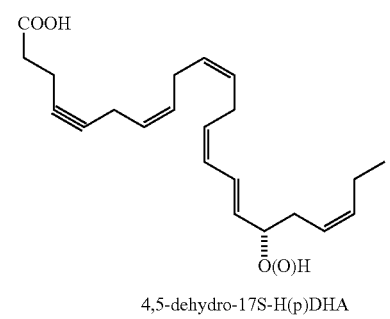

4,5-dehydro-17S-H(p)DHA

| NaBH4 reduction

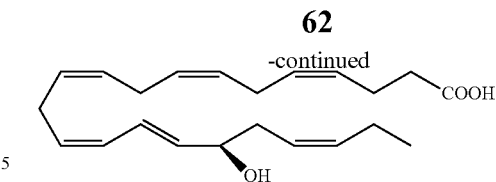

4,5-dehydro-17S-HDHA

| 15-lipoxygenase potato

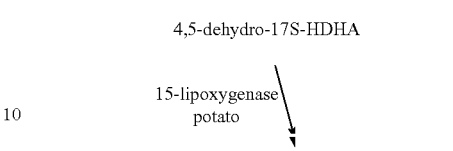

7S-hydro(peroxy),4,5-dehydro 17S-HDHA

| NaBH4 reduction

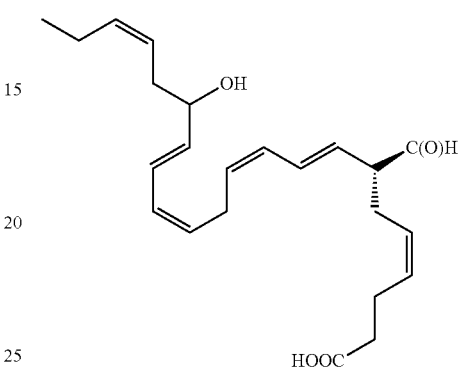

4,5-dehydro 7S,17S-diHDHA

Another example of this route for scale-up is given in Scheme E for the biogenic synthesis of a novel analog, 4,5-dehydro 10,17S-dihydroxy DHA (See also FIG. 17). In short, after addition of 15-LO that was converted to the 17S adduct, a second addition of the soybean 15-LO gave the LTA4-like synthase reaction to yield the 16(17) epoxide of the 4,5dehydro precursor that underwent hydrolysis to give the 4,5-dehydro 10,17S-dihydroxy DHA. This product at a 100 ng dose in murine zymosan A-induced peritonitis gave 40% inhibition of the PMN infiltration, indicating that this Resolvin analog is a potent anti-inflammatory agent in vivo.

FIG. 18 demonstrates that 4,17S-diHDHA is approximately half as potent as 10,17-docosatriene. By increasing the dose given by intravenous bolus to 200 ng, the two compounds are essentially equally effective. These results indicate that the 4,17S-diHDHA, although less potent on an equal quantity basis, is essentially equally effective in both regulating and inhibiting leukocyte infiltration and inflammation in the murine peritonitis model.

For FIG. 18, the 4,17S-diHDHA caused dose-dependent inhibition of PMN leukocyte infiltration. 100 ng of 10,17S-docosatrienes caused potent inhibition. Peritonitis was induced in 6 to 8 week old male FVB mice by peritoneal injection of 1 mg Zymosan A. Compounds 4,17S and 10,17S-diHDHA were injected by intravenous bolus injection, 1.5 minutes before Zymosan A treatment. Two hours after induction of peritonitis, rapid peritoneal lavages were collected and cell type enumeration was performed.

Scheme E example

17S-HDHA SERIES
Biogenic Synthesis

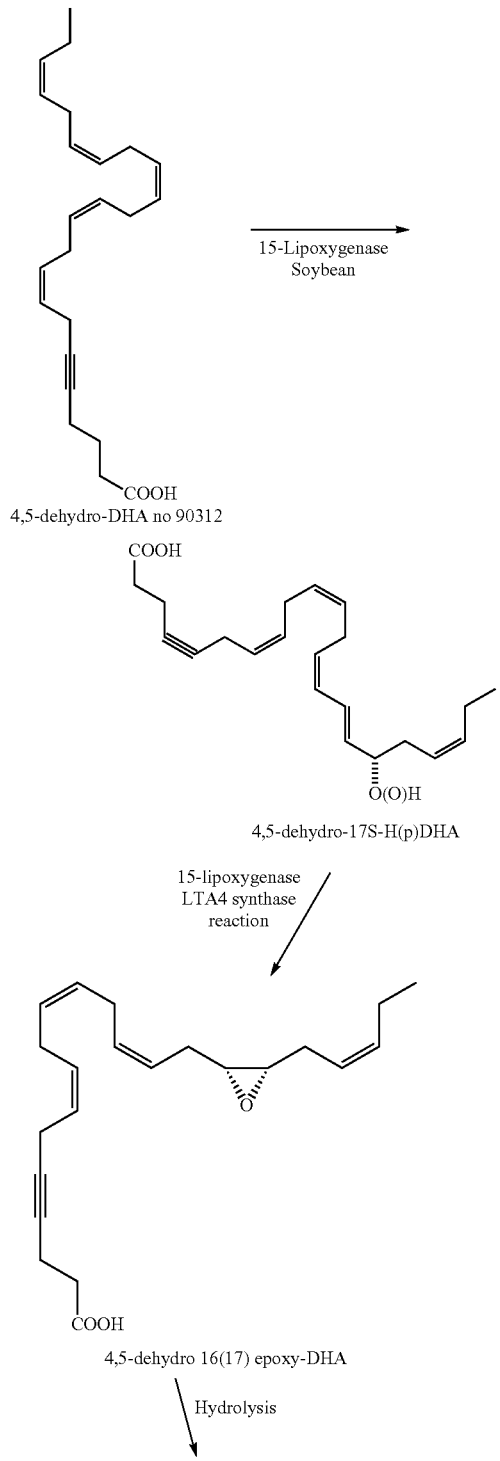

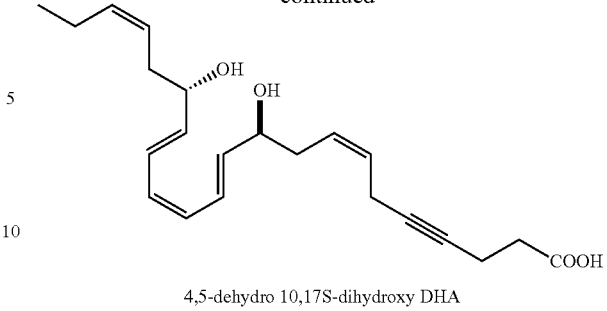

4,5-dehydro 10,17S-dihydroxy DHA

Organic Syntheses of Resolvin Analogs

The following synthetic routes exemplify methods to prepare the resolvin analog families of interest. The preparations are not intended to be limiting but serve as another means to prepare such analogs along more traditional practices and should be considered as complementary to the biogenic syntheses described above. Isolations methods include, column chromatography, HPLC, GC, crystallization and distillation if necessary. Characterization can be accomplished by UV, MS, MS/MS, GC/MS, NMR, etc. One skilled in the art can appreciate the various methods to prepare, isolate and characterize these novel compounds based upon the teachings herein.

The general synthetic schemes provided below depict methods to prepare the various "classes" or families of resolvins encompassed by the present invention. Throughout the syntheses of these families, R groups are used to indicate that various groups can be appended to the resolvin carbon chain. Each R group is independent selected, can be the same or different, and it can be envisioned that each R group is not necessarily present. In those instances, the attachment site would include a hydrogen atom. As described above, the R group is considered a "protecting R group" and can be an substituted or unsubstituted, branched or unbranched alkyl group, arylalkylgroup, alkylaryl group or a halogen atom.

Throughout the synthetic schemes, various hydroxylprotecting groups are depicted. These are not to be considered limiting; these are exemplary protecting groups that can be used and were chosen as illustrative.

The moiety designated as "U" as used throughout the synthetic schemes is described throughout the application and is incorporated herein by reference. "U" as used throughout the synthetic schemes herein is meant to include a terminal carbon atom. The terminal group can be a mono, di or tri substituted methyl group, a methylene (substituted or unsubstituted) attached to a phenoxy group (substituted or unsubstituted), a substituted or unsubstituted aryl group, arylalkyl groups, etc.

"Q" is defined throughout the specification is intended to include one or more substituents positioned about a ring structure. Suitable substituents include, hydrogen atoms, halogen atoms, alkyl groups (substituted and unsubstituted, branched and unbranched), alkylaryl groups, arylalkyl groups, esters, hydroxyls, etc.

The moiety designated as "X" as used throughout the synthetic schemes is described throughout the application and is incorporated herein by reference. "X" as used throughout the synthetic schemes is intended to include, an oxygen atoms, a methylene, a substituted or unsubstituted nitrogen atom or sulfur atom.

As described above, hydrogenation of acetylenic portions of the resolvin can be accomplished to provide one or more products. Selective hydrogenation can provide multiple reaction product dependent upon the degree of hydrogenation that is desired. The resultant product(s) can provide one or more geometric isomers (cis or trans) about the resultant double bond where hydrogenation has taken place. Additionally, selective hydrogenation can provide resolvin analogs that retain one or more acetylenic portions, thus providing still more additional analogs. All analogs are considered part of the present invention and are hereby explicitly incorporated herein. Separation and identification of the compounds can be accomplished by methods known in the art (TLC, HPLC, GC, etc.)

Retention of acetylenic portions within the resolvin analog is considered to be advantageous. The synthesis can be shortened (the hydrogenation step or steps can be eliminated or monitored so that only selective hydrogenation occurs). The resultant acetylenic containing resolvin compounds retain similar bioactivies to the corresponding fully hydrogenated olefinic containing resolvins. Additionally, it is believed to be advantageous to avoid hydrogenation of those olefinic bonds that are generated from acetylenic portions which correspond to "cis" configurational isomers with respect to naturally occurring DHA and EPA compounds. That is, retrosynthetically, it is advantageous to prepare DHA and EPA compounds having acetylenic portions where previously cis double bonds existed in the molecule.

For example, Scheme I provides for the general preparation of one class of resolvins

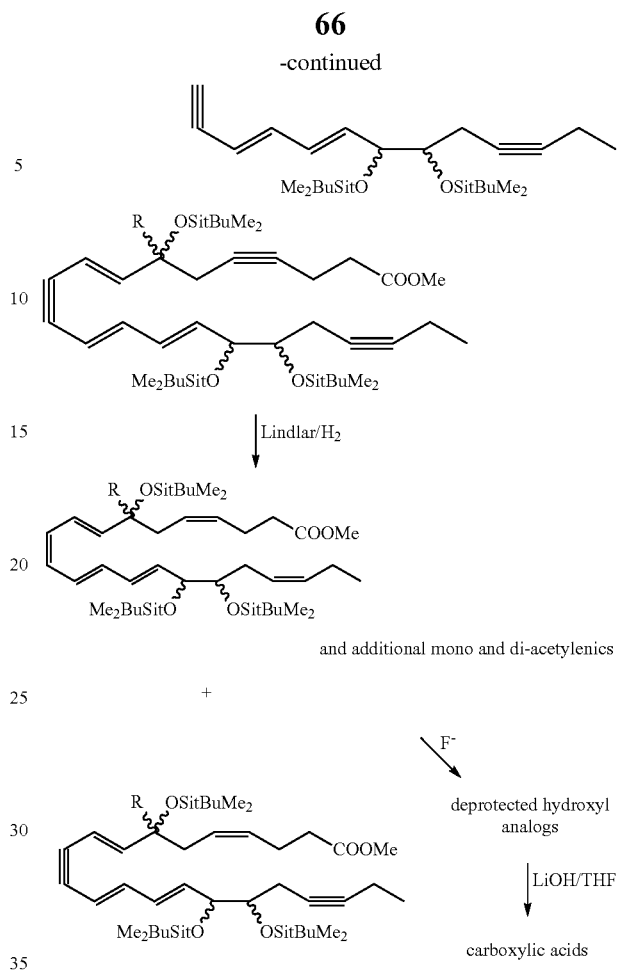

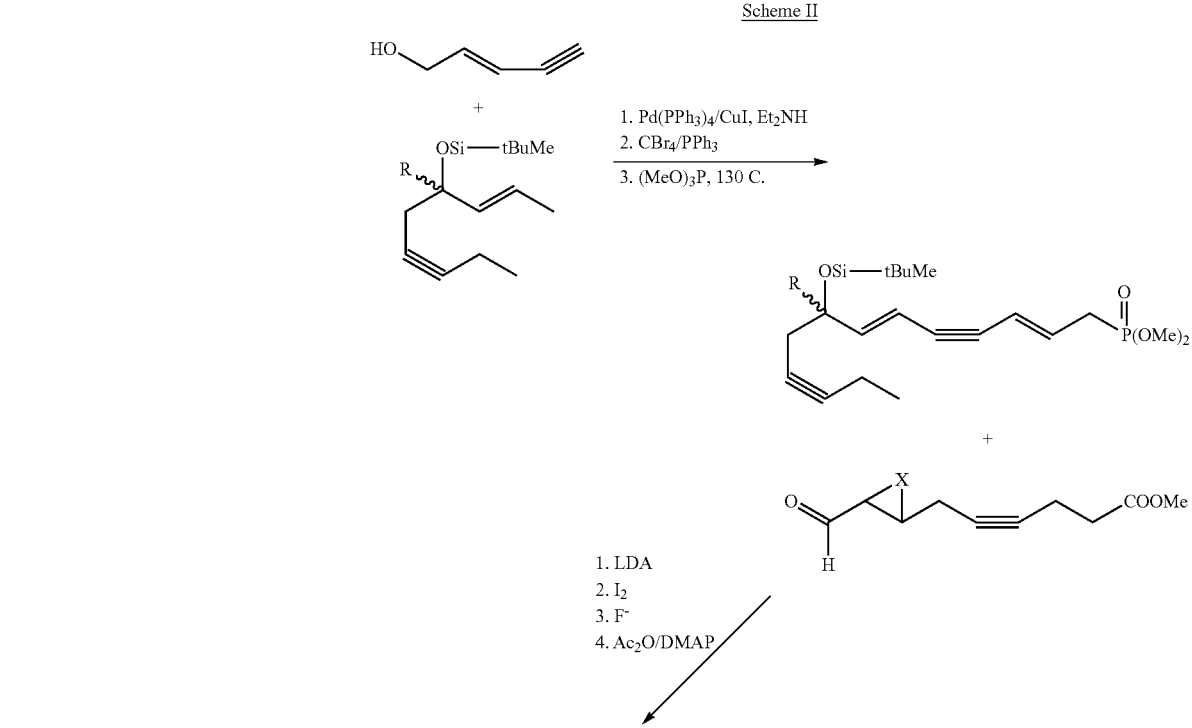

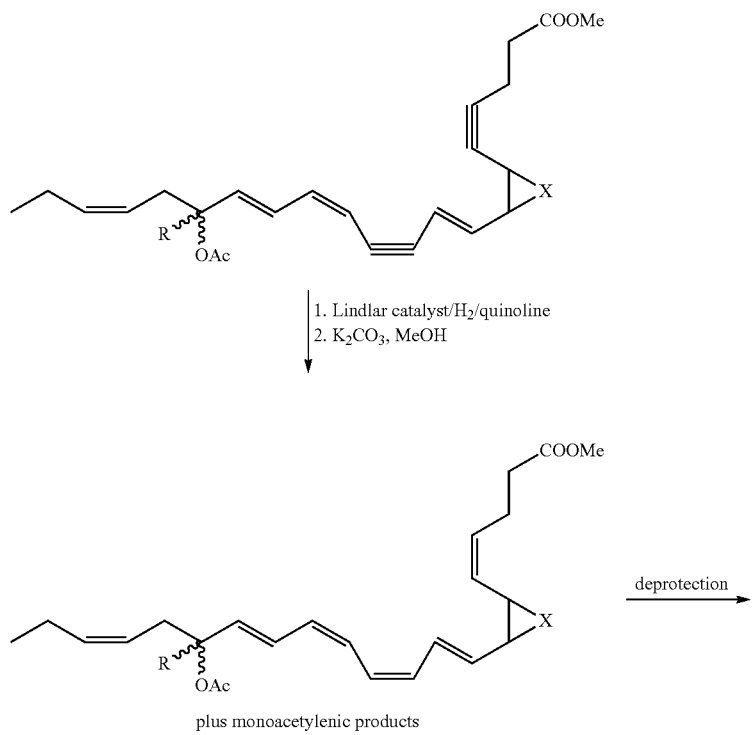

plus monoacetylenic products

It should be noted, for example, that the "R" groups are used as inhibitors for blocking oxidation of the 7-OH and/or 17-OH, forming ketones at the C-7 or C-17 position(s).

In synthetic scheme II, the synthesis of the 7(8)-methano-analog is based on the biotemplate of the epoxide intermediate in the biosynthesis of bioactive products generated by exudates and cell from DHA as the precursor. In this example, $Pd^0/Cu^I$ catalyzed coupling of the vinyl bromide acetylene with the alkynyl alcohol proceeds after bromination and phosphate production to give a phosphonate as an intermediate. The phosphonate is subject to condensation of the lithio derivate with the aldehyde to yield a mixture of Δ 9-10 cis(E) (Z) trans isomers. These can be converted by treatment with catalytic amounts of iodine. To protect the triple bonds, the silyl protecting group at carbon 17 is replaced by acetate. Lindlar catalytic reduction is used to reduce the triple bonds in quinoline. The product(s) are deacetylated to give the stable cyclopropyl 7(8) methano analog of the equivalent labile epoxide analog that is involved in resolvin biosynthesis of exudates in vivo and/or in cells, such as microlial cells of the brain or human leukocytes.

These analogs are important therapeutics because in addition to acting at the site/receptor for 7,8,17R-triHDHA resolvin as a mimetic to stop leukocyte recruitment as an agonist to stimulate/promote resolution and to pharmacologically inhibit inflammation, it also serves as an inhibitor of enzymes in vivo. Thus the compounds inhibit proinflammatory lipid mediators such as leukotrienes and also lead to an accumulation in situ of upstream resolvins in the biosynthetic pathway (See FIG. 8). Thus, these class of compounds serve a dual purpose: mimetic of resolvin 7,8,17-tri-HDHA and as a substrate level inhibitor.

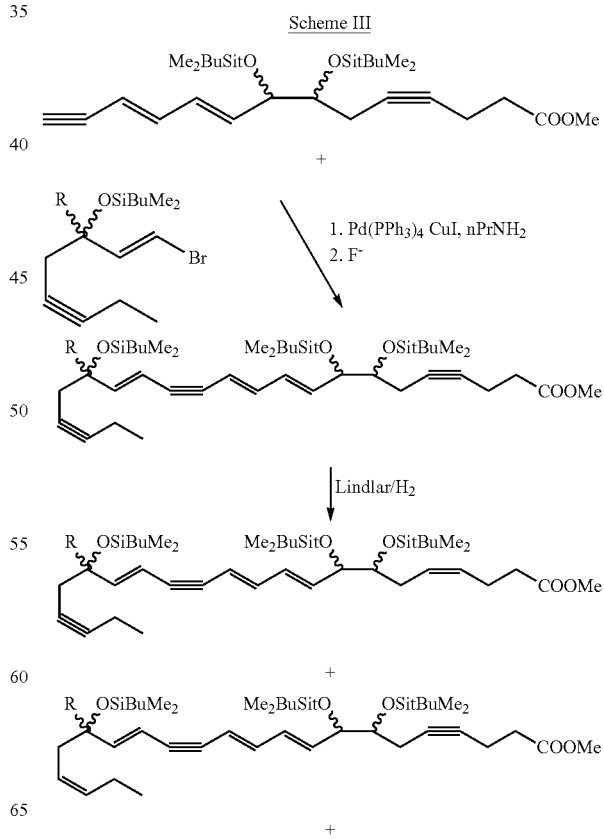

Scheme III

-continued
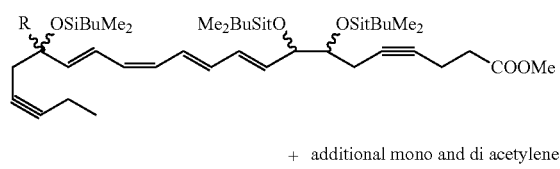
+ additional mono and di acetylenes
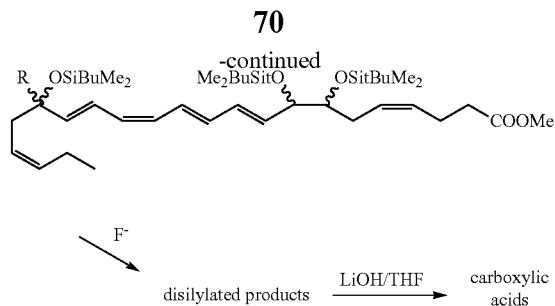
$\xrightarrow{F^-}$ disilylated products $\xrightarrow{LiOH/THF}$ carboxylic acids
Scheme IV
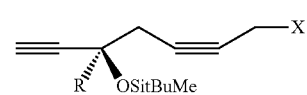
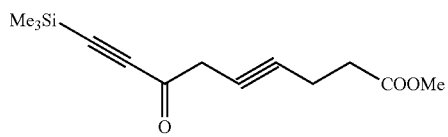
1. nBu$_3$SnH
2. Br$_2$
1. (-)-pinanyl-BBN
2. F$^-$
3. tBuPh$_2$SiCl/imidazole
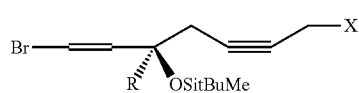
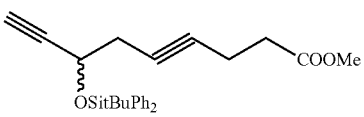
1. Pd(PPh$_3$)$_4$/CuI, nPrNH$_2$
2. AgNO$_3$/KCN
1. strong base, RX
2. tBu$_3$SnH
3. Br$_2$
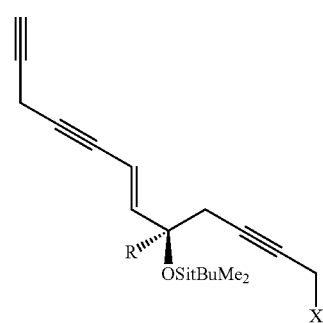
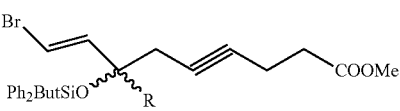
Pd(PPh$_3$)$_4$/CuI, nPrNH$_2$ 71 72
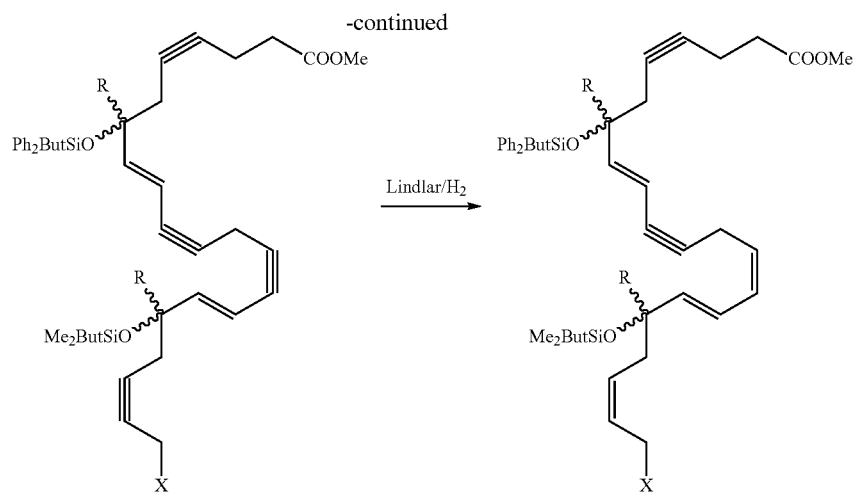
mono, di and tri-acetylenic products, including hexadienes, for example
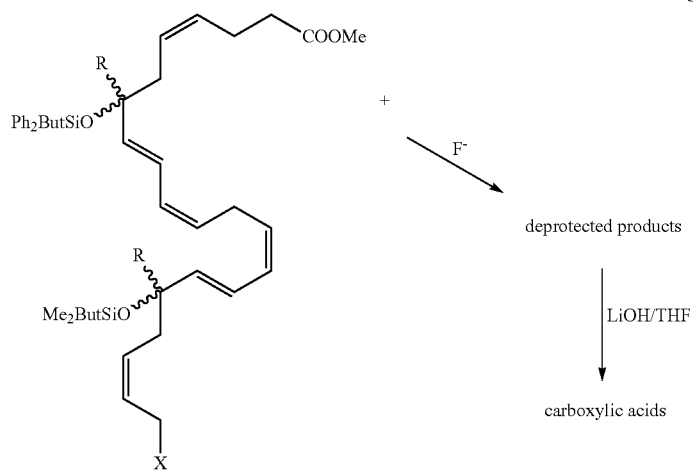
deprotected products
↓ LiOH/THF
carboxylic acids
Scheme V
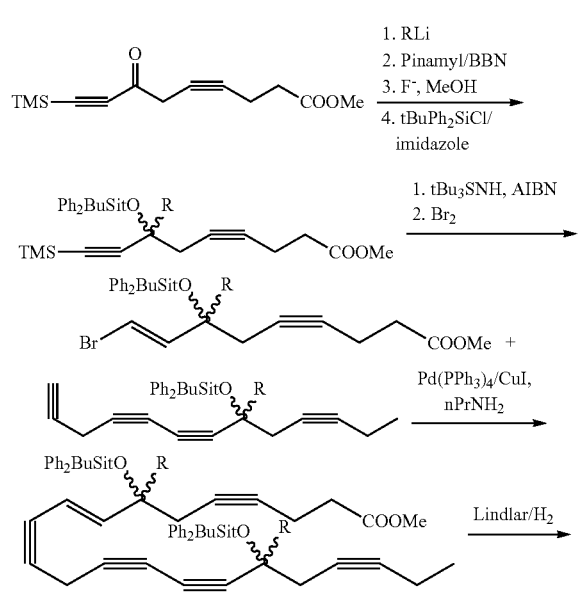
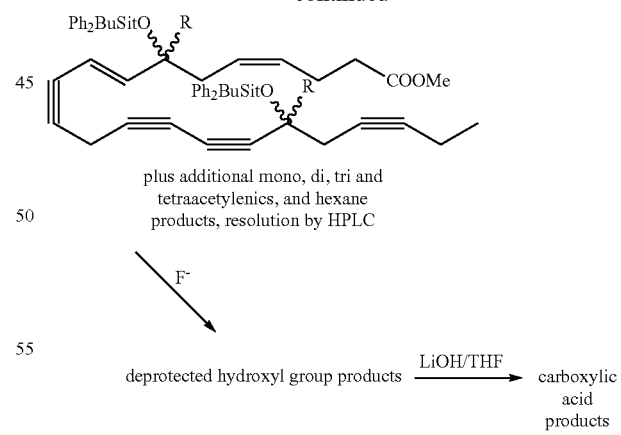
plus additional mono, di, tri and tetraacetylenics, and hexane products, resolution by HPLC
↓ F⁻
deprotected hydroxyl group products —LiOH/THF→ carboxylic acid products
Scheme V Alternative
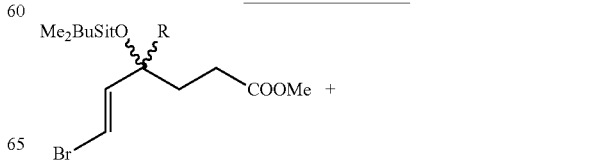

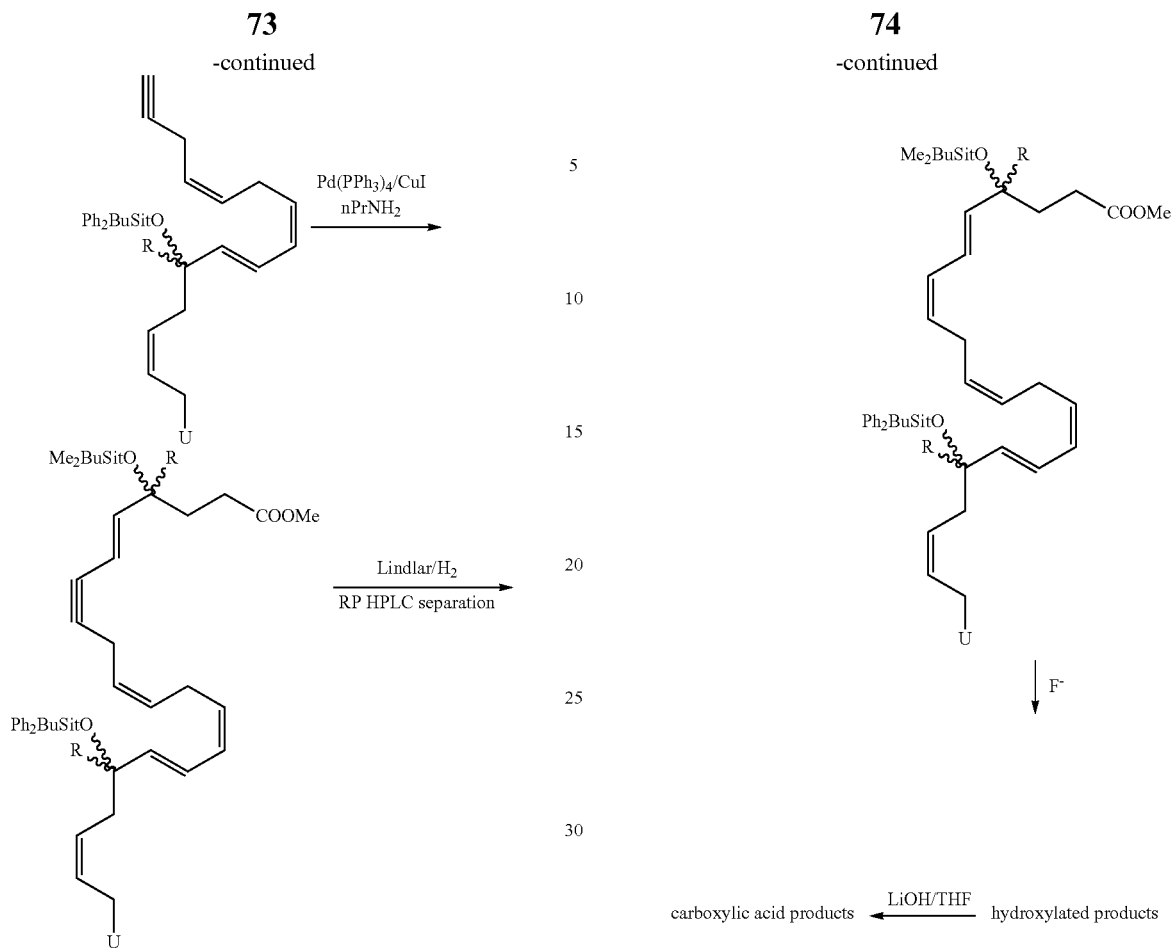
Scheme VI
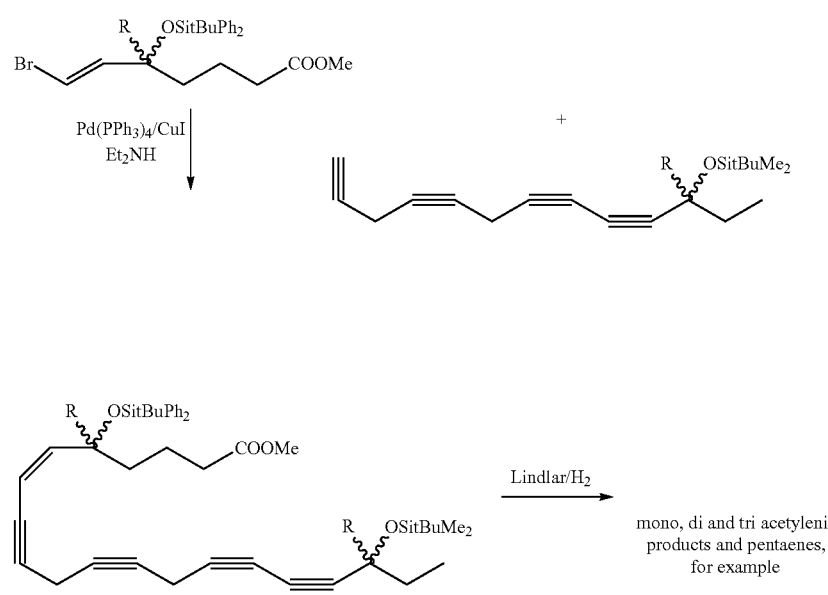

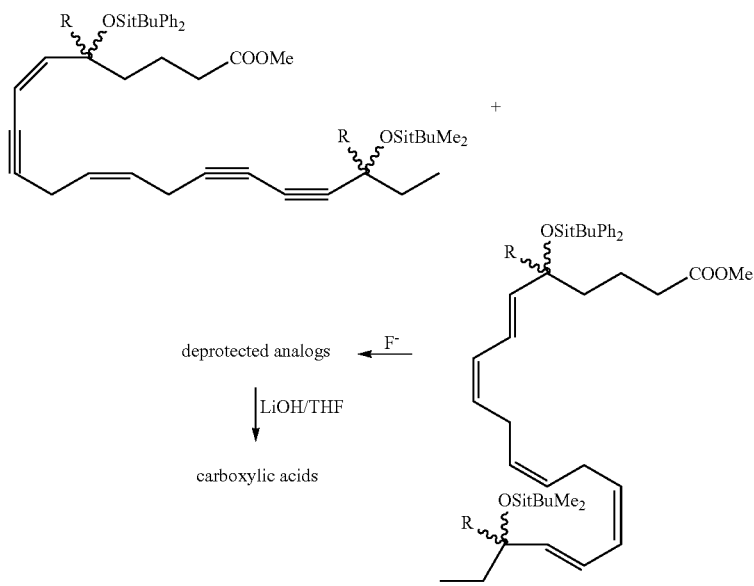

Scheme VI represents another class of compounds, where again, "protection" of the potentially oxidizable 5 and/or 18 hydroxyls to ketones. Use of "R" groups, as described herein, provides the ability to prevent the oxidation, and therefore the bioavailability of the bioactive compound.

The analogs within synthetic scheme VI can be prepared by coupling the vinyl bromide as prepared in K. C. Nicolaou et al. Angew. Chem. Int. Ed. Engl 30 (1991) 1100-1116) and coupled using Pd/Cu coupling chemistry. The resultant intermediate can be selectively hydrogenated with the Lindlar catalyst and hydrogen to produce various acetylenic products, as well as penatene containing products. Deprotection of the alcohols and conversion to carboxylic acids, esters, etc. can be accomplished by known methods.

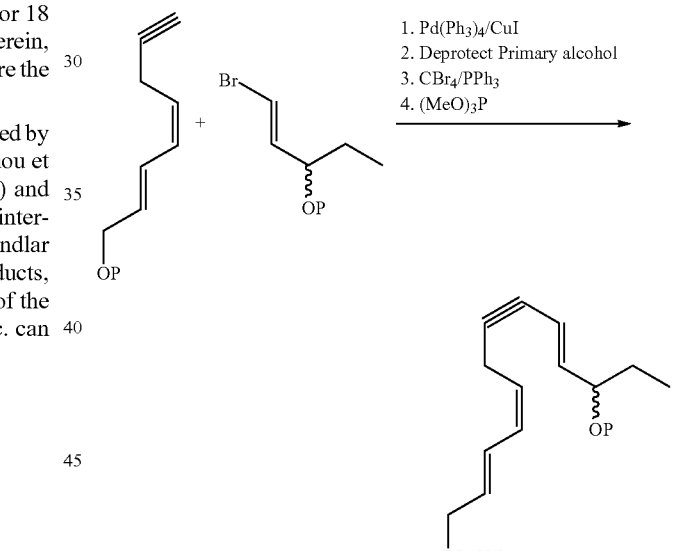

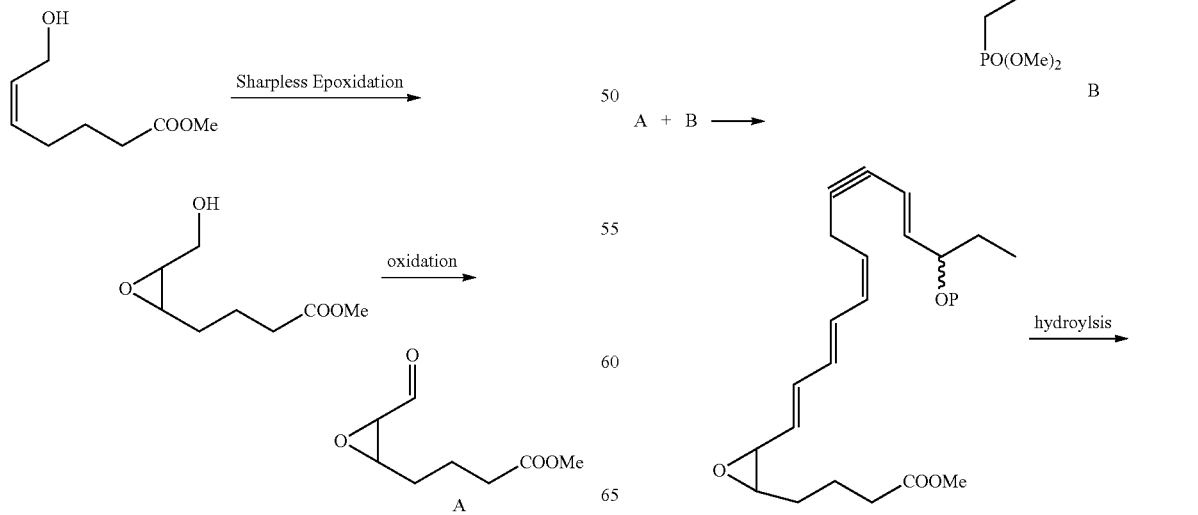

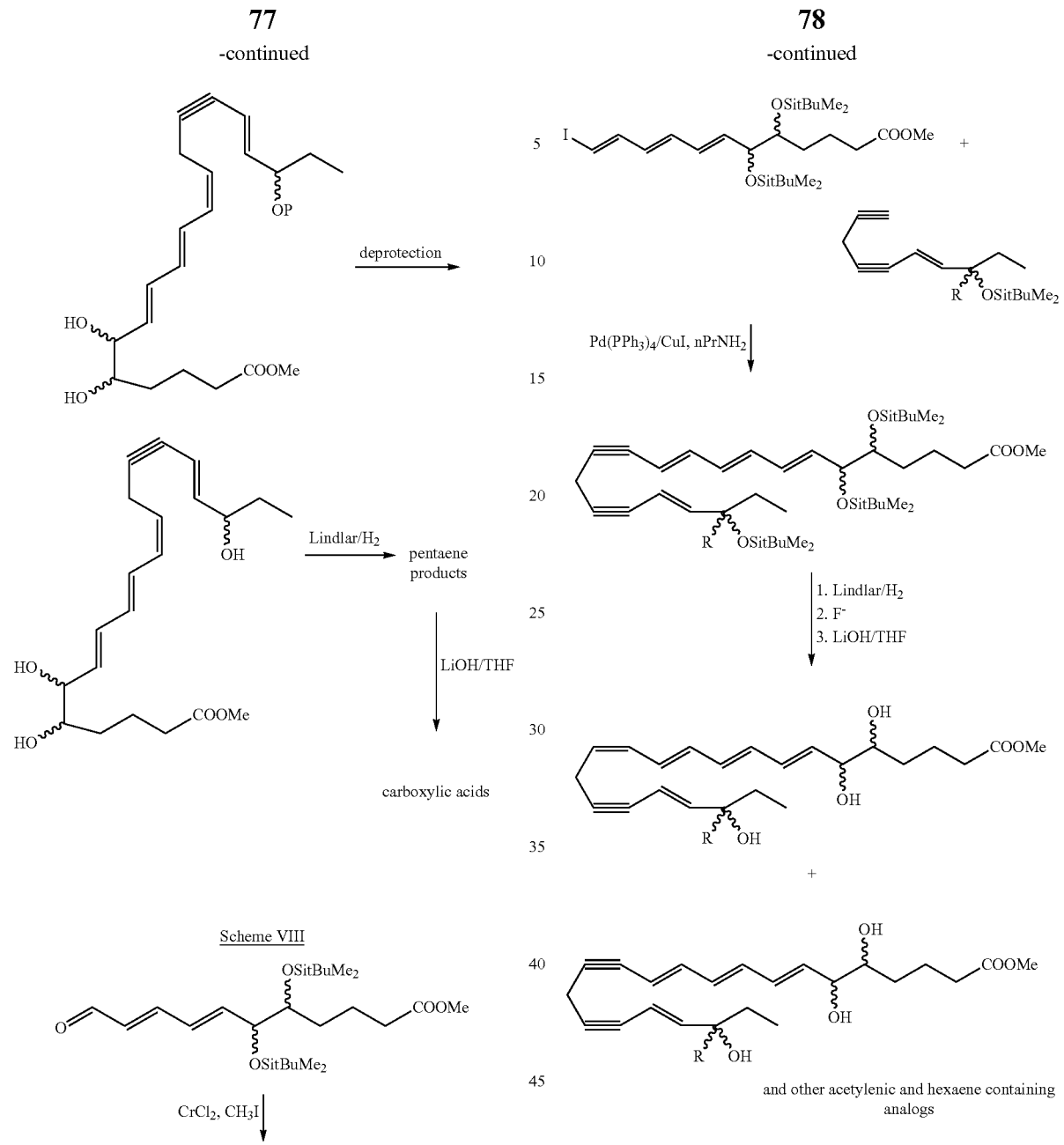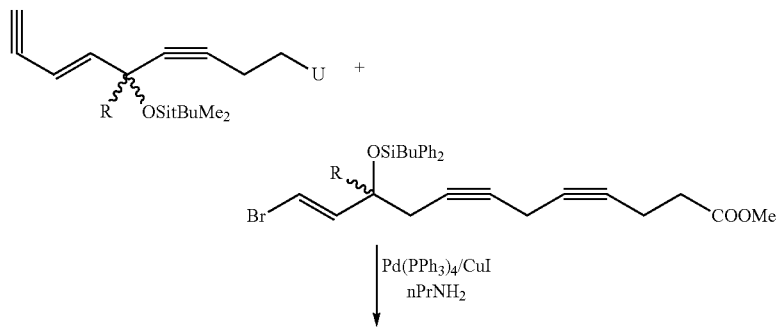

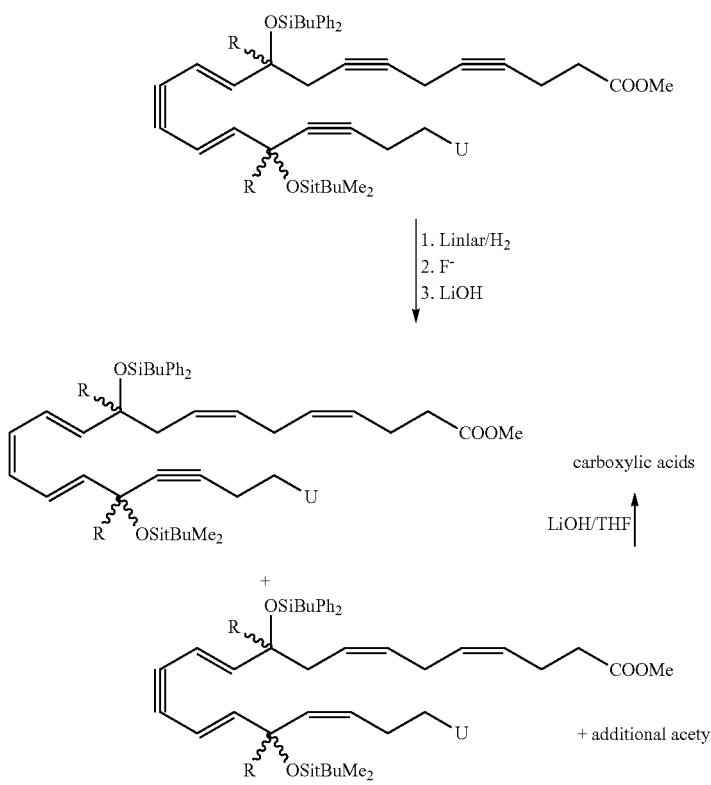

10,17 diHDHA's are depicted in FIG. 8 and are of interest because the biosynthesis of 10,17 di-HDHA differs from the other compounds of FIG. 8. It is produced via 15-lipoxygenase action on DHA (pH of about 8.5) under conditions that favor hydroperoxidation at the 17 position of DHA which is then converted into the 16, 17 epoxide. The 16(17) epoxide carries the conjugated triene chromophore and opens via a carbonium cation intermediate with OH attack at the 10 position to afford 10,17-diHDHA. Human tissues and isolated cells produce this via the 15-lipoxygenase as well as additional enzymes. This compound has been prepared by using soybean 15-lipoxygenase with DHA as the substrate at a pH of about 8.5, presented in micelle configuration. The 10,17 di-HDHA was isolated using RP-HPLC as described herein. It was found that the 10,17 di-HDHA inhibited both PMN migration into the peritoneum (zymosan induced peritonitis) of mice given Zymosan and inflammation. Hence, protection at the C-10 hyroxyl position with an "R protecting group" should prevent metabolic conversion and increase stability and activation to block PMN infiltration and acute inflammation.

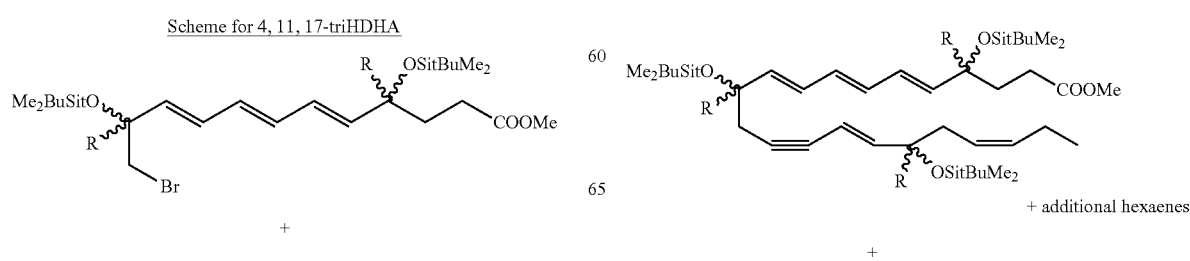

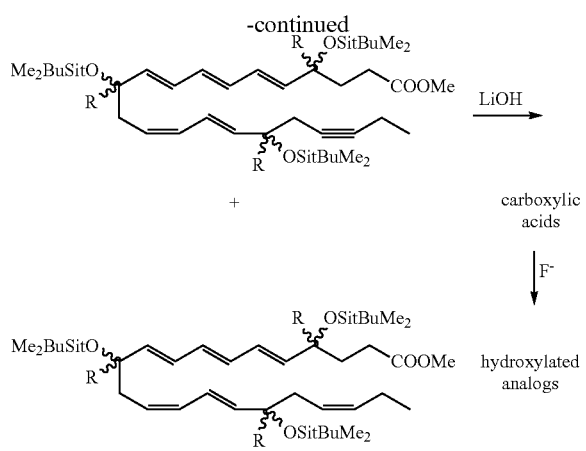

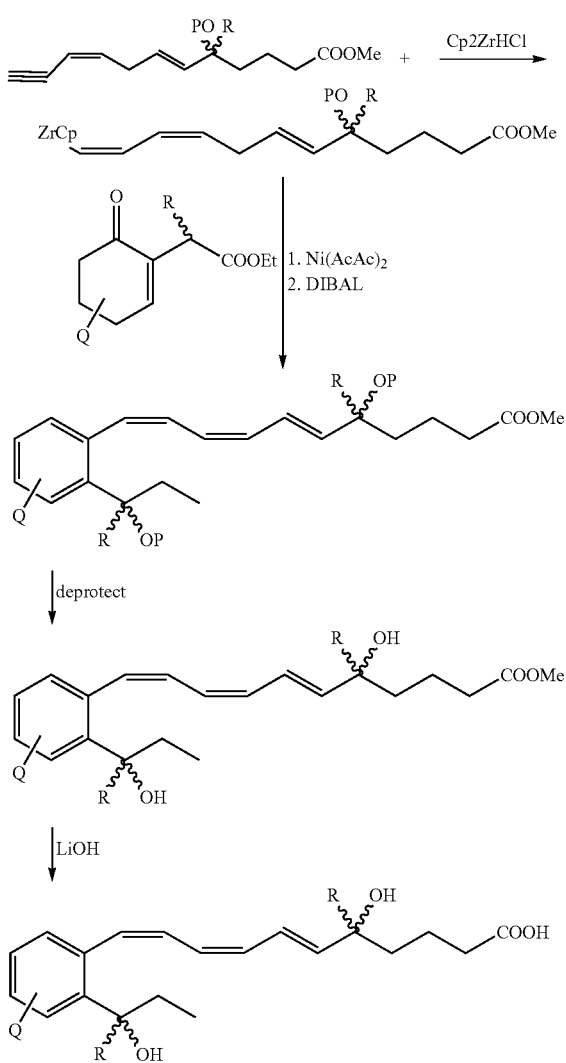

The preparation of 5,18-diHEPA analogs is achieved using a conjugated addition of a vinyl zirconium reagent 3-(1-octen-1-yl)cyclohexanone as in Sun, R. C., M. Okabe, D. L. Coffen, and J. Schwartz. 1992. Conjugate addition of a vinylzirconium reagent: 3-(1-octen-1-yl)cyclopentanone (cyclopentanone, 3-(1-octenyl)-, (E)-). In Organic Syntheses, vol. 71. L. E. Overman, editor. Organic Syntheses, Inc., Notre Dame, Ind. 83-88 using Schwartz's reagent as prepared in Buchwald, S. L., S. J. LaMaire, R. B. Nielsen, B. T. Watson, and S. M. King. 1992. Schwartz's reagent (zirconium, chlorobis(h5-2,4-cyclopentadien-1-yl)hydro-). In Organic Synthesis, vol. 71. L. E. Overman, editor. Organic Syntheses, Inc., Notre Dame, Ind. to construct the zirconiated intermediate. Treatment with DIBAL as in Ishiyama, T., N. Miyaura, and A. Suzuki. 1992. Palladium(0)-catalyzed reaction of 9-alkyl-9-borabicyclo[3.3.1]nonane with 1-bromo-1-phenylthioethene: 4-(3-cyclohexenyl)-2-phenylthio-1-butene. In Organic Syntheses, vol. 71. L. E. Overman, editor. Organic Syntheses, Inc., Notre Dame, Ind. provides the di-HEPA ring containing analog. It should be understood that the cyclohexanone reagent can be substituted with any number of substituents, thereby providing the resultant substituted or unsubstituted aromatic ring within the di-HEPA analog.

Again, it should be noted that inclusion of an "R protecting group" at C-5 and/or C-18 positions helps to inhibit oxidation of the hydroxyl group to a ketone. Additionally, it is believed that the use of a ring within the structure helps to constrain confirmation about the molecule and affects receptor ligand interaction(s).

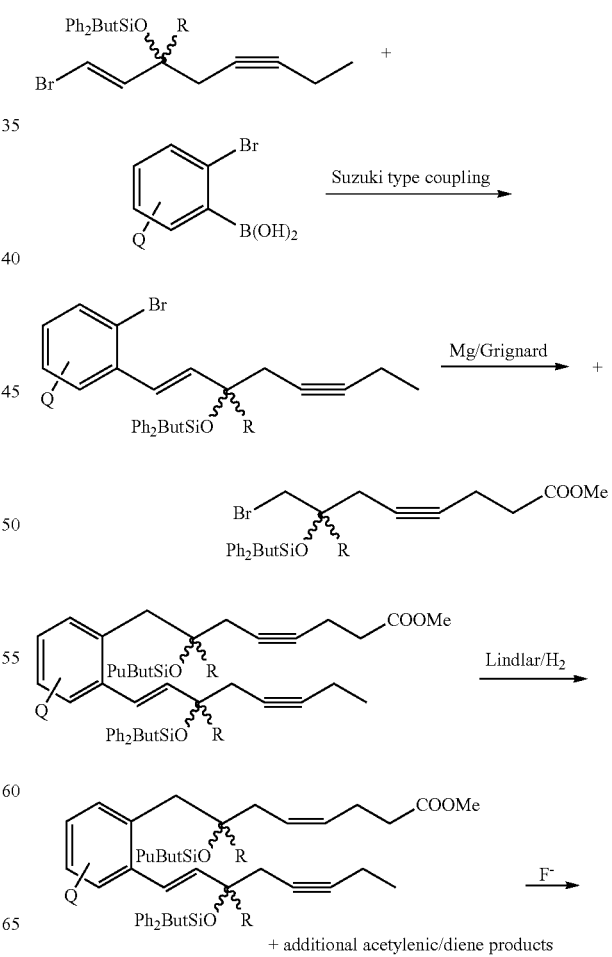

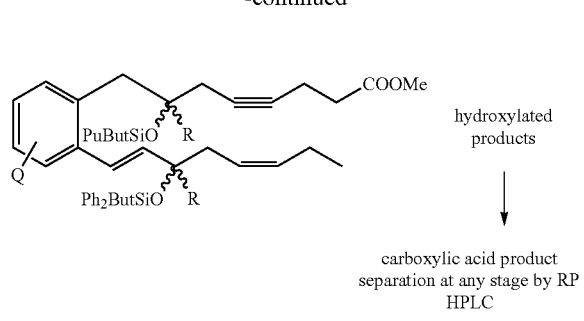
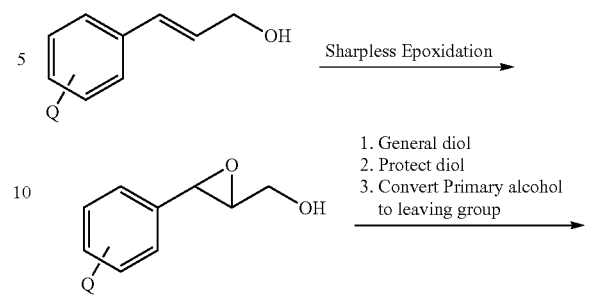
Scheme for 7, 16, 17-tri-HDHA ring analogs
Scheme for 7, 8, 17-trihdroxy-HDHA with ring structure
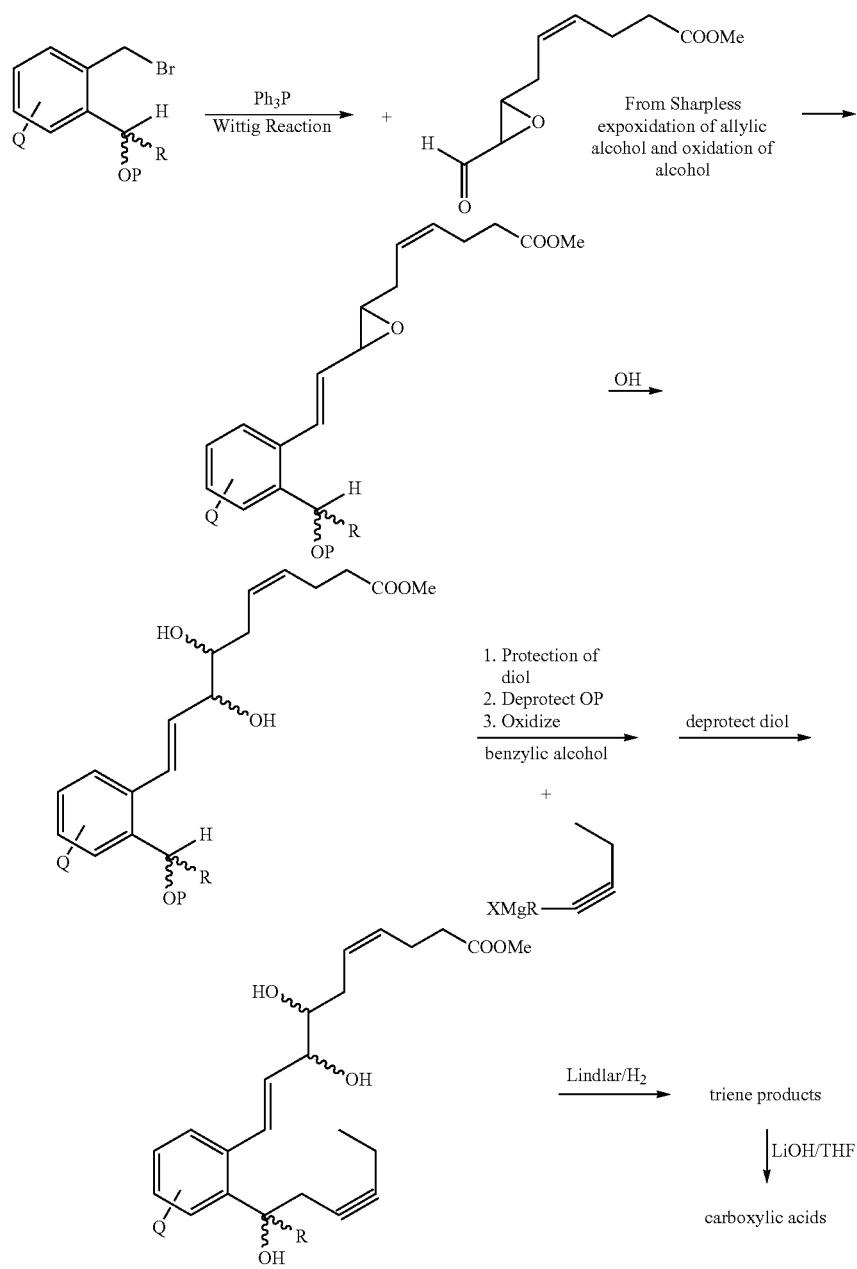

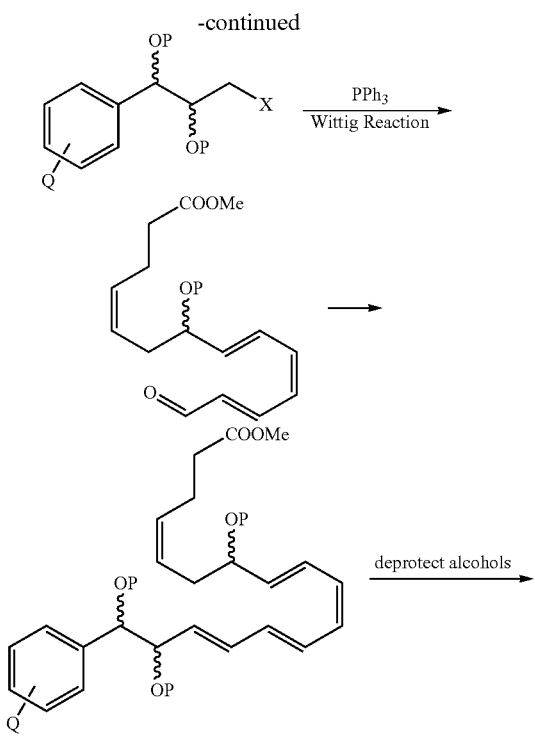

Results
Lipidomics of the Exudate Resolution Phase

It is well appreciated that orderly resolution in healthy individuals is influenced by both systemic and local host factors that include nutrition, metabolic status (i.e., diabetes is associated with delayed healing) and circulatory status as some of the key determinants in the duration of resolution (39). In experimental acute inflammatory challenge that undergoes spontaneous resolution, namely in the murine air pouch model of exudate formation and resolution, it was found a temporal dissociation between the formation and actions of local chemical mediators (10). Leukotrienes and prostaglandins are generated rapidly and appear with leukocyte recruitment to the air pouch exudate in line with their known actions as proinflammatory mediators. Lipoxin biosynthesis concurs with spontaneous resolution and the loss of PMN from the murine air pouch exudate, providing evidence that functionally distinct lipid mediator profiles switch from proinflammatory to anti-inflammatory mediators such as lipoxins during resolution (10).

Recently, it was found that EPA is transformed in murine exudates treated with ASA to novel products that possess anti-inflammatory properties, providing a potential mechanism for omega-3 beneficial actions in many diseases (2). Since DHA is cardioprotective (22), abundant in brain and retina and displays an impact in many physiologic processes (28-32), lipidomic analyses were undertaken to determine whether inflammatory exudates utilize DHA in the resolution phase with ASA treatment.

FIG. 9 depicts the approach developed to isolate, examine, characterize and separate the various components of the exudates. Until now, it was unappreciated how many different compounds are generated through the biochemical pathway. Each compound is unique and precise separation and characterization was required to isolate each component. In general, a sample of the exudates is extracted and then separated into components via solid phase extraction followed by chromatography and mass spectral analysis. GC-MS can also be employed to help identify separate components. UV analysis is also often helpful. The physical properties of the compounds are then identified and placed into a library to determine which compounds are unique and previously unknown. Further structural elucidation is undertaken (NMR, MS/MS, IR, etc.) prior to scale up. Production of the compounds can be accomplished via biogenic synthesis and or traditional organic synthesis, such as provided herein.

Inflammatory exudates obtained within the resolution phase formed within dorsal skin air pouches following injection of TNFα, DHA and aspirin treatment contained several previously unknown novel compounds revealed with LC-MS-MS analysis (FIG. 1). It is noteworthy that the Lab Diet 5001 used to feed these mice contained 1.86% DHA and 1.49% EPA with <0.25% arachidonic acid (Purina Mills). Additional mass spectral analysis employing both GC-MS (with derivatized products) and LC-UV-MS-MS-based analyses (which did not require derivatization) indicated that the inflammatory exudate-derived materials contained novel hydroxy acids produced from both DHA and EPA, namely these products were not known as reported lipid mediators. The EPA-derived products were recently established (2). Selected ion chromatograms and MS-MS from results acquired at m/z 343 were consistent with the production of 17-HDHA (FIG. 1, Panels A and B), with lesser amounts of 7S- and 4S-HDHA (FIG. 1, Panel A) within the exudates. These products co-eluted with authentic 17(R/S racemic)-HDHA and 4S-HDHA (qualified by NMR; see Methods) in 3 different chromatographic systems (not shown), and their basic structural properties were consistent with those of related DHA-derived products (cf. 28, 29, 30). ASA-treatment also gave novel di- and tri-hydroxy products carrying the DHA backbone within the inflammatory exudates; at this dose ASA completely inhibited the in vivo production of thromboxane and prostanoids. Importantly, ASA treatment in vivo and COX-2 gave previously unknown products from DHA that possess bioactive properties (vide infra).

Results in FIG. 1, Panel C show the MS-MS spectra of a dihydroxy-containing DHA with fragment ions consistent with the structure shown in the inset, namely 7,17-diHDHA; m/z 359 [M-H], m/z 341 [M-H—$H_2O$], m/z 323 [M-H-2$H_2O$], m/z 315 [M-H—$CO_2$], and m/z 297 [M-H—$CO_2$—$H_2O$]. Additional diagnostic ions consistent with the 7- and 17-hydroxy-containing positions were present at m/z 261, 247, and 217. A representative of the several novel trihydroxy-containing DHA-derived compounds also present in inflammatory exudates is shown in FIG. 1, Panel D. Ions present were consistent with its [M-H]=m/z 375, 357 [M-H—$H_2O$], 339 [M-H-2$H_2O$], 331 [M-H—$CO_2$], 313 [M-H—$CO_2$—$H_2O$], 306, 303, 276, 273, 255 [273-$H_2O$], 210, 195, and 180. These physical properties (i.e. MS-MS, UV, LC retention time) were used throughout to identify these and related compounds and to assess their bioimpact. These compounds were deemed of interest because transfer of materials extracted from inflammatory exudates in DHA plus ASA pouches to naïve mouse (i.v. or via i.p. administration) sharply reduced zymosan-induced PMN infiltration by ~60%, indicating the in vivo utilization of DHA and production of bioactive products within exudates (vide infra).

The Role of COX-2 and ASA in Biosynthesis of R-Containing HDHA

Chirality of the alcohol group at carbon-17 (FIG. 1B) was established for the product that matched exudate-derived 17-HDHA using a chiral HPLC column. The alcohol at carbon 17 position proved to be predominantly in the R configuration (>95%; n=4), indicating that this was indeed a novel product of enzymatic origin formed in vivo that was not known earlier. For example, 17S-HDHA is generated via 15-lipoxygenation or via autooxidation in racemic ~50:50 ratio of R/S mixtures cf. (40, 41). Hence, the presence of the alcohol group in the R configuration as 17R-HDHA from exudates (FIG. 1) was indicative of an enzymatic origin. The substrate channel of COX-2 is larger than COX-1 (26), suggesting the possibility of substrates larger than arachidonic acid. Consistent with this, DHA was transformed by rhCOX-2 to 13-HDHA (FIG. 2; left panel). The MS-MS obtained were consistent with oxygen addition at the 13 position (i.e., m/z 193 and m/z 221) and, when COX-2 was treated with aspirin to acetylate serine within the catalytic site (1, 26, 42), DHA was enzymatically converted to 17R-HDHA (FIG. 2; right panel). The MS-MS and diagnostic ions at m/z 343 [M-H], 325 [M-H—$H_2O$], 299 [M-H—$CO_2$], 281 [M-H—$H_2O$—$CO_2$], 245 and 274 consistent with 17-carbon alcohol group and chiral analysis using chiral HPLC with reference materials (see Methods) indicated that the conversion of DHA by aspirin-acetylated COX-2 yielded predominantly (>98%) 17R-HDHA. The product of COX-2 matched the physical properties of the dominant 17-hydroxy-containing DHA-derived compound identified in inflammatory exudates (FIG. 1) in vivo with aspirin treatment. Unlike cyclooxygenase-1, shown earlier not to convert DHA (43), results with recombinant COX-2 in Table 1 and FIG. 2 indicate that aspirin treatment of this enzyme generates predominantly 17R-HDHA. Other commonly used nonsteroidal anti-inflammatory drugs, i.e. indomethacin, acetaminophen, or the COX-2 inhibitor (e.g. NS-398), did not give appreciable amounts of 17R-HDHA. Treatment with aspirin gave a reciprocal relationship between 17 versus 13-position oxygenation. Also in these incubations, indomethacin, acetaminophen, and NS-398 each reduced the overall oxygenation of DHA [to 13- as well as 17-HDHA (see Table 1)], but did not share the ability of ASA to produce 17R-HDHA. For direct comparison, conversion of C20:4 by ASA-acetylated COX-2 to 15R-HETE (67%±5% substrate conversion; n=3) was monitored in parallel with the conversion of DHA to 17R-HDHA (52±3%; mean±S.E.M.; n=3).

Brain and Vascular Biosynthesis of the New Compounds

Figure 3B:
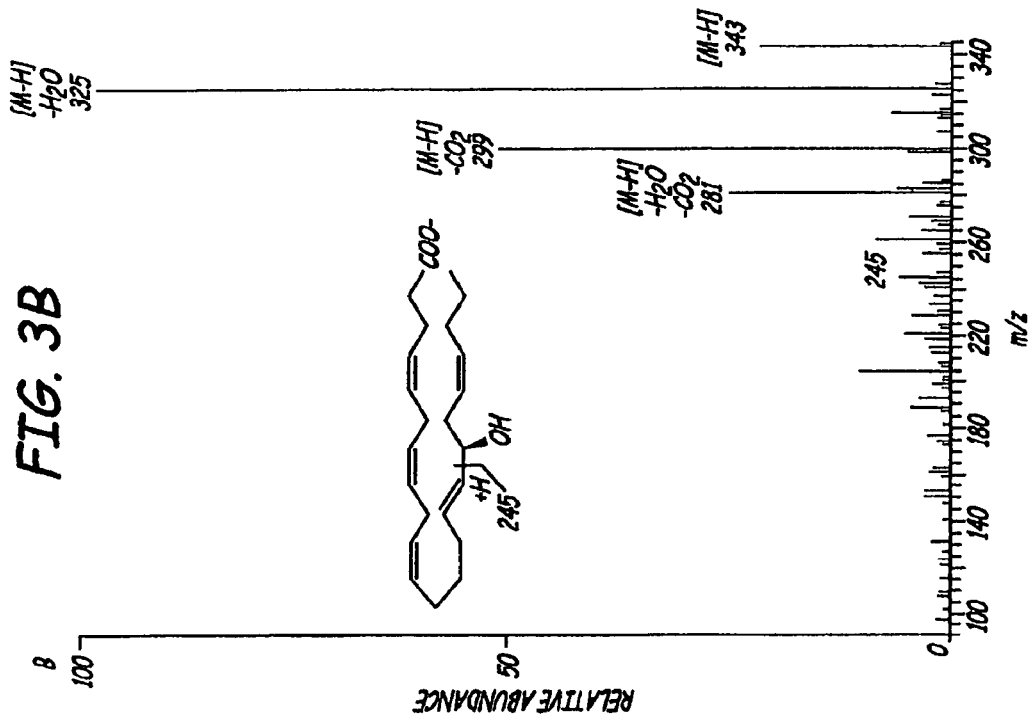
FIG. 3 depicts endogenous 17R-HDHA from brain and human microglial cells treated with aspirin. A) LC-MS-MS chromatogram obtained from brain for relative abundance at m/z 327 for DHA and m/z 343 for the monohydroxy product. B) MS-MS spectrum of brain 17R-HDHA (m/z 343). Murine brain samples were incubated with ASA (45 min, 37° C.). Results are representative of n=6 mice treated with ASA vs. 5 mice without ASA. C) Human microglial cells (HMG) treated with ASA; MS-MS spectrum of HMG 17R-HDHA. 10×10$^6$ cells were exposed to TNFα (50 ng/ml) and incubated (24 h, 37° C.). Cells were treated with ASA (500 μM, 30 min, 37° C.) followed by addition of ionophore A23187 (5μ, 1, 25-30 min). Incubations were stopped with MeOH, extracted and analyzed by tandem UV, LC-MS-MS (FIG. 3 inset shows UV-chromatogram plotted at 235 nm absorbance) (n=4, d=20). Both 17R-HDHA and DHA were identified on the basis of individual retention times, parent ions, and daughter ions obtained.
Figure 3A:
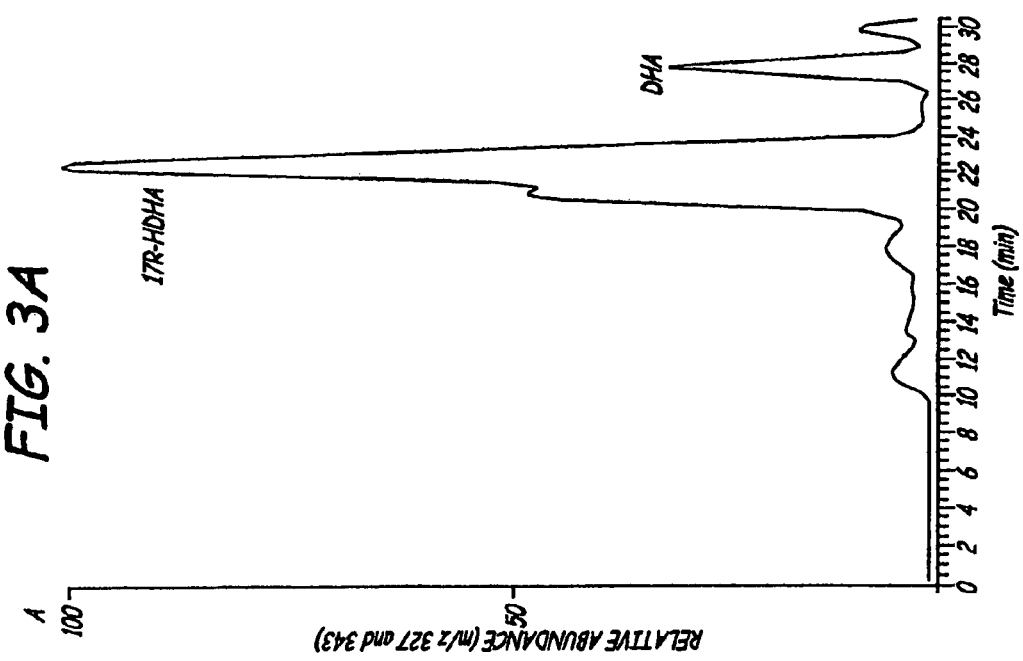
Figure 3C:
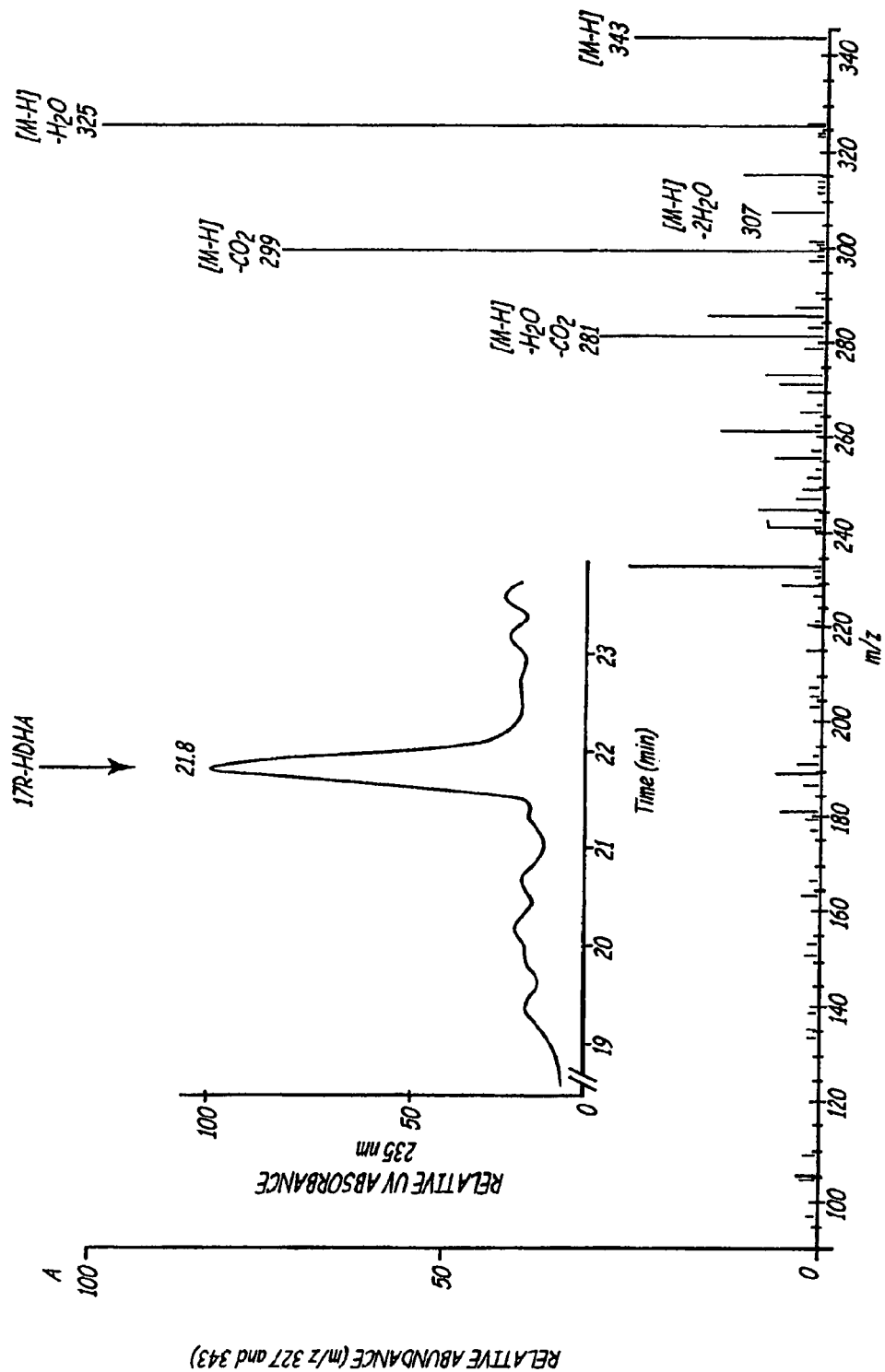
Figure 4:
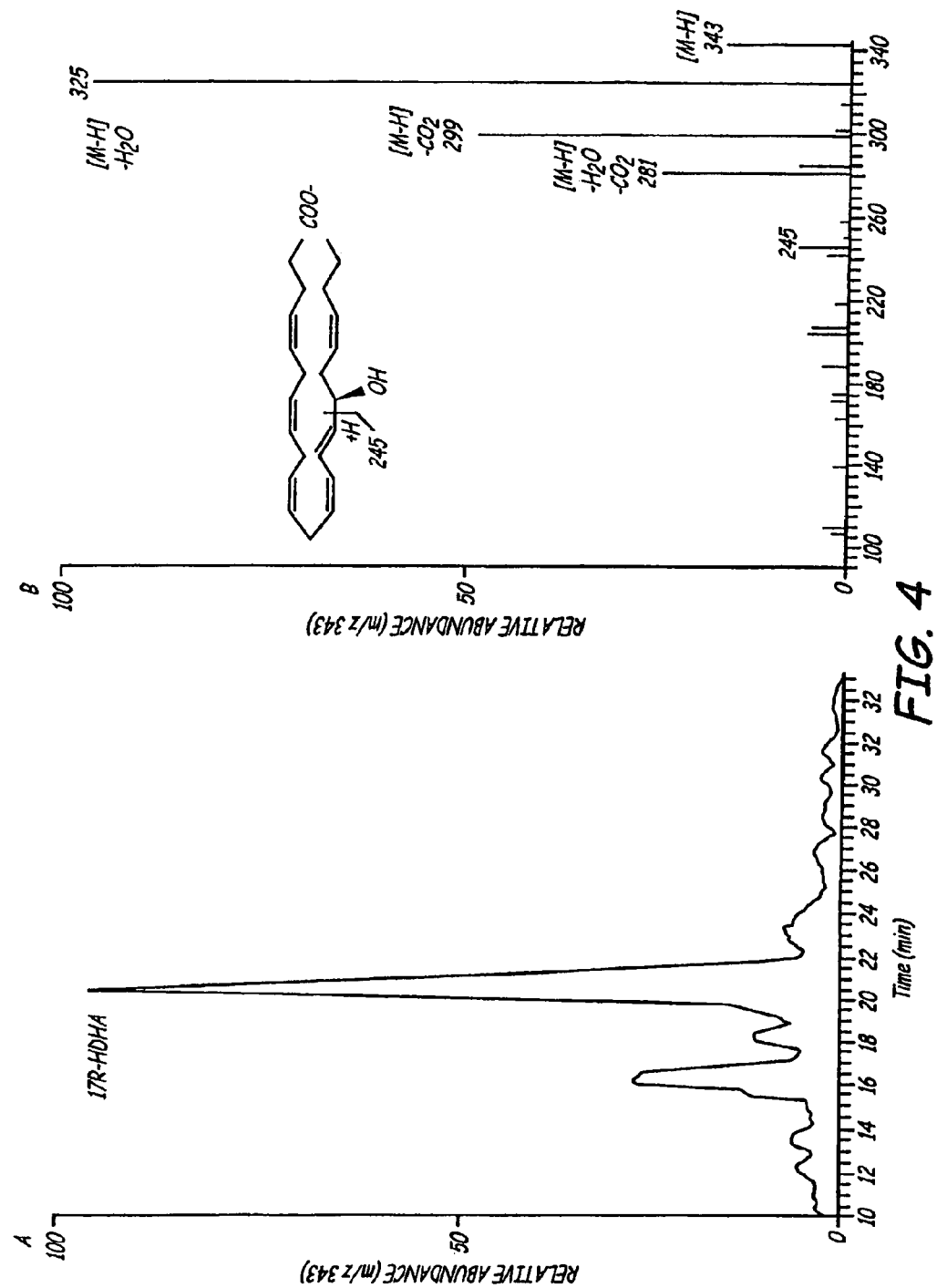
FIG. 4 depicts hypoxic HUVECs treated with ASA generate 17R-HDHA. HUVECs were exposed to TNFα and IL-1β (both 1 ng/ml) and placed in a hypoxia chamber (3 h). The cells were treated with ASA (500 μM, 30 min) followed by DHA (20 μg/$10^6$ cells/10 ml plate) and A23187 (2 μM, 60 min). Panel A: LC-MS-MS chromatogram of ion m/z 343 shows the presence of 17R-HDHA. Panel B: MS-MS spectrum (RT 21.2 min) of 17R-HDHA identified by retention time, parent ions, and daughter ions and matched with properties and authentic NMR qualified standard.

In brain, COX-2 is present in constitutive as well as in inducible pool(s) (28, 44). Results in FIG. 3 (A and B) indicate that aspirin-treated brain contained 17R-HDHA produced from the endogenous sources of DHA. To address the possible cell types involved in 17R-HDHA generation in brain, human microglial cells were exposed to TNFα, which up-regulated expression of COX-2, followed by treatment with ASA and the agonist ionophore A23187. Human microglial cells generated 17R-HDHA in an ASA-dependent fashion (FIG. 3C). Hypoxia is also known to induce COX-2 (45), and hypoxic endothelial cells exposed to cytokine IL-1β, as endothelial cells might encounter at inflammatory loci or with ischemic events (23), treated with aspirin were a source of 17R-HDHA (FIG. 4).

Of interest, in the absence of ASA treatment, 17S-HDHA and corresponding 17S-hydroxy-containing diHDHA and triHDHA were products in murine exudates and human cells. Their formation differs from the present biosynthesis in that, rather than COX-2-ASA, 15-lipoxygenase initiates biosynthesis in sequential lipoxygenation reactions to produce di- and trihydroxy-DHA (i.e., 7S,17S-diHDHA, 10,17S-diHDHA, 4S,17S-diHDHA, 4S,11,17S-triHDHA and 7S,8,17S-triHDHA; cf. Table 2) via epoxide intermediates.

Bioactions of the New Compounds

Figure 5A:
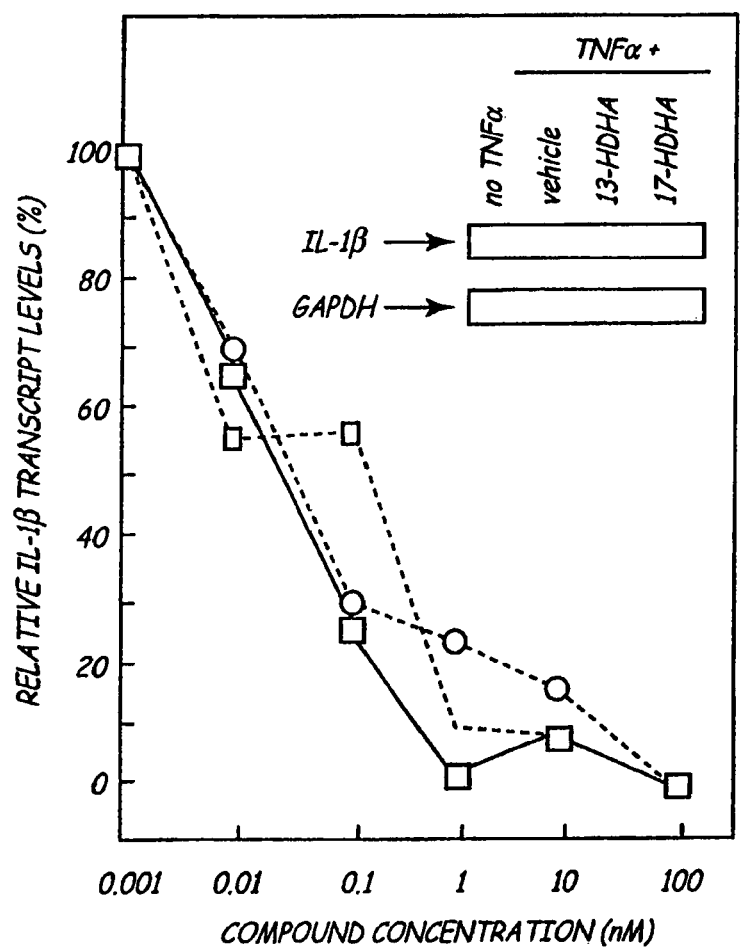
FIG. 5 depicts Bioimpact properties of omega-3-derived Resolvins. A) Human glioma cells: Inhibition of TNF-stimulated IL-1β transcripts DBTRG-05MG cells $10^6$/ml were stimulated with 50 ng/ml of human recombinant TNFα for 16 hours to induce expression of IL-1β transcripts. Concentration dependence with COX-2 products: 17-HDHA (n), 13-HDHA (l)and di-/tri-HDHA (n). The $IC_{50}$ for both compounds is ~50 pM. (insets) Results are representative of RT-PCR gels of MG cells exposed to 100 nM of 13-HDHA or 17-HDHA and graphed after normalization of the IL-1β transcripts using GAPDH. B) Influence of eicosanoids and docosanoids on fMLP-induced neutrophil migration across micovascular endothelial monolayers Neutrophils ($1\times10^6$ cells/monolayer) were exposed to vehicle containing buffer, or indicated concentrations of aspirin-triggered $LXA_4$ analog (closed diamonds) 5S,12,18R-triHEPE (closed squares), 17R-HDHA (closed circles) or 13-HDHA (closed triangles) for 15 minutes at 37° C. Neutrophils were then layered on HMVEC monolayers and stimulated to transmigrate by a $10^{-8}$ M fMLP gradient for 1 hr at 37° C. Transmigration was assessed by quantitation of the neutrophil marker myeloperoxidase. Results are presented as mean±SEM number of PMN (n=8-12 monolayers per condition). C) Reduction of PMN in murine peritonitis and skin pouch peritonitis: Compounds (100 ng in 120 μL sterile saline) were injected by intravenous bolus injection into the mouse tail vein and followed by 1 ml zymosan A (1 mg/ml) into the peritoneum. Peritoneal lavages were collected (2 h) and cell types were enumerated.
Figure 5B:
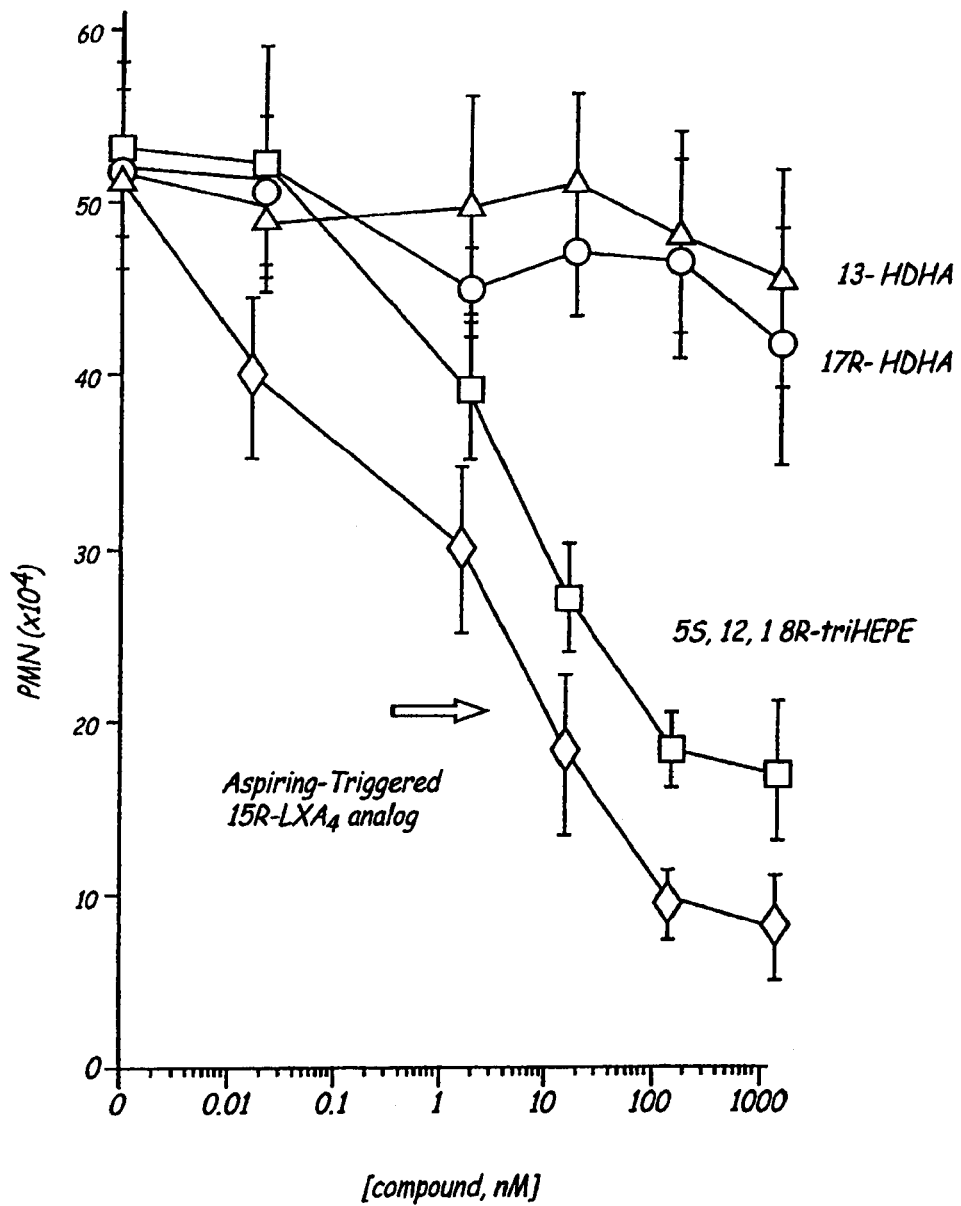

Since microglial cells are involved in host defense and inflammation in neural tissues, human microglial cells were incubated with the COX-2 products 13- and 17R-HDHA (each at 100 nM) to determine if they had an impact on the generation of inflammatory mediators (FIG. 5A inset). At nM concentrations, these novel cyclooxygenase-2 products inhibit TNFα-induced cytokine production with apparent $IC_{50}$~50 pM, as did the 17-containing di- and trihydroxy-HDHA compound (FIG. 5A). Next, the HDHA were tested for their ability to regulate transendothelial migration of human PMN. In the nM range, neither of the COX-2-derived monohydroxy-DHA products had a direct impact on PMN transmigration across endothelial cell monolayers (FIG. 5B). This finding contrasts results obtained with both EPA- and arachidonic acid-derived eicosanoid products that directly downregulate PMN transmigration in vitro (2, 3). For purposes of direct comparison, results with an ASA-triggered EPA pathway product 18R,5,12-triHEPE (P<0.01 by ANOVA) (cf. Ref. 2) were compared to those obtained with 15-epi-16-para(fluoro)-phenoxy-lipoxin $A_4$ (P<0.01 by ANOVA), a stable analog of aspirin-triggered 15R-lipoxin $A_4$ produced with aspirin treatment from arachidonic acid (10, 37).

Biosynthesis of Novel Docosanoids by Human PMN: Cell-Cell Interaction Products Matched in Exudates Next, since PMN interact with vascular cells during inflammation (7), the contribution of leukocytes was assessed in the production of the novel di- and tri-hydroxy compounds present in inflammatory exudates (FIG. 1A-D). To this end, human PMN were exposed to zymosan and 17R-HDHA produced via ASA-treated COX-2 or endothelial cells. PMN engaged in phagocytosis transform 17R-HDHA to both di- and tri-hydroxy-DHA (FIG. 6). The main conversions were to dioxygenation products including 7S,17R-diHDHA and 10,17R-diHDHA with lesser amounts of 4S,17R-diHDHA as the main dihydroxy-containing products present when monitored at m/z 359 (see FIG. 6). In addition, novel 17R-trihydroxy-containing products monitored at m/z 375 were present including 4S,11,17R-triHDHA as well as a set of trihydroxytetraene containing 7,8,17R-triHDHA (see Table 2). These compounds formed by human PMN match those produced within exudates generated in vivo in both their chromatographic behavior and prominent ions present in their respective mass spectra. LC-MS and on-line UV diode array profiles shown in FIG. 7 from exudates of mice treated with ASA indicate the in vivo production of both sets of 17R series di- and tri-hydroxy-containing products that carry triene and tetraene chromophores (see Table 2). Sources for these trihydroxy-DHA products as schematically illustrated include omega-1 hydroxylation at carbon 22 of either 7S,17R-diHDHA or 4S,17R-diHDHA via a p450-like reaction (see Ref. 6 and FIG. 8) that likely represents inactivation pathway products as with leukotrienes such as formation of 20-OH-$LTB_4$, a product of omega-oxidation of $LTB_4$ (2, 3, 6).

Transformation of 17R-HDHA by activated human PMN involved a 5-lipoxygenase and an $LTA_4$ synthase reaction that gave triHDHA products via the formation of respective 4S-hydro(peroxy)-17R-hydroxy- and 7S-hydro(peroxy)-17R-hydroxy-containing intermediates. Each was converted to epoxide-containing intermediates (i.e. 4(5) epoxide or 7(8) epoxide intermediates) that open via hydrolysis to give rise to 4S,11,17R-triHDHA or in a parallel route to diols such as the trihydroxytetraene set 7S,8,17R-triHDHA (see FIGS. 4, 7 and 8). The mechanism used by PMN to convert the 17R-HDHA precursor appeared similar to that established and identified for the epoxide generating capacity of the human PMN 5-lipoxygenase, which performs both a lipoxygenation and epoxidation step (2, 4) as demonstrated with the potato 5-lipoxygenase (46). The conversion of 17R-HDHA by human PMN displayed similar features as those established for the conversion of arachidonic acid to either leukotriene $B_4$ or lipoxins as well as the recently uncovered 18R series of EPA products (4, 9). These were modeled in vivo biosynthetic sequences of events using both plant (5-LO potato or 15-LO soybean) and human enzymes added in tandem "one pot" incubations that produce these compounds and matched those of human PMN and murine exudates (see Methods and Table 2). The findings with 17R-HDHA are of interest because the S isomer 17S-HDHA, a product of 15-lipoxygenase, can inhibit human neutrophil 5-lipoxygenase production of leukotrienes from endogenous substrate (47). Along these lines, it was found that 17R-HDHA was converted by isolated potato 5-LO to both 4S-hydro-(peroxy)-17R-hydroxy- and 7S-hydro-(peroxy)-17R-hydroxy-containing products that were reduced to 4S,17R-diHDHA and 7S,17R-diHDHA, respectively. These, as well as trihydroxy-DHA (see Table 2), are new products and indicate that 17R-HDHA is a substrate for 5-lipoxygenase and its epoxidase activity. The biogenic synthesis and physical properties of the compounds produced (i.e. major ions of the methyl ester trimethylsilyl-derivatives) with GC-MS analysis were consistent with the fragments obtained without derivatization using LC-MS-MS (see Table 2) and support the proposed structures as well as was both the murine exudate and human PMN biosynthesis from DHA (cf. 29 for monohydroxy products). Of interest, when added to human PMN, 17R-HDHA prevented formation of leukotrienes both in vitro with human PMN and in murine exudates (n=4; not shown).

Figure 5C:
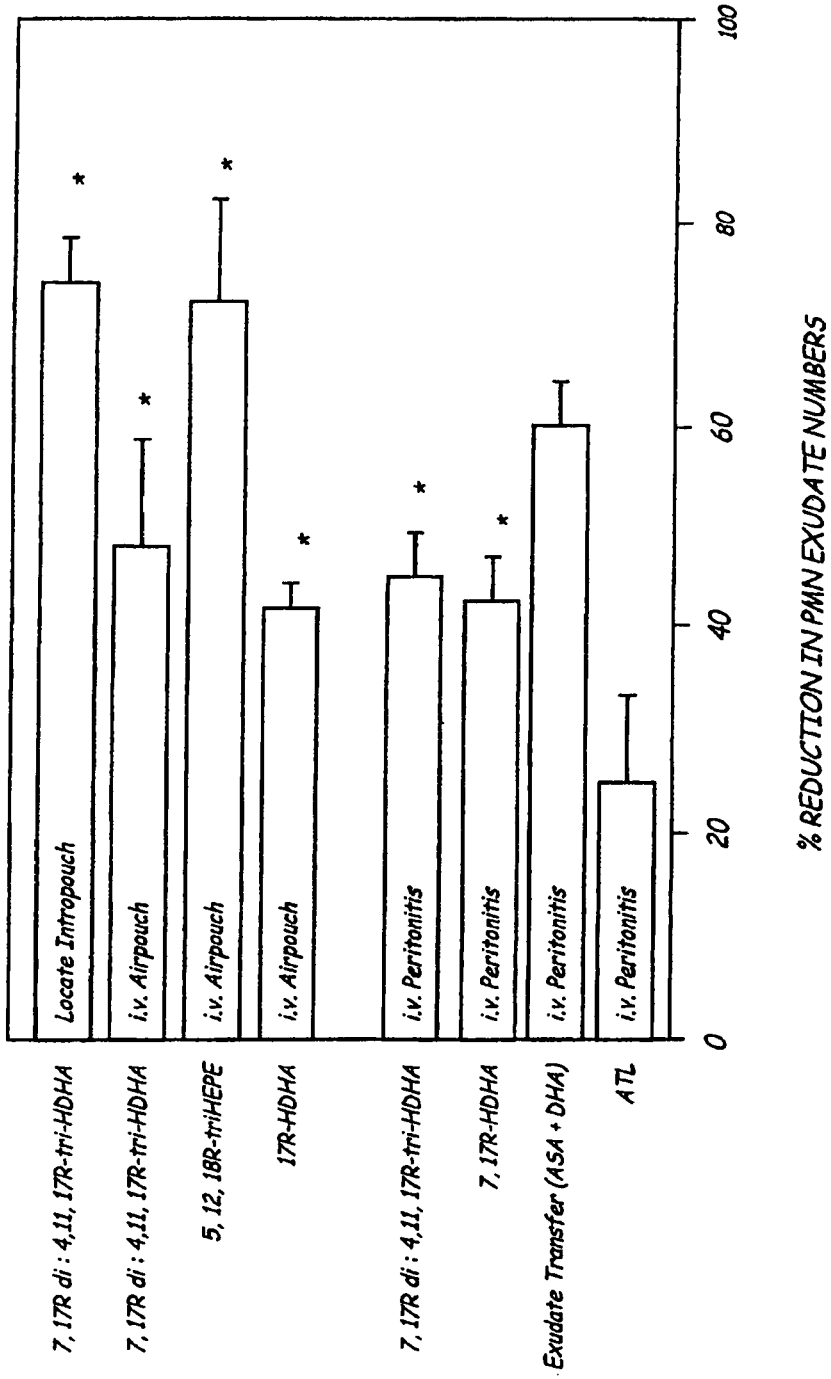

Inhibition of PMN Recruitment in Peritonitis and Air Pouch: Anti-Inflammatory Properties (i.v. And Topical) of Resolvins Although 17R-HDHA did not directly inhibit neutrophil transmigration in vitro (FIG. 5B), 17R-HDHA did regulate in vivo PMN exudate cell numbers in peritonitis as well as in the dermal air pouch (FIG. 5C). Also, 17R-HDHA was a potent inhibitor of zymosan-induced peritonitis, as were both the di- and tri-hydroxy-containing compounds (i.e. 7S,17R-diHDHA and 4S,11,17R-triHDHA). In addition to their ability to inhibit PMN recruitment when injected i.v. within zymosan-induced peritonitis, the 17R-hydroxy-HDHA-derived di- and trihydroxy-containing products proved to be potent regulators of leukocyte recruitment into the air pouch when administered i.v. as well as topically with local administration (FIG. 5C). Thus, the present results indicate that human and murine leukocytes convert 17R-HDHA to a novel series of 17R-hydroxy-containing di- and triHDHA; namely, an ASA-triggered circuit to utilize DHA to produce a 17R-series of docosanoids (FIG. 8).

The present results indicate that cells expressing cyclooxygenase-2 in exudates and brain treated with aspirin enzymatically transform omega-3 DHA to previously unrecognized compounds with bioactive properties in inflammation-resolution, i.e. a novel 17R series of di and tri-hydroxy-docosahexaenoic acids. The ASA-acetylated COX-2 present in these tissues generates predominantly 17R-HDHA that is converted further enzymatically to potent bioactive 17R series via lipoxygenation and epoxidation in leukocytes to both di- and tri-hydroxy-containing novel docosanoids (see FIG. 8). DHA is the most unsaturated of the omega-3 polyene family of fatty acids in mammalian and fish tissues. In humans, DHA is abundant in brain, retina, and testes (28, 48). The levels of DHA increase in adult human brain with age, which is required for optimal neural development (49) and DHA is rapidly esterified in retinal epithelium photoreceptors as well as into the phospholipids of resting human neutrophils (28, 50). At high micromolar values, DHA is held to possess both physiologic roles and direct action on neural voltage gated $K^+$ channels (51), binds RXR in neural tissues (52) and is held to be the active compound of fish oil supplements that is cardioprotective (21). Also, addition of DHA can correct and reverse the pathology associated with cystic fibrosis in cftr–/– mice (53). However, it is not clear from the results of these studies (21, 51, 52) or of the many reported clinical trials whether DHA is precursor to potent bioactive structures that are responsible for the many reported properties attributed to DHA itself in regulating biological systems of interest.

The three major lipoxygenases (i.e. 5-LO, 12-LO, and 15-LO) that act on arachidonate can each convert DHA to S-containing products, but their function in the immune system or elsewhere is not clear. In the brain, 12-lipoxygenase of pineal body converts DHA to 14S-HDHA and 15-lipoxygenase to 17S-HDHA (40). DHA can also be converted by human neutrophils to 7S-HDHA that does not stimulate chemotaxis (31), and retina converts DHA to both mono- and di-hydroxy products via lipoxygenase(s) (28). While not a substrate for COX-1 (43), oxidized isoprostane-like compounds can also be produced from DHA that appear to reflect oxidative free radical catalyzed events (54). Hence, the new 17R-hydroxy series of docosanoids generated by neural tissues, leukocytes, and inflammatory exudates uncovered in the present experiments and their role(s) are of interest in inflammation-resolution, a process now considered to be associated with many human diseases.

Although omega-3 fish oils encompassing both EPA and DHA could have a beneficial impact in the treatment of many chronic diseases (such as cardiovascular disease, atherosclerosis and asthma, as well as anti-tumor and anti-proliferative properties (15, 55)), the molecular rationale for their use remains of interest. Most of the earlier studies focused on uptake of omega-3 PUFA (i.e. EPA and DHA), namely their esterification into phospholipid and other lipid stores of many human tissues that in some cells reduces the availability of endogenous arachidonic acid for processing to pro-inflammatory prostaglandins (55). The body of results now available indicates that, in addition to pro-inflammatory roles, specific 15-lipoxygenase, 5-LO and/or LO-LO interaction products formed during cell-cell interactions such as lipoxins serve as endogenous anti-inflammatory mediators promoting resolution (9, 10, 12). Like other lipoxygenase-derived eicosanoids, lipoxins are potent-local acting in subnanomolar levels with precise stereochemical requirements for evoking their actions (4, 9). Hence, the production of 18R and 15R series products from EPA that inhibit PMN transmigration and inflammation within the low nanomolar range emphasizes the functional redundancies within chemical mediators produced from the omega-3 family of polyene fatty acids, namely the recently identified compounds from COX-2 EPA (2) or DHA-derived compounds as indicated from the present results (FIGS. 6-8). It is important to note that with these small molecular weight mediators subtle changes in chirality of alcohol—i.e. S to R—can change a compound from active to inactive or vice versa (3, 4, 9). In this regard, the 15R-hydroxy-containing compounds generated from either arachidonic acid or EPA and 18R series from EPA, as well as 17R-hydroxy series from DHA, each display similar functional redundancies in inflammation-resolution. Hence, uncovering the 17R series of both mono- and di-oxygenation products in inflammatory exudates and a role for COX-2 in the generation of the 17R-hydroxyl configuration in HDHA described here for the first time opens new avenues for considering the overall functional redundancies of mediators that dampen and/or counter the many pro-inflammatory signals to promote resolution.

Cyclooxygenase-2 is induced in most inflammatory cell types, but can also be constitutive in neural and vascular tissue (44, 56). The importance of the enlarged substrate tunnel in cyclooxygenase-2 becomes of interest when considering possible physiologic roles of this enzyme in these localities in vivo. It is now clear from numerous studies that aspirin has beneficial effects in and apart from other nonsteroidal anti-inflammatory drugs (57, 58). In this regard, aspirin has a unique ability to acetylate both isoforms of cyclooxygenase (COX-1 and COX-2). It is also noteworthy that DHA is cardioprotective in the ischemic heart (22) and that COX-2 is involved in preconditioning (19) as well as resolution (12). The present invention provides that DHA is a precursor and is converted to 17R-HDHA via aspirin-acetylated COX-2 at sites of inflammation in vivo (FIG. 1), murine brain (FIG. 3), and by acetylated recombinant COX-2 in vitro (FIG. 2). Both 13- and 17R-HDHA inhibit cytokine generation by microglial cells at the transcript level in the picomolar range (FIG. 5A). Human microglial cells generate these 17R-HDHA series products when given aspirin and TNF$\alpha$, which upregulate COX-2 expression (FIG. 3C). In addition, murine inflammatory exudates produced a family of novel di- and tri-hydroxy products that were also produced by human PMN via transcellular processing of 17R-HDHA. The proposed pathways for transcellular processing of acetylated COX-2-derived 17R-HDHA highlighting the generation of dioxygenated intermediates and epoxidation to form novel diHDHA during vascular inflammation-associated events are illustrated in FIG. 8.

It should be noted that these and related structures can be generated via cell-cell interactions or single cell types as depicted in FIG. 8, but could in theory also be produced via several sequential oxygenation routes by a single enzyme as well (see FIG. 8 legend). When these products were prepared by biogenic total synthesis and added back via topical administration into the air pouch, they inhibited TNF$\alpha$-induced leukocyte infiltration. Also, with i.v. administration these compounds inhibited leukocyte recruitment in both murine air pouch and in zymosan-induced peritonitis (FIG. 5). Taken together, these results indicate that aspirin-acetylated COX-2-derived products can downregulate cytokine generation and leukocyte (i.e., neutrophil) recruitment to sites of inflammation. The EPA-derived 5,12,18R series product proved to be as effective as a potent stable analog of 15-epi-lipoxin $A_4$ in preventing leukocyte diapedesis and exudate formation (see FIG. 5C). Since 17R-HDHA did not have a direct impact on human PMN transmigration in these conditions, but reduced exudate PMN numbers in vivo as well as regulates gene expression in human microglial cells, it is highly likely that a multi-level mechanism of action accounts for the in vivo properties of this ASA-triggered pathway. Moreover, there appear to be functional redundancies between the pathways in that the 18R series from EPA- and 17R series DHA-derived hydroxy-containing compounds share in their ability to regulate PMN exudate numbers (FIG. 5).

Emergence of the finding that arachidonic acid-derived lipoxins inhibit PMN trafficking and serve as endogenous anti-inflammatory mediators while activating monocytes in a nonphlogistic fashion (11, 59), as well as accelerating the uptake of apoptotic PMN by macrophages at sites of inflammation (28), indicates that not all lipoxygenase pathway products from the arachidonic acid precursor are "pro"-inflammatory. Given their longer half-life and bioavailability, the metabolically more stable analogs of these local-acting lipid mediators derived from arachidonate in vivo and prepared by total organic synthesis provide further evidence for their roles in promoting resolution (37). Moreover, these results suggest that the new resolving properties belong to a larger class of endogenous compounds with mechanisms directed towards enhancing resolution. Also, the link between anti-inflammation and enhanced endogenous antimicrobial activities (13) by lipoxins and aspirin-triggered lipoxins sets a unique precedent for the importance of cell-cell communication and transcellular biosynthesis in host defense and in the clearance and resolution of inflammatory sequelae.

The present results disclosing 17R series oxygenated DHA products and with the 15R and 18R series from eicosapentaenoic acid as prototypes (2), taken together, suggest that the generation of local-acting lipid mediators with beneficial actions relevant in human disease may not be restricted to arachidonic acid alone as an important precursor. Also, they indicate that transcellular biosynthesis unveils previously unrecognized pathways that are evoked by aspirin treatment with DHA. Acetylated COX-2 acts in an "R-oxygenation" mechanism to initiate the conversion of DHA to a 17R series of di- and tri-hydroxy docosanoids that display downregulatory actions in vivo in inflammation as do the omega-3 EPA-derived 18R-series-products. Hence, it follows that, once inflammation is initiated, upon aspirin treatment with omega-3 supplementation, these pathways can be operative in vascular tissues to generate products that appear to have properties as aspirin-triggered lipid mediators similar to those of either the 15-epi-lipoxins or 18R- and 15R series products from EPA. These compounds are generated via lipoxygenation followed by epoxidation and subsequent steps (FIG. 8 and cf. Ref. 2). Also of interest are the findings that, in the absence of aspirin, COX-2 converts DHA to 13-HDHA, a previously unknown route that might also be relevant in tissues that constitutively express COX-2, which is also converted to dihydroxy DHA products (4,13-diHDHA, 7,13-diHDHA, and 13,20-diHDHA), and during resolution, induction and conversion by 15-lipoxygenase (10) to 10,17S-diHDHA and 7S,17S-diHDHA (See FIGS. 10, 11, 12, and 14).

Since the properties of the omega-3-derived products from acetylated COX-2 via transcellular biosynthesis appear to dampen events in inflammation apparently in a functionally redundant fashion (i.e. 17R-HDHA series, 18R- and 15R-HEPA series), the term "Resolvins" is introduced for this family of new compounds and bioactions. Resolvins, by definition, are endogenously generated within the inflammatory resolution phase and downregulate leukocytic exudate cell numbers to prepare for orderly and timely resolution. The present results indicate that the 17R series of di- and trihydroxy DHA pathways are potent in models relevant in inflammation. It is likely that these compounds will also have actions in other tissues, in view of the many reports of the clinical actions for EPA and DHA, where high concentrations of these PUFA are used and required to evoke responses in vitro. The present results indicate that cell-cell interactions at sites of inflammation-resolution utilize omega-3 fatty acids to generate novel omega-3-derived products including 17R-HDHA series and 18R-HEPE series of oxygenated bioactive products termed Resolvins (FIGS. 8 and 13). Given their potent actions, the production of Resolvins may, in part, provide a rationale underlying the beneficial actions of omega-3 fatty acids (15-22) in chronic immune and vascular diseases as well as serve as new biotemplates for therapeutic development.

TABLE 1

Impact of NSAIDs on COX-2 conversion of DHA

| NSAID | % Inhibition of 13-HDHA | % Increase of 17-HDHA |
|---|---|---|
| ASA | 85.7 ± 5.6% | 97.8 ± 2.0% |
| Indomethacin | 89.8 ± 0.5% | 0.0% |
| Acetaminophen | 87.7 ± 4.3% | 0.0% |
| NS398 (COX-2 inhibitor) | 97.3 ± 1.0% | 0.0% |

Results are the mean±SEM, n=3. Products were extracted, identified, and quantitated using deuterium internal standards and LC-MS-MS (see Methods). NSAIDs were incubated 30 min with human recombinant COX-2 (see Methods); ASA [2 mM], indomethacin [200 µM], acetaminophen (500 µM), and NS398 (100 µM).

Airway Inflammation Discussions

Docosatrienes are newly identified natural chemical mediators derived from the essential ω-3 fatty acid docosahexaenoic acid (DHA) that reduce leukocyte transmigration and activation in vivo. In asthma, levels of DHA are decreased in the respiratory tract, so the formation of anti-inflammatory mediators derived from DHA and their actions are of interest in lung.

Methods and Findings:

Using an experimental model of asthma, the present invention provides the first evidence for the generation of Protectin D1 (PD1,10,17S-docosatriene) from DHA by respiratory tissues. When physiologic amounts were administered to allergic animals prior to allergen aerosol challenge, PD1 blocked airway inflammation and reduced airway hyper-responsiveness to inhaled methacholine. After allergen sensitization and aerosol challenge, PD1 selectively reduced airway eosinophils, lymphocytes and the levels of established pro-inflammatory mediators, including interleukin-13, cysteinyl leukotrienes and prostaglandin $D_2$.

The formation of this novel DHA-derived mediator during airway inflammation and its regulation of allergic airway responses provide evidence for endogenous PD1 (also coined neuroprotectin D1 when generated in neural tissues) as a pivotal counter-regulatory axis in the lung. Moreover, these results suggest new therapeutic strategies for asthma that focus on this new pathway in the lung.

Asthma is characterized by chronic airway inflammation with large numbers of eosinophils and T lymphocytes infiltrating respiratory tissues (Busse et al. 2001). These leukocytes further amplify the airway inflammation by trafficking into the lung an increased capacity to generate both pro-inflammatory peptides and lipid mediators, such as $T_H2$ cytokines and cysteinyl leukotrienes (CysLTs) (Busse and Lemanske 2001). In addition, $T_H2$ cytokines up-regulate the expression of biosynthetic enzymes for eicosanoids-including both LTs and lipoxins (LXs) (Levy et al. 2003). Surprising results recently indicated that arachidonic acid (C20:4) is not the only fatty acid precursor converted to potent bioactive mediators during inflammation and resolution. Distinct from their actions on C20:4, many biosynthetic enzymes for prostaglandins (PGs), LTs and LXs can also metabolize other essential fatty acids, including docosahexaenoic acid (DHA), to potent bioactive compounds (Serhan et al. 2000; Serhan et al. 2002; Hong et al. 2003).

DHA (C22:6, ω-3) is incorporated into cell membranes and rapidly released upon cell activation for conversion via independent pathways to potent local mediators with pro-resolving actions. Hence, their recent naming as "resolvins" (i.e., formed during resolution via cell-cell interactions) (Serhan, Hong et al. 2002; Gilroy et al. 2004). During cell-cell interactions, C22:6 is converted to 17S-hydroxy containing resolvins of the D series (because they are from DHA) and docosatrienes (e.g., 10,17S-dihydroxy-4,7,15,19-cis-11,13-trans-docosahexaenoic, also named neuroprotectin D1 (NPD1) when generated by neural cells (Mukherjee et al. 2004)). 10,17S-docosatriene (10,17S-DT) is generated via a 16,17S-epoxide intermediate, indicating a role for 15-lipoxygenase (LO)-like activity and/or related enzymes (Hong, Gronert et al. 2003). Human lung is rich in LO activities, particularly 15-LO (Hunter et al. 1985). During inflammation, increased numbers of leukocytes (that carry 5-LO) traffic to the lung (Busse and Lemanske 2001), and eosinophils (EOS), prominent in asthmatic lung, also carry 5- and 15-LO activity (Levy and Serhan 2003). Therefore, several potential biosynthetic routes that can participate in the biosynthesis of resolvins and docosatrienes are in place in the lung during allergic airway inflammation.

It is now discovered that 10,17S-DT is generated from endogenous sources in allergic airway inflammation and reduces both airway inflammation and hyper-responsiveness. On the basis of a protective role for this docosatriene in stroke and retina (Mukherjee, Marcheselli et al. 2004), this chemical mediator was coined NeuroprotectinD1 (NPD1) (Serhan et al. 2004). Like its local neuroprotective actions (Mukherjee, Marcheselli et al. 2004), 10,17S-DT is generated by human leukocytes in vitro and stops the recruitment and activation of murine neutrophils (PMNs) in vivo, providing evidence for more general counter-regulatory actions in inflammation (Hong, Gronert et al. 2003). Because 10,17S-DT (NPD1) also protects from the aberrant effects of excess airway inflammation when generated outside of the central nervous system, therefore, this same material be more generally termed Protectin D1 (PD 1).

PD1 is Endogenously Generated in Allergic Lung

To determine if DHA-derived products are present in inflamed respiratory tissues, we analyzed lipid extracts from the lungs of mice after sensitization and aerosol challenge with allergen. FIG. 19 shows that PD 1 was generated from endogenous sources during allergic airway inflammation (2.01+/−0.68 ng/mouse lungs, mean+/−SEM for n=3). Addition of exogenous DHA to a homogenate of the inflamed lungs ex vivo increased PD1 recovery by approximately 5-fold.

Allergic Airway Inflammation Decreases with PD1

To determine if PD1 and Resolvin E1 had properties of a counter-regulatory mediator during airway inflammation, physiologically relevant quantities (2, 20 or 200 ng) were administered by intravenous injection to allergen sensitized animals just prior (30 min) to aerosol challenge on 4 consecutive days. Animals receiving PD1 had substantially less eosinophils (EOS) and lymphocytes (Lymphs) in the peribronchiolar regions and airspaces compared to control mice that received only vehicle (FIG. 20). Morphometric analyses identified significant decreases in EOS tissue infiltration around vessels and in the large and peripheral airways (FIG. 21a). In addition, edema and epithelial hyperplasia were also markedly decreased. In BAL fluid, PD1 and Resolvin E1 decreased total leukocytes, EOS, and Lymphs in a concentration-dependent manner (FIGS. 21b and 24), and levels of peptide and lipid pro-inflammatory mediators were selectively reduced (FIG. 22). PD1 administration blocked allergen-induced increases in IL-13, CysLTs and $PGD_2$, all of which have been assigned pivotal roles in asthma pathobiology (Wills-Karp et al. 1998; Matsuoka et al. 2000; Vachier et al. 2003). In conjunction with decreased airway inflammation, levels of the counter-regulatory eicosanoid $LXA_4$ were also diminished in the presence of PD1 (data not shown). No behavioral or physical signs of toxicity with PD1 treatment were observed. Together, these results indicate that PD1, in nanogram quantities, significantly reduced allergic pulmonary inflammation, and suggests that its mechanism of action is distinct from LXs.

PD1 Blocks Airway Hyper-Responsiveness

Because increased airway reactivity is a diagnostic hallmark of asthma, it was also determined if PD 1 regulated airway hyper-responsiveness to inhaled methacholine. After allergen sensitization and aerosol challenge in the presence of PD 1 (0-200 ng), animals were ventilated and exposed (10 sec) to increasing concentrations of inhaled methacholine (0, 20, 50 and 75 mg). Consistent with the regulation of airway inflammation, PD1 also decreased both peak and average lung resistance in response to methacholine in a concentration-dependent manner (FIG. 23). These results indicate that methacholine-induced bronchoconstriction is significantly reduced by administration of PD 1.

The present invention provides PD1 as a natural product of a new C22:6 signaling pathway (Serhan, Hong et al. 2002; Hong, Gronert et al. 2003) during respiratory tract inflammation that displays potent counter-regulatory actions on key asthma phenotypes, namely airway leukocyte accumulation and hyper-responsiveness. Docosatrienes, such as PD1, were first identified in murine exudates and human brain, blood and glial cells that can serve as a single cell type for PD1 production (Hong, Gronert et al. 2003). Airway inflammation triggered PD1 formation in vivo with a product-precursor relationship to C22:6 in the lung. Similarly, the generation of PD1 occurs in the setting of multicellular events in vivo during brain ischemia-reperfusion injury and ex vivo by activated human whole blood (Hong, Gronert et al. 2003; Marcheselli et al. 2003). The biosynthesis of PD1 proceeds via enzymatic conversion of DHA to 17S-hydroperoxy and 16,17S-epoxide intermediates (Hong, Gronert et al. 2003). Lipoxygenases and epoxide hydrolases are both prominent classes of enzymes in asthmatic lung that are induced by pivotal regulators of allergy, including specific $T_H2$ cytokines (Munafo et al. 1994; Nassar et al. 1994; Pouliot et al. 1994; Zaitsu et al. 2000). This indicates the presence of specialized enzyme systems in the lung for this new DHA pathway for conversion to biologically active mediators during airway inflammation.

Eosinophilic airway inflammation and airway hyper-responsiveness are characteristic features of asthma. Eosinophil recruitment to the lung in asthma is primarily a consequence of $T_H2$ lymphocyte activation (Busse and Lemanske 2001), which was reduced by as little as 2 ng of PD1. Levels of $T_H2$ cytokines in BAL fluid and the number of lymphocytes in both BAL fluid and lung tissue were decreased. In addition, PD 1 dampened hyper-responsiveness to methacholine in the inflamed airway. Together, these findings provide evidence for potent, concentration-dependent reduction of both $T_H2$ lymphocytes and eosinophil responses in vivo. Lymphocyte and eosinophil activation in the lung are held to contribute to asthma pathobiology. In addition, PMN activation contributes to the pathobiology of asthma exacerbation (Fahy et al. 1995) and severity (Wenzel et al. 1997), and PD1 also carries systemic and topical anti-inflammatory actions for PMNs in vivo (Hong, Gronert et al. 2003; Marcheselli, Hong et al. 2003). PD1 is a potent negative regulator of PMN-mediated tissue injury and cytokine gene expression in experimental stroke (Mukherjee, Marcheselli et al. 2004). When discovered in the nervous system, this bioactive product was coined neuroprotectin D1 (NPD1) (Mukherjee, Marcheselli et al. 2004) because it decreased brain leukocyte infiltration, IL-1β-induced NFκB activation and COX-2 expression to elicit neuroprotection (Marcheselli, Hong et al. 2003; Mukherjee, Marcheselli et al. 2004). Slightly increased concentrations of PD1 were required for reduction of airway hyper-responsiveness than that observed for parameters of inflammation (e.g., BAL leukocytes, IL-13, $PGD_2$), suggesting potentially distinct sites and/or mechanisms of action for PD1 in airway resident cells and leukocytes. The local generation of PD1 in allergic inflammation together with counter-regulatory properties in the airway broadens its potential cellular sources in vivo and actions to new leukocyte classes and tissue resident cells and points to a more generalized counter-regulatory function as an autacoid in inflammation.

LXs are also generated in asthma and serve as potent inhibitors of both airway inflammation and airway hyper-responsiveness (Levy et al. 2002). While there is some overlap in the pattern of cytokine regulation for PD 1 and an aspirin-triggered LX stable analog in this murine model of asthma, some key differences were observed. First, while both mediators blocked IL-13 and CysLT generation and had no significant effect on IL-12 levels (Levy, De Sanctis et al. 2002), the inhibitory concentrations of PD1 were 1 to 2 log orders more potent than the LX analog. Secondly, IL-5 production was reduced by the LX stable analog, but not PD1. Third, administration of PD1 led to decreased airway levels of $LXA_4$, suggesting that the circuit for PD1 formation and actions is separate and independent of LX signaling in the murine lung. In aggregate, these findings indicate the presence of unique homeostatic pathways for DHA derived bioactive mediators in the lung.

It was noted that DHA levels in the respiratory tract are decreased in asthma and other diseases of excess airway inflammation, such as cystic fibrosis (Freedman et al. 2004). Moreover, formation of counter-regulatory LXs is defective in severe forms of both these illnesses (Sanak et al. 2000; Karp et al. 2004). The apparently low tissue levels of DHA in these conditions do not take into consideration the local concentrations in select tissue compartments or cell types that are likely to be enriched with DHA, such as that observed in the retina relative to whole brain (Mukherjee, Marcheselli et al. 2004). Given its counter-regulatory properties, decreased formation of PD 1 from low levels of DHA would adversely impact control of airway inflammation and hyper-responsiveness. While observational studies have identified an increased risk of asthma in populations with diets low in DHA, interventional trials with DHA supplementation have not consistently improved clinical outcomes (Woods et al. 2002), despite altering the responses of isolated leukocytes to inflammatory stimuli (Lee et al. 1984). In contrast, nutritional supplementation with ω-3 essential fatty acids has proven beneficial in cystic fibrosis and the acute respiratory distress syndrome, clinical disorders of excess PMN-mediated inflammation (Gadek et al. 1999; Beckles Willson et al. 2002). Because the molecular rationale for these beneficial effects is uncertain, there remain many potential reasons for the lack of clinical success with DHA feeding in asthma, including purity, dose, time course and difficulties tolerating the ingestion of large amounts of fish oils for extended periods of time (Spector et al. 2003). Identification of PD1 as a DHA-derived counter-regulatory autacoid in the lung opens the door to new mechanism-based therapeutic strategies in airway inflammation.

These results are the first demonstration of PD 1 formation in the lung from DHA and identify direct protective and regulatory roles for this novel mediator in allergic inflammation and airway hyper-responsiveness. In light of its ability to strongly reduce both of these key asthma phenotypes, the PD1 pathway may offer new therapeutic approaches for asthma. Moreover, the results indicate that endogenous conversion of DHA to PD1 represents a potential mechanism for the therapeutic benefits derived from diets rich in this ω-3 essential fatty acid in maintaining respiratory homeostasis.

Methods

Sensitization and Challenge Protocols.

Five to seven week old male FvB mice (Charles River Laboratories, Wilmington, Mass.) were housed in isolation cages under viral antibody-free conditions. Mice were fed a standard diet (Laboratory Rodent Diet 5001, PMI Nutrition International, Richmond, Ind.) that contained no less than 4.5% total fat with 0.26% omega-3 fatty acids and <0.01% C20:4. After Harvard Medical Area IRB approval (Protocol #02570), mice were sensitized with intraperitoneal injections of ovalbumin (OVA) (Grade III; Sigma Chemical Co., St. Louis, Mo.) (10 µg) plus 1 mg aluminum hydroxide (ALUM) (J. T. Baker Chemical Co.; Phillipsburg, N.J.) as adjuvant in 0.2 ml PBS on days 0 and 7. On days 14, 15, 16 and 17, the mice received PD1 (2, 20 or 200 ng), Resolvin E1 (200 ng) (products of biogenic synthesis (Hong, Gronert et al. 2003)), or PBS with 1.6 mM $CaCl_2$ and 1.6 mM $MgCl_2$ (0.1 ml) by intravenous injection 30 min prior to an aerosol challenge containing either PBS or 6% OVA for 25 min/day. On day 18, 24 h after the last aerosol challenge, airway responsiveness to aerosolized methacholine (0, 20, 50 and 75 mg, 10 sec) was measured, bilateral bronchoalveolar lavage (BAL) (2 aliquots of 1 ml PBS plus 0.6 mM EDTA) was performed or tissues were harvested for histological analysis. Lung resistance was measured using a Flexivent ventilator (SciReq, Montreal, Quebec). Resistance was measured as a function of time for each animal, and peak and average values for each dose of methacholine were recorded. No BAL or histological analysis was performed on those animals undergoing airway hyper-responsiveness or lipid extraction studies.

Allergen-Initiated Respiratory Inflammation.

Tissue morphometry was performed by a member (K. Haley) of the Lung Histopathology Core Laboratory at Brigham and Women's Hospital who was blinded to the experimental conditions prior to histological analyses. Three fields per slide were examined at 200× magnification for vessels, large airways and alveoli with EOS counted at 400× magnification in randomly assigned fields. Vessels were identified by perivascular smooth muscle, and large airways were identified by at least ½ their diameter either cuboidal or columnar epithelia. Measurement of inflammatory mediators was determined in cell-free BAL fluid (2000 g, 10 min) by sensitive and specific ELISAs, in tandem, for interleukin-5 (IL-5), IL-12, IL-13, $PGD_2$ (R&D Systems, Minneapolis, Minn.), cysteinyl LTs, (Cayman Chemical Co, Ann Arbor, Mich.), and $LXA_4$ (Neogen, Lexington, Ky.). Cells in BALF were resuspended in PBS, enumerated by hemocytometer, and concentrated onto microscope slides by cytocentrifuge (STATspin) (265 g). Cells were stained with a Wright-Giemsa stain (Sigma Chemical Co.) to determine leukocyte differentials (after counting ≥200 cells).

PD1 Extraction from Murine Lung.

After flushing blood from the pulmonary circulation with 2 ml PBS, whole murine lungs were removed from OVA-sensitized/OVA-challenged and control mice on Day 18. Using a manual dounce, lungs were gently homogenized for direct lipid extraction in MeOH or in some cases were warmed (5 min, 37° C.) in PBS, and incubated (40 min, 37° C.) in the absence or presence of DHA (100 µg). Reactions were stopped with 10 volumes of iced MeOH and stored at −20° C. overnight. Lipids were extracted using C18 cartridges (Alltech) and deuterium-labeled $PGE_2$ as an internal standard to correct for losses during extraction (Hong, Gronert et al. 2003). Materials eluting in the methyl formate fraction were taken to HPLC coupled to a photo-diode-array detector and tandem mass spectrometry (LC-PDA-MS-MS, ThermoFinnigan, San Jose, Calif.) for lipidomic analyses. PD1 was identified by retention time, UV absorbance (λmax 270 nm with shoulders at 260 and 281 nm) and at least 5 diagnostic MS-MS ions (m/z 359 [M-H], 341 ([M-H]-$H_2O$; base peak), 315 ([M-H]—$CO_2$), 297 ([M-H]-$2H_2O$, —$CO_2$), plus additional ions defining the C10 or C17 hydroxyl (i.e., 289, 261, 205, 181, and 153) (FIG. 1). The quantitation of PD1 was determined following LC-MS-MS analyses using a calibration curve ($r^2$=0.991) and the area beneath the peak obtained via selective ion monitoring.

REFERENCES

1. Clària, J., and C. N. Serhan. 1995. Aspirin triggers previously undescribed bioactive eicosanoids by human endothelial cell-leukocyte interactions. *Proc. Natl. Acad. Sci. USA* 92:9475-9479.
2. Serhan, C. N., C. B. Clish, J. Brannon, S. P. Colgan, N. Chiang, and K. Gronert. 2000. Novel functional sets of lipid-derived mediators with antiinflammatory actions generated from omega-3 fatty acids via cyclooxygenase 2-nonsteroidal antiinflammatory drugs and transcellular processing. *J. Exp. Med.* 192:1197-1204.
3. Samuelsson, B. 1982. From studies of biochemical mechanisms to novel biological mediators: prostaglandin endoperoxides, thromboxanes and leukotrienes. In Les Prix Nobel: Nobel Prizes, Presentations, Biographies and Lectures. Almqvist & Wiksell, Stockholm. 153-174.
4. Samuelsson, B., S. E. Dahlén, J. A. Lindgren, C. A. Rouzer, and C. N. Serhan. 1987. Leukotrienes and lipoxins: structures, biosynthesis, and biological effects. *Science* 237:1171-1176.
5. Gunstone, F. D., J. L. Harwood, and F. B. Padley. 1994. The Lipid Handbook. 2nd ed. Chapman & Hall, London. 551 pp.
6. Zeldin, D. C. 2001. Epoxygenase pathways of arachidonic acid metabolism. *J. Biol. Chem.* 276:36059-36062.
7. Marcus, A. J. 1999. Platelets: their role in hemostasis, thrombosis, and inflammation. In Inflammation: Basic Principles and Clinical Correlates. J. I. Gallin and R. Snyderman, editors. Lippincott Williams & Wilkins, Philadelphia. 77-95.
8. Palmantier, R., and P. Borgeat. 1991. Transcellular metabolism of arachidonic acid in platelets and polymorphonuclear leukocytes activated by physiological agonists: enhancement of leukotriene $B_4$ synthesis. In Cell-Cell Interactions in the Release of Inflammatory Mediators, vol. 314. P. Y.-K. Wong and C. N. Serhan, editors. Plenum, N.Y. 73-89.
9. Serhan, C. N., and E. Oliw. 2001. Unorthodox routes to prostanoid formation: new twists in cyclooxygenase-initiated pathways. *J. Clin. Invest.* 107:1481-1489.
10. Levy, B. D., C. B. Clish, B. Schmidt, K. Gronert, and C. N. Serhan. 2001. Lipid mediator class switching during acute inflammation: signals in resolution. *Nature Immunol.* 2:612-619.
11. McMahon, B., S. Mitchell, H. R. Brady, and C. Godson. 2001. Lipoxins: revelations on resolution. *Trends in Pharmacological Sciences* 22:391-395.
12. Bandeira-Melo, C., M. F. Serra, B. L. Diaz, R. S. B. Cordeiro, P. M. R. Silva, H. L. Lenzi, Y. S. Bakhle, C. N. Serhan, and M. A. Martins. 2000. Cyclooxygenase-2-derived prostaglandin $E_2$ and lipoxin $A_4$ accelerate resolution of allergic edema in *Angiostrongylus costaricensis*-infected rats: relationship with concurrent eosinophilia. *J. Immunol.* 164:1029-1036.

13. Canny, G., O. Levy, G. T. Furuta, S, Narravula-Alipati, R. B. Sisson, C. N. Serhan, and S. P. Colgan. 2002. Lipid mediator-induced expression of bactericidal/permeability-increasing protein (BPI) in human mucosal epithelia. *Proc. Natl. Acad. Sci. USA* 99:3902-3907.

14. Rowley, A. F., D. J. Hill, C. E. Ray, and R. Munro. 1997. Haemostasis in fish—an evolutionary perspective. *Thromb. Haemost.* 77:227-233.

15. De Caterina, R., S. Endres, S. D. Kristensen, and E. B. Schmidt, editors. 1993. *n-3 Fatty Acids and Vascular Disease*. Springer-Verlag, London.

16. Hibbeln, J. R. 1998. Fish consumption and major depression. *Lancet* 351:1213.

17. Olfson, M., S. C. Marcus, B. Druss, L. Elinson, T. Tanielian, and H. A. Pincus. 2002. National trends in the outpatient treatment of depression. *JAMA* 287:203-209.

18. Albert, C. M., H. Campos, M. J. Stampfer, P. M. Ridker, J. E. Manson, W. C. Willett, and J. Ma. 2002. Blood levels of long-chain n-3 fatty acids and the risk of sudden death. *N. Engl. J. Med.* 346:1113-1118.

19. Shinmura, K., X.-L. Tang, Y. Wang, Y.-T. Xuan, S.-Q. Liu, H. Takano, A. Bhatnagar, and R. Bolli. 2000. Cyclooxygenase-2 mediates the cardioprotective effects of the late phase of ischemic preconditioning in conscious rabbits. *Proc. Natl. Acad. Sci. USA* 97:10197-10202.

20. GISSI-Prevenzione Investigators. 1999. Dietary supplementation with n-3 polyunsaturated fatty acids and vitamin E after myocardial infarction: results of the GISSI-Prevenzione trial. Gruppo Italiano per lo Studio della Sopravvivenza nell'Infarto miocardico. *Lancet* 354(9177):447-455.

21. Marchioli, R., F. Barzi, E. Bomba, C. Chieffo, D. Di Gregorio, R. Di Mascio, M. G. Franzosi, E. Geraci, G. Levantesi, A. P. Maggioni, L. Mantini, R. M. Marfisi, G. Mastrogiuseppe, N. Mininni, G. L. Nicolosi, M. Santini, C. Schweiger, L. Tavazzi, G. Tognoni, C. Tucci, and F. Valagussa. 2002. Early protection against sudden death by n-3 polyunsaturated fatty acids after myocardial infarction: time-course analysis of the results of the Gruppo Italiano per lo Studio della Sopravvivenza nell'Infarto Miocardico (GISSI)-Prevenzione. *Circulation* 105:1897-1903.

22. McLennan, P., P. Howe, M. Abeywardena, R. Muggli, D. Raederstorff, M. Mano, T. Rayner, and R. Head. 1996. The cardiovascular protective role of docosahexaenoic acid. *Eur. J. Pharmacol.* 300:83-89.

23. Libby, P. 2002. Atherosclerosis: the new view. *Sci. Am.* 286:46-55.

24. Drazen, J. M., E. K. Silverman, and T. H. Lee. 2000. Heterogeneity of therapeutic responses in asthma. *Br. Med. Bull.* 56:1054-1070.

25. Vane, J. R., and R. M. Botting, editors. 2001. *Therapeutic Roles of Selective COX-2 Inhibitors*. William Harvey Press, London.

26. Rowlinson, S. W., B. C. Crews, D. C. Goodwin, C. Schneider, J. K. Gierse, and L. J. Marnett. 2000. Spatial requirements for 15-(R)-hydroxy-5Z,8Z,11Z,13E-eicosatetraenoic acid synthesis within the cyclooxygenase active site of murine COX-2. *J. Biol. Chem.* 275:6586-6591.

27. Gilroy, D. W., P. R. Colville-Nash, D. Willis, J. Chivers, M. J. Paul-Clark, and D. A. Willoughby. 1999. Inducible cycloxygenase may have anti-inflammatory properties. *Nature Med.* 5:698-701.

28. Bazan, N. G., E. B. Rodriguez de Turco, and W. C. Gordon. 1993. Pathways for the uptake and conservation of docosahexaenoic acid in photoreceptors and synapses: biochemical and autoradiographic studies. *Can. J. Physiol. Pharmacol.* 71:690-698.

29. Whelan, J., P. Reddanna, V. Nikolaev, G. R. Hildenbrandt, and T. S. Reddy. 1990. The unique characteristics of the purified 5-lipoxygenase from potato tubers and the proposed mechanism of formation of leukotrienes and lipoxins. In Biological Oxidation Systems, vol. 2. Academic Press. 765-778.

30. Fischer, S., C.v. Schacky, W. Siess, T. Strasser, and P. C. Weber. 1984. Uptake, release and metabolism of docosahexaenoic acid (DHA, C22:6$\omega$3) in human platelets and neutrophils. *Biochem. Biophys. Res. Commun.* 120:907-918.

31. Lee, T. H., J.-M. Mencia-Huerta, C. Shih, E. J. Corey, R. A. Lewis, and K. F. Austen. 1984. Effects of exogenous arachidonic, eicosapentaenoic, and docosahexaenoic acids on the generation of 5-lipoxygenase pathway products by ionophore-activated human neutrophils. *J. Clin. Invest.* 74:1922-1933.

32. Yergey, J. A., H.-Y. Kim, and N. Salem, Jr. 1986. High-performance liquid chromatography/thermospray mass spectrometry of eicosanoids and novel oxygenated metabolites of docosahexaenoic acid. *Anal. Chem.* 58:1344-1348.

33. Clish, C. B., B. D. Levy, N. Chiang, H.-H. Tai, and C. N. Serhan. 2000. Oxidoreductases in lipoxin $A_4$ metabolic inactivation. *J. Biol. Chem.* 275:25372-25380.

34. Colgan, S. P., C. N. Serhan, C. A. Parkos, C. Delp-Archer, and J. L. Madara. 1993. Lipoxin $A_4$ modulates transmigration of human neutrophils across intestinal epithelial monolayers. *Journal of Clinical Investigation* 92:75-82.

35. George, H. J., D. E. Van Dyk, R. A. Straney, J. M. Trzaskos, and R. A. Copeland. 1996. Expression purification and characterization of recombinant human inducible prostaglandin G/H synthase from baculovirus-infected insect cells. *Protein Expres. Purif.* 7:19-26.

36. Gronert, K., C. B. Clish, M. Romano, and C. N. Serhan. 1999. Transcellular regulation of eicosanoid biosynthesis. In Eicosanoid Protocols. E. A. Lianos, editor. Humana Press, Totowa, N.J. 119-144.

37. Serhan, C. N., J. F. Maddox, N. A. Petasis, I. Akritopoulou-Zanze, A. Papayianni, H. R. Brady, S. P. Colgan, and J. L. Madara. 1995. Design of lipoxin $A_4$ stable analogs that block transmigration and adhesion of human neutrophils. *Biochemistry* 34:14609-14615.

38. Qiu, F.-H., P. R. Devchand, K. Wada, and C. N. Serhan. 2001. Aspirin-triggered lipoxin $A_4$ and lipoxin $A_4$ up-regulate transcriptional corepressor NAB1 in human neutrophils. *FASEB J.*:10.1096/fj.1001-0576fje (available at www.fasebj.org).

39. Cotran, R. S., V. Kumar, and T. Collins. 1999. Cellular pathology I: cell injury and cell death. In Robbins Pathologic Basis of Disease. R. S. Cotran, V. Kumar and T. Collins, editors. W.B. Saunders, Philadelphia. 1-29.

40. Sawazaki, S., N. Salem, Jr., and H.-Y. Kim. 1994. Lipoxygenation of docosahexaenoic acid by the rat pineal body. *J. Neurochem.* 62:2437-2447.

41. Miller, C. C., W. Tang, V. A. Ziboh, and M. P. Fletcher. 1991. Dietary supplementation with ethyl ester concentrates of fish oil (n-3) and borage oil (n-6) polyunsaturated fatty acids induces epidermal generation of local putative anti-inflammatory metabolites. *J. Invest. Dermatol.* 96:98-103.

42. Xiao, G., A.-L. Tsai, G. Palmer, W. C. Boyar, P. J. Marshall, and R. J. Kulmacz. 1997. Analysis of hydroperoxide-induced tyrosyl radicals and lipoxygenase activity in aspirin-treated human prostaglandin H synthase-2. *Biochemistry* 36:1836-1845.

43. Corey, E. J., C. Shih, and J. R. Cashman. 1983. Docosahexaenoic acid is a strong inhibitor of prostaglandin but not leukotriene biosynthesis. *Proc. Natl. Acad. Sci. USA* 80:3581-3584.

44. O'Banion, M. K., V. D. Winn, and D. A. Young. 1992. *Proc. Natl. Acad. Sci. USA* 89:4888-4892.

45. Schmedtje, J. F., Jr., Y.-S. Ji, W.-L. Liu, R. N. DuBois, and M. S. Runge. 1997. Hypoxia induces cyclooxygenase-2 via the NF-κB p65 transcription factor in human vascular endothelial cells. *J. Biol. Chem.* 272:601-608.

46. Shimizu, T., O. Rådmark, and B. Samuelsson. 1984. Enzyme with dual lipoxygenase activities catalyzes leukotriene $A_4$ synthesis from arachidonic acid. *Proc. Natl. Acad. Sci. USA* 81:689-693.

47. Ziboh, V. A., C. C. Miller, and Y. Cho. 2000. Metabolism of polyunsaturated fatty acids by skin epidermal enzymes: generation of antiinflammatory and antiproliferative metabolites. *Am. J. Clin. Nutr.* 71(Suppl.):361S-366S.

48. Simopoulos, A. P., A. Leaf, and N. Salem, Jr. 1999. Workshop on the essentiality of an recommended dietary intakes for omega-6 and omega-3 fatty acids. *J. Am. Coll. Nutr.* 18:487-489.

49. Salem, N., Jr., B. Wegher, P. Mena, and R. Uauy. 1996. Arachidonic and docosahexaenoic acids are biosynthesized from their 18-carbon precursors in human infants. *Proc. Natl. Acad. Sci. USA* 93:49-54.

50. Tou, J.-s. 1986. Acylation of docosahexaenoic acid into phospholipids by intact human neutrophils. *Lipids* 21:324-327.

51. Poling, J. S., S. Vicini, M. A. Rogawski, and N. Salem, Jr. 1996. Docosahexaenoic acid block of neuronal voltage-gated $K^+$ channels: subunit selective antagonism by zinc. *Neuropharmacology* 35:969-982.

52. Mata de Urquiza, A., S. Liu, M. Sjöberg, R. H. Zetterstrom, W. Griffiths, J. Sjövall, and T. Perlmann. 2000. Docosahexaenoic acid, a ligand for the retinoid X receptor in mouse brain. *Science* 290:2140-2144.

53. Freedman, S. D., D. Weinstein, P. G. Blanco, P. Martinez-Clark, S. Urman, M. Zaman, J. D. Morrow, and J. G. Alvarez. 2002. Characterization of LPS-induced lung inflammation in cftr$^{-/-}$ mice and the effect of docosahexaenoic acid. *J. Appl. Physiol.* 92:2169-2176.

54. Reich, E. E., W. E. Zackert, C. J. Brame, Y. Chen, L. J. Roberts, II, D. L. Hachey, T. J. Montine, and J. D. Morrow. 2000. Formation of novel D-ring and E-ring isoprostane-like compounds ($D_4/E_4$-neuroprostanes) in vivo from docosahexaenoic acid. *Biochemistry* 39:2376-2383.

55. Lands, W. E. M., editor. 1987. *Proceedings of the AOCS Short Course on Polyunsaturated Fatty Acids and Eicosanoids*. American Oil Chemists' Society, Champaign, Ill.

56. Garcia-Cardena, G., J. Comander, K. R. Anderson, B. R. Blackman, and M. A. Gimbrone, Jr. 2001. Biomechanical activation of vascular endothelium as a determinant of its functional phenotype. *Proc. Natl. Acad. Sci. USA* 98:4478-4485.

57. Gum, P. A., M. Thamilarasan, J. Watanabe, E. H. Blackstone, and M. S. Lauer. 2001. Aspirin use and all-cause mortality among patients being evaluated for known or suspected coronary artery disease: a propensity analysis. *J.A.M.A.* 286:1187-1194.

58. Rosenberg, I. H. 2002. Fish—food to calm the heart. *N. Engl. J. Med.* 346:1102-1103.

59. Maddox, J. F., and C. N. Serhan. 1996. Lipoxin $A_4$ and $B_4$ are potent stimuli for human monocyte migration and adhesion: selective inactivation by dehydrogenation and reduction. *J. Exp. Med.* 183:137-146.

Beckles Willson, N., T. M. Elliott and M. L. Everard (2002). "Omega-3 fatty acids (from fish oils) for cystic fibrosis." *Cochrane Database of Systematic Reviews*. (3): CD002201.

Busse, W. W. and R. F. Lemanske, Jr. (2001). "Asthma." *New England Journal of Medicine* 344(5): 350-62.

Fahy, J. V., K. W. Kim, J. Liu and H. A. Boushey (1995). "Prominent neutrophilic inflammation in sputum from subjects with asthma exacerbation." *Journal of Allergy & Clinical Immunology*. 95(4): 843-52.

Freedman, S. D., P. G. Blanco, M. M. Zaman, J. C. Shea, M. Ollero, et al. (2004). "Association of cystic fibrosis with abnormalities in fatty acid metabolism. [see comment]." *New England Journal of Medicine*. 350(6): 560-9.

Gadek, J. E., S. J. DeMichele, M. D. Karlstad, E. R. Pacht, M. Donahoe, et al. (1999). "Effect of enteral feeding with eicosapentaenoic acid, gamma-linolenic acid, and antioxidants in patients with acute respiratory distress syndrome. Enteral Nutrition in ARDS Study Group." *Critical Care Medicine*. 27(8): 1409-20.

Gilroy, D. W., T. Lawrence, M. Perretti and A. G. Rossi (2004). "Inflammatory resolution: New opportunities for drug discovery." *Nature Reviews. Drug Discovery*. 3: 401-416.

Hong, S., K. Gronert, P. R. Devchand, R. L. Moussignac and C. N. Serhan (2003). "Novel docosatrienes and 17S-resolvins generated from docosahexaenoic acid in murine brain, human blood, and glial cells. Autacoids in anti-inflammation." *Journal of Biological Chemistry*. 278(17): 14677-87.

Hunter, J. A., W. E. Finkbeiner, J. A. Nadel, E. J. Goetzl and M. J. Holtzman (1985). "Predominant generation of 15-lipoxygenase metabolites of arachidonic acid by epithelial cells from human trachea." *Proceedings of the National Academy of Sciences of the United States of America* 82(14): 4633-7.

Karp, C. L., L. M. Flick, K. W. Park, S. Softic, T. M. Greer, et al. (2004). "Defective lipoxin-mediated anti-inflammatory activity in the cystic fibrosis airway." *Nature Immunology*. 5(4): 388-392.

Lee, T. H., J. M. Mencia-Huerta, C. Shih, E. J. Corey, R. A. Lewis, et al. (1984). "Effects of exogenous arachidonic, eicosapentaenoic, and docosahexaenoic acids on the generation of 5-lipoxygenase pathway products by ionophore-activated human neutrophils." *Journal of Clinical Investigation*. 74(6): 1922-33.

Levy, B. D., G. T. De Sanctis, P. R. Devchand, E. Kim, K. Ackerman, et al. (2002). "Multi-pronged inhibition of airway hyper-responsiveness and inflammation by lipoxin A(4)." *Nature Medicine*. 8(9): 1018-23.

Levy, B. D. and C. N. Serhan (2003). "Exploring new approaches to the treatment of asthma: potential roles for lipoxins and aspirin-triggered lipid mediators." *Drugs of Today*. 39(5): 373-84.

Marcheselli, V. L., S. Hong, W. J. Lukiw, X. H. Tian, K. Gronert, et al. (2003). "Novel docosanoids inhibit brain ischemia-reperfusion-mediated leukocyte infiltration and pro-inflammatory gene expression." *Journal of Biological Chemistry*. 278(44): 43807-17.

Matsuoka, T., M. Hirata, H. Tanaka, Y. Takahashi, T. Murata, et al. (2000). "Prostaglandin D2 as a mediator of allergic asthma." *Science.* 287(5460): 2013-7.

Mukherjee, P. K., V. L. Marcheselli, C. N. Serhan and N. G. Bazan (2004). "Neuroprotectin D1: a docosahexaenoic acid-derived docosatriene protects human retinal pigment epithelial cells from oxidative stress." *Proceedings of the National Academy of Sciences of the United States of America* 101: 8491-8496.

Munafo, D. A., K. Shindo, J. R. Baker and T. D. Bigby (1994). "Leukotriene A4 hydrolase in human bronchoalveolar lavage fluid." *Journal of Clinical Investigation.* 93(3): 1042-50.

Nassar, G. M., J. D. Morrow, L. J. d. Roberts, F. G. Lakkis and K. F. Badr (1994). "Induction of 15-lipoxygenase by interleukin-13 in human blood monocytes." *Journal of Biological Chemistry* 269(44): 27631-4.

Pouliot, M., P. P. McDonald, L. Khamzina, P. Borgeat and S. R. McColl (1994). "Granulocyte-macrophage colony-stimulating factor enhances 5-lipoxygenase levels in human polymorphonuclear leukocytes." *Journal of Immunology* 152(2): 851-8.

Sanak, M., B. D. Levy, C. B. Clish, N. Chiang, K. Gronert, et al. (2000). "Aspirin-tolerant asthmatics generate more lipoxins than aspirin-intolerant asthmatics." *European Respiratory Journal.* 16(1): 44-9.

Serhan, C. N., C. B. Clish, J. Brannon, S. P. Colgan, N. Chiang, et al. (2000). "Novel functional sets of lipid-derived mediators with antiinflammatory actions generated from omega-3 fatty acids via cyclooxygenase 2-nonsteroidal antiinflammatory drugs and transcellular processing." *Journal of Experimental Medicine.* 192(8): 1197-204.

Serhan, C. N., K. Gotlinger, S. Hong and M. Arita (2004). "Resolvins, Docosatrienes and Neuroprotectins, Novel Omega-3-Derived Mediators and Their Aspirin-Triggered Endogenous Epimers An Overview of Their Protective Roles in Catabasis." *Prostaglandins & Other Lipid Mediators.* 73: 155-172.

Serhan, C. N., S. Hong, K. Gronert, S. P. Colgan, P. R. Devchand, et al. (2002). "Resolvins: a family of bioactive products of omega-3 fatty acid transformation circuits initiated by aspirin treatment that counter proinflammation signals." *Journal of Experimental Medicine.* 196(8): 1025-37.

Spector, S. L. and M. E. Surette (2003). "Diet and asthma: has the role of dietary lipids been overlooked in the management of asthma?" *Annals of Allergy, Asthma, & Immunology.* 90(4): 371-7; quiz 377-8, 421.

Vachier, I., M. Kumlin, S. E. Dahlen, J. Bousquet, P. Godard, et al. (2003). "High levels of urinary leukotriene E4 excretion in steroid treated patients with severe asthma." *Respiratory Medicine* 97(11): 1225-9.

Wenzel, S. E., S. J. Szefler, D. Y. Leung, S. I. Sloan, M. D. Rex, et al. (1997). "Bronchoscopic evaluation of severe asthma. Persistent inflammation associated with high dose glucocorticoids." *American Journal of Respiratory & Critical Care Medicine.* 156(3 Pt 1): 737-43.

Wills-Karp, M., J. Luyimbazi, X. Xu, B. Schofield, T. Y. Neben, et al. (1998). "Interleukin-13: central mediator of allergic asthma." *Science.* 282(5397): 2258-61.

Woods, R. K., F. C. Thien and M. J. Abramson (2002). "Dietary marine fatty acids (fish oil) for asthma in adults and children. [update of Cochrane Database Syst Rev. 2000; (4):CD001283; PMID: 11034708]." *Cochrane Database of Systematic Reviews.* (3): CD001283.

Zaitsu, M., Y. Hamasaki, M. Matsuo, A. Kukita, K. Tsuji, et al. (2000). "New induction of leukotriene A(4) hydrolase by interleukin-4 and interleukin-13 in human polymorphonuclear leukocytes." *Blood.* 96(2): 601-9.

Although the present invention has been described with reference to preferred embodiments, persons skilled in the art will recognize that changes may be made in form and detail without departing from the spirit and scope of the invention. All publications and references cited herein, including those in the background section, are expressly incorporated herein by reference in their entirety.

---

We claim:

1. An isolated compound comprising the formula:

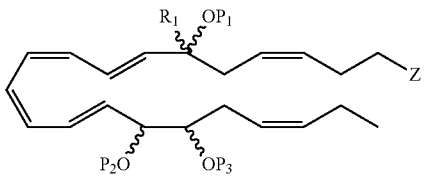

or pharmaceutically acceptable salts thereof, wherein:

each of $P_1$, $P_2$ and $P_3$ is independently a hydrogen atom or a protecting group;

$R_1$ is an optionally substituted alkyl; an optionally substituted aryl; an optionally substituted alkylaryl, halogen, or a hydrogen atom;

Z is a —C(O)OR$^d$, —C(O)NR$^c$R$^c$, —C(O)H, —C(NH)NR$^c$R$^c$, —C(S)H, —C(S)OR$^d$, —C(S)NR$^c$R$^c$, or —CN, wherein:

each R$^c$ is independently a protecting group or R$^a$, or, alternatively, two R$^c$ are taken together with the nitrogen atom to which they are bonded to form a 5 to 8-membered cycloheteroalkyl or heteroaryl optionally substituted with one or more of the same or different R$^a$ or R$^b$ groups;

each R$^d$ is independently a protecting group or R$^a$;

each R$^a$ is independently a hydrogen atom, (C1-C6) alkyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl, or 6-16 membered heteroarylalkyl;

each R$^b$ is independently a =O, —OR$^d$, (C1-C3) haloalkyloxy, —OCF$_3$, =S, —SR$^d$, =NR$^d$, =NOR$^d$, —NR$^c$R$^c$, halogen, —CF$_3$, —CN, —NC, —OCN, —SCN, —NO, —NO$_2$, =N$_2$, —N$_3$, —S(O)R$^d$, —S(O)$_2$R$^d$, —S(O)$_2$OR$^d$, —S(O)NR$^c$R$^c$, —S(O)$_2$NR$^c$R$^c$, —OS(O)R$^d$, —OS(O)$_2$R$^d$, —OS(O)$_2$OR$^d$, —OS(O)$_2$NR$^c$R$^c$, —C(O)R$^d$, —C(O)OR$^d$, —C(O)NR$^c$R$^c$, —C(NH)NR$^c$R$^c$, —C(NR$^a$)NR$^c$R$^c$, —C(NOH)R$^a$, —C(NOH)NR$^c$R$^c$, —OC(O)R$^d$, —OC(O)OR$^d$, —OC(O)NR$^c$R$^c$, —OC(NH)NR$^c$R$^c$, —OC(NR$^a$)N R$^c$R$^c$, —[NHC(O)]$_n$ R$^d$, —[NR$^a$C(O)]$_n$R$^d$, —[NHC(O)]$_n$OR$^d$, —[NR$^a$C(O)]$_n$OR$^d$, —[NHC(O)]$_n$NR$^c$R$^c$, —[NR$^a$C(O)]$_n$NR$^c$R$^c$, —[NHC(NH)]$_n$NR$^c$R$^c$, or —[NR$^a$C(NR$^a$)]$_n$NR$^c$R$^c$; and each n, independently is an integer from 0 to 3;

each double bond represents an E or a Z isomer.

2. A method to treat inflammation in a subject comprising the step of administering to the subject a therapeutically effective amount of an isolated compound of claim 1, wherein inflammation is treated.

3. A composition comprising an isolated compound of claim 1 and a pharmaceutically acceptable carrier.

4. A method to treat inflammation in a subject comprising the step of administering to the subject a therapeutically effective amount of the composition of claim 3, wherein inflammation is treated.

5. The isolated compound of claim 1, wherein the chiral carbon atom at the 7 position (C-7) has an S configuration and $R_1$ is a hydrogen atom.

6. A method to treat inflammation in a subject comprising the step of administering to the subject a therapeutically effective amount of an isolated compound of claim 5, wherein inflammation is treated.

7. A composition comprising an isolated compound of claim 5 and a pharmaceutically acceptable carrier.

8. A method to treat inflammation in a subject comprising the step of administering to the subject a therapeutically effective amount of the composition of claim 7, wherein inflammation is treated.

9. The isolated compound of claim 5, wherein Z is a —C(O)OR$^d$ and R$^d$ is a hydrogen atom or a (C1-C6) alkyl.

10. A method to treat inflammation in a subject comprising the step of administering to the subject a therapeutically effective amount of an isolated compound of claim 9, wherein inflammation is treated.

11. A composition comprising an isolated compound of claim 9 and a pharmaceutically acceptable carrier.

12. A method to treat inflammation in a subject comprising the step of administering to the subject a therapeutically effective amount of the composition of claim 11, wherein inflammation is treated.

13. The isolated compound of claim 1, wherein the chiral carbon atom at the 16 position (C-16) has an R configuration and $R_1$ is a hydrogen atom.

14. A method to treat inflammation in a subject comprising the step of administering to the subject a therapeutically effective amount of an isolated compound of claim 13, wherein inflammation is treated.

15. A composition comprising an isolated compound of claim 13 and a pharmaceutically acceptable carrier.

16. A method to treat inflammation in a subject comprising the step of administering to the subject a therapeutically effective amount of the composition of claim 15, wherein inflammation is treated.

17. The isolated compound of claim 13, wherein Z is a —C(O)OR$^d$ and R$^d$ is a hydrogen atom or a (C1-C6) alkyl.

18. A method to treat inflammation in a subject comprising the step of administering to the subject a therapeutically effective amount of an isolated compound of claim 17, wherein inflammation is treated.

19. A composition comprising an isolated compound of claim 17 and a pharmaceutically acceptable carrier.

20. A method to treat inflammation in a subject comprising the step of administering to the subject a therapeutically effective amount of the composition of claim 19, wherein inflammation is treated.

21. The isolated compound of claim 1, wherein the chiral carbon atom at the 17 position (C-17) has an S configuration and R$_1$ is a hydrogen atom.

22. A method to treat inflammation in a subject comprising the step of administering to the subject a therapeutically effective amount of an isolated compound of claim 21, wherein inflammation is treated.

23. The isolated compound of claim 21, wherein Z is a —C(O)OR$^d$ and R$^d$ is a hydrogen atom or a (C1-C6) alkyl.

24. A composition comprising an isolated compound of claim 23 and a pharmaceutically acceptable carrier.

25. A method to treat inflammation in a subject comprising the step of administering to the subject a therapeutically effective amount of the composition of claim 24, wherein inflammation is treated.

26. The isolated compound of claim 1, wherein the chiral carbon atom at the 7 position (C-7) has an S configuration, the chiral carbon atom at the 16 position (C-16) has an R configuration and the 17 position (C-17) has an S configuration and R$_1$ is a hydrogen atom.

27. A method to treat inflammation in a subject comprising the step of administering to the subject a therapeutically effective amount of an isolated compound of claim 26, wherein inflammation is treated.

28. A composition comprising an isolated compound of claim 26 and a pharmaceutically acceptable carrier.

29. A method to treat inflammation in a subject comprising the step of administering to the subject a therapeutically effective amount of the composition of claim 28, wherein inflammation is treated.

30. The isolated compound of claim 26, wherein Z is a —C(O)OR$^d$ and R$^d$ is a hydrogen atom or a (C1-C6) alkyl.

31. A method to treat inflammation in a subject comprising the step of administering to the subject a therapeutically effective amount of an isolated compound of claim 30, wherein inflammation is treated.

32. A composition comprising an isolated compound of claim 30 and a pharmaceutically acceptable carrier.

33. A method to treat inflammation in a subject comprising the step of administering to the subject a therapeutically effective amount of the composition of claim 32, wherein inflammation is treated.

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: oligonucleotide

<400> SEQUENCE: 1
ggaagatgct ggttccctgc                                                   20

<210> SEQ ID NO 2
<211> LENGTH: 20
<212> TYPE: DNA
<213> ORGANISM: Artificial Sequence
<220> FEATURE:
<223> OTHER INFORMATION: oligonucleotide

<400> SEQUENCE: 2
caacacgcag gacaggtaca                                                   20

<210> SEQ ID NO 3
<211> LENGTH: 21
<212> TYPE: DNA
<213> ORGANISM: Artificial Sequence
```

```
<220> FEATURE:
<223> OTHER INFORMATION: oligonucleotide

<400> SEQUENCE: 3
tccaccaccg tgttgctgta g                                        21

<210> SEQ ID NO 4
<211> LENGTH: 22
<212> TYPE: DNA
<213> ORGANISM: Artificial Sequence
<220> FEATURE:
<223> OTHER INFORMATION: oligonucleotide

<400> SEQUENCE: 4
gaccacagtc catgacatca ct                                       22
```